(12) United States Patent
Schwarz et al.

(10) Patent No.: US 11,484,725 B2
(45) Date of Patent: *Nov. 1, 2022

(54) METHODS AND DEVICES FOR AESTHETIC TREATMENT OF BIOLOGICAL STRUCTURES BY RADIOFREQUENCY AND MAGNETIC ENERGY

(71) Applicant: BTL Medical Solutions A.S., Prague 1 (CZ)

(72) Inventors: Tomás Schwarz, Prague (CZ); Frantisek Lang, Volyně (CZ)

(73) Assignee: BTL Medical Solutions A.S., Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/671,191

(22) Filed: Feb. 14, 2022

(65) Prior Publication Data

US 2022/0168584 A1   Jun. 2, 2022

Related U.S. Application Data

(63) Continuation of application No. 16/844,822, filed on Apr. 9, 2020, now Pat. No. 11,247,063.
(Continued)

(51) Int. Cl.
*A61N 2/00* (2006.01)
*A61B 18/14* (2006.01)
*A61N 1/40* (2006.01)

(52) U.S. Cl.
CPC .............. *A61N 2/002* (2013.01); *A61B 18/14* (2013.01); *A61N 1/403* (2013.01); *A61N 2/004* (2013.01)

(58) Field of Classification Search
CPC ...... A61B 18/14; A61B 18/082; A61N 2/004; A61N 1/36146; A61N 1/36167;
(Continued)

(56) References Cited

U.S. PATENT DOCUMENTS 1,973,387 A   9/1934   Neymann et al.
2,021,676 A   11/1935  Wood et al.
(Continued)

FOREIGN PATENT DOCUMENTS

AU   747678 B2      5/2002
AU   2011265424 B2  7/2014
(Continued)

OTHER PUBLICATIONS

US 10,398,895 B2, 09/2019, Tomás (withdrawn)
(Continued)

*Primary Examiner* — Christine H Matthews
*Assistant Examiner* — Joshua Daryl D Lannu
(74) *Attorney, Agent, or Firm* — Sterne, Kessler, Goldstein & Fox P.L.L.C.

(57) ABSTRACT

A treatment device for providing a magnetic treatment and a radiofrequency treatment to a body area of a patient. The device includes an energy storage device for storing electric energy, a magnetic field generating device, and a switching device to discharge the electrical energy from the energy storage device to the magnetic field generating device, such that a time-varying magnetic field is generated and provides muscle contraction to a muscle in the body area of the patient. The time-varying magnetic field may have a magnetic field density in a range of 0.1 Tesla to 7 Tesla and a repetition rate in a range of 0.1 Hz to 700 Hz. The device may also include a radiofrequency electrode to generate radiofrequency waves to heat a tissue in the body of the patient. A body of the radiofrequency electrode may include a plurality of openings in a range of 5 to 1000 openings.

30 Claims, 47 Drawing Sheets

Related U.S. Application Data

(60) Provisional application No. 62/832,738, filed on Apr. 11, 2019, provisional application No. 62/832,688, filed on Apr. 11, 2019, provisional application No. 62/932,259, filed on Nov. 7, 2019.

(58) Field of Classification Search
CPC ............ A61N 1/36171; A61N 1/36178; A61N 2/002; A61N 2/02; A61N 1/403; A61N 5/025

See application file for complete search history.

(56) References Cited

U.S. PATENT DOCUMENTS

| | | |
|---|---|---|
| 3,163,161 A | 12/1964 | Jacques et al. |
| 3,566,877 A | 3/1971 | Smith et al. |
| 3,658,051 A | 4/1972 | Maclean et al. |
| 3,841,306 A | 10/1974 | Hallgren et al. |
| 3,915,151 A | 10/1975 | Kraus |
| 3,946,349 A | 3/1976 | Haldeman, III |
| 3,952,751 A | 4/1976 | Yarger |
| 3,971,387 A | 7/1976 | Mantell |
| 4,068,292 A | 1/1978 | Berry et al. |
| 4,143,661 A | 3/1979 | LaForge et al. |
| 4,197,851 A | 4/1980 | Fellus |
| 4,237,898 A | 12/1980 | Whalley |
| 4,305,115 A | 12/1981 | Armitage |
| 4,315,503 A | 2/1982 | Ryaby et al. |
| 4,392,040 A | 7/1983 | Rand et al. |
| 4,454,883 A | 6/1984 | Fellus |
| 4,456,001 A | 6/1984 | Pescatore |
| 4,550,714 A | 11/1985 | Talish et al. |
| 4,556,056 A | 12/1985 | Fischer et al. |
| 4,665,898 A | 5/1987 | Costa et al. |
| 4,674,482 A | 6/1987 | Waltonen et al. |
| 4,674,505 A | 6/1987 | Pauli et al. |
| 4,723,536 A | 2/1988 | Rauscher et al. |
| 4,850,959 A | 7/1989 | Findl |
| 4,889,526 A | 12/1989 | Rauscher et al. |
| 4,957,480 A | 9/1990 | Morenings |
| 4,989,604 A | 2/1991 | Fang |
| 4,993,413 A | 2/1991 | Mcleod et al. |
| 5,061,234 A | 10/1991 | Chaney |
| 5,067,940 A | 11/1991 | Liboff et al. |
| 5,085,626 A | 2/1992 | Frey |
| 5,143,063 A | 9/1992 | Fellner |
| 5,156,587 A | 10/1992 | Montone |
| 5,181,902 A | 1/1993 | Erickson et al. |
| 5,199,951 A | 4/1993 | Spears |
| 5,334,181 A | 8/1994 | Rubinsky et al. |
| 5,344,384 A | 9/1994 | Ostrow et al. |
| 5,401,233 A | 3/1995 | Erickson et al. |
| 5,415,617 A | 5/1995 | Kraus |
| 5,419,344 A | 5/1995 | Dewitt |
| 5,433,737 A | 7/1995 | Aimone |
| 5,433,740 A | 7/1995 | Yamaguchi |
| 5,584,863 A | 12/1996 | Rauch et al. |
| 5,620,463 A | 4/1997 | Drolet |
| 5,660,836 A | 8/1997 | Knowlton |
| 5,674,218 A | 10/1997 | Rubinsky et al. |
| 5,690,692 A | 11/1997 | Fleming |
| 5,691,873 A | 11/1997 | Masaki |
| 5,718,662 A | 2/1998 | Jalinous |
| 5,725,471 A | 3/1998 | Davey et al. |
| 5,755,753 A | 5/1998 | Knowlton |
| 5,766,124 A | 6/1998 | Polson |
| 5,782,743 A | 7/1998 | Russell |
| 5,807,232 A | 9/1998 | Espinoza et al. |
| 5,857,957 A | 1/1999 | Lin |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa et al. |
| 6,017,337 A | 1/2000 | Pira |
| 6,032,675 A | 3/2000 | Rubinsky |
| 6,038,485 A | 3/2000 | Axelgaard |
| 6,047,215 A | 4/2000 | McClure et al. |
| 6,063,108 A | 5/2000 | Salansky et al. |
| 6,067,474 A | 5/2000 | Schulman et al. |
| 6,086,525 A | 7/2000 | Davey et al. |
| 6,094,599 A | 7/2000 | Bingham et al. |
| 6,099,459 A | 8/2000 | Jacobson |
| 6,099,523 A | 8/2000 | Kim et al. |
| 6,117,066 A | 9/2000 | Abrams et al. |
| 6,132,361 A | 10/2000 | Epstein et al. |
| 6,141,985 A | 11/2000 | Cluzeau et al. |
| 6,155,966 A | 12/2000 | Parker |
| 6,161,757 A | 12/2000 | Morris |
| 6,179,769 B1 | 1/2001 | Ishikawa et al. |
| 6,179,770 B1 | 1/2001 | Mould |
| 6,179,771 B1 | 1/2001 | Mueller |
| 6,200,259 B1 | 3/2001 | March |
| 6,213,933 B1 | 4/2001 | Lin |
| 6,223,750 B1 | 5/2001 | Ishikawa et al. |
| 6,246,905 B1 | 6/2001 | Mogul |
| 6,255,815 B1 | 7/2001 | Davey |
| 6,261,301 B1 | 7/2001 | Knesch et al. |
| 6,273,862 B1 | 8/2001 | Privitera et al. |
| 6,273,884 B1 | 8/2001 | Altshuler et al. |
| 6,280,376 B1 | 8/2001 | Holcomb |
| 6,282,448 B1 | 8/2001 | Katz et al. |
| D447,806 S | 9/2001 | Davey et al. |
| 6,311,090 B1 | 10/2001 | Knowlton |
| 6,324,430 B1 | 11/2001 | Zarinetchi et al. |
| 6,324,432 B1 | 11/2001 | Rigaux et al. |
| 6,334,069 B1 | 12/2001 | George et al. |
| 6,334,074 B1 | 12/2001 | Spertell |
| 6,350,276 B1 | 2/2002 | Knowlton |
| 6,402,678 B1 | 6/2002 | Fischell et al. |
| 6,413,255 B1 | 7/2002 | Stern |
| 6,418,345 B1 | 7/2002 | Tepper et al. |
| 6,424,864 B1 | 7/2002 | Matsuura |
| 6,425,852 B1 | 7/2002 | Epstein et al. |
| 6,443,883 B1 | 9/2002 | Ostrow et al. |
| 6,445,955 B1 | 9/2002 | Michelson et al. |
| 6,447,440 B1 | 9/2002 | Markoll |
| 6,453,202 B1 | 9/2002 | Knowlton |
| 6,461,375 B1 | 10/2002 | Baudry et al. |
| 6,491,620 B1 | 12/2002 | Davey |
| 6,500,110 B1 | 12/2002 | Davey et al. |
| 6,520,903 B1 | 2/2003 | Yamashiro |
| 6,527,694 B1 | 3/2003 | Ishikawa et al. |
| 6,527,695 B1 | 3/2003 | Davey et al. |
| 6,537,197 B1 | 3/2003 | Ruohonen et al. |
| 6,569,078 B2 | 5/2003 | Ishikawa et al. |
| 6,605,080 B1 | 8/2003 | Altshuler et al. |
| 6,635,053 B1 | 10/2003 | Lalonde et al. |
| 6,658,301 B2 | 12/2003 | Loeb et al. |
| 6,662,054 B2 | 12/2003 | Kreindel et al. |
| 6,663,556 B2 | 12/2003 | Barker |
| 6,663,659 B2 | 12/2003 | McDaniel |
| 6,701,185 B2 | 3/2004 | Burnett et al. |
| 6,735,481 B1 | 5/2004 | Bingham et al. |
| 6,738,667 B2 | 5/2004 | Deno et al. |
| 6,749,624 B2 | 6/2004 | Knowlton |
| 6,827,681 B2 | 12/2004 | Tanner et al. |
| 6,849,040 B2 | 2/2005 | Ruohonen et al. |
| 6,860,852 B2 | 3/2005 | Schonenberger et al. |
| 6,871,099 B1 | 3/2005 | Whitehurst et al. |
| 6,879,859 B1 | 4/2005 | Boveja |
| 6,889,090 B2 | 5/2005 | Kreindel |
| 6,920,883 B2 | 7/2005 | Bessette et al. |
| 6,939,287 B1 | 9/2005 | Ardizzone et al. |
| 6,960,202 B2 | 11/2005 | Cluzeau et al. |
| 6,990,427 B2 | 1/2006 | Kirsch et al. |
| 7,024,239 B2 | 4/2006 | George et al. |
| 7,030,764 B2 | 4/2006 | Smith et al. |
| 7,041,100 B2 | 5/2006 | Kreindel |
| 7,083,580 B2 | 8/2006 | Bernabei |
| 7,186,209 B2 | 3/2007 | Jacobson et al. |
| 7,217,265 B2 | 5/2007 | Hennings et al. |
| 7,276,058 B2 | 10/2007 | Altshuler et al. |
| 7,309,309 B2 | 12/2007 | Wang et al. |
| 7,318,821 B2 | 1/2008 | Lalonde et al. |

(56) References Cited

U.S. PATENT DOCUMENTS

| | | |
|---|---|---|
| 7,351,252 B2 | 4/2008 | Altshuler et al. |
| 7,367,341 B2 | 5/2008 | Anderson et al. |
| 7,369,895 B2 | 5/2008 | Hurtado |
| 7,372,271 B2 | 5/2008 | Roozen et al. |
| 7,376,460 B2 | 5/2008 | Bernabei |
| 7,396,326 B2 | 7/2008 | Ghiron et al. |
| 7,496,401 B2 | 2/2009 | Bernabei |
| 7,520,849 B1 | 4/2009 | Simon |
| 7,520,875 B2 | 4/2009 | Bernabei |
| 7,532,926 B2 | 5/2009 | Bernabei |
| 7,571,003 B2 | 8/2009 | Pozzato |
| 7,591,776 B2 | 9/2009 | Phillips et al. |
| 7,601,115 B2 | 10/2009 | Riehl |
| 7,608,035 B2 | 10/2009 | Farone |
| 7,618,429 B2 | 11/2009 | Mulholland |
| 7,630,774 B2 | 12/2009 | Karni et al. |
| 7,643,883 B2 | 1/2010 | Kreindel |
| 7,697,998 B2 | 4/2010 | Axelgaard |
| 7,699,768 B2 | 4/2010 | Kishawi et al. |
| 7,740,574 B2 | 6/2010 | Pilla et al. |
| 7,744,523 B2 | 6/2010 | Epstein |
| 7,783,348 B2 | 8/2010 | Gill et al. |
| 7,785,358 B2 | 8/2010 | Lach |
| 7,854,754 B2 | 12/2010 | Ting et al. |
| 7,909,786 B2 | 3/2011 | Bonnefin et al. |
| 7,914,469 B2 | 3/2011 | Torbati |
| 7,945,321 B2 | 5/2011 | Bernabei |
| 7,946,973 B2 | 5/2011 | Peterchev |
| 7,953,500 B2 | 5/2011 | Bingham et al. |
| 7,998,053 B2 | 8/2011 | Aho |
| 8,035,385 B2 | 10/2011 | Tomiha et al. |
| RE43,007 E | 12/2011 | Lalonde et al. |
| 8,088,058 B2 | 1/2012 | Juliana et al. |
| 8,128,549 B2 | 3/2012 | Testani et al. |
| 8,133,191 B2 | 3/2012 | Rosenberg et al. |
| 8,137,258 B1 | 3/2012 | Dennis et al. |
| 8,172,835 B2 | 5/2012 | Leyh et al. |
| 8,192,474 B2 | 6/2012 | Levinson |
| 8,204,446 B2 | 6/2012 | Scheer et al. |
| 8,251,986 B2 | 8/2012 | Chornenky et al. |
| 8,265,763 B2 | 9/2012 | Fahey |
| 8,271,090 B1 | 9/2012 | Hartman et al. |
| 8,275,442 B2 | 9/2012 | Allison |
| 8,285,390 B2 | 10/2012 | Levinson et al. |
| 8,335,566 B2 | 12/2012 | Muller et al. |
| 8,337,539 B2 | 12/2012 | Ting et al. |
| 8,366,756 B2 | 2/2013 | Tucek et al. |
| 8,376,825 B2 | 2/2013 | Guinn et al. |
| 8,376,925 B1 | 2/2013 | Dennis et al. |
| 8,454,591 B2 | 6/2013 | Leyh et al. |
| 8,457,751 B2 | 6/2013 | Pozzato |
| 8,475,354 B2 | 7/2013 | Phillips et al. |
| 8,523,927 B2 | 9/2013 | Levinson et al. |
| 8,548,599 B2 | 10/2013 | Zarsky et al. |
| 8,565,888 B2 | 10/2013 | Buhlmann et al. |
| 8,579,953 B1 | 11/2013 | Dunbar et al. |
| 8,588,930 B2 | 11/2013 | DiUbaldi et al. |
| 8,593,245 B2 | 11/2013 | Zeng et al. |
| 8,603,073 B2 | 12/2013 | Allison |
| 8,646,239 B2 | 2/2014 | Rulon |
| 8,666,492 B2 | 3/2014 | Muller et al. |
| 8,676,338 B2 | 3/2014 | Levinson |
| 8,684,901 B1 | 4/2014 | Zabara |
| 8,700,176 B2 | 4/2014 | Azar et al. |
| 8,702,774 B2 | 4/2014 | Baker et al. |
| 8,725,270 B2 | 5/2014 | Towe |
| 8,771,326 B2 | 7/2014 | Myeong et al. |
| 8,788,060 B2 | 7/2014 | Nebrigic et al. |
| 8,795,148 B2 | 8/2014 | Schneider et al. |
| 8,834,547 B2 | 9/2014 | Anderson et al. |
| 8,840,608 B2 | 9/2014 | Anderson et al. |
| 8,864,641 B2 | 10/2014 | Riehl et al. |
| 8,868,177 B2 | 10/2014 | Simon et al. |
| 8,906,009 B2 | 12/2014 | Nebrigic et al. |
| 8,915,948 B2 | 12/2014 | Altshuler et al. |
| 8,932,338 B2 | 1/2015 | Lim et al. |
| 8,979,727 B2 | 3/2015 | Ron et al. |
| 8,985,331 B2 | 3/2015 | Guenter et al. |
| 8,998,791 B2 | 4/2015 | Ron Edoute et al. |
| 9,002,477 B2 | 4/2015 | Burnett |
| 9,028,469 B2 | 5/2015 | Jones et al. |
| 9,037,247 B2 | 5/2015 | Simon et al. |
| 9,044,595 B2 | 6/2015 | Araya et al. |
| 9,061,128 B2 | 6/2015 | Hall et al. |
| 9,072,891 B1 | 7/2015 | Rao |
| 9,078,634 B2 | 7/2015 | Gonzales et al. |
| 9,089,719 B2 | 7/2015 | Simon et al. |
| 9,101,524 B2 | 8/2015 | Aghion |
| 9,132,031 B2 | 9/2015 | Levinson et al. |
| 9,149,650 B2 | 10/2015 | Shanks et al. |
| 9,168,096 B2 | 10/2015 | Kreindel |
| 9,233,257 B1 | 1/2016 | Zabara |
| 9,254,395 B1 | 2/2016 | Shambayati |
| 9,261,574 B2 | 2/2016 | Boskamp et al. |
| 9,265,690 B2 | 2/2016 | Kriksunov et al. |
| 9,308,120 B2 | 4/2016 | Anderson et al. |
| 9,314,368 B2 | 4/2016 | Allison et al. |
| 9,326,910 B2 | 5/2016 | Eckhouse et al. |
| 9,339,641 B2 | 5/2016 | Rajguru et al. |
| 9,358,068 B2 | 6/2016 | Schomacker et al. |
| 9,358,149 B2 | 6/2016 | Anderson et al. |
| 9,375,345 B2 | 6/2016 | Levinson et al. |
| 9,387,339 B2 | 7/2016 | Sham et al. |
| 9,398,975 B2 | 7/2016 | Müller et al. |
| 9,408,745 B2 | 8/2016 | Levinson et al. |
| 9,414,759 B2 | 8/2016 | Lang et al. |
| 9,433,797 B2 | 9/2016 | Pilla et al. |
| 9,439,805 B2 | 9/2016 | Gonzales et al. |
| 9,446,258 B1 | 9/2016 | Schwarz |
| 9,468,774 B2 | 10/2016 | Zarsky et al. |
| 9,532,832 B2 | 1/2017 | Ron Edoute et al. |
| 9,545,523 B2 | 1/2017 | Nanda |
| 9,561,357 B2 | 2/2017 | Hall et al. |
| 9,586,057 B2 | 3/2017 | Ladman et al. |
| 9,596,920 B2 | 3/2017 | Shalev et al. |
| 9,610,429 B2 | 4/2017 | Harris et al. |
| 9,610,459 B2 | 4/2017 | Burnett et al. |
| 9,615,854 B2 | 4/2017 | Matsushita |
| 9,636,516 B2 | 5/2017 | Schwarz |
| 9,636,519 B2 | 5/2017 | Ladman et al. |
| 9,649,220 B2 | 5/2017 | Anderson et al. |
| 9,655,770 B2 | 5/2017 | Levinson et al. |
| 9,694,194 B2 | 7/2017 | Ron Edoute et al. |
| 9,737,238 B2 | 8/2017 | Wright et al. |
| 9,737,434 B2 | 8/2017 | Allison |
| 9,757,584 B2 | 9/2017 | Burnett |
| 9,782,324 B2 | 10/2017 | Crunick et al. |
| 9,814,897 B2 | 11/2017 | Ron Edoute et al. |
| 9,844,460 B2 | 12/2017 | Weber et al. |
| 9,844,461 B2 | 12/2017 | Levinson et al. |
| 9,855,166 B2 | 1/2018 | Anderson et al. |
| 9,861,421 B2 | 1/2018 | O'Neil et al. |
| 9,861,520 B2 | 1/2018 | Baker et al. |
| 9,867,996 B2 | 1/2018 | Zarsky et al. |
| 9,901,743 B2 | 2/2018 | Ron Edoute et al. |
| 9,919,161 B2 | 3/2018 | Schwarz et al. |
| 9,937,358 B2 | 4/2018 | Schwarz et al. |
| 9,962,553 B2 | 5/2018 | Schwarz et al. |
| 9,968,797 B2 | 5/2018 | Sham et al. |
| 9,974,519 B1 | 5/2018 | Schwarz et al. |
| 9,974,684 B2 | 5/2018 | Anderson et al. |
| 9,980,765 B2 | 5/2018 | Avram et al. |
| 9,981,143 B2 | 5/2018 | Ron Edoute et al. |
| 9,999,780 B2 | 6/2018 | Weyh et al. |
| 10,037,867 B2 | 7/2018 | Godyak |
| 10,039,929 B1 | 8/2018 | Schwarz et al. |
| 10,080,906 B2 | 9/2018 | Schwarz |
| 10,092,346 B2 | 10/2018 | Levinson |
| 10,111,770 B2 | 10/2018 | Harris et al. |
| 10,111,774 B2 | 10/2018 | Gonzales et al. |
| 10,124,187 B2 | 11/2018 | Schwarz et al. |
| 10,183,172 B2 | 1/2019 | Ghiron et al. |
| 10,195,453 B2 | 2/2019 | Schwarz et al. |
| 10,195,454 B2 | 2/2019 | Yamashiro |

(56) References Cited

U.S. PATENT DOCUMENTS

| | | |
|---|---|---|
| 10,201,380 B2 | 2/2019 | Debenedictis et al. |
| 10,245,439 B1 | 4/2019 | Schwarz et al. |
| 10,271,900 B2 | 4/2019 | Marchitto et al. |
| 10,342,988 B2 | 7/2019 | Midorikawa et al. |
| 10,413,745 B2 | 9/2019 | Riehl |
| 10,463,869 B2 | 11/2019 | Ron Edoute et al. |
| 10,471,269 B1 | 11/2019 | Schwarz et al. |
| 10,478,588 B2 | 11/2019 | Walpole et al. |
| 10,478,633 B2 | 11/2019 | Schwarz et al. |
| 10,478,634 B2 | 11/2019 | Schwarz et al. |
| 10,493,293 B2 | 12/2019 | Schwarz et al. |
| 10,518,098 B2 | 12/2019 | Hong et al. |
| 10,549,109 B2 | 2/2020 | Schwarz et al. |
| 10,549,110 B1 | 2/2020 | Schwarz et al. |
| 10,556,121 B2 | 2/2020 | Gurfein |
| 10,556,122 B1 | 2/2020 | Schwarz et al. |
| 10,569,094 B2 | 2/2020 | Schwarz et al. |
| 10,569,095 B1 | 2/2020 | Schwarz et al. |
| 10,583,287 B2 | 3/2020 | Schwarz |
| 10,596,386 B2 | 3/2020 | Schwarz et al. |
| 10,610,696 B1 | 4/2020 | Peled |
| 10,632,321 B2 | 4/2020 | Schwarz et al. |
| 10,639,490 B2 | 5/2020 | Simon et al. |
| 10,661,093 B2 | 5/2020 | Ron Edoute et al. |
| 1,068,831 A1 | 6/2020 | Worthington |
| 10,675,819 B2 | 6/2020 | Li et al. |
| 10,688,310 B2 | 6/2020 | Schwarz et al. |
| 10,695,575 B1 | 6/2020 | Schwarz et al. |
| 10,695,576 B2 | 6/2020 | Schwarz et al. |
| 10,709,894 B2 | 7/2020 | Schwarz et al. |
| 10,709,895 B2 | 7/2020 | Schwarz et al. |
| 10,806,943 B2 | 10/2020 | Sokolowski |
| 10,821,295 B1 | 11/2020 | Schwarz et al. |
| 10,849,784 B2 | 12/2020 | Jurna et al. |
| 11,141,219 B1 | 10/2021 | Schwarz |
| 11,185,690 B2 | 11/2021 | Schwarz |
| 11,247,039 B2 | 2/2022 | Schwarz |
| 2001/0018547 A1 | 8/2001 | Mechlenburg et al. |
| 2001/0031906 A1 | 10/2001 | Ishikawa et al. |
| 2002/0010414 A1 | 1/2002 | Coston et al. |
| 2002/0049483 A1 | 4/2002 | Knowlton |
| 2002/0082466 A1 | 6/2002 | Han |
| 2002/0128686 A1 | 9/2002 | Minogue et al. |
| 2002/0143365 A1 | 10/2002 | Herbst |
| 2002/0160436 A1 | 10/2002 | Markov et al. |
| 2002/0165590 A1 | 11/2002 | Crowe et al. |
| 2003/0028072 A1 | 2/2003 | Fischell et al. |
| 2003/0032900 A1 | 2/2003 | Ella |
| 2003/0032950 A1 | 2/2003 | Altshuler et al. |
| 2003/0050527 A1 | 3/2003 | Fox et al. |
| 2003/0074037 A1 | 4/2003 | Moore et al. |
| 2003/0078646 A1 | 4/2003 | Axelgaard |
| 2003/0093133 A1 | 5/2003 | Crowe et al. |
| 2003/0130711 A1 | 7/2003 | Pearson et al. |
| 2003/0149451 A1 | 8/2003 | Chomenky et al. |
| 2003/0153958 A1 | 8/2003 | Yamazaki et al. |
| 2003/0158585 A1 | 8/2003 | Burnett |
| 2003/0216729 A1 | 11/2003 | Marchitto et al. |
| 2003/0220674 A1 | 11/2003 | Anderson et al. |
| 2003/0236487 A1 | 12/2003 | Knowlton |
| 2004/0015163 A1 | 1/2004 | Buysse et al. |
| 2004/0034346 A1 | 2/2004 | Stern et al. |
| 2004/0039279 A1 | 2/2004 | Ruohonen |
| 2004/0073079 A1 | 4/2004 | Altshuler et al. |
| 2004/0077977 A1 | 4/2004 | Ella et al. |
| 2004/0093042 A1 | 5/2004 | Altshuler et al. |
| 2004/0102768 A1 | 5/2004 | Cluzeau et al. |
| 2004/0162583 A1 | 8/2004 | Bingham et al. |
| 2004/0193003 A1 | 9/2004 | Mechlenburg et al. |
| 2004/0206365 A1 | 10/2004 | Knowlton |
| 2004/0210214 A1 | 10/2004 | Knowlton |
| 2004/0210282 A1 | 10/2004 | Flock et al. |
| 2004/0210287 A1 | 10/2004 | Greene |
| 2004/0230226 A1 | 11/2004 | Bingham et al. |
| 2005/0038313 A1 | 2/2005 | Ardizzone |
| 2005/0049543 A1 | 3/2005 | Anderson et al. |
| 2005/0075701 A1 | 4/2005 | Shafer |
| 2005/0075702 A1 | 4/2005 | Shafer |
| 2005/0090814 A1 | 4/2005 | Lalonde et al. |
| 2005/0107656 A1 | 5/2005 | Jang et al. |
| 2005/0134193 A1 | 6/2005 | Myers et al. |
| 2005/0187599 A1 | 8/2005 | Sharkey et al. |
| 2005/0203504 A1 | 9/2005 | Wham et al. |
| 2005/0215987 A1 | 9/2005 | Slatkine |
| 2005/0216062 A1 | 9/2005 | Herbst |
| 2005/0251120 A1 | 11/2005 | Anderson et al. |
| 2006/0004244 A1 | 1/2006 | Phillips et al. |
| 2006/0020236 A1 | 1/2006 | Ben-Nun |
| 2006/0036300 A1 | 2/2006 | Kreindel |
| 2006/0094924 A1 | 5/2006 | Riehl |
| 2006/0106375 A1 | 5/2006 | Werneth et al. |
| 2006/0152301 A1 | 7/2006 | Rohwedder |
| 2006/0184214 A1 | 8/2006 | McDaniel |
| 2006/0187607 A1 | 8/2006 | Mo |
| 2006/0195168 A1 | 8/2006 | Dunbar et al. |
| 2006/0199992 A1 | 9/2006 | Eisenberg et al. |
| 2006/0206103 A1 | 9/2006 | Altshuler et al. |
| 2006/0206180 A1 | 9/2006 | Alcidi |
| 2006/0253176 A1 | 11/2006 | Caruso et al. |
| 2006/0259102 A1 | 11/2006 | Slatkine |
| 2006/0271028 A1 | 11/2006 | Altshuler et al. |
| 2006/0287566 A1 | 12/2006 | Zangen et al. |
| 2006/0293719 A1 | 12/2006 | Naghavi |
| 2007/0010766 A1 | 1/2007 | Gil et al. |
| 2007/0010861 A1 | 1/2007 | Anderson et al. |
| 2007/0016274 A1 | 1/2007 | Boveja et al. |
| 2007/0027411 A1 | 2/2007 | Ella et al. |
| 2007/0083237 A1 | 4/2007 | Teruel |
| 2007/0088413 A1 | 4/2007 | Weber et al. |
| 2007/0088419 A1 | 4/2007 | Fiorina et al. |
| 2007/0135811 A1 | 6/2007 | Hooven |
| 2007/0142886 A1 | 6/2007 | Fischell et al. |
| 2007/0173749 A1 | 7/2007 | Williams et al. |
| 2007/0173805 A1 | 7/2007 | Weinberg et al. |
| 2007/0179534 A1 | 8/2007 | Firlik et al. |
| 2007/0198071 A1 | 8/2007 | Ting et al. |
| 2007/0232966 A1 | 10/2007 | Applebaum et al. |
| 2007/0244530 A1 | 10/2007 | Ren |
| 2007/0255355 A1 | 11/2007 | Altshuler et al. |
| 2007/0255362 A1 | 11/2007 | Levinson et al. |
| 2007/0260107 A1 | 11/2007 | Mishelevich et al. |
| 2007/0270795 A1 | 11/2007 | Francischelli et al. |
| 2007/0270925 A1 | 11/2007 | Levinson |
| 2007/0282156 A1 | 12/2007 | Konings |
| 2007/0293911 A1 | 12/2007 | Crowe et al. |
| 2007/0293918 A1 | 12/2007 | Thompson et al. |
| 2008/0009885 A1 | 1/2008 | Del Giglio |
| 2008/0046053 A1 | 2/2008 | Wagner et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0082094 A1 | 4/2008 | McPherson et al. |
| 2008/0082153 A1 | 4/2008 | Gadsby et al. |
| 2008/0103565 A1 | 5/2008 | Altshuler et al. |
| 2008/0132971 A1 | 6/2008 | Pille et al. |
| 2008/0183251 A1 | 7/2008 | Azar et al. |
| 2008/0188915 A1 | 8/2008 | Mills et al. |
| 2008/0228520 A1 | 9/2008 | Day et al. |
| 2008/0234534 A1 | 9/2008 | Mikas et al. |
| 2008/0249350 A1 | 10/2008 | Marchitto et al. |
| 2008/0255572 A1 | 10/2008 | Zeller et al. |
| 2008/0255637 A1 | 10/2008 | Oishi |
| 2008/0262287 A1 | 10/2008 | Dussau |
| 2008/0262574 A1 | 10/2008 | Briefs et al. |
| 2008/0287839 A1 | 11/2008 | Rosen et al. |
| 2008/0287948 A1 | 11/2008 | Newton et al. |
| 2008/0306325 A1 | 12/2008 | Burnett et al. |
| 2008/0306326 A1 | 12/2008 | Epstein |
| 2008/0312647 A1 | 12/2008 | Knopp et al. |
| 2009/0005631 A1 | 1/2009 | Simenhaus et al. |
| 2009/0018384 A1 | 1/2009 | Boyden et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |

(56) References Cited

U.S. PATENT DOCUMENTS

| | | |
|---|---|---|
| 2009/0018626 A1 | 1/2009 | Levinson et al. |
| 2009/0018627 A1 | 1/2009 | Levinson et al. |
| 2009/0018628 A1 | 1/2009 | Burns et al. |
| 2009/0024192 A1 | 1/2009 | Mulholland |
| 2009/0024193 A1 | 1/2009 | Altshuler et al. |
| 2009/0036958 A1 | 2/2009 | Mehta |
| 2009/0043293 A1 | 2/2009 | Pankratov et al. |
| 2009/0099405 A1 | 4/2009 | Schneider et al. |
| 2009/0108969 A1 | 4/2009 | Sims et al. |
| 2009/0118722 A1 | 5/2009 | Ebbers et al. |
| 2009/0118790 A1 | 5/2009 | Van Herk |
| 2009/0149300 A1 | 6/2009 | Chen |
| 2009/0149929 A1 | 6/2009 | Levinson et al. |
| 2009/0149930 A1 | 6/2009 | Schenck |
| 2009/0156958 A1 | 6/2009 | Mehta et al. |
| 2009/0221938 A1 | 9/2009 | Rosenberg et al. |
| 2009/0227831 A1 | 9/2009 | Burnett et al. |
| 2009/0234423 A1 | 9/2009 | Vetanze |
| 2009/0248004 A1 | 10/2009 | Altshuler et al. |
| 2009/0254154 A1 | 10/2009 | De Taboada et al. |
| 2009/0270945 A1 | 10/2009 | Markoll et al. |
| 2009/0284339 A1 | 11/2009 | Choi et al. |
| 2009/0306648 A1 | 12/2009 | Podhajsky et al. |
| 2009/0326571 A1 | 12/2009 | Mulholland |
| 2010/0004536 A1 | 1/2010 | Rosenberg |
| 2010/0004715 A1 | 1/2010 | Fahey |
| 2010/0016761 A1 | 1/2010 | Rosenberg |
| 2010/0036191 A1 | 2/2010 | Walter et al. |
| 2010/0036368 A1 | 2/2010 | England et al. |
| 2010/0049188 A1 | 2/2010 | Nelson et al. |
| 2010/0069704 A1 | 3/2010 | Peterchev |
| 2010/0081971 A1 | 4/2010 | Allison |
| 2010/0087699 A1 | 4/2010 | Peterchev |
| 2010/0087816 A1 | 4/2010 | Roy |
| 2010/0121131 A1 | 5/2010 | Mathes |
| 2010/0130945 A1 | 5/2010 | Laniado et al. |
| 2010/0145399 A1 | 6/2010 | Johari et al. |
| 2010/0152522 A1 | 6/2010 | Roth et al. |
| 2010/0152824 A1 | 6/2010 | Allison |
| 2010/0160712 A1 | 6/2010 | Burnett et al. |
| 2010/0168501 A1 | 7/2010 | Burnett et al. |
| 2010/0179372 A1 | 7/2010 | Glassman |
| 2010/0185042 A1 | 7/2010 | Schneider et al. |
| 2010/0217253 A1 | 8/2010 | Mehta |
| 2010/0222629 A1 | 9/2010 | Burnett et al. |
| 2010/0228250 A1 | 9/2010 | Brogna |
| 2010/0256438 A1 | 10/2010 | Mishelevich et al. |
| 2010/0256439 A1 | 10/2010 | Schneider et al. |
| 2010/0261992 A1 | 10/2010 | Axelgaard |
| 2010/0274327 A1 | 10/2010 | Carroll et al. |
| 2010/0274329 A1 | 10/2010 | Bradley et al. |
| 2010/0280582 A1 | 11/2010 | Baker et al. |
| 2010/0286470 A1 | 11/2010 | Schneider et al. |
| 2010/0286691 A1 | 11/2010 | Kerr et al. |
| 2010/0298623 A1 | 11/2010 | Mishelevich et al. |
| 2010/0309689 A1 | 12/2010 | Coulson |
| 2010/0324611 A1 | 12/2010 | Deming et al. |
| 2010/0331602 A1 | 12/2010 | Mishelevich et al. |
| 2010/0331603 A1 | 12/2010 | Szecsi |
| 2011/0004261 A1 | 1/2011 | Sham et al. |
| 2011/0007745 A1 | 1/2011 | Schultz et al. |
| 2011/0009737 A1 | 1/2011 | Manstein |
| 2011/0015464 A1 | 1/2011 | Riehl et al. |
| 2011/0021863 A1 | 1/2011 | Burnett et al. |
| 2011/0046432 A1 | 2/2011 | Simon et al. |
| 2011/0046523 A1 | 2/2011 | Altshuler et al. |
| 2011/0066216 A1 | 3/2011 | Ting et al. |
| 2011/0077451 A1 | 3/2011 | Marchitto et al. |
| 2011/0082383 A1 | 4/2011 | Cory et al. |
| 2011/0087312 A1 | 4/2011 | Shanks et al. |
| 2011/0105826 A1 | 5/2011 | Mishelevich et al. |
| 2011/0112520 A1 | 5/2011 | Michael |
| 2011/0118722 A1 | 5/2011 | Lischinsky et al. |
| 2011/0125203 A1 | 5/2011 | Simon et al. |
| 2011/0130618 A1 | 6/2011 | Ron et al. |
| 2011/0130713 A1 | 6/2011 | Dufay |
| 2011/0130796 A1 | 6/2011 | Louise |
| 2011/0152967 A1 | 6/2011 | Simon et al. |
| 2011/0172735 A1 | 7/2011 | Johari |
| 2011/0172752 A1 | 7/2011 | Bingham et al. |
| 2011/0190569 A1 | 8/2011 | Simon et al. |
| 2011/0196438 A1 | 8/2011 | Mnozil et al. |
| 2011/0202058 A1 | 8/2011 | Eder et al. |
| 2011/0218464 A1 | 9/2011 | Iger |
| 2011/0224761 A1 | 9/2011 | Manstein |
| 2011/0237921 A1 | 9/2011 | Askin, III et al. |
| 2011/0238050 A1 | 9/2011 | Allison et al. |
| 2011/0238051 A1 | 9/2011 | Levinson et al. |
| 2011/0245900 A1 | 10/2011 | Turner et al. |
| 2011/0263925 A1 | 10/2011 | Bratton |
| 2011/0273251 A1 | 11/2011 | Mishelevich et al. |
| 2011/0275927 A1 | 11/2011 | Wagner et al. |
| 2011/0276108 A1 | 11/2011 | Crowe et al. |
| 2011/0300079 A1 | 12/2011 | Martens et al. |
| 2011/0306943 A1 | 12/2011 | Dunbar et al. |
| 2011/0319700 A1 | 12/2011 | Schneider |
| 2012/0016359 A1 | 1/2012 | Podhajsky |
| 2012/0022518 A1 | 1/2012 | Levinson |
| 2012/0029394 A1 | 2/2012 | Babaev |
| 2012/0035608 A1 | 2/2012 | Marchitto et al. |
| 2012/0046598 A1 | 2/2012 | Kardos et al. |
| 2012/0046653 A1 | 2/2012 | Welches et al. |
| 2012/0053449 A1 | 3/2012 | Moses et al. |
| 2012/0101326 A1 | 4/2012 | Simon et al. |
| 2012/0108883 A1 | 5/2012 | Peterchev |
| 2012/0108884 A1 | 5/2012 | Bechler et al. |
| 2012/0109241 A1 | 5/2012 | Rauscher |
| 2012/0116271 A1 | 5/2012 | Caruso et al. |
| 2012/0150079 A1 | 6/2012 | Rosenberg |
| 2012/0157747 A1 | 6/2012 | Rybski et al. |
| 2012/0158100 A1 | 6/2012 | Schomacker |
| 2012/0172653 A1 | 7/2012 | Chornenky et al. |
| 2012/0197361 A1 | 8/2012 | Gonzales et al. |
| 2012/0215210 A1 | 8/2012 | Brown et al. |
| 2012/0226272 A1 | 9/2012 | Chernov et al. |
| 2012/0226330 A1 | 9/2012 | Kolen et al. |
| 2012/0239123 A1 | 9/2012 | Weber et al. |
| 2012/0240940 A1 | 9/2012 | Paraschac et al. |
| 2012/0245483 A1 | 9/2012 | Lundqvist |
| 2012/0253098 A1 | 10/2012 | George et al. |
| 2012/0271206 A1 | 10/2012 | Shalev et al. |
| 2012/0271294 A1 | 10/2012 | Barthe et al. |
| 2012/0277587 A1 | 11/2012 | Adanny et al. |
| 2012/0302821 A1 | 11/2012 | Burnett |
| 2012/0303076 A1 | 11/2012 | Fahey |
| 2012/0310033 A1 | 12/2012 | Muntermann |
| 2012/0310035 A1 | 12/2012 | Schneider et al. |
| 2012/0310311 A1 | 12/2012 | Elkah |
| 2012/0330090 A1 | 12/2012 | Sham et al. |
| 2013/0006039 A1 | 1/2013 | Sadler |
| 2013/0012755 A1 | 1/2013 | Slayton |
| 2013/0030239 A1 | 1/2013 | Weyh et al. |
| 2013/0035745 A1 | 2/2013 | Ahmed et al. |
| 2013/0053620 A1 | 2/2013 | Susedik et al. |
| 2013/0066309 A1 | 3/2013 | Levinson |
| 2013/0079684 A1 | 3/2013 | Rosen et al. |
| 2013/0096363 A1 | 4/2013 | Schneider et al. |
| 2013/0103127 A1 | 4/2013 | Mueller et al. |
| 2013/0116758 A1 | 5/2013 | Levinson et al. |
| 2013/0116759 A1 | 5/2013 | Levinson et al. |
| 2013/0123568 A1 | 5/2013 | Hamilton et al. |
| 2013/0123629 A1 | 5/2013 | Rosenberg et al. |
| 2013/0123764 A1 | 5/2013 | Zarsky et al. |
| 2013/0123765 A1 | 5/2013 | Zarsky et al. |
| 2013/0131764 A1 | 5/2013 | Grove |
| 2013/0137918 A1 | 5/2013 | Phillips et al. |
| 2013/0144280 A1 | 6/2013 | Eckhouse et al. |
| 2013/0150653 A1 | 6/2013 | Borsody |
| 2013/0158440 A1 | 6/2013 | Allison |
| 2013/0158634 A1 | 6/2013 | Ron et al. |
| 2013/0158636 A1 | 6/2013 | Ting et al. |
| 2013/0178764 A1 | 7/2013 | Eckhouse et al. |
| 2013/0184693 A1 | 7/2013 | Neev |
| 2013/0190744 A1 | 7/2013 | Avram et al. |

(56) References Cited

U.S. PATENT DOCUMENTS

| | | |
|---|---|---|
| 2013/0238043 A1 | 9/2013 | Beardall et al. |
| 2013/0238061 A1* | 9/2013 | Ron Edoute ............ A61B 18/14 607/101 |
| 2013/0238062 A1 | 9/2013 | Ron Edoute et al. |
| 2013/0245731 A1 | 9/2013 | Allison |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0261374 A1 | 10/2013 | Elder |
| 2013/0261683 A1 | 10/2013 | Soikum et al. |
| 2013/0267943 A1 | 10/2013 | Hancock |
| 2013/0289433 A1 | 10/2013 | Jin et al. |
| 2013/0303904 A1 | 11/2013 | Barthe et al. |
| 2013/0304159 A1 | 11/2013 | Simon et al. |
| 2013/0317281 A1 | 11/2013 | Schneider et al. |
| 2013/0317282 A1 | 11/2013 | Ron Edoute et al. |
| 2013/0331637 A1 | 12/2013 | Greff |
| 2014/0005758 A1 | 1/2014 | Ben-Yehuda et al. |
| 2014/0005760 A1 | 1/2014 | Levinson et al. |
| 2014/0012064 A1 | 1/2014 | Riehl et al. |
| 2014/0018767 A1 | 1/2014 | Harris et al. |
| 2014/0025033 A1 | 1/2014 | Mirkov et al. |
| 2014/0025142 A1 | 1/2014 | Zarksy et al. |
| 2014/0046423 A1 | 2/2014 | Rajguru et al. |
| 2014/0066786 A1 | 3/2014 | Naghavi et al. |
| 2014/0067025 A1 | 3/2014 | Levinson et al. |
| 2014/0081359 A1 | 3/2014 | Sand |
| 2014/0148870 A1 | 5/2014 | Burnett |
| 2014/0194958 A1 | 7/2014 | Chabal et al. |
| 2014/0200388 A1 | 7/2014 | Schneider et al. |
| 2014/0221990 A1 | 8/2014 | Kreindel |
| 2014/0235928 A1 | 8/2014 | Zangen et al. |
| 2014/0243933 A1 | 8/2014 | Ginggen |
| 2014/0249355 A1 | 9/2014 | Martinez |
| 2014/0249609 A1 | 9/2014 | Zarsky et al. |
| 2014/0257071 A1 | 9/2014 | Curran et al. |
| 2014/0257443 A1 | 9/2014 | Baker et al. |
| 2014/0276248 A1 | 9/2014 | Hall et al. |
| 2014/0276693 A1 | 9/2014 | Altshuler et al. |
| 2014/0277219 A1 | 9/2014 | Nanda |
| 2014/0277302 A1 | 9/2014 | Weber et al. |
| 2014/0303425 A1 | 10/2014 | Pilla et al. |
| 2014/0303525 A1 | 10/2014 | Sitharaman |
| 2014/0303696 A1 | 10/2014 | Anderson et al. |
| 2014/0303697 A1 | 10/2014 | Anderson et al. |
| 2014/0316393 A1 | 10/2014 | Levinson |
| 2014/0324120 A1 | 10/2014 | Bogie et al. |
| 2014/0330067 A1 | 11/2014 | Jordan |
| 2014/0350438 A1 | 11/2014 | Papirov et al. |
| 2014/0357935 A1 | 12/2014 | Ilmoniemi et al. |
| 2014/0364841 A1 | 12/2014 | Kornstein |
| 2014/0371515 A1 | 12/2014 | John |
| 2014/0378875 A1 | 12/2014 | Ron Edoute et al. |
| 2015/0005569 A1 | 1/2015 | Missoli |
| 2015/0005759 A1 | 1/2015 | Welches et al. |
| 2015/0018667 A1 | 1/2015 | Radman et al. |
| 2015/0025299 A1 | 1/2015 | Ron et al. |
| 2015/0080769 A1 | 3/2015 | Lotsch |
| 2015/0088105 A1 | 3/2015 | Fatemi |
| 2015/0094788 A1 | 4/2015 | Pierenkemper |
| 2015/0112412 A1 | 4/2015 | Anderson et al. |
| 2015/0119849 A1 | 4/2015 | Aronhalt et al. |
| 2015/0123661 A1 | 5/2015 | Yui et al. |
| 2015/0127075 A1 | 5/2015 | Ward et al. |
| 2015/0133717 A1 | 5/2015 | Ghiron et al. |
| 2015/0133718 A1 | 5/2015 | Schneider et al. |
| 2015/0141877 A1 | 5/2015 | Feldman |
| 2015/0148858 A1 | 5/2015 | Kaib |
| 2015/0157873 A1 | 6/2015 | Sokolowski |
| 2015/0165226 A1 | 6/2015 | Simon et al. |
| 2015/0165232 A1 | 6/2015 | Altshuler et al. |
| 2015/0165238 A1 | 6/2015 | Slayton et al. |
| 2015/0174002 A1 | 6/2015 | Burbank et al. |
| 2015/0202454 A1 | 7/2015 | Burnett |
| 2015/0216719 A1 | 8/2015 | Debenedictis et al. |
| 2015/0216720 A1 | 8/2015 | Debenedictis et al. |
| 2015/0216816 A1 | 8/2015 | O'Neil et al. |
| 2015/0223975 A1 | 8/2015 | Anderson et al. |
| 2015/0238248 A1 | 8/2015 | Thompson et al. |
| 2015/0238771 A1 | 8/2015 | Zarsk et al. |
| 2015/0272776 A1 | 10/2015 | Gonzales et al. |
| 2015/0283022 A1 | 10/2015 | Lee et al. |
| 2015/0297909 A1 | 10/2015 | Peashock |
| 2015/0314133 A1 | 11/2015 | Yamashiro |
| 2015/0328077 A1 | 11/2015 | Levinson |
| 2015/0328475 A1 | 11/2015 | Kim et al. |
| 2015/0342661 A1 | 12/2015 | Ron Edoute |
| 2015/0342780 A1 | 12/2015 | Levinson et al. |
| 2015/0360045 A1 | 12/2015 | Fischell et al. |
| 2015/0367141 A1 | 12/2015 | Goetz et al. |
| 2015/0375005 A1 | 12/2015 | Segal |
| 2016/0015995 A1 | 1/2016 | Leung et al. |
| 2016/0016013 A1 | 1/2016 | Capelli et al. |
| 2016/0020070 A1 | 1/2016 | Kim et al. |
| 2016/0022349 A1 | 1/2016 | Woloszko et al. |
| 2016/0030763 A1 | 2/2016 | Midorikawa et al. |
| 2016/0045755 A1 | 2/2016 | Chun et al. |
| 2016/0051401 A1 | 2/2016 | Yee et al. |
| 2016/0051827 A1 | 2/2016 | Ron et al. |
| 2016/0066977 A1 | 3/2016 | Neal, II et al. |
| 2016/0066994 A1 | 3/2016 | Shanks |
| 2016/0067516 A1 | 3/2016 | Schneider et al. |
| 2016/0067517 A1 | 3/2016 | Burnett |
| 2016/0089550 A1 | 3/2016 | Debenedictis et al. |
| 2016/0106982 A1 | 4/2016 | Cakmak et al. |
| 2016/0121112 A1 | 5/2016 | Azar |
| 2016/0129273 A1* | 5/2016 | Park ................ A61N 1/36021 607/3 |
| 2016/0129274 A1 | 5/2016 | Park |
| 2016/0136462 A1 | 5/2016 | Lewis, Jr. et al. |
| 2016/0150494 A1 | 5/2016 | Tabet et al. |
| 2016/0151637 A1 | 6/2016 | Abe et al. |
| 2016/0158574 A1 | 6/2016 | Eckhouse et al. |
| 2016/0175193 A1 | 6/2016 | Jung |
| 2016/0184601 A1 | 6/2016 | Gleich et al. |
| 2016/0193466 A1 | 7/2016 | Burnett |
| 2016/0213924 A1 | 7/2016 | Coleman et al. |
| 2016/0220834 A1 | 8/2016 | Schwarz |
| 2016/0250494 A1 | 9/2016 | Sakaki et al. |
| 2016/0256702 A1 | 9/2016 | Schwarz et al. |
| 2016/0256703 A1 | 9/2016 | Schwarz et al. |
| 2016/0270951 A1 | 9/2016 | Martins et al. |
| 2016/0317346 A1 | 11/2016 | Kovach |
| 2016/0317827 A1 | 11/2016 | Schwarz et al. |
| 2016/0324684 A1 | 11/2016 | Levinson et al. |
| 2016/0346561 A1 | 12/2016 | Ron Edoute et al. |
| 2016/0354237 A1 | 12/2016 | Gonzales et al. |
| 2017/0001024 A1 | 1/2017 | Prouza |
| 2017/0001025 A1 | 1/2017 | Schwarz et al. |
| 2017/0001026 A1 | 1/2017 | Schwarz et al. |
| 2017/0001027 A1 | 1/2017 | Ladman et al. |
| 2017/0001028 A1 | 1/2017 | Ladman et al. |
| 2017/0001029 A1 | 1/2017 | Pribula et al. |
| 2017/0001030 A1 | 1/2017 | Pribula et al. |
| 2017/0007309 A1 | 1/2017 | Debenedictis et al. |
| 2017/0036019 A1 | 2/2017 | Matsushita |
| 2017/0043177 A1 | 2/2017 | Ron Edoute et al. |
| 2017/0050019 A1 | 2/2017 | Ron Edoute et al. |
| 2017/0072212 A1 | 3/2017 | Ladman et al. |
| 2017/0087373 A1 | 3/2017 | Schwarz |
| 2017/0100585 A1 | 4/2017 | Hall et al. |
| 2017/0105869 A1 | 4/2017 | Frangineas, Jr. |
| 2017/0106201 A1 | 4/2017 | Schwarz et al. |
| 2017/0106203 A1 | 4/2017 | Schneider et al. |
| 2017/0120067 A1 | 5/2017 | Prouza |
| 2017/0143958 A1 | 5/2017 | Shalev et al. |
| 2017/0156907 A1 | 6/2017 | Harris et al. |
| 2017/0173347 A1 | 6/2017 | Schwarz et al. |
| 2017/0182334 A1 | 6/2017 | Altshuler et al. |
| 2017/0182335 A1 | 6/2017 | Altshuler et al. |
| 2017/0189707 A1 | 7/2017 | Zabara |
| 2017/0196731 A1 | 7/2017 | Debenedictis et al. |

(56) References Cited

U.S. PATENT DOCUMENTS

| | | |
|---|---|---|
| 2017/0209708 A1 | 7/2017 | Schwarz |
| 2017/0239079 A1 | 8/2017 | Root et al. |
| 2017/0239467 A1 | 8/2017 | Shalev et al. |
| 2017/0259077 A1 | 9/2017 | Jin |
| 2017/0280889 A1 | 10/2017 | Koch |
| 2017/0304642 A1 | 10/2017 | Ron Edoute et al. |
| 2017/0319378 A1 | 11/2017 | Anderson et al. |
| 2017/0325992 A1 | 11/2017 | Debenedictis et al. |
| 2017/0325993 A1 | 11/2017 | Jimenez et al. |
| 2017/0326042 A1 | 11/2017 | Zeng et al. |
| 2017/0326346 A1 | 11/2017 | Jimenez et al. |
| 2017/0333705 A1 | 11/2017 | Schwarz |
| 2017/0348143 A1 | 12/2017 | Rosen et al. |
| 2017/0348539 A1 | 12/2017 | Schwarz et al. |
| 2017/0354530 A1 | 12/2017 | Shagdar et al. |
| 2017/0361095 A1 | 12/2017 | Mueller et al. |
| 2018/0000347 A1 | 1/2018 | Perez et al. |
| 2018/0001106 A1 | 1/2018 | Schwarz |
| 2018/0001107 A1* | 1/2018 | Schwarz ............... A61F 7/007 |
| 2018/0021565 A1 | 1/2018 | Dar et al. |
| 2018/0028831 A1 | 2/2018 | Ron Edoute et al. |
| 2018/0036548 A1 | 2/2018 | Nusse |
| 2018/0043151 A1 | 2/2018 | Ejiri et al. |
| 2018/0071544 A1 | 3/2018 | Ghiron et al. |
| 2018/0103991 A1 | 4/2018 | Linhart et al. |
| 2018/0125416 A1 | 5/2018 | Schwarz et al. |
| 2018/0133498 A1 | 5/2018 | Chornenky et al. |
| 2018/0153736 A1 | 6/2018 | Mills et al. |
| 2018/0153760 A1 | 6/2018 | Rosen et al. |
| 2018/0161197 A1 | 6/2018 | Baker et al. |
| 2018/0177996 A1 | 6/2018 | Gozani et al. |
| 2018/0185081 A1 | 7/2018 | O'Neil et al. |
| 2018/0185189 A1 | 7/2018 | Weber et al. |
| 2018/0214300 A1 | 8/2018 | Anderson et al. |
| 2018/0228646 A1 | 8/2018 | Gonzales et al. |
| 2018/0229048 A1 | 8/2018 | Sikora et al. |
| 2018/0236254 A1 | 8/2018 | Schwarz et al. |
| 2018/0250056 A1 | 9/2018 | Avram et al. |
| 2018/0263677 A1 | 9/2018 | Hilton et al. |
| 2018/0264245 A1 | 9/2018 | Edwards et al. |
| 2018/0271767 A1 | 9/2018 | Jimenez et al. |
| 2018/0296831 A1 | 10/2018 | Matsushita |
| 2018/0310950 A1 | 11/2018 | Yee et al. |
| 2018/0345012 A1 | 12/2018 | Schwarz et al. |
| 2018/0353767 A1 | 12/2018 | Biginton |
| 2019/0000524 A1 | 1/2019 | Rosen et al. |
| 2019/0000529 A1 | 1/2019 | Kothare et al. |
| 2019/0000663 A1 | 1/2019 | Anderson et al. |
| 2019/0029876 A1 | 1/2019 | Anderson et al. |
| 2019/0030356 A1 | 1/2019 | Schwarz |
| 2019/0053941 A1 | 2/2019 | Samson |
| 2019/0111255 A1 | 4/2019 | Errico et al. |
| 2019/0117965 A1 | 4/2019 | Iger et al. |
| 2019/0134414 A1 | 5/2019 | Schwarz |
| 2019/0151655 A1 | 5/2019 | Hall et al. |
| 2019/0168012 A1 | 6/2019 | Biginton |
| 2019/0183562 A1 | 6/2019 | Widgerow |
| 2019/0192219 A1 | 6/2019 | Kreindel |
| 2019/0192853 A1 | 6/2019 | Kim et al. |
| 2019/0192872 A1 | 6/2019 | Schwarz et al. |
| 2019/0192873 A1 | 6/2019 | Schwarz et al. |
| 2019/0192875 A1 | 6/2019 | Schwarz et al. |
| 2019/0201705 A1 | 7/2019 | Schwarz et al. |
| 2019/0201706 A1 | 7/2019 | Schwarz et al. |
| 2019/0209836 A1 | 7/2019 | Yakoub et al. |
| 2019/0255346 A1 | 8/2019 | Ghiron |
| 2019/0269909 A1 | 9/2019 | Gozani et al. |
| 2019/0275320 A1 | 9/2019 | Kim et al. |
| 2019/0299018 A1 | 10/2019 | Chornenky et al. |
| 2019/0314629 A1 | 10/2019 | Kreindel |
| 2019/0314638 A1 | 10/2019 | Kreindel |
| 2019/0329065 A1 | 10/2019 | Gandel |
| 2019/0336783 A1 | 11/2019 | Sokolowski |
| 2019/0344091 A1 | 11/2019 | Fischer |
| 2019/0350646 A1 | 11/2019 | Kreindel |
| 2019/0365462 A1 | 12/2019 | Casalino et al. |
| 2019/0388698 A1 | 12/2019 | Schwarz et al. |
| 2020/0001103 A1 | 1/2020 | Schwarz et al. |
| 2020/0016422 A1 | 1/2020 | Ron Edoute et al. |
| 2020/0016423 A1 | 1/2020 | Ron Edoute et al. |
| 2020/0054890 A1 | 2/2020 | Schwarz et al. |
| 2020/0061385 A1 | 2/2020 | Schwarz et al. |
| 2020/0061386 A1 | 2/2020 | Schwarz et al. |
| 2020/0094066 A1 | 3/2020 | Heath |
| 2020/0114160 A1 | 4/2020 | Blendermann |
| 2020/0129759 A1 | 4/2020 | Schwarz |
| 2020/0139148 A1 | 5/2020 | Schwarz et al. |
| 2020/0155221 A1 | 5/2020 | Marchitto et al. |
| 2020/0171297 A1 | 6/2020 | Kirson et al. |
| 2020/0197696 A1 | 6/2020 | Nagel et al. |
| 2020/0206524 A1 | 7/2020 | Katznelson et al. |
| 2020/0237424 A1 | 7/2020 | Hunziker et al. |
| 2020/0281642 A1 | 9/2020 | Kreindel |
| 2020/0289838 A1 | 9/2020 | Schwarz et al. |
| 2020/0330782 A1 | 10/2020 | Zabara |
| 2020/0352633 A1 | 11/2020 | Treen et al. |
| 2020/0353244 A1 | 11/2020 | Yamazaki |
| 2020/0353273 A1 | 11/2020 | Zucco |
| 2020/0360681 A1 | 11/2020 | Lay |
| 2021/0008369 A1 | 1/2021 | Crosson |
| 2021/0038894 A1 | 2/2021 | Mowery et al. |
| 2021/0146150 A1 | 5/2021 | Frangineas, Jr. et al. |
| 2021/0275825 A1 | 9/2021 | Kreindel |
| 2021/0283395 A1 | 9/2021 | Kreindel |
| 2021/0361938 A1 | 11/2021 | Gershonowitz |

FOREIGN PATENT DOCUMENTS

| | | |
|---|---|---|
| AU | 2012244313 B2 | 11/2014 |
| AU | 2014203094 B2 | 7/2015 |
| AU | 2013207657 B2 | 11/2015 |
| BR | PI0812502 A2 | 6/2015 |
| CA | 2484880 A1 | 4/2006 |
| CA | 2604112 C | 7/2016 |
| CA | 3019140 A1 | 10/2017 |
| CA | 3019410 A1 | 10/2017 |
| CA | 3023821 A1 | 11/2017 |
| CH | 714113 A2 | 3/2019 |
| CN | 86204070 U | 9/1987 |
| CN | 87203746 U | 12/1987 |
| CN | 87215926 U | 7/1988 |
| CN | 1026953 C | 12/1994 |
| CN | 1027958 C | 3/1995 |
| CN | 2192348 Y | 3/1995 |
| CN | 1206975 C | 6/2005 |
| CN | 101234231 A | 8/2008 |
| CN | 101327358 A | 12/2008 |
| CN | 201906360 U | 7/2011 |
| CN | 102319141 A | 1/2012 |
| CN | 102711706 A | 10/2012 |
| CN | 102847231 A | 1/2013 |
| CN | 202637725 U | 1/2013 |
| CN | 203169831 U | 9/2013 |
| CN | 102319141 B | 8/2014 |
| CN | 106540375 A | 3/2017 |
| CN | 107613914 A | 1/2018 |
| CN | 108882992 A | 11/2018 |
| CN | 109310516 A | 2/2019 |
| CN | 112221015 A | 1/2021 |
| DE | 718637 C | 3/1942 |
| DE | 1118902 B | 12/1961 |
| DE | 2748780 A1 | 5/1978 |
| DE | 3205048 A1 | 8/1983 |
| DE | 3340974 A1 | 5/1985 |
| DE | 3610474 A1 | 10/1986 |
| DE | 3825165 A1 | 1/1990 |
| DE | 3340974 C2 | 7/1994 |
| DE | 69318706 T2 | 1/1999 |
| DE | 10062050 A1 | 4/2002 |
| DE | 102004006192 A1 | 9/2005 |
| DE | 60033756 T2 | 6/2007 |
| DE | 102009023855 A1 | 12/2010 |
| DE | 102009050010 A1 | 5/2011 |
| DE | 102010004307 A1 | 7/2011 |

(56) References Cited

FOREIGN PATENT DOCUMENTS

| | | |
|---|---|---|
| DE | 102011014291 A1 | 9/2012 |
| DE | 102013211859 B4 | 7/2015 |
| DE | 102016116399 A1 | 3/2018 |
| DE | 202016008884 U1 | 7/2020 |
| DE | 102010014157 B4 | 2/2021 |
| DK | 0633008 T3 | 3/1999 |
| EA | 000494 B1 | 8/1999 |
| EA | 002087 B1 | 12/2001 |
| EA | 002179 B1 | 2/2002 |
| EA | 003851 B1 | 10/2003 |
| EA | 007347 B1 | 8/2006 |
| EA | 007975 B1 | 2/2007 |
| EP | 0048451 A1 | 3/1982 |
| EP | 0209246 A1 | 1/1987 |
| EP | 0459101 A1 | 12/1991 |
| EP | 0459401 A1 | 12/1991 |
| EP | 0633008 A1 | 1/1995 |
| EP | 0788813 A1 | 8/1997 |
| EP | 0633008 B1 | 5/1998 |
| EP | 0692993 B1 | 9/1999 |
| EP | 1022034 A1 | 7/2000 |
| EP | 1916013 A1 | 4/2008 |
| EP | 2124800 B1 | 11/2010 |
| EP | 1917935 B1 | 1/2011 |
| EP | 2308559 A2 | 4/2011 |
| EP | 2139560 B1 | 5/2012 |
| EP | 2461765 A1 | 6/2012 |
| EP | 2069014 B1 | 6/2013 |
| EP | 2614807 A1 | 7/2013 |
| EP | 2676700 A2 | 12/2013 |
| EP | 2694159 A2 | 2/2014 |
| EP | 2749259 A1 | 7/2014 |
| EP | 2814445 A1 | 12/2014 |
| EP | 2856986 A1 | 4/2015 |
| EP | 3009167 A1 | 4/2016 |
| EP | 2501352 B1 | 7/2016 |
| EP | 3209246 A1 | 8/2017 |
| EP | 3342379 A1 | 7/2018 |
| EP | 3389532 A1 | 10/2018 |
| EP | 3434323 A1 | 1/2019 |
| EP | 3721939 A1 | 10/2020 |
| ES | 2118925 T3 | 10/1998 |
| ES | 2300569 T3 | 6/2008 |
| ES | 2305698 T3 | 11/2008 |
| ES | 2359581 T3 | 5/2011 |
| ES | 2533145 A2 | 4/2015 |
| ES | 2533145 B1 | 7/2016 |
| ES | 2533145 R1 | 10/2018 |
| FR | 3041881 A1 | 4/2017 |
| FR | 3061012 A1 | 6/2018 |
| GB | 260116 A | 10/1926 |
| GB | 304587 A | 3/1930 |
| GB | 390500 A | 4/1933 |
| GB | 871672 A | 6/1961 |
| GB | 2188238 A | 9/1987 |
| GB | 2176009 B | 12/1989 |
| GB | 2261820 A | 6/1993 |
| GB | 2286660 A | 8/1995 |
| GB | 2395907 B | 12/2004 |
| GB | 2504984 A | 2/2014 |
| GB | 2521240 A | 6/2015 |
| GB | 2552004 A | 1/2018 |
| GR | 3027678 T3 | 11/1998 |
| IT | 1217550 B | 3/1990 |
| IT | RE20120010 A1 | 8/2013 |
| IT | UB20159823 A1 | 7/2017 |
| JP | 2003305131 A | 10/2003 |
| JP | 2006130055 A | 5/2006 |
| JP | 4178762 B2 | 11/2008 |
| JP | 4324673 B2 | 9/2009 |
| JP | 2010207268 A | 9/2010 |
| JP | 2010533054 A | 10/2010 |
| JP | 2011194176 A | 10/2011 |
| JP | 2013063285 A | 4/2013 |
| JP | 2017518857 A | 7/2017 |
| JP | 2018501927 A | 1/2018 |
| JP | 2018018650 A | 2/2018 |
| KR | 20030065126 A | 8/2003 |
| KR | 100484618 B1 | 4/2005 |
| KR | 100491988 B1 | 5/2005 |
| KR | 200407524 Y1 | 1/2006 |
| KR | 100556230 B1 | 3/2006 |
| KR | 200410065 Y1 | 3/2006 |
| KR | 100841596 B1 | 6/2008 |
| KR | 20090063618 A | 6/2009 |
| KR | 20090095143 A | 9/2009 |
| KR | 100936914 B1 | 1/2010 |
| KR | 1020100026107 A | 3/2010 |
| KR | 101022244 B1 | 3/2011 |
| KR | 20110123831 A | 11/2011 |
| KR | 20120037011 A | 4/2012 |
| KR | 101233286 B1 | 2/2013 |
| KR | 101233287 B1 | 2/2013 |
| KR | 20130072244 A | 7/2013 |
| KR | 101292289 B1 | 8/2013 |
| KR | 20130128391 A | 11/2013 |
| KR | 101413022 B1 | 7/2014 |
| KR | 101415141 B1 | 7/2014 |
| KR | 101447532 B1 | 10/2014 |
| KR | 101511444 B1 | 4/2015 |
| KR | 20150058102 A | 5/2015 |
| KR | 101539633 B1 | 7/2015 |
| KR | 20150079619 A | 7/2015 |
| KR | 20150106379 A | 9/2015 |
| KR | 101650155 B1 | 8/2016 |
| KR | 101673182 B1 | 11/2016 |
| KR | 20170090654 A | 8/2017 |
| KR | 20170107603 A | 9/2017 |
| KR | 101794269 B1 | 11/2017 |
| KR | 20180059114 A | 6/2018 |
| KR | 20180092020 A | 8/2018 |
| KR | 101941863 B1 | 1/2019 |
| KR | 20190005981 A | 1/2019 |
| KR | 102000971 B1 | 7/2019 |
| KR | 20190001779 U | 7/2019 |
| KR | 200491572 Y1 | 5/2020 |
| KR | 20200000889 U | 5/2020 |
| KR | 20200052602 A | 5/2020 |
| KR | 20200056692 A | 5/2020 |
| KR | 20200056693 A | 5/2020 |
| KR | 20200056801 A | 5/2020 |
| KR | 20200056802 A | 5/2020 |
| KR | 20200057154 A | 5/2020 |
| KR | 20210002973 A | 1/2021 |
| KR | 20210002974 A | 1/2021 |
| MX | 2012012158 A | 4/2014 |
| NL | 7510644 A | 3/1977 |
| NL | 1037451-02 | 5/2011 |
| RU | 2212909 C2 | 9/2003 |
| RU | 2226115 C2 | 3/2004 |
| RU | 2281128 C2 | 8/2006 |
| RU | 2373971 C2 | 11/2009 |
| RU | 2392979 C2 | 6/2010 |
| RU | 2395267 C2 | 7/2010 |
| RU | 2496532 C2 | 10/2013 |
| RU | 2529471 C2 | 9/2014 |
| RU | 2596053 C2 | 8/2016 |
| RU | 2637104 C2 | 11/2017 |
| RU | 2645923 C2 | 2/2018 |
| SI | 24921 A | 8/2016 |
| TW | 200423986 A | 11/2004 |
| WO | WO-9312835 A1 | 7/1993 |
| WO | WO-9521655 A1 | 8/1995 |
| WO | WO-9527533 A1 | 10/1995 |
| WO | WO-9932191 A1 | 7/1999 |
| WO | WO-0013749 A1 | 3/2000 |
| WO | WO-0044346 A1 | 8/2000 |
| WO | WO-0107111 A2 | 2/2001 |
| WO | WO-0112089 A1 | 2/2001 |
| WO | WO-0193797 A2 | 12/2001 |
| WO | WO-0225675 A1 | 3/2002 |
| WO | WO-03078596 A2 | 9/2003 |
| WO | WO-03079916 A1 | 10/2003 |
| WO | WO-03090863 A1 | 11/2003 |

(56) References Cited

FOREIGN PATENT DOCUMENTS

| | | |
|---|---|---|
| WO | WO-03103769 A1 | 12/2003 |
| WO | WO-2004078255 A1 | 9/2004 |
| WO | WO-2004087255 A1 | 10/2004 |
| WO | WO-2004095385 A2 | 11/2004 |
| WO | WO-2004095835 A1 | 11/2004 |
| WO | WO-2004096343 A2 | 11/2004 |
| WO | WO-2004108211 A1 | 12/2004 |
| WO | WO-2005032660 A1 | 4/2005 |
| WO | WO-2005107866 A1 | 11/2005 |
| WO | WO-2006115120 A1 | 11/2006 |
| WO | WO-2007096206 A1 | 8/2007 |
| WO | WO-2007140584 A1 | 12/2007 |
| WO | WO-2008012827 A2 | 1/2008 |
| WO | WO-2008049775 A1 | 5/2008 |
| WO | WO-2008060494 A2 | 5/2008 |
| WO | WO-2008109058 A1 | 9/2008 |
| WO | WO-2008127011 A2 | 10/2008 |
| WO | WO-2008145260 A2 | 12/2008 |
| WO | WO-2009011708 A1 | 1/2009 |
| WO | WO-2009013729 A2 | 1/2009 |
| WO | WO-2009036040 A1 | 3/2009 |
| WO | WO-2009042863 A1 | 4/2009 |
| WO | WO-2009044400 A2 | 4/2009 |
| WO | WO-2009047628 A2 | 4/2009 |
| WO | WO-2009083915 A2 | 7/2009 |
| WO | WO-2010007614 A2 | 1/2010 |
| WO | WO-2010022278 A1 | 2/2010 |
| WO | WO-2010007614 A3 | 5/2010 |
| WO | WO-2010135425 A1 | 11/2010 |
| WO | WO-2010139376 A1 | 12/2010 |
| WO | WO-2011011749 A1 | 1/2011 |
| WO | WO-2011016019 A1 | 2/2011 |
| WO | WO-2011021184 A1 | 2/2011 |
| WO | WO-2011045002 A1 | 4/2011 |
| WO | WO 2011053607 A1 | 5/2011 |
| WO | WO-2011058565 A2 | 5/2011 |
| WO | WO-2011156495 A2 | 12/2011 |
| WO | WO-2012005766 A1 | 1/2012 |
| WO | WO-2012029065 A2 | 3/2012 |
| WO | WO-2012040243 A1 | 3/2012 |
| WO | WO-2012073232 A1 | 6/2012 |
| WO | WO-2012103632 A1 | 8/2012 |
| WO | WO-2012119293 A1 | 9/2012 |
| WO | WO-2012138169 A2 | 10/2012 |
| WO | WO-2013021380 A1 | 2/2013 |
| WO | WO-2013026393 A1 | 2/2013 |
| WO | WO-2013035088 A1 | 3/2013 |
| WO | WO-2013074576 A2 | 5/2013 |
| WO | WO-2013098815 A1 | 7/2013 |
| WO | WO-2013191699 A1 | 12/2013 |
| WO | WO-2014009875 A2 | 1/2014 |
| WO | WO-2014016820 A2 | 1/2014 |
| WO | WO-2014109653 A1 | 7/2014 |
| WO | WO-2014137344 A1 | 9/2014 |
| WO | WO-2014141229 A1 | 9/2014 |
| WO | WO-2014149021 A2 | 9/2014 |
| WO | WO-2014151431 A2 | 9/2014 |
| WO | WO-2014163020 A1 | 10/2014 |
| WO | WO-2014164926 A1 | 10/2014 |
| WO | WO-2015004540 A2 | 1/2015 |
| WO | WO-2015012639 A1 | 1/2015 |
| WO | WO-2015012672 A1 | 1/2015 |
| WO | WO-2015052705 A1 | 4/2015 |
| WO | WO-2015083305 A1 | 6/2015 |
| WO | WO-2015137733 A1 | 9/2015 |
| WO | WO-2015157725 A1 | 10/2015 |
| WO | WO-2015179571 A1 | 11/2015 |
| WO | WO-2016116747 A1 | 7/2016 |
| WO | WO-2016140871 A1 | 9/2016 |
| WO | WO-2017002065 A1 | 1/2017 |
| WO | WO-2017103923 A1 | 6/2017 |
| WO | WO-2017159959 A1 | 9/2017 |
| WO | WO-2017160097 A2 | 9/2017 |
| WO | WO-2017176621 A1 | 10/2017 |
| WO | WO-2017196548 A1 | 11/2017 |
| WO | WO-2017212253 A1 | 12/2017 |
| WO | WO-2018006086 A1 | 1/2018 |
| WO | WO-2018008023 A1 | 1/2018 |
| WO | WO-2018044825 A1 | 3/2018 |
| WO | WO-2018121998 A2 | 7/2018 |
| WO | WO-2018122535 A1 | 7/2018 |
| WO | WO-2017160097 A3 | 9/2018 |
| WO | WO-2018208992 A1 | 11/2018 |
| WO | WO-2019120420 A1 | 6/2019 |
| WO | WO-2019150378 A1 | 8/2019 |
| WO | WO-2019166965 A1 | 9/2019 |
| WO | WO-2019173866 A1 | 9/2019 |
| WO | WO-2019183622 A1 | 9/2019 |
| WO | WO-2020002801 A1 | 1/2020 |
| WO | WO-2020035852 A2 | 2/2020 |
| WO | WO-2020041502 A1 | 2/2020 |
| WO | WO-2020142470 A1 | 7/2020 |
| WO | WO-2020144486 A1 | 7/2020 |
| WO | WO-2020174444 A1 | 9/2020 |
| WO | WO-2020183508 A1 | 9/2020 |
| WO | WO-2020190514 A1 | 9/2020 |
| WO | WO-2020208590 A1 | 10/2020 |
| WO | WO-2020264263 A1 | 12/2020 |
| WO | WO-2021013654 A1 | 1/2021 |
| WO | WO-2021102365 A1 | 5/2021 |

OTHER PUBLICATIONS

Jalinous, R., "Technical and Practical Aspects of Magnetic Nerve Stimulation," Journal of Clinical Neurophysiology 8(1):10-25, Raven Press, Ltd., New York (1991).

*Lumenis Be Ltd. v. BTL Healthcare Technologies A.S.*, PTAB-IPR2022-00451, U.S. Pat. No. 10,806,943 Petition for Inter Partes Review, Jan. 24, 2022, 87 pages.

*Lumenis Be Ltd. v. BTL Healthcare Technologies A.S.*, PTAB-IPR2022-00451, Declaration of Dr. Marom Bikson (EX1002), Jan. 24, 2022, 236 pages.

*Lumenis Be Ltd. v. BTL Healthcare Technologies A.S.*, PTAB-IPR2022-00452, U.S. Pat. No. 10,806,943 Petition for Inter Partes Review, Jan. 24, 2022, 81 pages.

*Lumenis Be Ltd. v. BTL Healthcare Technologies A.S.*, PTAB-IPR2022-00452, Declaration of Dr. Marom Bikson (EX1002), Jan. 24, 2022, 229 pages.

Operating Manual: Magstim® $200^2$, P/N 3001-23-04, The Magstim Company Limited, Mar. 18, 2005, 34 pages.

Stallknecht, B., et al., "Are blood flow and lipolysis in subcutaneous adipose tissue influenced by contractions in adject muscles in humans?," Am J Physiol Endocrinol Metab 292: E394-E399 (Feb. 2007).

Weyh, T., et al., "Marked differences in the thermal characteristics of figure-of-eight shaped coils used for repetitive transcranial magnetic stimulation," Clinical Neurophysiology 116: 1477-1486, Elsevier Ireland Ltd. (Mar. 2005).

2018 Cutera University, Clinical Forum, Cutera 20, 26 pages.

501 (k) K030708 Slendertone Flex Letter from Department of Health and Humane Serivces, Public Health Service, Jun. 25, 2003, 6 pages.

501 (k) K163165 AM-100 Letter from Department of Health and Human Services, Public Health Service, Feb. 16, 2017, 9 pages.

Abulhasan, J.F., et al., "Peripheral Electrical and Magnetic Stimulation to Augment Resistance Training," Journal of Functional Morphology and Kinesiology, 1(3):328-342, (Sep. 2016).

Accent Radiofrequency System, Operator's Manual, Alma Lasers, Wellbeing Through Technology, 2008, 82 Pages.

Agilent Technologies, Inc., "Agilent 33500 Series 30 MHz Function/Arbitrary Waveform Generator User's Guide," Publication No. 33520-90001 (Dec. 2010), 278 pages.

Agilent Technologies, Inc., "Agilent Announces 30 MHz Function/Arbitrary Waveform Generators," Microwave J., URL: (Aug. 3, 2010), 8 pages.

*Allergan, Inc. et al. v. BTL Healthcare Technologies A.S.*, PTAB-PGR2021-00015, Paper 16 (Decision Denying Institution of Post-Grant Review), Jun. 17, 2021, 20 pages.

(56) References Cited

OTHER PUBLICATIONS

*Allergan, Inc. et al.* v. *BTL Healthcare Technologies A.S.*, PTAB-PGR2021-00016, Paper 16 (Decision Denying Institution of Post-Grant Review), Jun. 17, 2021, 20 pages.
*Allergan, Inc. et al.* v. *BTL Healthcare Technologies A.S.*, PTAB-PGR2021-00017, Paper 16 (Decision Denying Institution of Post-Grant Review), Jun. 16, 2021, 33 pages.
*Allergan, Inc. et al.* v. *BTL Healthcare Technologies A.S.*, PTAB-PGR2021-00018, Paper 16 (Decision Denying Institution of Post-Grant Review), Jun. 16, 2021, 42 pages.
*Allergan, Inc. et al.* v. *BTL Healthcare Technologies A.S.*, PTAB-PGR2021-00020, Paper 16 (Decision Denying Institution of Post-Grant Review), Jun. 16, 2021, 35 pages.
*Allergan, Inc. et al.* v. *BTL Healthcare Technologies A.S.*, PTAB-PGR2021-00021, Paper 17 (Decision Denying Institution of Post-Grant Review), Jun. 16, 2021, 33 pages.
*Allergan, Inc. et al.* v. *BTL Healthcare Technologies A.S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.
Alma Lasers., "Accent Radiofrequency System, Operator's Manual," Wellbeing Through Technology, 2008, Chapters 1-8, Appendix A.
Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).
Avram, M.M and Harry, R.S.,"Cryolipolysis for Subcutaneous Fat Layer Reduction," Lasers in Surgery and Medicine, 41(10)703-708, Wiley-Liss, United States (Dec. 2009).
Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).
Baranov, A., Krion, Whole Body Cryotherapy, Russia, 19 Pages.
Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).
Barker, A.T., et al., "Non-Invasive Magnetic Stimulation of Human Motor Cortex," Lancet 1(8437):1106-1107, Elsevier, England (May 1985).
Barker, A.T., "The History and Basic Principles of Magnetic Nerve Stimulation," Electroencephalography and Clinical Neurophysiology 51:3-21, Elsevier, Netherlands (1999).
Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jan. 14, 2004).
Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).
Beilin, G., et al., "Electromagnetic Fields Applied to the Reduction of Abdominal Obesity," Journal of Cosmetic & Laser Therapy, 14(1):24-42, Informa Healthcare, England, (Feb. 2012).
Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams & Wilkins, United States (2015).
Benton, et al., "Functional Electrical Stimulation—A Practical Clinical Guide," Second Edition, The Professional Staff Association of the Rancho Los Amigos Hospital, Inc., 42 pages (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-Macleod, S.A., et al., "Force Output of Cat Motor Units Stimulated with Trains of Linearly Varying Frequency," Journal of Neurophysiology 61(1):208-217, American Physiological Society, United States (Jan. 1989).
Binder-Macleod, S.A., et al., "Use of a Catchlike Property of Human Skeletal Muscle to Reduce Fatigue," Muscle & Nerve 14(9):850-857, John Wiley & Sons, United States (Sep. 1991).
Bio Medical Research Limited., "Slendertone Flex Abdominal Training System, Instructions for Use," All pages (Aug. 2006).
Bio Medical Research Limited., "Slendertone Flex Max Instruction Manual," All pages (Apr. 2006).
Bio-Medical Research Ltd., K010335, 510(k) Summary, Slendertone Flex, All pages (Sep. 2001).
Bio-Medical Research Ltd., K022855 510(k) Summary, Slendertone, 1-6 (Mar. 2003).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical & Biological Engineering & Computing 28(2):196-198, Springer, United States (Mar. 1990).
BTL Industries, Inc., K163165 510(k) Summary, AM-100, All pages (Feb. 2017).
BTL Industries, Inc., K180813 510(k) Summary, Emsculpt, All pages (Mar. 2018).
*BTL Industries, Inc.* v. *Allergan Ltd. et al.* DDE-1-20-cv-01046, Complaint for Patent Infringement and Exhibits 1-38, 821 pages (Aug. 2020).
*BTL Industries, Inc.* v. *Allergan Ltd. et al.*, DDE-1-20-cv-01046, Order Administratively Closing Case, Jul. 26, 2021, 1 page.
*BTL Industries, Inc.* v. *Allergan Ltd. et al* DDE-1-20-cv-01046, Order Granting Motion to Stay Pending Resolution of Proceedings at the International Trade Commission (Unopposed), 2 pages (Oct. 2020).
*BTL Industries, Inc.* v. *Allergan PLC et al* DDE-1-19-cv-02356, Complaint for Patent Infringement and Exhibits 1-34, 375 pages (Dec. 2019).
*BTL Industries, Inc.* v. *Allergan PLC et al* DDE-1-19-cv-02356, Order Granting Stipulation to Stay, Oct. 1, 2020, 1 page.
*BTL Industries, Inc.* v. *Allergan USA, Inc. et al.*, DDE-1-19-cv-02356, Order Administratively Closing Case, Jul. 26, 2021, 1 page.
Buenos Aires, Oct. 14, 2014, Venus Concept, Provision No. 7246, 56 pages (With Machine Translation).
Burge, S.M and Dawber, R.P.,"Hair Follicle Destruction and Regeneration in Guinea Pig Skin After Cutaneous Freeze Injury," Cryobiology, 27(2):153-163, Elsevier, Netherlands (Apr. 1990).
Busso, M. and Denkova, R., "Efficacy of High Intensity Focused Electro-Magnetic (HIFEM) Field Therapy When Used For Non-Invasive Buttocks Augmentation and Lifting: A Clinical Study" American Society for Laser Medicine and Surgery Abstracts, 382 (2018).
Bustamante, V., et al., "Muscle Training With Repetitive Magnetic Stimulation of the Quadriceps in Severe COPD Patients," Respiratory Medicine, 104(2):237-245, Elsevier, England, (Feb. 2010).
Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).
Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).
Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).
Caress, J.B., et al., "A Novel Method of Inducing Muscle Cramps Using Repetitive Magnetic Stimulation," Muscle Nerve, 23(1):126-128, John Wiley & Sons, United States, (Jan. 2000).

(56) References Cited

OTHER PUBLICATIONS

Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.
Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.
Certain Non-Invasive Aesthetic Body Contouring Devices, Components Thereof, and Methods of Using the Same, Inv. No. 337-TA-1219, Complaint, Aug. 5, 2020, 93 pages.
Certain Non-Invasive Aesthetic Body Contouring Devices, Components Thereof, and Methods of Using the Same, Inv. No. 337-TA-1219, Joint Claim Construction Chart, Dec. 14, 2020, 15 pages.
Certain Non-Invasive Aesthetic Body Contouring Devices, Components Thereof, and Methods of Using the Same; Inv. No. 337-TA-1219, Joint Claim Construction Chart, Dec. 18, 2020, 15 pages.
Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 5 pages.
Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.
Certain Non-Invasive Aesthetic Body Contouring Devices, Components Thereof, and Methods of Using the Same; Inv. No. 337-TA-1219, Respondents' List of Proposed Claim Constructions and Their Intrinsic and Extrinsic Support, filed Dec. 15, 2020, 23 pages.
Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.
Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.
Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.
Certain Non-Invasive Aesthetic Body-Contouring Devices, Components Thereof, and Methods of Using the Same, Inv. No. 337-TA-1219, Order No. 21 (Initial Determination), Apr. 28, 2021, 5 pages.
Certain Non-Invasive Aesthetic Body-Contouring Devices, Components Thereof, and Methods of Using the Same, Inv. No. 337-TA-1219, Order No. 30 (Order Concerning the Procedural Schedule), Aug. 4, 2021, 3 pages.
Certain Non-Invasive Aesthetic Body-Contouring Devices, Componesnts Thereof, and Methods of Using the Same, Inv. No. 337-TA-1219, Order No. 17: Amending Procedural Schedule, Apr. 9, 2021, 4 pages.
Certified English Translation of Belyaev, A.G., "Effect of Magnetic Stimulation on the Strength Capacity of Skeletal Muscles," Ph.D. Thesis Abstract, Smolensk State Academy of Physical Culture, Sport, and Tourism, Dec. 11, 2020, 23 pages.
Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.
Chattanooga Group of Encore Medical, L.P., "Intelect SWD 100 User Manual, Operation & Installation Instructions for Intelect SWD 00—Model 1600," All pages (2009).

Chesterton, L.S., et al.,"Skin Temperature Response to Cryotherapy," Archives of Physical Medicine and Rehabilitation, 83(4):543-549, W.B. Saunders, United States (Apr. 2002).
Collins, D.F., et al., "Large Involuntary Forces Consistent With Plateau-Like Behavior of Human Motoneurons," Journal of Neuroscience 21 (11):4059-4065, Society for Neuroscience, United States (Jun. 2001).
Colson, S., et al., "Re-Examination of Training Effects by Electrostimulation in the Human Elbow Musculoskeletal System," International Journal of Sports Medicine 21(4):281-288, Stuttgart, Thieme (May 2000).
Course in Physical Therapy, Presentation, Jan. 4, 2013, 156 pages.
CR Technologies, "Salus Talent Pop Manual KFDA First Approval Document" (English Translation), Nov. 25, 2011, 47 pages.
CR Technologies, "Notification of medical device manufacturing item permission, Salus Talent Pop KFDA Approval Document" (English Translation), 3 pages (Sep. 2011).
CR Technology Co, Ltd., "Salus-Talent Double Sales Brochure" 2 pages, (Oct. 2020).
CR Technology Co. Ltd., "Medical Laser Irradiator Salus-Talent-Pop User Manual Version 1.00" (Nov. 2020).
CR Technology Co. Ltd., Salus Talent Pop User Manual, Ver. 1.00, All pages, Approx. 2012.
CR Technology, Salus-Talent, Technical File of Electro-magnetic Stimulator, Document No. TF-C05, 2008, 241 pages.
CR Technology, Technology for Health and Business for Human Being, investor relations, 2008, 21 pages.
Currier, D. P., "Effects of Electrical and Electromagnetic Stimulation after Anterior Cruciate Ligament Reconstruction," The Journal of Orthopaedic and Sports Physical Therapy 17(4):177-84, Williams And Wilkins, United States (1993).
Cutera, truSculptflex, Brochure, dated 2019, 2 pages.
Cynosure, SculpSure TM, The New Shape of Energy-Based bodyContouring, 2015, Cynosure Inc, 2 pages.
Cynosure,Smooth Shapes XV, Now with Smoothshape petite, Transforming non-invasive Body Shaping,Retrieved from the Internet: (www.cynosure.com), 2011, Cynosure Inc, 8 pages.
Davies, C.T., et al., "Contractile Properties of the Human Triceps Surae With Some Observations on the Effects of Temperature and Exercise," European Journal of Applied Physiology and Occupational Physiology 49(2):255-269, Springer Verlag, Germany (Aug. 1982).
Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).
Depatment of Health and Human Services, 501(k) Letter and Summary for K092476 Body Control System 4M Powered Muscle Stimulator, dated May 7, 2010, 5 pages.
Depatment of Health and Human Services, 501(k) Letter and Summary for K160992 HPM-6000 Powered Muscle Stimulator, dated Oct. 21, 2016, 9 pages.
Depatment of Health and Human Services, 501(k) Letter and Summary for K163415 SlimShape System Powered Muscle Stimulator, dated Apr. 20, 2017, 8 pages.
Depatment of Health and Human Services, 501(k) Letter and Summary for K182106 BTL 799-2T Powered Muscle Stimulator, dated Oct. 23, 2018, 9 pages.
Depatment of Health and Human Services, 501(k) Letter and Summary for K190456 BTL 799-2L Powered Muscle Stimulator, dated Jul. 5, 2019, 9 pages.
Depatment of Health and Human Services, 501(k) Letter and Summary for K192224 BTL 899 Powered Muscle Stimulator, dated Dec. 5, 2019, 11 pages.
Doucet, B., et al., "Neuromuscular Electrical Stimulation for Skeletal Muscle Function," Yale Journal of Biology & Medicine 85:201-215, Yale Journal of Biology and Medicine, United States (Jun. 2012).
Dudley, G. and Stevenson, S., "Use of Electrical Stimulation in Strength and Power Training," Special Problems in Strength and Power Training :426-435 (2003).
Duncan, D., et al., "Noninvasive Induction of Muscle Fiber Hypertrophy and Hyperplasia: Effects of High-Intensity Focused Electro-

(56) References Cited

OTHER PUBLICATIONS magnetic Field Evaluated in an In-Vivo Porcine Model: A Pilot Study," Aesthetic Surgery Journal 40(5):568-574, Oxford University Press, United States (Apr. 2020).

DuoMAG Magnetic Stimulator, Alien Technik User Manuel, Jun. 26, 2012,48 pages, Version 2.1.

Dybek, T., et al.."Impact of 10 Sessions of Whole Body Cryostimulation on Aerobic and Anaerobic Capacity and on Selected Blood Count Parameters," Biology of Sport, 29(1):39-43 (Jan. 2012).

Dynatronics., "Better Rehab Solutions for Better Outcomes," Rehabilitation Products Guide 2.3, 2017, 52 pages.

Effective PEMF Magnetic Fat Reduction Slimming Body Beauty Salon Machine (PEMF Star), Wolfbeauty 1980, PEMF Star, China, Retrieved from the Internet: (URL: https://www.ec21.com/product-details/Effective-PEMF-Magnetic-Fat-Reduction--8928746.html), 2019, 5 pages.

Elamed, Magnetic Therapeutic Apparatus for Running Pulse Magfield small-sized ALMAG-01 Manual, allegedly accessed on Nov. 18, 2020, All pages.

Eliminate Stubborn Fat without Surgery or Downtime and Feel Great From Every Angle, Fear No Mirror®, Consultation Guide, Coolsculpting, 2014, 20 pages.

Energist Ltd—Acquired Chromogenez—Old Account, iLipo—Laser Liposuction (i-Lipo), Video Screenshots, Aug. 10, 2009, 5 pages.

Enoka, R.M., "Muscle Strength and Its Development," Sports Medicine 6:146-168, Springer (Oct. 1988).

Epstein, C., et al., "The Oxford Handbook of Transcranial Stimulation," 773 pages (2008).

European Commission, "Neurogenerative Disorders," 10 pages printed Dec. 27, 2016.

European Patent Office, International Search Report and Written Opinion for International Application No. PCT/IB2016/053930, dated Dec. 12, 2016, 19 pages.

Exilis, Operator's Manual, BTL, 2012, 44 Pages.

Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).

Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).

Fisher, R., et al., "ILAE Official Report: a Practical Clinical Definition of Epilepsy," Epilepsia, 55(4):475-482, Blackwell Science, United States (Apr. 2014).

Fujimura, K., et al., "Effects of Repetitive Peripheral Magnetic Stimulation on Shoulder Subluxations Caused by Stroke: A Preliminary Study," Neuromodulation : Journal of the International Neuromodulation Society 23(6):847-851, Wiley-Blackwell, United States (Nov. 2020).

Gaines, M., "Slendertone Abdominal Training System, the First FDA-Cleared Abdominal Belt, Introduced in United States by Compex Technologies on Time for Holiday Gift-Giving," Business Wire 44199 (Oct. 2003).

Geddes, L.A., "History of Magnetic Stimulation of the Nervous System," Journal of Clinical Neurophysiology 8(1):3-9, Lippincott Williams & Wilkins, United States (Jan. 1991).

Goetz, S.M., et al., "Coil Design for Neuromuscular Magnetic Stimulation Based on a Detailed 3-D Thigh Model," IEEE Transactions On Magnetics, 50(6):10, IEEE, (Jun. 2014).

Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).

Gorgey, A., et al., "Effects of Electrical Stimulation Parameters on Fatigue in Skeletal Muscle," The Journal of Orthopaedic and Sports Physical Therapy 39(9):684-692, Williams And Wilkins, United States (Sep. 2009).

Gorodnichev, R.M., et al., "The Effect of Electromagnetic Stimulation on the Parameters of Muscular Strength," Human Physiology 40:65-69 (2014).

Gorodnichev, R.M., "Magnetic Stimulation of Muscles as New Method to Enhance Their Strength," Velikie Luki State Academy of Physical Culture and Sport, Velikie Luki, 2016, 5 pages.

Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).

Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).

Han, B.H., et al., "Development of four-channel magnetic nerve stimulator," 2001 Proceedings of the 23rd Annual EMBS International Conference, pp. 1325-1327, Turkey (2001).

Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).

Harkey, M.S., "Disinhibitory Interventions and Voluntary Quadriceps Activation: A Systematic Review," Journal of Athletic Training 49(3):411-421, National Athletic Trainers' Association, United States (2014).

Heidland, A., et al., "Neuromuscular Electrostimulation Technigues: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).

Heisel, Jurgen, Physikalische Medizin, Stuttgart: Georg Thieme Verlag KG, 2005. ISBN 3-13-139881-7. p. 159.

Hera Estetik Medikal, "LIPOSTAR" dated Jul. 7, 2014, accessed at https://www.youtube.com/watch?v=R7OnFIK9go, accessed on Dec. 15, 2021.

Hera Estetik Medikal, "Lipostar Manyetik Incelme", accessed at https://www.heraestetik.com/en/urundetay/liposter-manyetik-incelme, accessed on Dec. 15, 2021.

Hill, A., "The Influence of Temperature on the Tension Developed in an Isometric Twitch," Proceeding of the Royal Society B 138:349-354, (Sep. 1951).

Hirvonen, H.E., et al.,"Effectiveness of Different Cryotherapies on Pain and Disease Activity in Active Rheumatoid Arthritis. A Randomised Single Blinded Controlled Trial,"Clinical and Experimental Rheumatology, 24(3):295-301, Clinical and Experimental Rheumatology S.A. S, Italy (May-Jun. 2006).

Hovey, C. and Jalinous, R., "The Guide to Magnetic Stimulation" Magstim, Pioneers in Nerve Stimulation and Monitoring, pp. 1-44 (2016).

Hovey, C., et al., "The Guide to Magnetic Stimulation," The Magstim Company Limited, 48 pages (Jul. 2006).

Huang, Y.Z., et al., "Theta Burst Stimulation of the Human Motor Cortex," Neuron 45(2):201-206, Cell Press, United States (Jan. 2005).

I-Lipo by Chromo genex, i-Lipo Ultra is the Intelligent, Non-Surgical Alternative to Liposuction, 2011, 2 pages.

Increasing Physiotherapy Presence in Cosmetology, Spa Inspirations, Jan. 2012, pp. 34-35.

Irazoqui P., Post Grant Review of U.S. Pat. No. 10,695,576, PTAB-PGR2021-00024, filed as EX1085, Dec. 14, 2020, 25 pages.

Iskra Medical, Magneto System, 2012, 2 pages.

Iskra Medical, "TESLA Stym—Functional Magnetic Stimulation FMS," Nov. 2013, http://ww.iskramedical.eu/magneto-therapy-medical/tesla-stym, 5 pages.

Iskra Medical, "TESLA Stym Website," URL: https://web.archive.org/web/20131106123126/http:/www.iskramedical.eu:80/magneto-therapy-medical/tesla-stym (Nov. 6, 2013).

(56) References Cited

OTHER PUBLICATIONS

Izumiya, Y., et al., "Fast/Glycolytic Muscle Fiber Growth Reduces Fat Mass and Improves Metabolic Parameters in Obese Mice", Cell Metabolism 7(2):159-172, Cell Press, United States (Feb. 2008).
Jacob, C., et al., "High Intensity Focused Electro-Magnetic Technology (HIFEM) for Non-Invasive Buttock Lifting and Toning of Gluteal Muscles: A Multi-Center Efficacy And Safety Study," Journal of Drugs in Dermatology 17(11):1229-1232, Physicians Continuing Education Corporation, United States (Nov. 2018).
Jacob, C.I., et al., "Safety And Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).
Jacobm C., and Paskova, "A Novel Non-Invasive Technology Based on Simultaneous Induction of Changes in Adipose and Muscle Tissues: Safety and Efficacy of a High Intensity Focused Electro-Magnetic (HIFEM) Field Device Used For Abdominal Body Shaping," American Society for Laser Medicine and Surgery, 2018 Electronic Posters (ePosters) Town Hall and ePosters, 369, p. 1, Wiley Periodicals, Inc. (2018).
Johari Digital Healthcare Ltd., 510(k)—K062439 Powertone Letter from Department of Health and Humane Services Summary, Public Health Service, Jan. 8, 2007, 6 pages.
Johari Digital Healthcare Ltd., "510(k)—K131291 Torc Body Letter from Department of Health and Humane Services", Public Health Service, Jun. 14, 2013, 10 pages.
Johari Digital Healthcare Ltd., K131291 510(k) Summary, TorcBody, All pages (Jun. 2013).
Jutte, L.S., et al.,"The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).
Katuscakova, Z.L., et al., High Induction Magnet Therapy in Rehabilitation, Department of Physiactric Rehabilitation, 2012, 72 pages.
Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).
Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams & Wilkins, United States (Dec. 2019).
Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).
Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).
Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).
Kim, Y.H., et al.,"The Effect of Cold Air Application on Intra-Articular and Skin Temperatures in the Knee," Yonsei Medical Journal, 43(5):621-626, Yonsei University, Korea (South) (Oct. 2002).
Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).

Kocbach et al., "A Simulation Approach to Optimizing Performance of Equipment for Thermostimulation of Muscle Tissue using COMSOL Multiphysics" Article in Biophysics & Bioeng. dated 2011, 26 pages.
Kolin, A., et al., "Stimulation of Irritable Tissues by means of an Alternating Magnetic Field," Proceedings of the Society for Experimental Biology and Medicine 102:251-253, Blackwell Science, United States (Oct. 1959).
Korman, P., et al.."Temperature Changes In Rheumatoid Hand Treated With Nitrogen Vapors and Cold Air," Rheumatology International, 32(10):2987-2992, Springer International, Germany (Oct. 2012).
Kotz, Y., "Theory and Practice of Physical Culture," Training of Skeletal Muscle With Method of Electrostimulation, 64-67 (Mar. 1971).
Kotz, Y., "Theory and Practice of Physical Culture," Training of Skeletal Muscle With Method of Electrostimulation, 66-72 (Apr. 1971).
Krueger, N. et al., "Safety and Efficacy of a New Device Combining Radiofrequency and Low-Frequency Pulsed Electromagnetic Fields for the Treatment of Facial Rhytides," Journal of Drugs in Dermatology 11(11):1306-1309, Physicians Continuing Education Corporation, United States (Nov. 2012).
Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).
Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).
Langford, J. and Mccarthy, P.W., "Randomised controlled clinical trial of magnet use in chronic low back pain; a pilot study," Clinical Chiropractic 8(1):13-19, Elsevier (Mar. 2005).
Lee, P.B., et al., "Efficacy of Pulsed Electromagnetic Therapy for Chronic Lower Back Pain: a Randomized, Double-blind, Placeb-controlled Study," The Journal of International Medical Research 34(2):160-167, Cambridge Medical Publications, England (Mar.-Apr. 2006).
Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).
Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).
Letter from Department of Health and Human Services, Public Health Service, Dec. 19, 2014, 7 pages.
Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).
Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).
Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).
Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).
Lin, V.W., et al., "Functional Magnetic Stimulation of the Respiratory Muscles in Dogs," Muscle & Nerve 21(8):1048-1057, John Wiley & Sons, United States (Aug. 1998).
Linehan, C., et al., Brainwave the Irish EpilepsyAssoication, "The Prevalence of Epilepsy in Ireland" Summary Report,pp. 1-8 (May 2009).

(56) References Cited

OTHER PUBLICATIONS

Lotz, B.P., et al., "Preferential Activation of Muscle Fibers with Peripheral Magnetic Stimulation of the Limb," Muscle & Nerve, 12(8):636-639, John Wiley & Sons, United States (Aug. 1989).
*Lumenis Be Ltd. v. BTL Healthcare Technologies A.S.*, PTAB-IPR2021-01402, Declaration of Dr. Marom Bikson (EX1002), Sep. 13, 2021, 244 pages.
*Lumenis Be Ltd. v. BTL Healthcare Technologies A.S.*, PTAB-IPR2021-01402, U.S. Pat. No. 10,821,295 Petition for Inter Partes Review, Sep. 13, 2021, 81 pages.
*Lumenis Be Ltd. v. BTL Healthcare Technologies A.S.*, PTAB-IPR2021-01403, Declaration of Dr. Marom Bikson (EX1002), Sep. 13, 2021, 243 pages.
*Lumenis Be Ltd. v. BTL Healthcare Technologies A.S.*, PTAB-IPR2021-01403, U.S. Pat. No. 10,821,295 Petition for Inter Partes Review, Sep. 13, 2021, 84 pages.
*Lumenis Be Ltd. v. BTL Healthcare Technologies A.S.*, PTAB-IPR2021-01404, Declaration of Dr. Marom Bikson (EX1002), Sep. 13, 2021, 245 pages.
*Lumenis Be Ltd. v. BTL Healthcare Technologies A.S.*, PTAB-IPR2021-01404, U.S. Pat. No. 10,124,187 Petition for Inter Partes Review, Sep. 13, 2021, 82 pages.
*Lumenis Be Ltd. v. BTL Healthcare Technologies A.S.*, PTAB-IPR2021-01405, Declaration of Dr. Marom Bikson (EX1002), Sep. 13, 2021, 247 pages.
*Lumenis Be Ltd. v. BTL Healthcare Technologies A.S.*, PTAB-IPR2021-01405, U.S. Pat. No. 10,124,187 Petition for Inter Partes Review, Sep. 13, 2021, 86 pages.
*Lumenis Ltd. v. BTL Healthcare Technologies A.S.*, PTAB-IPR2021-01273, Declaration of Dr. Marom Bikson (EX1002), Aug. 13, 2021, 225 pages.
*Lumenis Ltd. v. BTL Healthcare Technologies A.S.*, PTAB-IPR2021-01273, U.S. Pat. No. 10,478,634, Petition for Inter Partes Review, Aug. 13, 2021, 70 pages.
*Lumenis Ltd. v. BTL Healthcare Technologies A.S.*, PTAB-IPR2021-01275, Declaration of Dr. Marom Bikson (EX1002), Aug. 5, 2021, 282 pages.
*Lumenis Ltd. v. BTL Healthcare Technologies A.S.*, PTAB-IPR2021-01275, U.S. Pat. No. 10,632,321, Petition for Inter Partes Review, Aug. 5, 2021, 92 pages.
*Lumenis Ltd. v. BTL Healthcare Technologies A.S.*, PTAB-IPR2021-01276, Declaration of Dr. Marom Bikson (EX1002), Aug. 5, 2021, 241 pages.
*Lumenis Ltd. v. BTL Healthcare Technologies A.S.*, PTAB-IPR2021-01276, U.S. Pat. No. 10,965,575, Petition for Inter Partes Review, Aug. 5, 2021, 79 pages.
*Lumenis Ltd. v. BTL Healthcare Technologies A.S.*, PTAB-IPR2021-01278, Declaration of Dr. Marom Bikson (EX1002), Aug. 13, 2021, 255 pages.
*Lumenis Ltd. v. BTL Healthcare Technologies A.S.*, PTAB-IPR2021-01278, U.S. Pat. No. 10,709,894, Petition for Inter Partes Review, Aug. 13, 2021, 85 pages.
*Lumenis Ltd. v. BTL Healthcare Technologies A.S.*, PTAB-IPR2021-01279, Declaration of Dr. Marom Bikson (EX1002), Aug. 5, 2021, 258 pages.
*Lumenis Ltd. v. BTL Healthcare Technologies A.S.*, PTAB-IPR2021-01279, U.S. Pat. No. 10,709,895, Petition for Inter Partes Review, Aug. 5, 2021, 88 pages.
*Lumenis Ltd. v. BTL Healthcare Technologies A.S.*, PTAB-IPR2021-01280, Declaration of Dr. Marom Bikson (EX1002), Aug. 13, 2021, 235 pages.
*Lumenis Ltd. v. BTL Healthcare Technologies A.S.*, PTAB-IPR2021-01280, U.S. Pat. No. 10,478,634, Petition for Inter Partes Review, Aug. 13, 2021, 69 pages.
*Lumenis Ltd. v. BTL Healthcare Technologies A.S.*, PTAB-IPR2021-01282, Declaration of Dr. Marom Bikson (EX1002), Aug. 5, 2021, 267 pages.
*Lumenis Ltd. v. BTL Healthcare Technologies A.S.*, PTAB-IPR2021-01282, U.S. Pat. No. 10,632,321, Petition for Inter Partes Review, Aug. 5, 2021, 89 pages.
*Lumenis Ltd. v. BTL Healthcare Technologies A.S.*, PTAB-IPR2021-01283, Declaration of Dr. Marom Bikson (EX1002), Aug. 5, 2021, 241 pages.
*Lumenis Ltd. v. BTL Healthcare Technologies A.S.*, PTAB-IPR2021-01283, U.S. Pat. No. 10,695,575, Petition for Inter Partes Review, Aug. 5, 2021, 84 pages.
*Lumenis Ltd. v. BTL Healthcare Technologies A.S.*, PTAB-IPR2021-01284, Declaration of Dr. Marom Bikson (EX1002), Aug. 5, 2021, 279 pages.
*Lumenis Ltd. v. BTL Healthcare Technologies A.S.*, PTAB-IPR2021-01284, U.S. Pat. No. 10,709,895, Petition for Inter Partes Review, Aug. 5, 2021, 93 pages.
*Lumenis Ltd. v. BTL Healthcare Technologies A.S.*, PTAB-IPR2021-01285, Declaration of Dr. Marom Bikson (EX1002), Aug. 13, 2021, 249 pages.
*Lumenis Ltd. v. BTL Healthcare Technologies A.S.*, PTAB-IPR2021-01285, U.S. Pat. No. 10,709,894, Petition for Inter Partes Review, Aug. 13, 2021, 79 pages.
Madariaga, V.B., et al., "[Magnetic Stimulation of the Quadriceps: Analysis of 2 Stimulators Used for Diagnostic and Therapeutic Applications]," Archives De Bronconeumologia, 43(7):411-417, Elsevier Espana, Spain, (Jul. 2007).
Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).
Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).
Mag Venture, Magnetic Stimulation, Accessories Catalogue, Accessories Catalogue, 2011, 54 pages.
Magstim Company Limited, K051864 510(k) Summary, Magstim Rapid and Magstim Super Rapid, All pages (Dec. 2005).
Magstim Company US, LLC, K060847 510(k) Summary, Magstim Model 200-2 with Double 70mm Remote Coil, All pages (Sep. 2006).
Magstim Corporation US, K992911 510(k) Summary, Magstim Rapid, All pages (Jan. 2000).
MagVenture, MagPro® by MagVenture®, Versatility in Magnetic Stimulation, World Leading Transcranial Magnetic Stimulation Systems, 2011, 6 Pages.
Man, W.D-C., et al., "Magnetic Stimulation for the Measurement of Respiratory and Skeletal Muscle Function," The European Respiratory Journal 24(5):846-60, European Respiratory Society, England (2004).
Manstein, D., et al.,"Selective Cryolysis: A Novel Method of Non-Invasive Fat Removal," Lasers in Surgery and Medicine, 40(9):595-604, Wiley-Liss, United States (Nov. 2008).
Mantovani, A., et al., "Applications of Transcranial Magnetic Stimulation to Therapy in Pyschiatry," Psychiatric Times 21(9), Intellisphere, 29 pages (Aug. 2004).
Marek Heinfarth, "Lipostar" dated Jan. 9, 2013, accessed at https://www.youtube.com/watch?v=hZurkn8iU_U, accessed on Dec. 15, 2021.
Markov, M.S., "Pulsed Electromagnetic Field Therapy History, State of the Art and Future," Environment Systems and Decisions 27(4):465-475, Springer (Dec. 2007).
MecoTec Freezing Technology, Presentation Cryoair Whole Body Cryotherapy Chambers, Germany, Jul. 2017, 52 Pages.
Medline, Body Temperature Norms, 2 pages (Year: 2019).
Mekawy et al., "Influence of Electro-lipolysis on Lipid Profile and Central Obesity in Obese Premenopausal Women" Bull. Fac. Ph. Th. Cairo Univ., vol. 17, No. (1), dated Jan. 2012, pp. 59-68.
Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).
Mogyoros, I., et al., "Strength-Duration Properties of Human Peripheral Nerve," Brain 119(Pt 2):439-447, Oxford University Press, England (Apr. 1996).

(56) References Cited

OTHER PUBLICATIONS

Moon, Chi-Woong"Study on the Pulsed Electromagnetic Fields Effect of Adipocyte Decomposition" Final Report of a Middle-grade Researcher Support Project, Inje University, 2017.

Morrissey. M., "Electromyostimulation from a Clinical Perspective," Sports Medicine 6(1):29-41, Springer International, New Zealand (Aug. 1988).

Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).

Nadler, S.F., et al.,"The Physiologic Basis and Clinical Applications of Cryotherapy and Thermotherapy for the Pain Practitioner," Pain Physician, 7(3):395-399, American Society of Interventional Pain Physicians, United States (Jul. 2004).

Nassab, R.,"The Evidence Behind Noninvasive Body Contouring Devices," Aesthetic Surgery Journal, 35(3):279-293, Oxford University Press, England (Mar. 2015).

National Institute of Neurological Disorders and Stroke, Epilepsy Information Page, www.ninds.nih.gov/disorders/epilepsy/epilepsy.htm, pp. 1-6 (Feb. 1, 2016).

Neotonus, Inc., K973096 510(k) Summary, Neotonus Model 1000 Muscle Stimulator System, All pages (Jun. 1998).

Neotonus, Inc., K973929 510(k) Summary and FDA Correspondence, Neotonus, All pages (May 1998).

Neuro Star, TMS Therapy, Bringing Hope to Patients with Depression, 2013, 6 Pages.

Neurosoft, Ivanovo, Since 1992, Magnetic Stimulator, NEUROMS, Technical Manual, Neurosoft Ltd, Ivanovo, Russia, 2006, 67 Pages.

Nexstim NBS System, Navigated Brain Stimulation, Noninvasive, direct cortical mapping, 2012, 5 Pages.

Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).

Nielsen, J.F., et al., "A New High-frequency Magnetic Stimulator With an Oil-cooled Coil," Journal of Clinical Neurophysiology 12(5):460-467, Lippincott Williams & Wilkins, United States (Sep. 1995).

Non Final Office Action dated Jun. 23, 2017, in U.S. Appl. No. 15/473,390, Schwarz, T., et al., filed Mar. 29, 2017.

Novickij, V., et al., "Compact Microsecond Pulsed Magnetic Field Generator for Application in Bioelectronics," Elektronika ir Elektrotechnika 19(8):25-28 (Oct. 2013).

Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).

Novickij, V., et al., "Magneto-Permeabilization of Viable Cell Membrane Using High Pulsed Magnetic Field," IEEE Transactions on Magnetics 51(9), All pages (Sep. 2015).

Novickij, V., et al., "Programmable Pulsed Magnetic Field System for Biological Applications," IEEE Transactions on Magnetics 50(11):5 (Nov. 2014).

NPF Electroapparat, Amplipulse-5Br Manual, allegedly accessed on Nov. 18, 2020, All pages.

Nuerosoft Ltd., "Neurosoft—Neuro-MS Transcranial Magnetic Simulator Technical Manual," All pages (Nov. 2014).

Obsluze, N.K.,Usage Instructions, User's Manual, Device for high-induction magnetic stimulation of type designation:Saluter Moti, 2016,88 Pages.

Oliveira, P.De., et al., "Neuromuscular Fatigue After Low-and Medium-frequency Electrical Stimulation in Healthy Adults," Muscle & Nerve 58(2):293-299, John Wiley & Sons, United States (Aug. 2018).

Operating Manual: Magstim D70$^2$ Coil, MOP06-EN, Revision 01, The Magstim Company Limited, Feb. 2012, 14 Pages.

Operating Manual: Magstim Magstim 2002, MOP01-EN, Revision 01, The Magstim Company Limited, Sep. 2011, 25 Pages.

Operating Manual: Magstim, Magstim Alpha Coil Range, MOP11-EN, Revision 01, Oct. 2012, 18 Pages.

Operating Manual: Magstim, Magstim Bistim$^2$, MOP02-EN, Revision, The Magstim Company Limited, 01, Sep. 2011, 27 Pages.

Operating Manual, Magstim, Model 200, P/N 3001-01, Double 70mm, Remote Coil, P/N 3190-00, The Magstim Company Limited, 2006, 32 pages.

Operating Manual: Magstim R, 2nd, Generation Coil Family, 3100-23-02, Magstim Coils, The Magstim Company Limited, Nov. 2002, 14 Pages.

Operating Manual, Magstim R Air-Cooled Double 70mm Coil System, 1600-23-04, The Magstim Company Limited, 1999, 18 Pages.

Operating Manual: Magstim R, Bistim System, P/N 3234-23-01, The Magstim Company Limited, Nov. 2004, 30 Pages.

Operating Manual: Magstim R, Coils & Accessories, 1623-23-07, Magstim Coils & Accessories, May 2010, 24 Pages.

Operating Manual: MAGSTIM, RAPID2, P/N 3576-23-09, The MAGSTIM Company LTD, Nov. 2009, 61 Pages.

Operator's Manual: BTL Emsculpt, BTL Industries Ltd, United Kingdom, 2018, 35 pages.

Operator's Manual: BTL, HPM-6000U, BTL Industries Ltd, United Kingdom, Dec. 2016, 36 pages.

Otte, J.S., et al.,"Subcutaneous Adipose Tissue Thickness Alters Cooling Time During Cryotherapy,"Archives of Physical Medicine and Rehabilitation, 83(11):1501-1505, W.B. Saunders, United States (Nov. 2002).

Pain Management Technologies, "Pain Management Technologies Product Catalog," (2012).

Papimi, For Scientific Research, Pap Ion Magnetic Inductor, Presentation, Magnetotherapeutic Device, Nov. 2009, 61 Pages.

Periso SA, CTU mega Diamagnetic Pump 20: Device For Diamagnetic Therapy, CTU Mega 20 Manual, dated Aug. 28, 2019, 44 pages, Pazzallo Switzerland.

Photograph, Alleged Photograph of Components of a Salus Talent Pop Double Device with An Alleged Manufacture date of Nov. 14, 2012, 1 page.

Physiomed, MAG-Expert, Physiomed Manual, Dec. 19, 2012.

Platil, A., "Magnetopneumography Using Optical Position Reference," Sensor Letters 11(1):69-73, ResearchGate (2013).

Podebradsky.K., et al., Clinical study of high-inductive electromagnetic stimulator SALUS talent, 2010, 8 pages.

Pohanka, J., et al., "An Embedded Stereovision System: Aspects of Measurement Precision," 12th Biennial Baltic Electronics Conference, pp. 157-160 (Oct. 2010).

Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.

Polkey M.I., et al., "Functional Magnetic Stimulation of the Abdominal Muscles in Humans," American Journal of Respiratory and Critical Care Medicine 160(2):513-522, American Thoracic Society, United States (Aug. 1999).

Polkey, M.I., et al., "Quadriceps Strength and Fatigue Assessed by Magnetic Stimulation of the Femoral Nerve in Man," Muscle Nerve 19(5):549-555, John Wiley & Sons, United States, (May 1996).

Pollogen, Maximus Non-invasive body shaping System, User Manual, dated May 1, 2012, 44 pages.

Pollogen, TriFractional FAQs, User Manual, dated Aug. 2011, 4 pages.

Pollogen, TriLipo MED Procedure, Brochure, dated Apr. 7, 2021, 76 pages.

Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).

Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).

(56) References Cited

OTHER PUBLICATIONS

Pribula, O. and Fischer, J., "Real Time Precise Position Measurement Based on Low-Cost CMOS Image Sensor," IEEE, 5 pages (2011).
Pribula, O., et al., "cost-effective Image Acquisition System for Precise Pc-based Measurements," Przeglad Elektrotechniczny (Electrical Review), 259-263, 2011.
Pribula, O., et al., "Optical Position Sensor Based on Digital Image Processing: Magnetic Field Mapping Improvement," Radioengineering 20 (1):55-60, (Apr. 2011).
Pribula, O., et al., "Real-Time Video Sequences Matching Spatio-Temporal Fingerprint," IEEE, 911-916 (Jun. 2010).
Prouza, O., et al., "High-Intensity Electromagnetic Stimulation Can Reduce Spasticity in Post-Stroke Patients," International Journal of Physiotherapy 5(3):87-91 (2018).
Prouza, O., "Ex-Post Analyza Spot Rebnich Dani," All pages, (2008).
Prouza, O., "Targeted Radiofrequency Therapy for Training Induced Muscle Fatigue—Effective or Not?," International Journal of Physiotherapy 3(6):707-710 (Dec. 2016).
PTAB-IPR2021-00296, U.S. Pat. No. 10,493,293, Petition for Inter Partes Review, Dec. 14, 2020, 117 pages.
PTAB-IPR2021-00312, U.S. Pat. No. 10,478,634, Petition for Inter Partes Review, Dec. 14, 2020, 108 pages.
PTAB-PGR2021-00015, U.S. Pat. No. 10,709,895, Petition for Post-Grant Review, Dec. 14, 2020, 140 pages.
PTAB-PGR2021-00016, U.S. Pat. No. 10,709,895, Petition for Post-Grant Review, Dec. 14, 2020, 144 pages.
PTAB-PGR2021-00017, U.S. Pat. No. 10,632,321, Petition for Post-Grant Review, Dec. 14, 2020, 121 pages.
PTAB-PGR2021-00018, U.S. Pat. No. 10,632,321, Petition for Post-Grant Review, Dec. 14, 2020, 140 pages.
PTAB-PGR2021-00020, U.S. Pat. No. 10,695,575, Petition for Post-Grant Review, Dec. 14, 2020, 112 pages.
PTAB-PGR2021-00021, U.S. Pat. No. 10,695,575, Petition for Post-Grant Review, Dec. 14, 2020, 117 pages.
PTAB-PGR2021-00022, U.S. Pat. No. 10,709,894, Petition for Post-Grant Review, Dec. 14, 2020, 119 pages.
PTAB-PGR2021-00023, U.S. Pat. No. 10,709,894, Petition for Post-Grant Review, Dec. 14, 2020, 136 pages.
PTAB-PGR2021-00024, U.S. Pat. No. 10,695,576, Petition for Post-Grant Review, Dec. 14, 2020, 136 pages.
PTAB-PGR2021-00025, U.S. Pat. No. 10,695,576, Petition for Post-Grant Review, Dec. 14, 2020, 135 pages.
Publication of Medical Device Manufacturing Approval of Salus-TALENT-Pro, approval date Mar. 11, 2014, 39 pages.
Quick Start Manuals, Magstim Super Rapid Plus Quick Start, Aalto TMS Laboratory, Aalto School of Science, 2013, 7 Pages.
Radakovic T. and Radakovic N., "The Effectiveness of the Functional Magnetic Stimulation Therapy in Treating Sciatica Syndrome," Open Journal of Therapy and Rehabilitation 3(3):63-69 (2015).
Reaction User Manual, Viora, Doc No. MK-004 A, 2008, 53 Pages.
Reshaping the Future of Your Practice, Cool sculpting, A Revolution in Aesthetic Fat Reduction, 2011, 10 Pages.
Riehl., M., "Chapters: TMS Stimulator Design" The Oxford Handbook of Transcranial Stimulation, Wasserman, E.M., ed., pp. 13-23, Oxford University Press, 26 pages, United Kingdom (2008).
Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).
Ruiz-Esparza, J. and J. Barba Gomez, "The Medical Face Lift: A Noninvasive, Nonsurgical Approach to Tissue Tightening in Facial Skin Using Nonablative Radiofrequency," Dermatologic Surgery 29(4):325-332, Williams & Wilkins, United States (Apr. 2003).
Russian excerpt of Werner, R., Magnetotherapy, Pulsating energy resonance therapy, 41-67 (Jun. 2007).
Rutkove, S., "Effects of Temperature on Neuromuscular Electrophysiology," Muscle & Nerve 24(7):867-882, John Wiley & Sons, United States (Jul. 2001).
Salus Talent Pop, The first sales bill, Authorization No. 20120221-41000096-66667961, 2 pages, (Feb. 2012).
Salus Talent-A, Remed, User Guide, High Intensity Electro Magnetic Field Therapy, 2017, 37 pages.
Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).
Schaefer, D.J., et al., "Review of Patient Safety in Time-Varying Gradient Fields," Journal of Magnetic Resonance Imaging 12:20-29, Wiley-Liss, United States (Jul. 2000).
Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).
Silinskas, V., et al., "Effect of Electrical Myostimulation on the Function of Lower Leg Muscles," Journal of strength and Conditioning Research 31(6):1577-1584, Human Kinetics Pub, United States (2017).
Sport-Elec S.A., K061914 510(k) Summary, Sport-Elec, All pages (Jul. 2007).
Sport-Elec S.A., K081026 510(k) Summary, Sport-Elec, All pages (Nov. 2008).
Starbelle, PEMF Shape, Webpage, dated Feb. 10, 2020, 3 pages, available at http://www.starbelle.cn/info/PEMFShape.html.
Stedman, T.L., "Aponeurosis—Apparatus," in Stedman's Medical Dictionary, 27th Edition, Pugh, M.B., ed., pp. 113-114, Lippincott Williams & Wilkins, Baltimore, MD (2000).
Stevens, J.E., et al., "Neuromuscular Electrical Stimulation for Quadriceps Muscle Strengthening After Bilateral Total Knee Arthroplasty: A Case Series," Journal of Orthopaedic and Sports Physical Therapy 34(1):21-29, Williams And Wilkins, United States (Jan. 2004).
Struppler, A., et al., "Facilitation of Skilled Finger Movements by Repetitive Peripheral Magnetic Stimulation (RPMS)—A New Approach In Central Paresis.," NeuroRehabilitation 18(1):69-82, IOS Press, Amsterdam (2003).
Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).
Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).
Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).
Szecsi, J., et al., "A Comparison of Functional Electrical and Magnetic Stimulation for Propelled Cycling of Paretic Patients," Archives of Physical Medicine and Rehabilitation 90(4):564-570, W.B. Saunders, United States, (Apr. 2009).
Szecsi, J., et al., "Force-pain Relationship in Functional Magnetic and Electrical Stimulation of Subjects With Paresis and Preserved Sensation," Clinical Neurophysiology 121(9):1589-1597, Elsevier, Netherlands, (Sep. 2010).
Taylor, J.L, "Magnetic Muscle Stimulation Produces Fatigue Without Effort," Journal of Applied Physiology (1985) 103(3):733-734, American Physiological Society, United States, (Sep. 2007).
Tesla Stym, Iskra Medical, Tone the inner muscle with FMS Functional Magnetic Stimulation, 2013, 4 pages.
The Burn Centre Care, Education, 3 pages, printed from internet Nov. 13, 2017.
The Magstim Company Ltd, K080499 510(k) Summary, Magstim Double 70mm Air Film Coil, All pages (Dec. 2008).
The Magstim Company Ltd., K130403 510(k) Summary, Magstim D702 coil, All pages (Aug. 2013).

(56) References Cited

OTHER PUBLICATIONS

Thermi Launches Arvati, powered by Thermi, with newest advances in True Temperature Controlled Radiofrequency Technology, 5 pages (2018).
Thompson, M.T., "Inductance Calculation Techniques—Part II: Approxmiations and Handbook Methods," Power Control and Intelligent Motion, 11 pages (Dec. 1999) http://www.pcim.com/.
Thompson, M.T., "Inductance Calculation Techniques—Part II: Classical Methods," Power Control and Intelligent Motion, 25(12):40-45, (Dec. 1999) http://www.pcim.com/.
Tomek, J., et al., "Magnetopneumography—Incorporation of optical position reference," Journal of Electrical Engineering, All pages (2012).
Torbergsen, T., "Abstracts of the International Course and Symposium in Single Fibre EMG and Quantitative EMG Analysis. Tromsø, Norway, Jun. 4-8, 1984," Muscle & Nerve 9(6):562-574, John Wiley & Sons, United States (Jul.-Aug. 1986).
TSEM Med Swiss SA, Diamagnetic Therapy: A Revolutionary Therapy, CTU Mega 20 Catalogue, dated 2016, 24 pages, Lugano Switzerland.
Turley, J., "Agilent Technologies Announces 30 MHz Function/Arbitrary Waveform Generators with Unparalleled Signal Accuracy," Elec. Eng'g J., URL: (Aug. 4, 2010), 8 pages.
Ultra Slim Professional, The very best body Contouring, Wardphotonics LLC, 2018, 16 pages.
U.S. Appl. No. 60/848,720, inventor Burnett, D., filed Sep. 30, 2006 (Not Published).
U.S. Appl. No. 62/331,060, inventor Schwarz, T., filed May 3, 2016 (Not Published).
U.S. Appl. No. 62/331,072, inventor Schwarz, T., filed May 3, 2016 (Not Published).
U.S. Appl. No. 62/331,088, inventor Schwarz, T., filed May 3, 2016 (Not Published).
U.S. Appl. No. 62/333,666, inventor Schwarz, T., filed May 9, 2016 (Not Published).
U.S. Appl. No. 62/351,156, inventor Schwarz, T., filed Jun. 16, 2016 (Not Published).
U.S. Appl. No. 62/357,679, inventor Schwarz, T., filed Jul. 1, 2016 (Not Published).
U.S. Appl. No. 62/440,905, inventors Schwarz, T. et al., filed Dec. 30, 2016 (Not Published).
U.S. Appl. No. 62/440,912, inventors Schwarz, T. et al., filed Dec. 30, 2016 (Not Published).
U.S. Appl. No. 62/440,922, inventor Schwarz, T., filed Dec. 30, 2016 (Not Published).
U.S. Appl. No. 62/440,936, inventor Schwarz, T., filed Dec. 30, 2016 (Not Published).
U.S. Appl. No. 62/440,940, inventor Schwarz, T., filed Dec. 30, 2016 (Not Published).
U.S. Appl. No. 62/441,805, inventor Prouza, O., filed Jan. 3, 2017 (Not Published).
U.S. Appl. No. 62/786,731, inventor Schwarz, T., filed Dec. 31, 2018 (Not Published).
User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.
User Guide, Salus Talent Pro, REMED, High Intensity Electro magnetic Field Therapy—2 Channel, 2017, Version M-1.0.0, 45 pages.
User Guide, Salus Talent, REMED, High Intensity Electro magnetic Field Therapy, Version. M-1.0.0, 2017, 40 pages.
User's Manual: BTL-6000, Super Inductive System Elite, BBTL Industries Ltd, United Kingdom, Sep. 2016, 36 pages.
User Manual: Electro-magnetic Stimulator, Salus-Talent, Version 1.00, Rehabilitation Medical Company,2013, 34 Pages.
User Manual: Regenetron PRO, System Information, Regenetron PRO User Manual, Nov. 2014, 7 Pages.
Vance, C., et al., "Effects of Transcutaneous Electrical Nerve Stimulation on Pain, Pain Sensitivity, and Function in People with Knee Osteoarthritis," Physical Therapy 92:898-910 (2012).
Vanquish Operator's Manual, BTL, 2012, 48 Pages.
Venus Concept Ltd., VenusFreeze MP2, User Manual, dated Jun. 2012, 46 pages.
Venus Concept Ltd., VenusViva, User Manual, dated Aug. 2013, 51 pages.
Venus Legacy, User Manual International, 2009, Venus Concept, 49 pages.
Verges S., et al., "Comparison of Electrical and Magnetic Stimulations to Assess Quadriceps Muscle Function," Journal of Applied Physiology (1985) 106(2):701-710, American Physiological Society, United States, (Feb. 2009).
Wada, K., et al., "Design and Implementation of Multi-Frequency Magnetic Field Generator Producing Sinusoidal Current Waveform for Biological Researches," IEEE, 9 pages (2016).
Wanitphakdeedecha, R., et al., "Treatment of Abdominal Cellulite and Circumference Reduction With Radiofrequency and Dynamic Muscle Activation" Article in Journal of Cosmetic and Laser Therapy, dated Apr. 6, 2015, 7 pages.
Ward, A.R. and Shkuratova, N., "Russian Electrical Stimulation: The Early Experiments," Physical therapy 82(10):1019-1030, Oxford University Press, United States (2002).
Wasilewski, M.L., Academy of Aesthetic and Anti-Aging Medicine, Application of magnetic fields with deep stimulation in the fight against local obesity of lower limbs, BTL, 2012, 4 pages.
Web MD, what is normal body temperature? 3 pages, printed Mar. 4, 2019.
Weight to volume aluminum, 2 pages, printed from internet Sep. 25, 2018.
Weight to volume copper, 2 pages printed from internet Sep. 25, 2018.
Weiss, R.A., et al., "Induction of Fat Apoptosis by a Non-Thermal Device: Mechanism of Action of Non-Invasive High-Intensity Electromagnetic Technology in a Porcine Model," Lasers in surgery and medicine 51(1):47-53, Wiley-Liss, United States (Jan. 2019).
Weng, O., "Electromagnetic Activation of the Calf Muscle Pump," UMI Dissertation Publishing (2014).
Woehrle, J., et al., "Dry Needling and its Use in Health Care—A Treatment Modality and Adjunct for Pain Management," Journal of Pain & Relief 4(5):1-3, (Aug. 2015).
Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).
Zao Okb Ritm, Electroneurostimulants, Transdermal Scenar-NT Instructions, All Pages (Nov. 2013).
Zao Okb Ritm, Percutaneous Electrical Stimulators With Individual Biofeedback Dosing Impact on Reflex Zones, All pages (2017).
Zelickson, B., et al.,"Cryolipolysis For Noninvasive Fat Cell Destruction: Initial Results From a Pig Model," Dermatologic Surgery 35(10):1462-1470, Hagerstown, MD Lippincott, Williams & Wilkins, United States (Oct. 2009).
ZELTIQ System User Manual—Print and Binding Specifications, ZELTIQ Aesthetics, Inc, Mar. 2011, 88 pages.
Zerona R-Z6 by Erchonia, Specifications,Retrieved from the Internet: (www.myzerona.com), 2015, 1 page.
Zhang, G., et al., "A Method of Nerve Electrical Stimulation by Magnetic Induction," Annual International Conference of the IEEE Engineering in Medicine and Biology Society 2009:622-625, IEEE, United States (2009).
Zhi-De, D., "Electromagnetic Field Modeling of Transcranial Electric and Magnetic Stimulation: Targeting, Individualization, and Safety of Convulsive and Subconvulsive Applications," Academic Commons (2013).
Zhu, Y., et al., "Magnetic Stimulation of Muscle Evokes Cerebral Potentials by Direct Activation of Nerve Afferents: A Study During Muscle Paralysis," Muscle & Nerve 19(12):1570-1575, John Wiley & Sons, United Sates (Dec. 1996).
Mantis, The non-invasive solution that restores natural beauty, improves health, and offers a renewed psychophysical sense of balance, MR991 theramagnetic, 2020, 8 pages.

(56) References Cited

OTHER PUBLICATIONS

Mantis Theramagnetic Compact: the compact that guarantees utmost efficiency and maximum performance, theramagnetic, 2020, 8 pages.

Pollegen, K200545, Legend Pro DMA, Indications for use, dated Oct. 20, 2021, 11 pages.

Pascual-Leone, Alvaro et al. "Handbook of Transcranial Magnetic Stimulation" 2002 Arnold Publishers, Chapters 1-4, 58 pages.

\* cited by examiner

METHODS AND DEVICES FOR AESTHETIC TREATMENT OF BIOLOGICAL STRUCTURES BY RADIOFREQUENCY AND MAGNETIC ENERGY

CROSS-REFERENCE TO RELATED APPLICATIONS

This application is a Continuation of U.S. application Ser. No. 16/844,822, filed Apr. 9, 2020, which claims the benefit of U.S. Provisional Application No. 62/832,738, filed Apr. 11, 2019; U.S. Provisional Application No. 62/832,688, filed Apr. 11, 2019; and U.S. Provisional Application No. 62/932,259, filed Nov. 7, 2019, all of which are incorporated herein by reference in their entireties.

BACKGROUND OF THE INVENTION

Aesthetic medicine includes all treatments resulting in enhancing a visual appearance according to a patient's criteria. Patients want to minimize all imperfections including, for example, unwanted body fat in specific body areas, improve body shape, and remove effects of natural aging. Patients require quick, non-invasive procedures that provide satisfactory results with minimal health risks.

The most common methods used for non-invasive aesthetic applications are based on application of mechanical waves, such as ultrasound or shock wave therapy, or electromagnetic waves, such as radiofrequency treatment or light treatment including laser treatment. The effect of mechanical waves on tissue is based on cavitation, vibration, and/or heat-inducing effects. The effect of applications using electromagnetic waves is based on heat production in the biological structure.

A mechanical treatment using mechanical waves and/or pressure can be used for treatment of cellulite or adipose cells. However, such mechanical treatments have several drawbacks, such as a risk of panniculitis, destruction of untargeted tissues, and/or non-homogenous results.

A thermal treatment including heating is applied to a patient for enhancing a visual appearance of the skin and body by, for example, increasing production of collagen and/or elastin, smoothing the skin, reducing cellulite, and/or removing adipose cells. However, thermal treatment has several drawbacks, such as risk of overheating a patient or even causing thermal damage of unwanted biological structures. A risk of a panniculitis and/or non-homogenous results may be a very common side effect of existing thermal treatments. Further, insufficient blood and/or lymph flow during and/or after the treatment may lead to panniculitis and other health complications after the treatment. Further, the treatment may be uncomfortable, and may be painful.

Muscle stimulation by time-varying magnetic field provides several benefits over known methods for treating biological structures, and allows for non-invasive stimulation of muscles located beneath other muscles. Further, time-varying magnetic fields may be used to provide muscle stimulation to cause muscle contraction through thick layer of adipose tissue. Electrostimulation in order to provide a muscle contraction needs to deliver an electric current from an electrode, through an adipose tissue, to a nerve and/or neuromuscular plate linked with the muscle. The adipose tissue has resistivity higher than the muscle tissue and delivery of electric current from the electrode through insulating adipose tissue to muscle tissue may be less efficient. Targeting of the electric current to an exact muscle may not be precise and stimulating muscle may be very difficult nearly impossible. Additionally, with thicker adipose tissue, electric current delivered by electrotherapy has to be higher and such high amount of electric current propagating and dissipating during long distance may be very uncomfortable for a patient. On the other hand, time-varying magnetic fields induce electric current in the muscle, neuromuscular plate and/or in the nerve, so targeting and muscle stimulation by time-varying magnetic field is easier, more precise, comfortable and more effective. Time-varying magnetic field also enable comfortable stimulation or large number of muscles and/or muscle groups and applicator may not be in direct contact with the patient's body that may also improve hygiene and other parameters of a treatment.

Combination of a radiofrequency (RF) treatment that provides heating up of patient's soft tissue and a magnetic treatment that provides stimulation of patient's muscle tissue may have outstanding synergic effect. Combined treatment may provide improved treatment, may result in shorter treatment periods, increase of patient's comfort during the treatment, enable to combine different treatment effects with a synergic result, improve patient safety and others deeply described later in this document.

To reach the best synergic effect it is preferred to target magnetic treatment providing muscle stimulation and RF treatment to one body area (e.g. same body area) wherein at least one RF electrode providing the RF treatment should be flat and/or correspond with patient's skin to ensure homogenous heating of the patient's soft tissue. To target the RF treatment and the magnetic treatment to the same body area requires to position a magnetic field generating device and an RF electrode nearby each other, e.g. with at least partial overlay of the magnetic field generating device and RF electrode. However, arranging an RF electrode and the magnetic field generating device in close proximity may be problematic, because the time-varying magnetic field generated by the magnetic field generating device may induce unwanted physical effects, such as eddy currents, skin effect and/or other physical effects in the RF electrode. Unwanted physical effects may cause significant energy loss, inefficiency of such device arrangement and also heating of the RF electrode, influencing of the device function, such as incorrect tuning of the device, inaccurate targeting of produced energies, degeneration of produced magnetic, electromagnetic fields and/or other. The RF electrode may be influenced by the magnetic field generating device and vice versa.

A device and method described in this document presents a solution for providing the RF and magnetic treatment with maximized synergic effect and also preserve safety and efficiency of the delivered magnetic and RF (electromagnetic) fields.

SUMMARY OF THE INVENTION

The invention provides a treatment device and method for providing one or more treatment effects to at least one biological structure in at least one body area. The treatment device provides a unique opportunity how to shape human or animal bodies, improve visual appearance, restore muscle functionality, increase muscle strength, change (e.g. increase) muscle volume, change (e.g. increase) muscle tonus, cause muscle fibre hypertrophy, cause muscle fibre hyperplasia, decrease number and volume of adipose cells and adipose tissue, remove cellulite and/or other. The treatment device and the method may use the application of a radiofrequency (RF) treatment and a magnetic treatment to cause heating of at least one target biological structure within the body area and cause muscle stimulation including muscle contraction, within the proximate or same body area. The treatment device may use an RF electrode as a treatment energy source to produce RF energy (which may be referred as RF field) to provide RF treatment, and a magnetic field generating device as a treatment energy source for generating a time-varying magnetic field to provide magnetic treatment.

In order to enhance efficiency and safety of the treatment, to minimize energy loss and unwanted physical effect induced in at least one RF electrode and/or magnetic field generating device, the device may use the one or more segmented RF electrodes, wherein the segmented RF electrode means RF electrode with e.g. one or more apertures, cutouts and/or protrusions to minimize the effects of a nearby time-varying magnetic field produced by the magnetic field generating device. Aperture may be an opening in the body of the RF electrode. The cutout may be an opening in the body of the RF electrode along the border of the RF electrode. Openings in the body of the RF electrode may be defined by view from floor projection, which shows a view of the RF electrode from above. The apertures, cutouts and/or areas outside of protrusions may be filed by air, dielectric and/or other electrically insulating material. The apertures, cutouts and/or protrusions of the RF electrode may minimize induction of eddy currents in the RF electrode, minimize energy loss, and inhibit overheating of the treatment device. Further, the apertures, cutouts and/or protrusions may minimize the influence of the magnetic treatment on the produced RF treatment. The proposed design of the RF electrode enables the same applicator to include a magnetic field generating device and the RF electrode with at least partial overlay, according to the applicator's floor projection, while enabling targeting of RF treatment and magnetic treatment to the same area of the patient's body with the parameters described herein. Incorporation of an RF electrode and a magnetic field generating device in one applicator enables enhanced treatment targeting and positive treatment results with minimal negative effects mentioned above.

Also mutual insulation of at least one RF circuit and at least one magnet circuit prevent interaction between electric and/or electromagnetic signals.

The magnetic field generating device in combination with an energy storage device enables production of a magnetic field with an intensity (which may be magnetic flux density) which evokes a muscle contraction. Energy storage device may be used to store electrical energy enabling accumulation of an electric field having a voltage in a range from 500 V to 15 kV. The energy storage device may supply the magnetic field generating device with the stored electrical energy in an impulse of several microseconds to several milliseconds.

The method of treatment enables heating of at least one body area where is also evoked a muscle contraction that minimizes muscle and/or ligament injury, such as tearing or inflammation. Heating of a skin, a contracted muscle, a contracting muscle, a relaxed muscle, adipose tissue, adipose tissue, and/or adjacent biological structure of the treated body area may shift the threshold when a patient may consider treatment to be uncomfortable.

Therefore, heating may allow a higher amount of electromagnetic energy, (e.g. RF and/or magnetic field) to be delivered to the patient's body in order to provide more muscle work through muscle contractions and subsequent relaxation. Another benefit of application of the RF treatment and the magnetic treatment in the same body area is that the muscle work (provided e.g. by repetitive muscle contractions and relaxations) accelerates blood and lymph flow in the targeted area and so improves dissipation of thermal energy created by the RF treatment. Application of the RF treatment and the magnetic treatment also improves homogeneity of biological structure heating that prevents creation of hot spots, edge effects and/or other undesirable effects. The method of treatment causing muscle stimulation and heating to the same body area may result in hyperacidity of extracellular matrix that leads to apoptosis or necrosis of the adipose tissue. The RF treatment may provide selective heating of adipose tissue that leads to at least one of apoptosis, necrosis, decrease of volume of adipose cells, and cellulite removal.

BRIEF DESCRIPTION OF THE DRAWINGS

The accompanying drawings, which are incorporated herein and form a part of the specification, illustrate the present disclosure and, together with the description, further serve to explain the principles thereof and to enable a person skilled in the pertinent art to make and use the same.

DETAILED DESCRIPTION

Figure 1A:
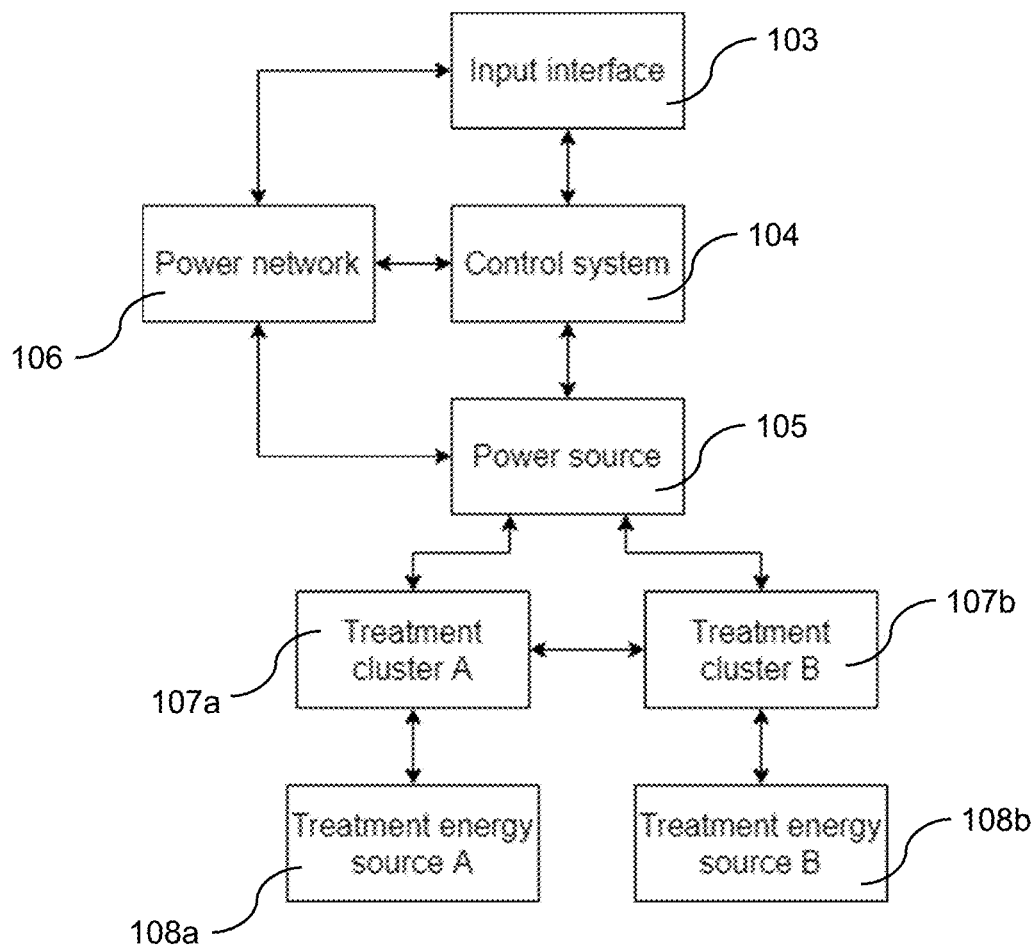
FIGS. 1a-1e illustrate exemplary diagrams of a treatment device.

The present treatment device and method of use provide new physiotherapy and/or aesthetic treatment by combination of RF treatment and treatment providing muscle stimulation targeted to various treatment effects, such as rejuvenate, heal and/or provide remodeling at least part of at least one biological structure of patient's tissue in at least one body area.

The biological structure may be any tissue in a human and/or animal body which may have of identical function, structure and/or composition. The biological structure may include or be at least part of any type of tissue like: connective tissue (e.g. tendons, ligaments, collagen, elastin fibres), adipose tissue (e.g. adipose cells of subcutaneous adipose tissue and/or visceral adipose tissue), bones, dermis and/or other tissue, such as at least one neuron, neuromuscular plate (neuromuscular junction), muscle cell, one or more individual muscles, muscle group, at least part of a muscle fibre, volume of extracellular matrix, endocrine gland, neural tissue (e.g. peripheral neural tissue, neuron, neuroglia, neuromuscular plate) and/or joint or part of joint. For the purpose of this application, the biological structure may be called target biological structure.

A treatment effect provided to at least part of at least one target biological structure may include muscle contraction (including supramaximal contractions and/or tetanic contractions), muscle twitch, muscle relaxation and heating of biological structure. Also, the treatment effect may include e.g. remodelling of the biological structure, reducing a number and/or a volume of adipose cells by apoptosis and/or necrosis, muscle strengthening, muscle volume increase, causing of a muscle fibre hypertrophy, muscle fibre hyperplasia, restoration of muscle functionality, myosatellite cells proliferation and/or differentiation into muscle cells, improvement of muscle shape, improving of muscle endurance, muscle definition, muscle relaxation, muscle volume decrease, restructuring of collagen fibre, neocollagenesis, elastogenesis, collagen treatment, improving of blood and lymph flow, accelerate of at least part of at least one target biological structure and/or other functions or benefits. During treatment of body area by the treatment device, more than one treatment effect may be provided and variable treatment effects may be combined.

The treatment effect provided to target biological structure may results in body shaping, improving contour of the body, body toning, muscle toning, muscle shaping, body shaping, breast lifting, buttock lifting, buttock rounding and/or buttock firming. Further, providing a treatment effect may result in body rejuvenation, such as wrinkle reduction, skin rejuvenation, skin tightening, unification of skin colour, reduction of sagging flesh, lip enhancement, cellulite removing, reduction of stretch marks and/or removing of scars. The treatment effect may also lead to accelerating of healing process, anti-edematic effect and/or other physiotherapeutic and treatment result.

The treatment device may provide one or more types of treatment energy wherein treatment energy may include magnetic field (also referred as magnetic energy) and RF field (also referred as RF energy) and/or magnetic field (also referred as magnetic energy). The magnetic field is provided during magnetic treatment. The RF field provided during RF treatment may include electrical component of RF field and magnetic component of RF field. The electrical component of RF field may be referred as RF wave or RF waves. The RF electrode may generate RF field, RF waves and/or other components of RF field.

The magnetic field and/or RF field may be characterized by intensity. In case of magnetic field, the intensity may include magnetic flux density or amplitude of magnetic flux density. In case of RF field, the intensity may include energy flux density of the RF field or RF waves.

A body area may include at least part of patient's body including at least a muscle or a muscle group covered by other soft tissue structure like adipose tissue, skin and/or other. The body area may be treated by the treatment device. The body area may be body part, such as a buttock, saddlebag, love handle, abdominal area, hip, leg, calf, thigh, arm, torso, shoulder, knee, neck, limb, bra fat, face or chin and/or any other tissue. For the purpose of the description the term "body area" may be interchangeable with the term "body region".

Skin tissue is composed of three basic elements: epidermis, dermis and hypodermis so called subcutis. The outer and also the thinnest layer of skin is the epidermis. The dermis consists of collagen, elastic tissue and reticular fibres. The hypodermis is the lowest layer of the skin and contains hair follicle roots, lymphatic vessels, collagen tissue, nerves and also fat forming a subcutaneous white adipose tissue (SWAT). Adipose tissue may refer to at least one lipid rich cell, e.g. adipose cell like adipocyte. The adipose cells create lobules which are bounded by connective tissue or fibrous septa (retinaculum cutis).

Another part of adipose tissue, so called visceral adipose tissue, is located in the peritoneal cavity and forms visceral white adipose tissue (VWAT) located between parietal peritoneum and visceral peritoneum, closely below muscle fibres adjoining the hypodermis layer.

A muscle may include at least part of a muscle fibre, whole muscle, muscle group, neuromuscular plate, peripheral nerve and/or nerve innervating of at least one muscle.

Deep muscle may refer to a muscle that is at least partially covered by superficial muscles and/or to a muscle covered by a thick layer of other tissue, such as adipose tissue wherein the thickness of the covering layer may be at least 4, 5, 7, 10 or more centimetres up to 15 cm thick.

Individual muscles may be abdominal muscles including rectus abdominalis, obliquus abdominalis, transversus abdominis, and/or quadratus lumborum. Individual muscles may be muscle of the buttocks including gluteus maximus, gluteus medius and/or gluteus minimus. Individual muscles may be muscles of lower limb including quadriceps femoris, Sartorius, gracilis, biceps femori, adductor magnus longus/brevis, tibialis anterior, extensor digitorum longus, extensor hallucis longus, triceps surae, gastroenemiis lateralis/medialis, soleus, flexor hallucis longus, flexor digitorum longus, extensor digitorum brevis, extensor hallucis brevis, adductor hallucis, abductor halluces, ab/adductor digiti minimi, abductor digiti minimi and/or interossei plantares). Ligament may be Cooper's ligament of breast.

One example may be application of the treatment device and method to patient's abdomen that may provide (or where the treatment may eventually result in) treatment effect such as reducing a number and volume of adipose cells, muscle strengthening, fat removal, restructuring of collagen fibres, accelerate of neocollagenesis and elastogenesis, muscle strengthening, improving of muscle functionality, muscle endurance and muscle shape. These treatment effects may cause circumferential reduction of the abdominal area, removing of saggy belly and/or firming of abdominal area, cellulite reduction, scar reduction and also improving of the body posture by strengthening the abdominal muscles that may also improve contour of the body, body look and patient's health.

One other example may be application of the treatment device and method to body area comprising buttock that may provide (or where the treatment may eventually result in) treatment effect such as reducing a number and volume of adipose cells, restructuring of collagen fibres, accelerate of neocollagenesis and elastogenesis, muscle strengthening, muscle toning and muscle shaping. These treatment effects may cause waist or buttock circumferential reduction, buttock lifting, buttock rounding, buttock firming and/or cellulite reduction.

Another example may be application of the treatment device and method to body area comprising thighs that may provide (or where the treatment may eventually result in) reduction of a number and volume of adipose cells, muscle strengthening, muscle shaping and muscle toning. The application of the treatment device and method to body area comprising thigh may cause circumferential reduction of the thigh, removing of saggy belly and cellulite reduction.

Still another example may be application of the treatment device and method to body area comprising arm that may provide (or where the treatment may eventually result in) reduction of a number and volume of adipose cells, muscle strengthening, muscle shaping and muscle toning. The application of the treatment device and method to body area comprising arm may cause circumferential reduction of the abdomen, removing of saggy belly and cellulite reduction.

The one or more treatment effects provided to one or more target biological structures may be based on selective targeting of a RF field into one or more biological structures and providing heating together with application of magnetic field causing muscle stimulation (including muscle contraction). The RF treatment may cause selective heating of one or more biological structures, polarizing of extracellular matrix and/or change of cell membrane potential in a patient's body. The magnetic field may be time-varying magnetic field or static magnetic field. When the time-varying magnetic field is used, the magnetic treatment may be referred as time-varying magnetic treatment. The magnetic treatment may cause muscle contraction, muscle relaxation, cell membrane polarization, eddy currents induction and/or other treatment effects caused by generating time-varying magnetic field in at least part of one or more target biological structures. The time-varying magnetic field may induce electric current in biological structure, The induced electric current may lead to muscle contraction. The muscle contractions may be repetitive. Muscle contraction provided by magnetic field may include supramaximal contraction, tetanic contraction and/or incomplete tetanic contraction. In addition, magnetic field may provide muscle twitches.

The treatment effect provided by using of the treatment device and by application of magnetic treatment and RF treatment may be combined. For example, reduction of a number and volume of adipose cells may be achieved together with muscle strengthening, muscle shaping and/or muscle toning during actual treatment or during a time (e.g. three or six months) after treatment. Furthermore, the effect provided by using of the treatment device by application of magnetic treatment and RF treatment may be cumulative. For example, the muscle toning may be achieved by combined reduction of a number and volume of adipose cells may be achieved together with muscle strengthening.

The method of treatment may provide the treatment effect to at least one of target biological structure by thermal treatment provided by RF field in combination with applied magnetic treatment. The treatment effect to a target biological structure may be provided by heating at least one biological structure and evoking at least a partial muscle contraction or muscle contraction of a muscle by magnetic treatment.

The method of treatment may enable heating of the body area where the muscle contraction by the magnetic field is evoked. The heating may minimize muscle injury and/or ligament injury including tearing or inflammation. Heating of a contracting muscle and/or adjacent biological structure may also shift the threshold of uncomfortable treatment. Therefore, heating caused by the RF field may allow a higher amount of magnetic energy to be delivered into patient's biological structure to do more muscle work. Heating of the muscle and/or adjacent biological structure may also improve the quality of and/or level of muscle contraction. Because of heating provided by RF field, more muscle fibres and/or longer part of the muscle fibre may be able to contract during the magnetic treatment. Heating may also improves penetration of muscle stimuli generated by the magnetic treatment. Additionally, when at least partial muscle contraction or muscle contraction is repeatedly evoked, the patient's threshold of uncomfortable heating may also be shifted higher. Such shifting of the threshold may allow more RF energy to be delivered to the patient's body.

Repeated muscle contraction followed by muscle relaxation in combination with heating may suppress the uncomfortable feeling caused by muscle stimulation (e.g. muscle contraction). Muscle stimulation in combination with heating may provide better regeneration after treatment and/or better prevention of panniculitis and other tissue injury.

Repeated muscle contraction followed by muscle relaxation in combination with RF heating (according to preliminary testing) may have positive results in treatment and/or suppressing symptoms of diabetes. The repetitive muscle contraction induced by provided magnetic field together with heating of the biological structure by RF field may also improve the outcome of diabetes symptoms or positively influence results of diabetes symptoms drug treatment. Success of treatment of diabetes symptoms may be caused by penetration of high amount of radiofrequency energy deep to patient's abdomen area. Such penetration may be caused by simultaneous application of magnet treatment that may cause suppressing of patient's uncomfortable feelings related to high amount of RF energy flux density and increased temperature in the tissue. Also, magnet treatment may cause polarization and depolarization of patient's tissue that may also increase RF energy penetration to patient's body. The RF treatment and/or magnetic treatment may influence glucose metabolism or help with weight loss that may suppress diabetes symptoms. It is a believe that weight loss and exercise of patients with diabetes symptoms may help suppress diabetes symptoms.

Application of RF treatment by RF field combined with magnetic treatment by magnetic field may also positively influence proliferation and differentiation of myosatellite cells into muscle cells. Tests suggest that magnet treatment including time periods with different duration, repetition rate and magnetic flux density (e.g. pulses or trains as defined below) may provide a stimulation needed to start proliferation and differentiation of myosatellite cells.

Testing also suggest that method of treatment providing magnetic field including at least two or at least three successive time periods with different duration, repetition rate and magnetic flux density (e.g. pulses, bursts or trains as defined below) may provide a shock to the muscle. As a consequence, the regeneration process resulting in proliferation and differentiation of myosatellite cells may be started and further accelerated by delivered RF field. Proliferation and differentiation of myosatellite cells may result in muscle strengthening, restoration of muscle functionality, increasing muscle volume and improvement of muscle shape, body tone or muscle tone.

The method of application of at least partial muscle stimulation or muscle contraction together with heating to the same body area may result in hyperacidity of the extracellular matrix. Hyperacidity may lead to apoptosis of adipose tissue and acceleration of weight loss and body volume loss. Hyperacidity may be caused by release of fatty acids into the extracellular matrix, wherein the release of fatty acids may be caused by concentrated high intensity muscle work. Concentrated high intensity muscle work may be provided by high number of repetitive muscle contractions causes by application of time-varying magnetic field generated by described magnetic field generating device and treatment device.

The treatment effect of the RF treatment may be enhanced by magnetic treatment, such as by reducing or eliminating the risk of panniculitis or local skin inflammation since any clustering of the treated adipocytes may be prevented by the improved metabolism. The improved blood and/or lymph flow may contribute to removing adipocytes. The removal of adipocytes may be promoted by a higher number of cells phagocytosing the adipocytes as well. Synergic effects of magnetic treatment and radiofrequency (RF) treatment significantly improves metabolism. Therefore, the possibility of adverse event occurrence is limited and treatment results induced by the present invention are reached in shorter time period.

The treatment device and the method of a treatment may provide treatment of the same patient's body area, wherein the magnetic treatment and the RF treatment may be targeted into at least part of one or more biological structures. One or more volumes of patient's body tissue affected by targeted RF and/or magnetic treatment may be in proximity. The volume of at least part of at least one or more affected biological structures of patient's body tissue may be defined as an affected tissue volume wherein the treatment effect provided by treatment device and/or method of treatment described above takes place. The treatment effect may be caused by repeated muscle contraction (provided e.g. magnetic treatment) changing of a tissue temperature (provided e.g. RF treatment), and/or by at least partial polarization and acceleration of molecules in the patient's tissue (preferably provided by RF treatment and magnetic treatment). Changing of a tissue temperature may include e.g. an increasing tissue temperature of at least 3° C. or 4° C. or 5° C. or 6° C. or 7° C. or 10° C. with reference to normal tissue temperature. Further, changing of a tissue temperature may include an increase or decrease of tissue temperature in the range of 1° C. to 50° C. or 2° C. to 30° C. or 2° C. to 25° C. as compared to the untreated tissue located in the same or different body area. Changed tissue temperature may be interpreted as change of temperature in any volume or any area of the biological tissue.

Proximity of affected tissue volumes by at least one RF treatment and/or by at least one magnetic treatment has meaning of a distance between two affected tissue volumes. At least two proximate affected tissue volumes may have at least partial overlay wherein 2% to 15% or 5% to 30% or 2% to 100% or 30% to 60% or 80% to 100% or 40% to 85% of smaller affected tissue volume may be overlaid by larger affected tissue volume. Also the distance between volumes of affected tissue may be in a range of 0.01 cm to 10 cm or in the range of 0.01 cm to 5 cm, 0.01 cm to 3 cm, or 0.01 cm to 1 cm. Alternatively, the overlay in the ranges mentioned above may apply for two or more affected tissue volumes having an identical volume without any differentiation between smaller or larger tissue volumes.

FIGS. 1a-1e show exemplary schematic diagrams of the treatment device. The diagrams may apply only to main unit and applicator. The treatment device may include input interface 103, control system 104, power source 105, power network 106, one or more treatment clusters 107 and one or more treatment energy sources 108.

Plurality of treatment energy sources 108 may be coupled to or communicate with at least one treatment cluster 107. Control system 104 may be coupled to and communicate with each treatment cluster.

Shown parts of treatment device in FIGS. 1a-1e may be electrical elements of circuitry. Also, one or more shown parts of diagrams in FIGS. 1a-1e may include plurality of individual electrical elements. Electrical elements may generate, transfer, modify, receive or transmit electromagnetic signal (e.g. electrical) signal between individual electrical elements. The electromagnetic signal may be characterized by current, voltage, phase, frequency, envelope, value of the current, amplitude of the signal and/or their combination. When the electromagnetic signal reaches the treatment energy source, the respective treatment energy source may generate treatment energy and/or field.

Input interface 103 may receive input from a user. Input interface may include human machine interface (HMI). The HMI may include one or more displays, such as a liquid crystal display (LCD), a light emitting diode (LED) display, an organic LED (OLED) display, which may also include a touch-screen display. HMI may include one or more controlling elements for adjustment or controlling treatment device. Controlling element may be at least one button, lever, dial, switch, knob, slide control, pointer, touchpad and/or keyboard. The input interface may communicate or be coupled to control system or power network.

The user may be an operator (e.g. medical doctor, technician, nurse) or patient himself, however the treatment device may be operated by patient only. In most cases, the treatment device may be operated by the user having an appropriate training. The user may be any person influencing treatment parameters before or during the treatment in most cases with exception of the patient.

Control system 104 may include a master unit or one or more control units. Control system may be an integral part of the input interface 103. Control system 104 may be controlled through the input interface 103. Control system may include one or more controlling elements for adjustment or controlling any part or electrical elements of treatment device. Master unit is a part of treatment device (e.g. applicator and/or main unit) or electrical element of circuitry that may be selected by the user and/or treatment device in order to provide master-slave communication including high priority instructions to other parts of the treatment device. For example, master unit may be a control unit or part of input interface providing high priority instructions to other parts of the treatment device. The treatment device may include a chain of master-slave communications. For example, treatment cluster 107 may include one control unit providing instructions for electrical elements of the treatment cluster 107, while the control unit of treatment cluster 107 is slave to master unit. Control system 104 may be coupled or communicate with input interface 103, one or all power source 105, power network 106, and/or with one or all treatment clusters present in the treatment device. The control system 104 may include one or more processors (e.g. a microprocessors) or process control blocks (PCBs).

The power source 105 may provide electrical energy including electrical signal to one or more treatment clusters. The power source may include module converting AC voltage to DC voltage.

The power network 106 may represent a plug. The power network may represent a connection to power grid. However, the power network may represent a battery for operation of the treatment device without need of a power grid. The power network may provide electrical energy needed to operation to whole treatment device and/or its parts. As shown on exemplary diagrams in FIGS. 1a-1e, the power network provides electrical energy to input interface 103, control system 104 and power source 105.

The treatment cluster 107 may include one or more electrical elements related to generation of respective treatment energy. For example, the treatment cluster for magnetic treatment (referred as HIFEM) may include e.g. an energy storage element and switching device. For another example, the treatment cluster for RF treatment (referred as RF cluster) may include e.g. power amplifier and/or filter.

The treatment energy source 108 may include a specific source of treatment energy. In case of magnetic treatment, the treatment energy source of magnetic field may be a magnetic field generating device e.g. a magnetic coil. In case of RF treatment, the treatment energy source of RF energy (including RF waves) may be RF electrode.

The treatment device may include one or more treatment circuits. One treatment circuit may include a power source, electrical elements of one treatment cluster and one respective treatment energy source. In case of magnetic treatment, the magnetic circuit may include a power source, HIFEM cluster and magnetic field generating device. In case of RF treatment, the RF circuit may include a power source, RF cluster and magnetic field generating device. The electromagnetic signal generated and/or transmitted within a treatment circuit for RF treatment may be referred as RF signal. The wiring connecting respective electrical elements of the one treatment cluster may also be included in the respective cluster. Each of the treatment clusters in FIGS. 1a-1e described in the detail below may be any of HIFEM, RF or combination.

The one or more treatment circuits and/or their parts may be independently controlled or regulated by any part of control system 104. For example, the speed of operation of HIFEM cluster of one treatment circuit may be regulated independently on the operation of HIFEM cluster of another treatment circuit. In another example, the amount of energy flux density of delivered by operation of RF electrode of one treatment circuit may be set independently from the operation of RF electrode of another treatment circuit.

FIG. 1a shows an exemplary diagram of the treatment device including input interface 103, control system 104, power source 105, power network 106, two treatment clusters including treatment cluster A 107a, treatment cluster B 107b, treatment energy source A 108a and treatment energy source B 108b. In such case, treatment device may include two treatment circuits. One treatment circuit may include a power source 105, treatment cluster A 107a and/or treatment energy source A 108a. Another treatment circuit may include a power source 105, treatment cluster B 107b and/or treatment energy source B 108b. Treatment clusters 107a and 107b may communicate with each other.

Figure 1B:
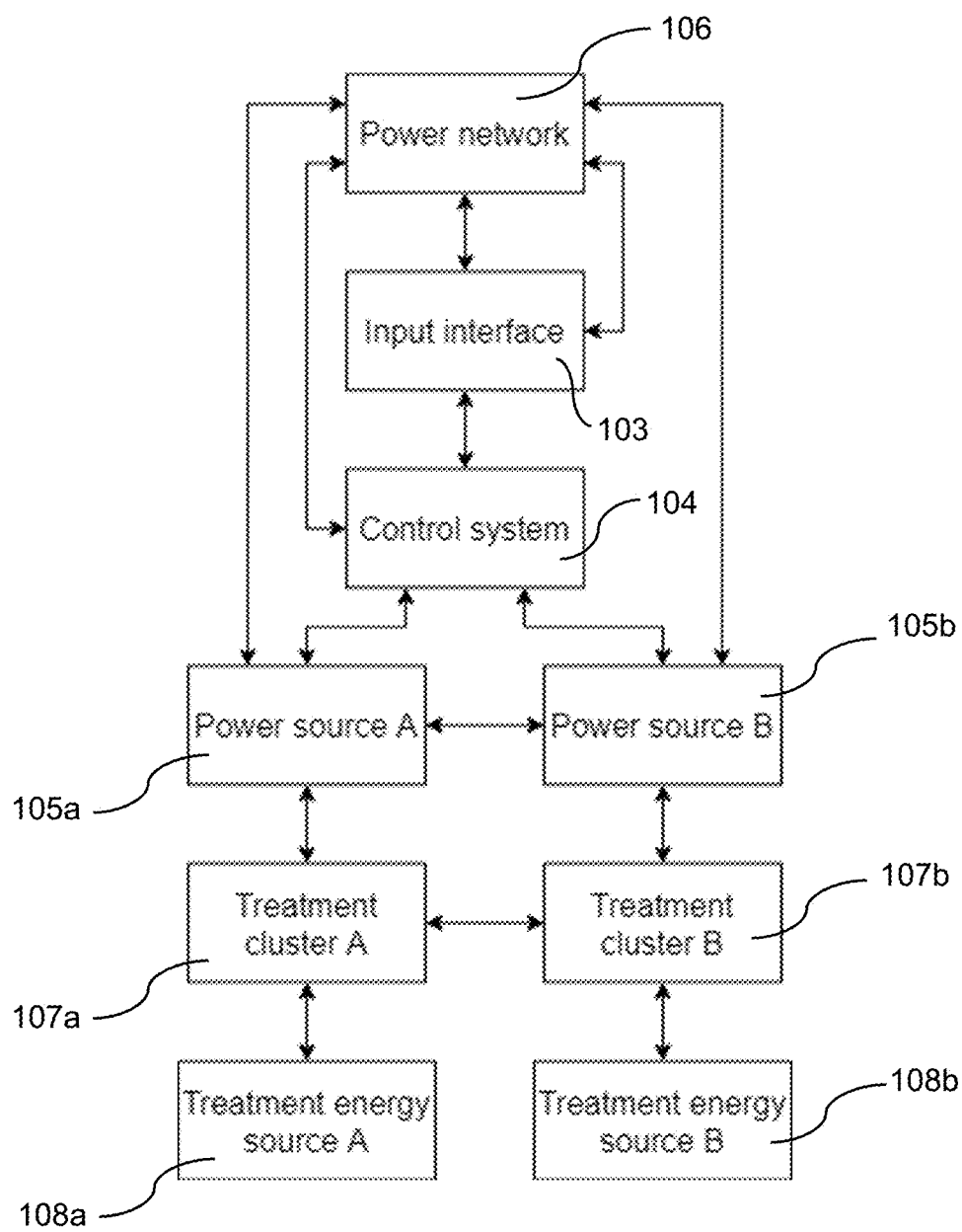

FIG. 1b shows an exemplary diagram of the treatment device including input interface 103, control system 104, two power sources including a power source A 105a and a power source B 105*b*, power network 106, two treatment clusters including treatment cluster A 107*a* and treatment cluster B 107*b*, treatment energy source A 108*a* and treatment energy source B 108*b*. In such case, treatment device may include two treatment circuits. One treatment circuit may include a power source 105*a*, treatment cluster A 107*a* and/or treatment energy source A 108*a*. Another treatment circuit may include a power source B 105*b*, treatment cluster B 107*b* and/or treatment energy source B 108*b*. Treatment clusters 107*a* and 107*b* may communicate with each other.

Figure 1C:
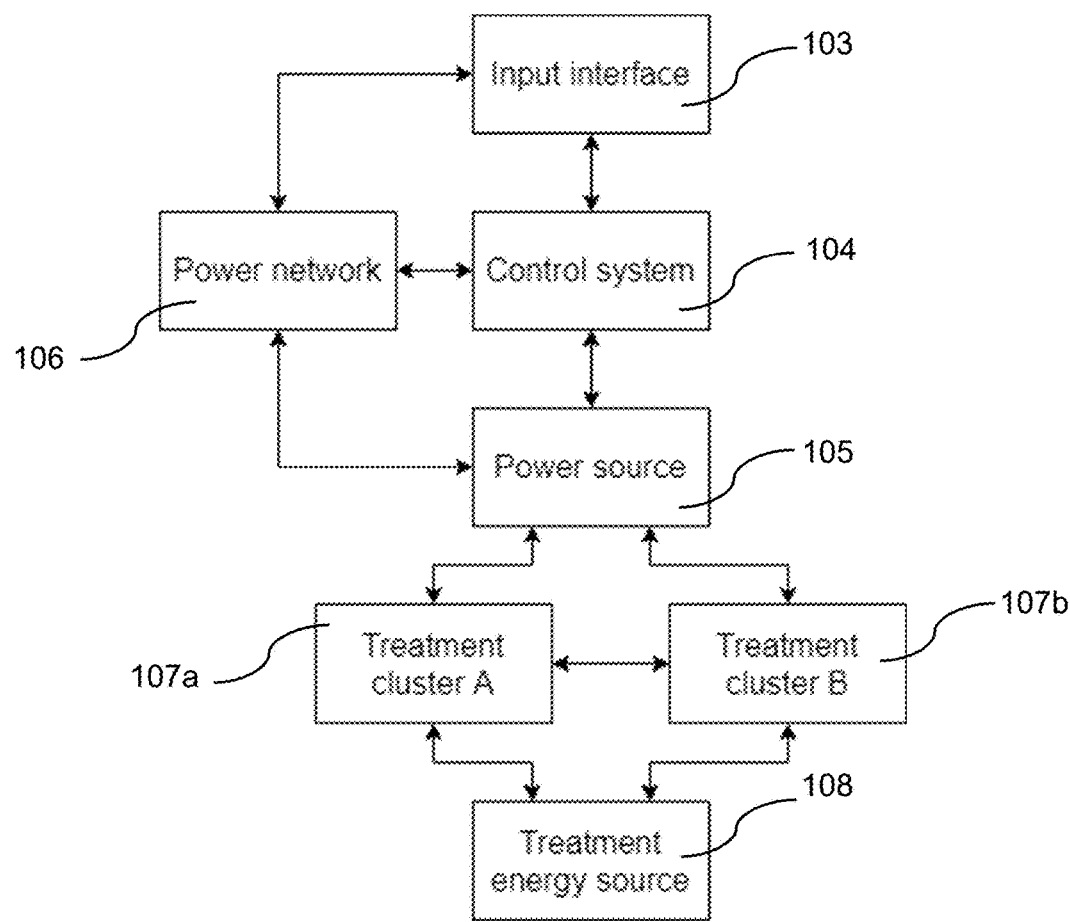

FIG. 1*c* shows an exemplary diagram of the treatment device including input interface 103, control system 104, power source 105, power network 106, two treatment clusters including treatment cluster A 107*a* and treatment cluster B 107*b* and one treatment energy source 108. In such case, treatment device may include two treatment circuits. One treatment circuit may include a power source 105, treatment cluster A 107*a* and/or treatment energy source 108. Another treatment circuit may include the power source 105, treatment cluster B 107*b* and/or treatment energy source 108. Treatment clusters 107*a* and 107*b* may communicate with each other. The shown diagram may include a magnetic field generating device providing both RF treatment and magnetic treatment.

Figure 1D:
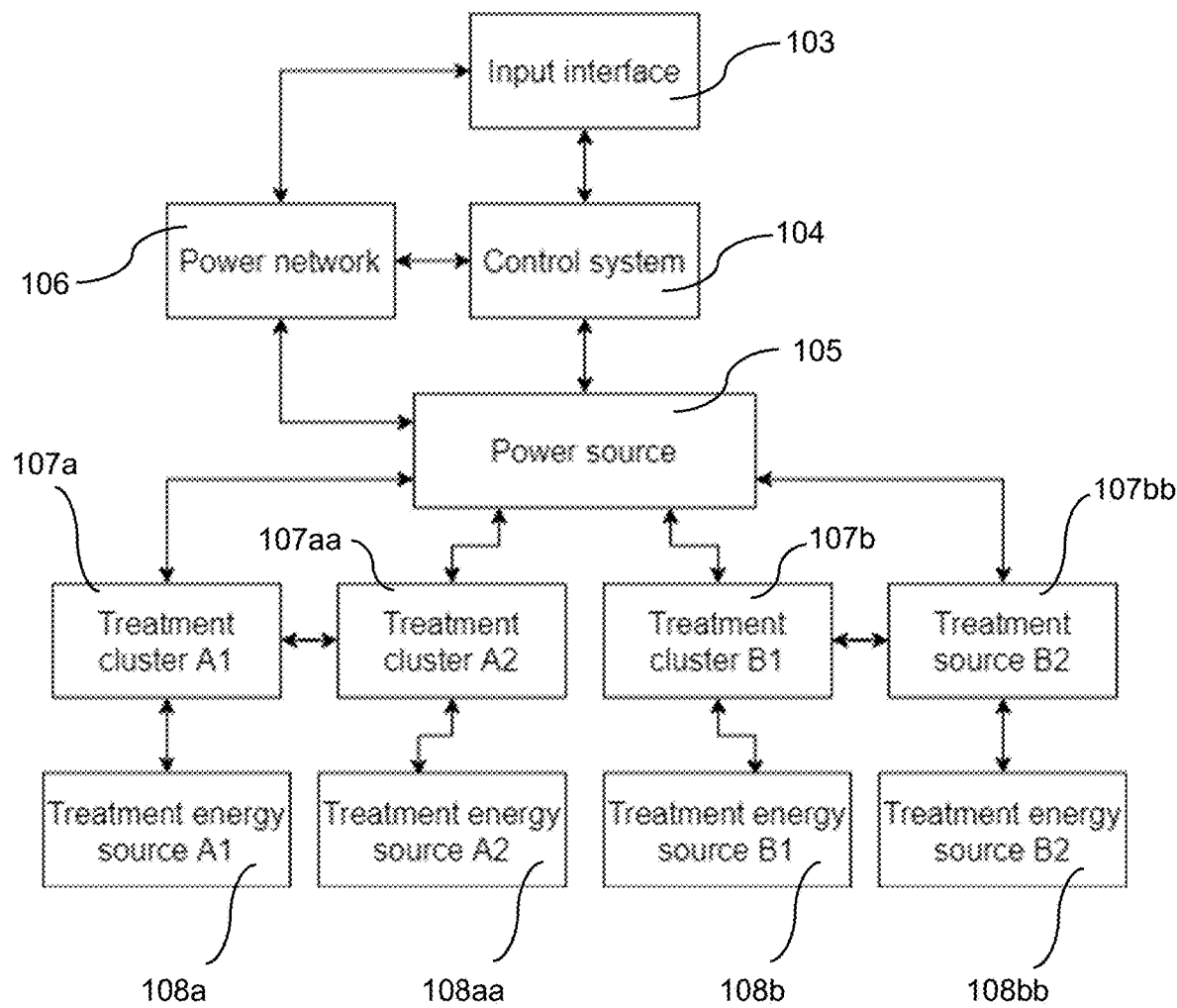

FIG. 1*d* shows an exemplary diagram of the treatment device including input interface 103, control system 104, power source 105, power network 106, four treatment clusters including treatment cluster A1 107*a*, treatment cluster A2 107*aa*, treatment cluster B1 107*b*, treatment cluster B2 107*bb* and four treatment energy sources including treatment energy source A1 108*a*, treatment energy source A2 108*aa*, treatment energy source B1 108*b* and treatment energy source B2 108*bb*. In such case, treatment device may include four treatment circuits. First treatment circuit may include a power source 105, treatment cluster A1 107*a* and/or treatment energy source 108*a*. Second treatment circuit may include the power source 105, treatment cluster A2 107*aa* and/or treatment energy source A2 108*aa*. Third treatment circuit may include a power source 105, treatment cluster B1 107*b* and/or treatment energy source B1 108*b*. Fourth treatment circuit may include a power source 105, treatment cluster B2 107*bb* and/or treatment energy source B2 108*bb*. The treatment energy sources of the first treatment circuit and second treatment circuit may be positioned in one applicator, while the treatment energy sources of the third treatment circuit and fourth treatment circuit may be positioned in another applicator.

Figure 1E:
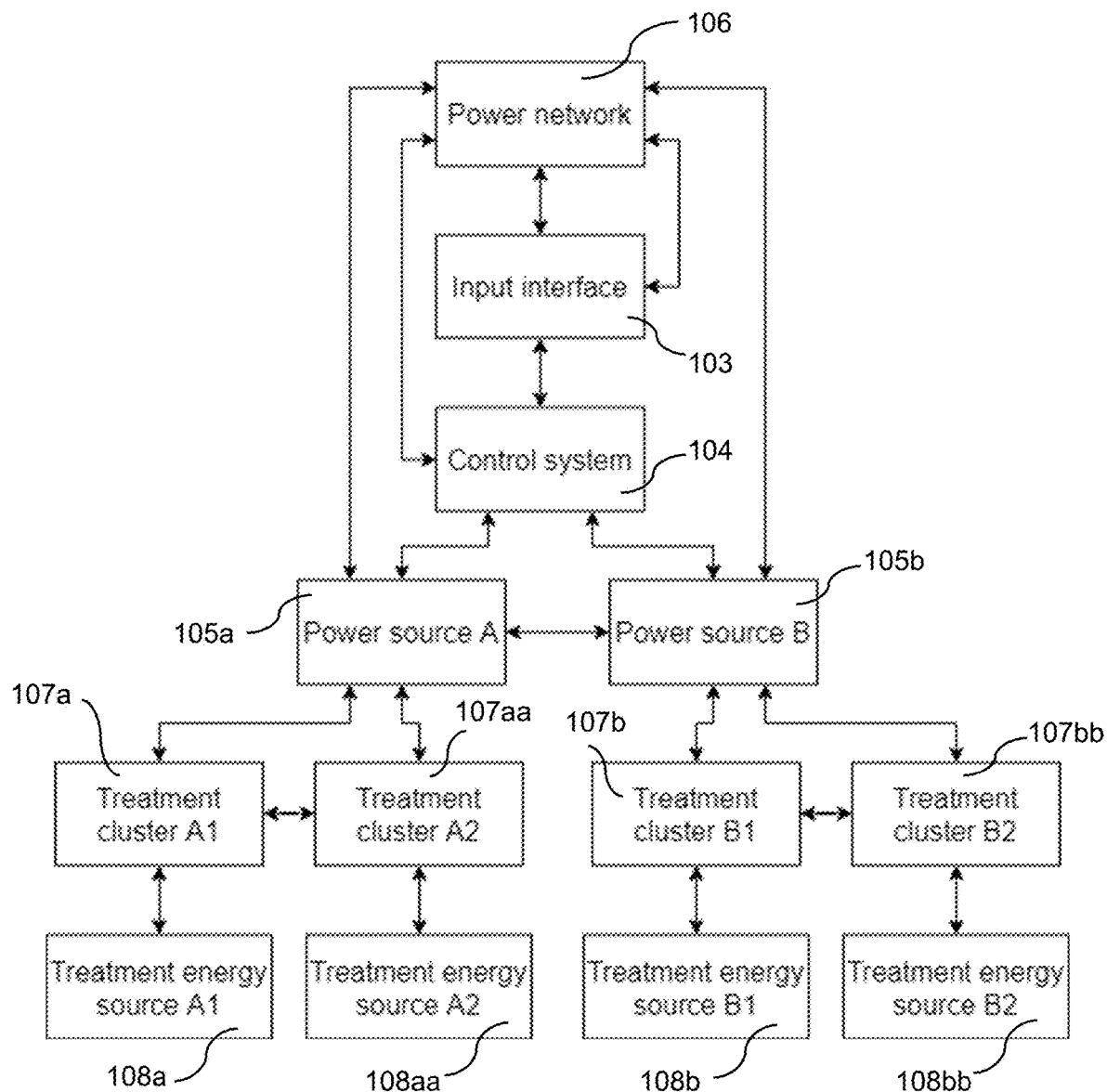

FIG. 1*e* shows an exemplary diagram of the treatment device including input interface 103, control system 104, two power sources including power source A 105*a* and power source B 105*b*, power network 106, four treatment clusters including treatment cluster A1 107*a*, treatment cluster A2 107*aa*, treatment cluster B1 107*b*, treatment cluster B2 107*bb* and four treatment energy sources including treatment energy source A1 108*a*, treatment energy source A2 108*aa*, treatment energy source B1 108*b* and treatment energy source B2 108*bb*. In such case, treatment device may include four treatment circuits. First treatment circuit may include a power source A 105*a*, treatment cluster A1 107*a* and/or treatment energy source 108*a*. Second treatment circuit may include a power source A 105*a*, treatment cluster A2 107*aa* and/or treatment energy source A2 108*aa*. Third treatment circuit may include a power source B 105*b*, treatment cluster B1 107*b* and/or treatment energy source B1 108*b*. Fourth treatment circuit may include a power source B 105*b*, treatment cluster B2 107*bb* and/or treatment energy source B2 108*bb*. The treatment energy sources of the first treatment circuit and second treatment circuit may be positioned in one applicator, while the treatment energy sources of the third treatment circuit and fourth treatment circuit may be positioned in another applicator.

Figure 1F:
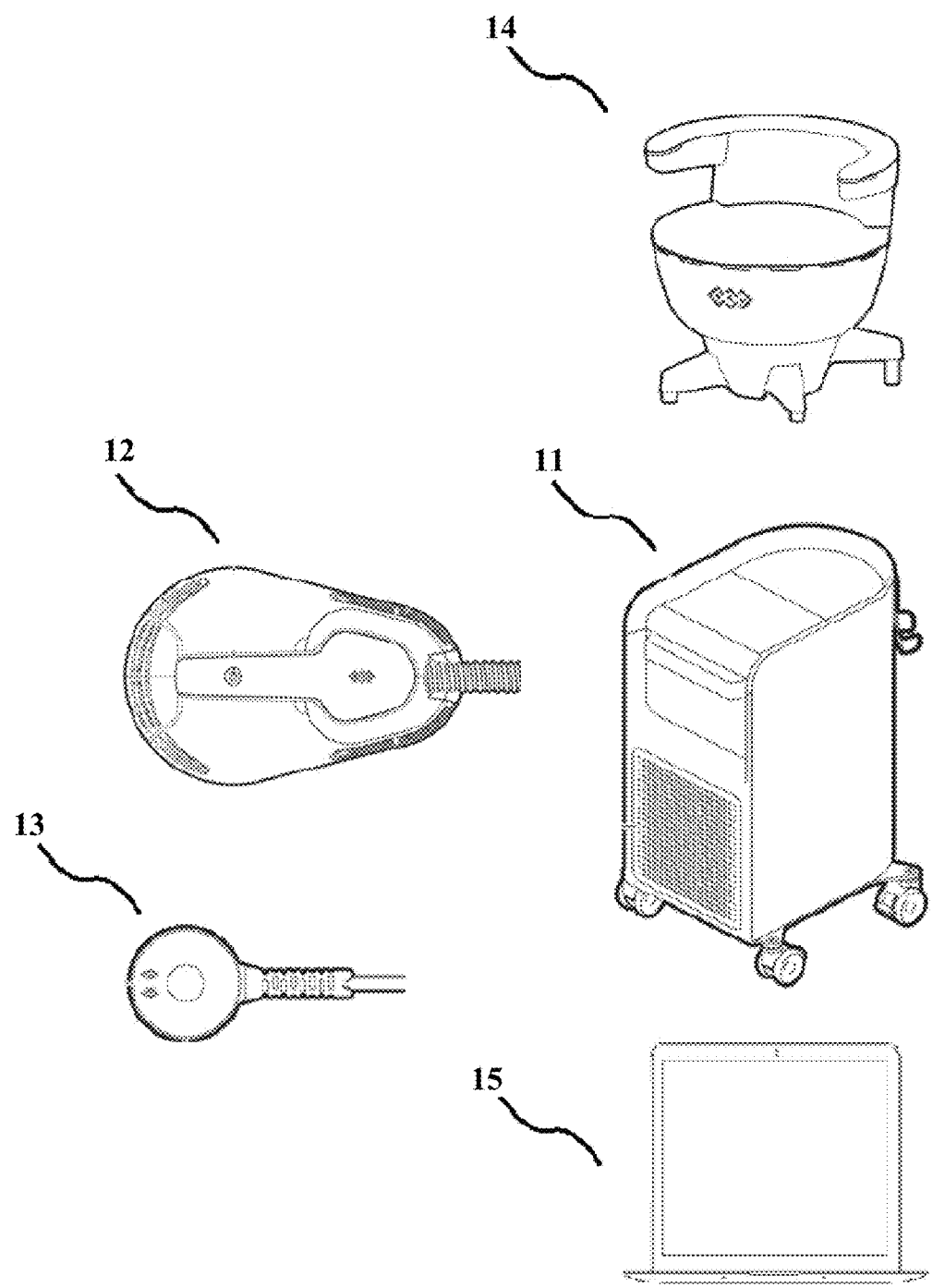
FIG. 1f illustrates exemplary individual parts of a treatment device.

FIG. 1*f* illustrates individual parts of the treatment device, including a main unit 11 connected or coupled to at least one applicator 12, a remote control 13, an additional or additional treatment device 14, and/or a communication device 15. The additional treatment device may be on the same level of independency as the whole treatment device.

The treatment device may include a remote control 13. Remote control 13 may include a discomfort button for safety purposes so that when a patient feels any discomfort during the treatment, the user may press the discomfort button. When the discomfort button is pressed, remote control 13 may send a signal to a main unit and stop treatment. Also, the remote control 13 may inform the user through a human machine interface (HMI). In order to stop treatment during discomfort, the operation of the discomfort button may override the instructions from master unit. Alternatively, the discomfort button may be coupled to or be part of the main unit 11.

The main unit 11 may be coupled or connected to one or more additional treatment devices 14 that may be powered by the main unit 11. However, the treatment device including main unit 11 may be paired by software with the one or more additional treatment devices 14. Also, one or more additional treatment devices 14 may be also powered by their own source or sources of energy. The communication device 15, additional treatment device 14, remote control 13 and at least one applicator 12 may each communicate with the main unit 11. Communication may include sending and/or receiving information. Communication may be provided by wire and/or wirelessly, such as by internet network, local network, RF waves, acoustic waves, optical waves, 3G, 4G, 5G, GSM, HUB switch, LTE network, GSM network, Bluetooth and/or other communication methods or protocols.

The additional treatment device 14 may be any device that is able to provide at least one type of treatment energy (e.g.: RF field, magnetic field, ultrasound, light, time-varied mechanical pressure, shock wave, or electric current) to a patient's body to cause treatment effect to at least one target biological structure. The additional treatment device 14 may include at least one electrical element generating treatment energy for at least one treatment e.g. magnet, radiofrequency, light, ultrasound, heating, cooling, massage, plasma and/or electrotherapy. The additional treatment device 14 may be able to provide at least one treatment without instructions from the main unit 11. The additional treatment device 14 may communicate with the main unit 11, communication device 15 and/or other additional treatment devices 14. The additional treatment devices 14 may be any other device of the same or other company wherein the device may be able to provide specific one or more type of treatment energy. The additional treatment device 14 may be an extension of the treatment device, wherein the additional treatment device 14 may provide treatment energy with parameters defined by the HMI of the main unit 11.

The communication device 15 may be connected by wire and/or wirelessly to the main unit 11. The communication device 15 may be a computer, such as a laptop or desktop computer, or a mobile electronic device, such as a smartphone, or an electronic tablet. The communication device may send and/or receive information linked with a treatment, functionality of the treatment device, and/or other information. The additional treatment device 14 and/or the communication device 15 may communicate directly with the main unit 11 or indirectly with the main unit 11 through one or more additional or communication devices. In order to provide communication the communication device may include receiver, transmitter and a control unit to process sent and/or received information.

Sent and/or received information from or to an individual part of the treatment device may include data from communication between communication device 15 and the main unit 11, data from communication between applicator 12 and the main unit 11, data from communication between additional treatment device 14 and the main unit 11 and/or data from communication between the remote control 13 and the main unit 11. Sent and/or received information may be stored in a black box, cloud storage space and/or other storage devices. The black box may be part of the main unit 11 or any other part of the treatment device. Other storage device may be USB, other memory device and/or also communication device with internal memory. At least part of sent and/or received information may be also displayed by HMI. Sent and/or received information may be displayed, evaluated and/or changed by the user through the HMI and/or automatically by control system. One type of the sent and/or received information may be predetermined or current value or selection of one or more treatment parameters or patient information. Patient information may include e.g. gender of a patient, age and/or body type of the patient.

Sent and/or received information may also inform external authorities, like a support centre, e.g. a service and/or a sale department, that are also subset of communication devices. Sent and/or received information to external authorities may include information about the condition of the treatment device, history of one or more provided treatments, operational history of the treatment device, software update information, wear out information, durability of the RF electrode, durability of the magnetic field generating device, treatment warnings, treatment credit/billing information, such as information of number of paid treatments or credits, and/or other operation and usage information.

One possible type of sent and/or received information may be recognition of connection of one or more applicators 12, the remote control 13, additional treatment devices 14, and/or communication devices 15, According to information the treatment device may manually or automatically recognize type of connected additional treatment device 14 and/or applicator 12. Automatic recognition may be provided by control system. Based on information about connection of one or more applicators 12, connection of additional treatment devices 14 and/or communication devices 15, the treatment device may provide actualization of HMI, show notification about the connection to applicators and/or possible optimization of new treatment options. Possible optimization of new treatment options may include e.g. adjusting of at least one treatment parameter, implementing additional treatment energy source, change of parameters of new treatment energy source and/or other. The treatment device (e.g. control system) may automatically adjust or offer adjustment of treatment parameters based on newly connected applicator 12 and/or additional treatment devices 14. Recognition of connected applicator 12, additional treatment device 14 and/or communication device 15 may be based on by specific connectors (e.g., a specific pin connector). Also, the recognition of connection may be provided by a specific physical characteristic like an impedance of connected part or by a specific signal provided by the applicator or its connected part to the main unit 11. Connection between individual parts of the treatment device such as the main unit 11, the applicator 12, the remote control 13, the additional treatment device 14 and/or the communication device 15 may be provided by wire and/or wirelessly (e.g. by RFID tag, RF, Bluetooth, and/or light electromagnetic pulses). The applicator 12 may by connected to the main unit 11 by a wire to be powered sufficiently. Alternatively, the application may be connected through a wireless connection in order to communicate with the main unit 11 and/or with communication device 15. Connected applicator 12, additional treatment device 14 and/or communication device 15 may be recognized by software recognition, specific binary ID, manual recognition of the parts selected from the list implemented in the treatment device, and/or by a pairing application.

The connector side in the main unit 11 may include a unit able to read and/or recognize information included in the connector side of the applicator and/or connector side of the additional treatment device. Based on read and/or recognized information, the applicator and/or the additional treatment device may be recognized by main unit 11. The connector side of the main unit 11 may serve as a first side connector of the connection, wherein the connection of the applicator or additional treatment device may serve as a second side connector of the connection. Sending of the information, receiving of the information and/or recognition of the second side connector by the first side connector may be based on binary information received by conductive contact between these two connector sides, by optical reading and/or by recognition provided by the first side connector. Optical recognition may be based on, for example, reading of specific QR codes, barcodes and the like for the specific applicators 12.

The first side connector located in the main unit 11 may include a unit able to read/recognize binary information implemented in the second side connector of a cable from the applicator 12 and/or additional treatment device 14. Implemented information in the second side connector may be stored in an SD card. Based on such implemented information any part of the treatment device may be recognized by the main unit 11.

Communication between individual parts of the treatment device (including e.g. the main unit 11, the remote control, one or more applicators, one or more additional treatment devices and/or communication devices) may be based on peer-to-peer (referred as P2P) and/or master-slave communication. During P2P communication, the individual parts of the treatment device have the same priority of its commands and/or may communicate directly between each other. P2P communication may be used during initial recognition of connected individual parts of the treatment device. P2P communication may be used between some parts of the treatment device during a treatment, such as between communication devices.

Master-slave communication may be used between individual parts of the treatment device for at least a short time during, before and/or after each treatment of individual patient. During master-slave communication, one part of the treatment device may provide commands with the highest priority. The individual part of the treatment device, e.g. as the main unit 11 may provide commands with the highest priority and is referred as master unit. The treatment device may include at least one master-slave communication between an individual electrical element, such as a power source and or one or more control units, where the one or more control units act as master.

The master unit may be selected by a user before, after and/or during the treatment. The user may select master unit from available individual parts or electrical elements of the treatment device. Therefore, the user may select the main unit 11, the applicator 12, the remote control 13, the additional treatment device 14 or the communication device 15 as the master unit. The master unit may be a control unit in selected present in individual part of the treatment device e.g. a control unit in the main unit 11. The user may select the master unit in order to facilitate adjusting of treatment parameters. The user may also select the communication device 15 as a master unit, wherein the communication device selected as master device may provide control of more than one treatment device. The main unit 11 may include a control unit as a master unit that monitor and evaluate at least one parameter of the treatment, such as patient's temperature, voltage on individual elements of the treatment device and/or other, that enable to provide safe treatment even if the connection between. Also, the master unit may be independent electrical element outside of human machine interface. The master unit may be controlled by user through human machine interface.

Alternatively, the master unit may be selected automatically based on a predetermined priority value of the connected parts of the treatment device. Selected master unit may remain unchanged and already selected part of the treatment device may act as the master unit during the whole treatment. However, the selection of master unit may be changed during the treatment based on command priority and/or choice of the user. The master unit may be also determined according to manufacturing configuration or being dependent on factory reset. For example, the remote control 13 may provide command with the highest priority to stop the treatment when patient feels discomfort and the treatment will be stopped without relevance of which individual part of the treatment device was set as the master unit and set parameters of the treatment.

FIGS. 2-5 illustrate several possible master-slave communication schemes that may be used in communication between the main unit 11 and one or more applicators 12, remote controls 13, additional treatment devices 14, and/or communication devices 15. According to FIG. 2, one or more therapy generators 201 generate a modified electrical signal in order to provide a signal to a treatment energy source, such as the RF electrode and/or the magnetic field generating device. The therapy generators 201 may include a group of electrical elements or at least two members of the group of electrical elements present in the circuitry of the treatment device and/or main unit. The group of electrical elements may include a control unit, power source, system of coaxial cables, one or more switches, one or more energy storage devices, one or more pin diodes, one or more LC circuits, one or more LRC circuits, one or more power amplifiers and/or other part of the treatment device actively modifying electrical signal in controlled manner. The therapy generator may provide modifying of electrical signal in controlled manner.

Modifying electrical signal in controlled manner may include e.g. providing and/or controlling impedance adjustment of provided RF treatment based on impedance matching measured across patient's tissue and/or RF electrodes. Actively modified electrical signal may be interpreted such that electrical signal may have different parameters, such as frequency, symmetrisation, amplitude, voltage, phase, intensity, etc. The parameters of electrical signal may be based on requirements of treatment including the type of the patient, treatment parameters. In addition, the parameters of electrical signal may be modified on feedback information, such as measured standing wave ratio of RF energy, temperature of tissue, temperature of RF electrode, temperature of the inside of the applicator, temperature of the surface of the applicator, electric current and voltage of individual elements of the treatment device and/or other.

Figure 2:
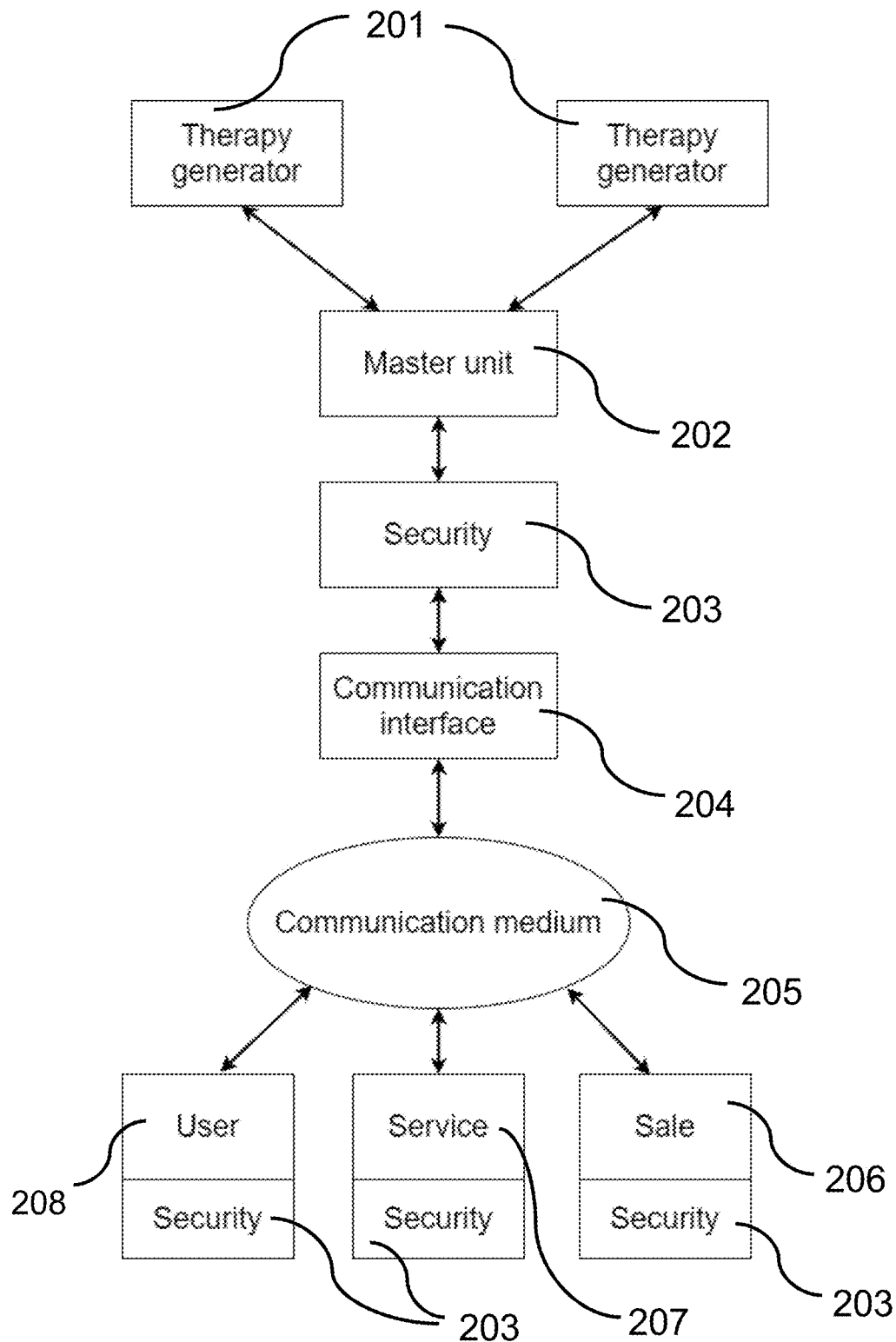
FIG. 2 illustrates an exemplary communication diagram between parts of the treatment device such as an applicator, a remote control, an additional treatment device and a communication device.

The diagram of FIG. 2 shows a security 203 that prevent any unauthorized intrusion to the treatment device communication and protects personal user data and/or account. The security 203 may protect the treatment device from computer viruses, unauthorized access and/or protect the communication between individual parts of the treatment device from reading or change by unauthorized medium or person. The security 203 may provide coding of the information used in communication and/or antivirus services preventing intrusion of unwanted binary code into the treatment device and/or communication. The security 203 may correct mistakes created during the communication. The security 203 may block connection of unauthorized/unwanted external device to the treatment device.

The security 203 in FIG. 2 may be located in the communication diagram between the master unit 202 and a communication interface 204. The security 203 may also be part of an element user 208, a service 207, and/or a sale 206. The security 203 may be located also between the communication interface 204 and a communication medium 205, the therapy generator 201, and/or may be part of them.

The communication interface 204 may include hardware and/or software components that enables to translate electric, electromagnetic, infrared and/or other signal into readable form to enable communication between at least two parts of the treatment device and/or other communicating sides or medium. The communication interface 204 may provide communication and/or coding of the information and/or data. The communication interface 204 may be, for example, a modem or GSM module providing communication between the treatment device and online network or server. The communication interface 204 may be part of the master unit 202, the therapy generator 201, and/or other part of the treatment device.

The communication medium 205 may be medium transferring communication data. The communication medium 205 may be used in communication between the treatment device and the user 208, the service 207 and/or the sale 206. The communication medium 205 may be a wire, SD card, flash memory, coaxial wire, any conductive connection, server, some kind of network on principle, such as RF waves, acoustic waves, optic waves, GSM, 3G, 4G, 5G, HUB switch, Bluetooth, Wi-Fi and/or other medium which may include one or more servers.

Communication data/information may be redirected to the individual parts of the treatment device and/or to individual users or services, such as the user 208, the service 207 and/or the sale 206. Communication data/information may be redirected by the master unit 202, the communication medium 205 and/or the therapy generator 201. For example, server may filter data for the user 208 and filter other communication information that will be redirecting to the service 207, control unit and/or other part of the treatment device.

The element called "user 208" of FIG. 2 may be a representation of the HMI controlled by a user. Alternatively, the element called "user 208" of FIG. 2 may a representation of the other communication device (personal computer, laptop, mobile, tablet, etc.) controlled by user, wherein the communication device may send information to at least one part of the treatment device and/or receive information from at least one part of the treatment device.

Information provided by this communication channel may be a type of a treatment protocol, information about treatment effect, actual value and/or predetermined value of one or more treatment parameters, feedback information, selection of treated body area, recommendations of behaviour before and after the treatment and/or other information. At least part of the information may be sent to the user controlling the treatment device and also to the patient, such as by an software application for mobile phone, tablet or laptop.

The service 207 in FIG. 2 may represent a service department that has authorized access to information about the treatment device. The service 207 may be the service department of the company providing or manufacturing the treatment device wherein the communication between the service department of the company and the user may be provided through the HMI, a communication device and/or automatically through pre-programmed software interface. Information provided by this communication channel may include wear of individual electrical element of the treatment device, durability of any RF electrode and/or magnetic field generating device, malfunction of an individual electrical element, possible software optimization and/or actualization of the device, providing applications for connection of another additional treatment device and/or other. Optimization and/or actualization of the treatment device may include e.g. a remote access to the treatment device software and/or fixing errors.

The sale 206 in FIG. 2 may be a sales department with authorized access to information about the treatment device. The sale 206 may inform the user about a type of accessories which may be added to the treatment device. Further the sale 206 may mediate sales of the plug-in modules and/or mediate sales of accessories of the treatment device. Furthermore, the sale 206 may provide an offer linked with billing and renting system. Information exchanged by communication to or from sale 206 may be, for example, the number of treatments, time of treatments, and/or type of applied treatment, information about applicators and/or others.

The treatment device may include a black box for storing a data regarding the treatment history, operational history, communication between individual parts of the treatment device, data from or for a billing and renting system, operational errors, and/or other information. The data may be accessible to the sale 206, to the service 207 and/or to the user 208 via the communication medium (e.g., a storage cloud and/or server). The treatment device may include a billing and renting system to manage charges for using of the treatment device and/or respective additional treatment devices. The billing and renting system may send such information to a provider in order to prepare the billing invoice. Data from the black box may be downloaded by verified authorized personnel, such as a service technician, accountant and/or other person with administrator access. Verification of the authorized person may be provided by specific key, password, software code of several bits and/or by specific interconnecting cable.

The billing and renting system may be based on credits subtracted from a user account. Credits may be predefined by the provider of the treatment device, e.g. a producer of the treatment device. Credits may be recharged during the time when the treatment device is in operation and/or may be recharged to online account linked with one or more treatment devices of the user and/or provider. Credits may be subtracted according to the selected treatment protocol or body area. Credit value for individual one or more treatments and/or part of the treatment may be displayed to the user before treatment starts, during the treatment and/or after the treatment. If the credit in the user's account runs out, the treatment device may not enable any further treatment until credits are recharged. Credits may be used as a currency changed for individual treatment wherein different treatment may cost a different amount of credits based on the type of the treatment, the duration of the treatment, the number of used applicators, and/or other factors. Credits may be also used for renting or buying individual part of the treatment device, whole treatment device, hardware or software extensions of the treatment device and/or other consumables and spare parts belonging to the treatment device. Interface where the credit system may be recharged may be part of the treatment device, HMI and/or online accessible through website interface.

One or more software extension (e.g. software applications) may be linked with the treatment device and method of treatment. One or more software extensions may be downloaded to any communication device, such as a smartphone, tablet, computer and/or other electronic device. The software extension may communicate with the main unit and/or other part of the treatment device. The communication device with installed software extension may be used for displaying or adjusting of one or more treatment parameters or information associated to the treatment. Such displayable treatment parameters and information associated to the treatment may include e.g. time progress of the treatment, measured size of treated body area before and/or after individual treatments, schematic illustrations of applied bursts or trains, remaining time of the treatment, heart rate of the patient, temperature of patient's body e.g. temperature of the body surface, provided types of treatment, type of the treatment protocol, comparison of patient's body parameters against previous treatment (e.g., body fat percentage) and/or actual treatment effect of the treatment (e.g. muscle contraction or muscle relaxation). The software extension may be also provided to the patient in order to inform them about the schedule of treatments, mapping progress between individual treatments, percentile of treatment results compared to other people and/or recommendations of behaviour before and/or after the treatment. Recommendations of behaviour may include e.g. recommendation what volume of water should patient drink during the day, how should patient's diet look like, what type and volume of exercise should patient provide before and/or after treatment and/or other information that may improve results of treatment.

Communication between individual elements of the communication diagram, such as the therapy generator 201, the master unit 202, the security 203, the communication interface 204, the communication medium 205, the user 208, the service 207 and/or the sale 206 may be bidirectional or multidirectional.

Connection between the user 208, the service 207, the sale 206, communication medium 205 and/or connection between the therapy generator 201 and the master unit 202 may be secured by the security 203 to provide safe communication and eliminate errors. The security 203 may be located between the master unit 202 and the communication interface 204 and/or between the communication medium 205 and the communication interface 204.

Figure 3:
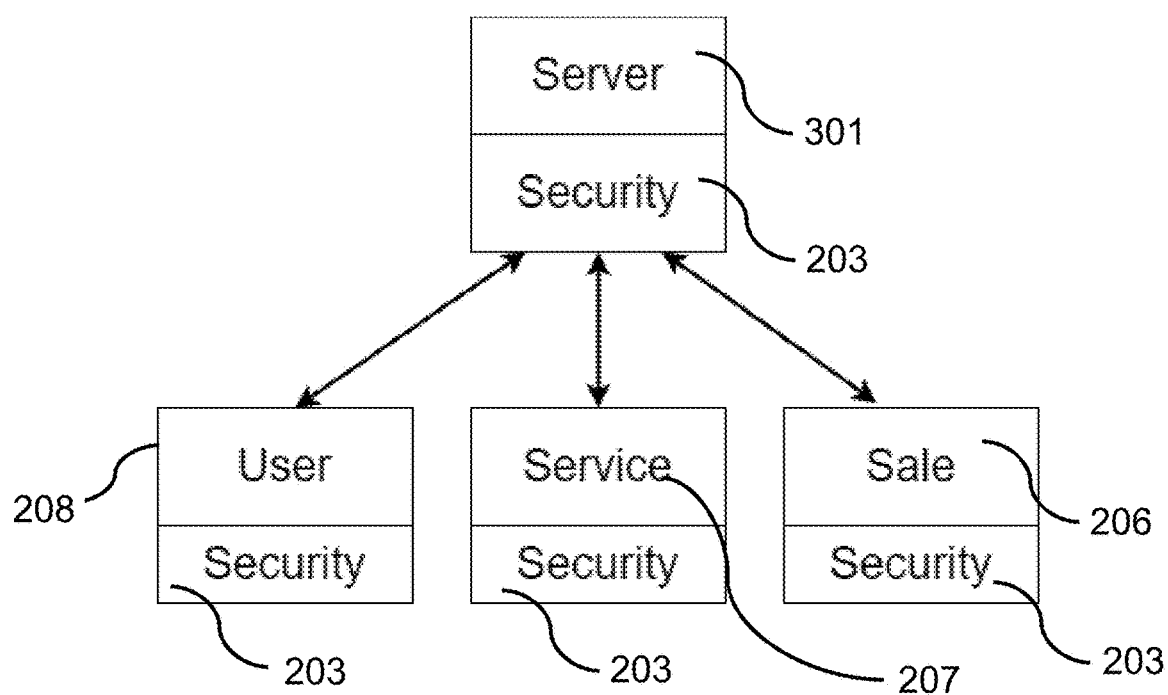
FIG. 3 illustrates an exemplary communication diagram between a server and part of the treatment device such as applicators, remote control and additional treatment devices.

As shown on FIG. 3, another option of remote access communication between the user 208, the service 207, and/or the sale 206 and the treatment device may be provided by a server 301. The server 301 may include the security 203. The security 203 may be implemented in individual access of the user 208, the service 207, and/or the sale 206.

Figure 4:
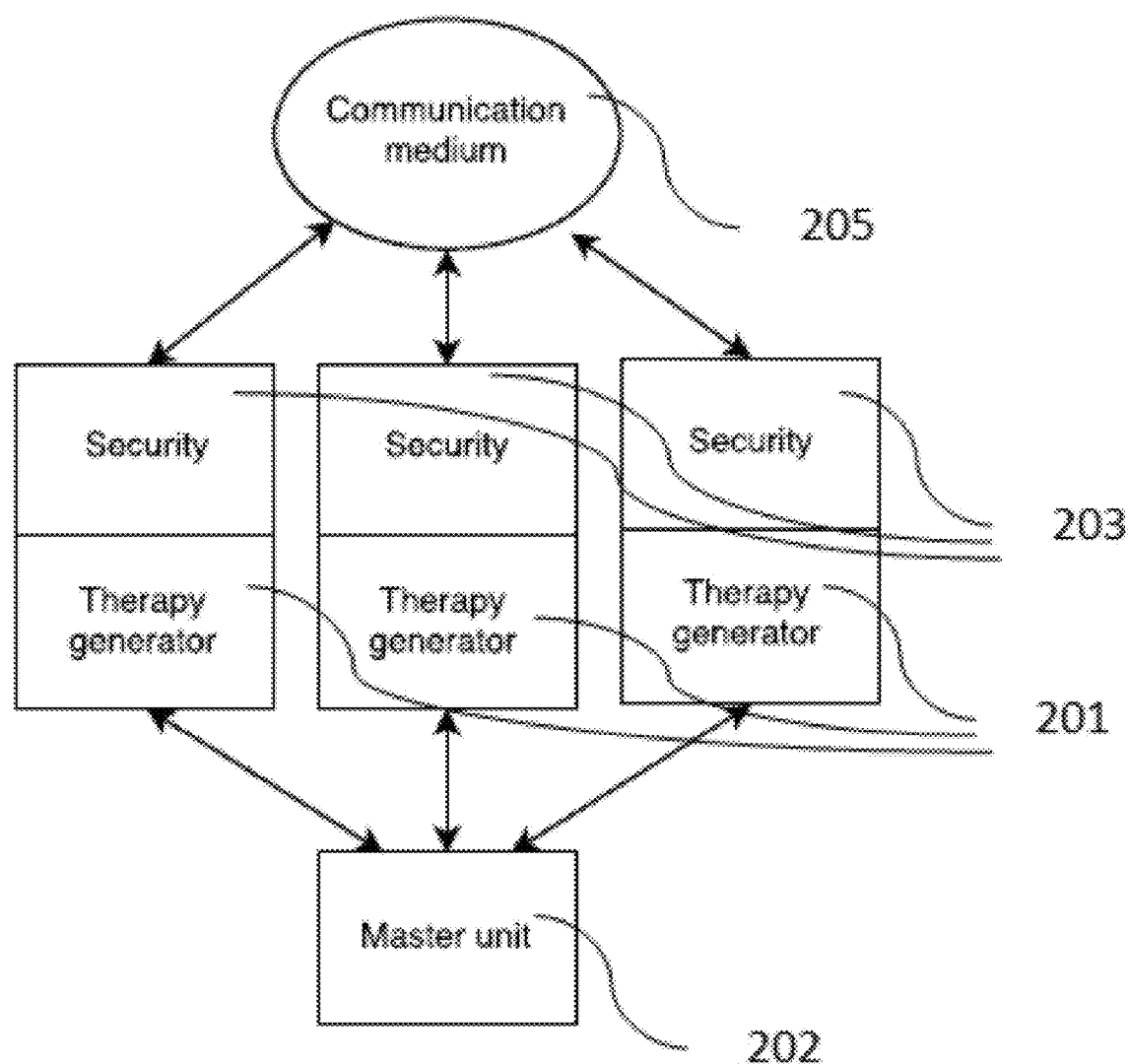
FIG. 4 illustrates an exemplary communication diagram between a communication medium, a therapy generator and a master unit of the treatment device.

As shown in FIG. 4, the communication medium 205 may communicate with one or more therapy generators 201. One or more therapy generator 201 may communicate with the master unit 202. The information from the communication medium 205 may be verified by the security 203 before the therapy generator 201 sends information to the master unit 202.

Figure 5:
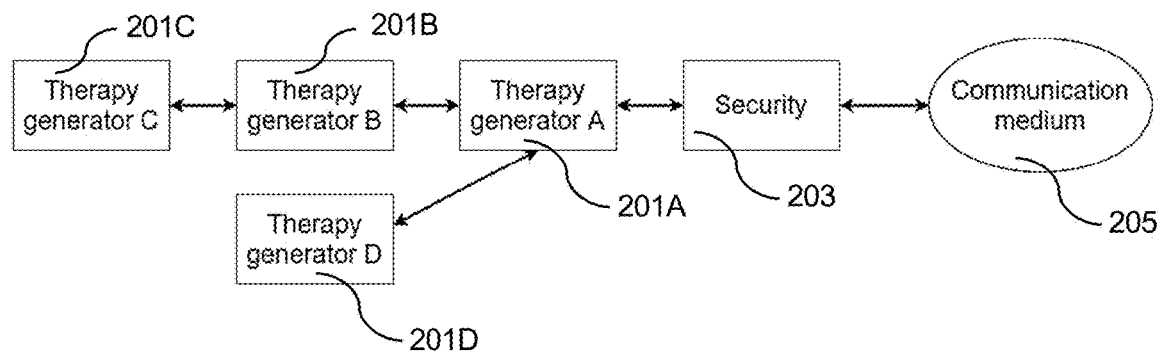
FIG. 5 illustrates a communication between a communication medium and a therapy generator of the treatment device.

FIG. 5 shows a schematic diagram of communication between the communication medium 205 and one or more therapy generators 201A-201D. The therapy generator A 201A may communicate with at least one or more therapy generator 201B-201D. Another therapy generator B 201B may also communicate with one or more therapy generators 201A, 201C, 201D. Therapy generator C 201C may not directly communicate with the therapy generator A 201A and may communicate through therapy generator B 201B. The security 203 may be in the communication pathway between each therapy generator 201A-201D and/or between the therapy generator 201A and the communication medium 205.

Figure 6:
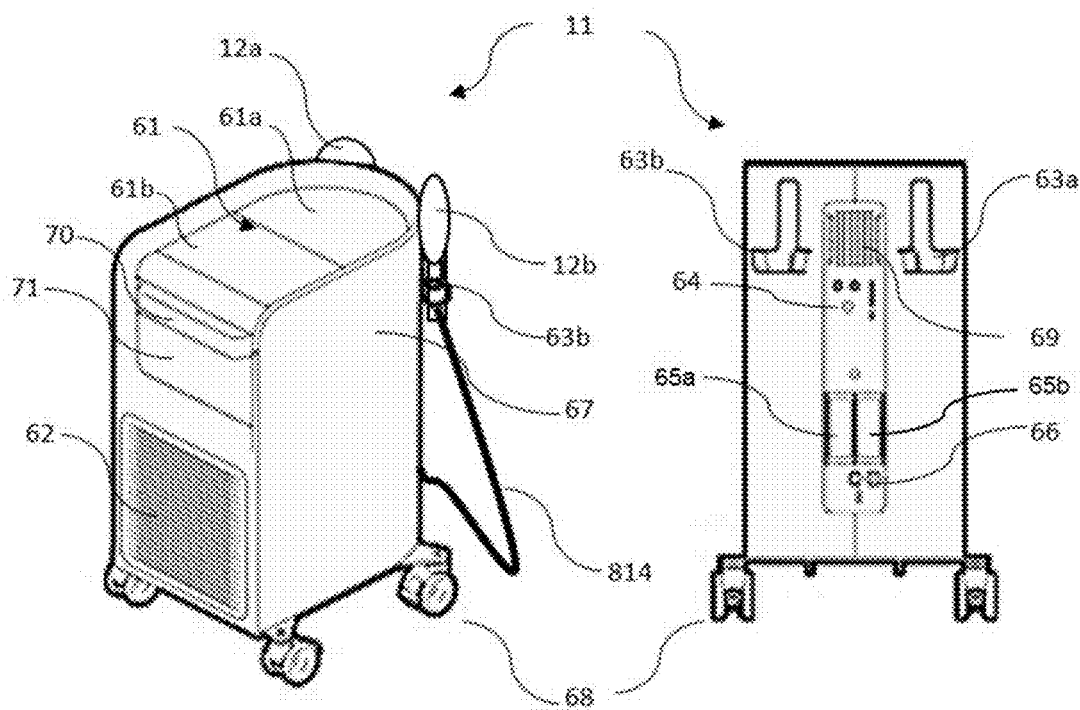
FIG. 6 illustrates different views of an exemplary main unit of the treatment device.

FIG. 6 show the main unit 11 of the treatment device. The main unit 11 may include a HMI 61, a ventilator grid 62, at least one applicator holders 63a and 63b, at least one device control 64, applicator connectors 65a and 65b, at least one main power supply input 66, a curved cover 67 of the main unit 11, wheels 68, a main unit cover opening 69, a main unit handle 70, and/or a logo area 71. The main power supply input 66 may provide coupling or connection to the power grid or power network.

The ventilator grid 62 of the treatment device may be designed as one piece and/or may be divided into multiple ventilator grids 62 to provide heat dissipation. The ventilator grid 62 may be facing toward a person operating the main unit 11, facing the floor and not being visible and/or ventilator grid 62 may be on the sides of the main unit 11. The floor-facing location of the ventilator grid may be used to minimize disturbing noise for the patient, because processes like cooling of the main unit 11 and/or electrical elements powered by electric energy may produce noise. Surface area of all ventilator grids 62 on the surface of the main unit 11 may be in a range from 100 cm$^2$ to 15000 cm$^2$, or from 200 cm$^2$ to 1000 cm$^2$, or from 300 cm$^2$ to 800 cm$^2$.

Manipulation with the main unit 11 may be provided by rotating wheels 68 on the bottom of the main unit 11 and/or by the main unit handle 70. The logo area 71 of the company providing the treatment device may be located below the main unit handle 70 and/or anywhere on the curved cover 67 and HMI 61.

As shown in FIG. 6, the front side of the main unit 11 facing the patient may be designed as a curved cover 67 of the main unit. The front side of the main unit 11 facing the patient may have no right angles according to floor projection of the main unit 11. The front side of the main unit 11 facing the patient may be designed as one, two or more pieces covering the inside of the main unit 11. The main unit 11 with curved facing side may improve manipulation of the main unit 11 itself nearby patient's support wherein the risk of collision main unit 11 and various sensitive body parts of the patient (e.g. fingers) is minimized. Facing side of the main unit 11 may also include the main unit cover opening 69. The main unit cover opening 69 may include a thermal camera for monitoring the temperature of the patient or treated body area, a camera for monitoring the location of one or more applicators, movement of the patient and/or other. The main unit cover opening 69 may be represented by opening in the curved cover 67 of the main unit. The main unit cover opening 69 may include one or more connectors for connecting additional treatment devices. Further, the main unit cover opening 69 may include one or more sensors, such as camera, infrared sensor to scan patient's movement, heating of treated body area and/or biological structure. Based on information from such sensors, actual value and/or predetermined value of one or more treatment parameters may be optimized when patient moves, skin surface reach temperature threshold limit, determine treated body area and/or other. The front side of the main unit 11 may also include one or more applicator connectors 65a and/or 65b.

Applicator connectors 65a and 65b facing the patient may be closer to patient's body than applicators connected to side facing the operator (e.g. doctor or technician). Accordingly the length of the connecting tube 814 connecting the applicator with the main unit 11 may be minimized. Manipulation with the applicator and/or plurality of the applicators connected by shorter connecting tubes 814 may be easier than with the applicator connected with the longer connecting tube 814. The front side of the main unit 11 may have no corners and/or angles and may include at least partially elliptical and/or circular curvature. The curvature may have a radius of curvature in a range of 20 cm to 150 cm, 30 cm to 100 cm, 30 cm to 70 cm, or 40 to 60 cm, An angle of the main unit 11 front side curvature may be in a range of 30° to 200°, or of 50° to 180°, or of 90° to 180°. The angle of the curvature may be defined with the same principle as it is defined an angle 30 of a section 26 in FIG. 23 as discussed in further detail below.

The main unit 11 may include one or more an applicator holder e.g. 63a and 63b. Alternatively, one or more applicator holders may be coupled to the main unit 11. Each applicator holder 63a and 63b may have specific design for different types of the applicator. The applicator holder 63a and 63b may each hold a single applicator 12a or 12b. Each applicator holder 63a, 63b may have several functions. For example, the applicator holders 63a and 63b may be used for pre-heating or pre-cooling of at least part of the applicator. Further, the applicator holders 63a and 63b may include another HMI and be used for displaying information about selected treatment, actual value and/or predetermined value of one or more treatment parameters. Also, the applicator holder 63a and/or 63b may provide indication whether an applicator is ready to use. Furthermore, the applicator holder 63a and/or 63b may indicate a current value temperature of at least part of the applicator. The indication may be provided by color flashing or vibration. The applicator holder 63a and/or 63b may be used to set actual value and/or predetermined value of one or more treatment parameters and/or applicator parameters, such as a temperature of applicator's part contacting the patient.

The main unit 11 may include device control 64 for switching on and off the main unit 11, manual setting of power input parameters and/or other functions. The applicator connectors 65a and 65b may be used for transfer of electrical and/or electromagnetic signal from the main unit 11 and applicators. The applicator connectors 65a and 65b may be used for connecting of one or more applicators (via the connecting tube 814), the communication device, the additional treatment device and/or memory storage devices such as USB, SSD disc, diagnostic devices, and/or other memory storage devices known in the state of art. The applicator connectors 65 (e.g. 65a and/or 65b) for connecting of one, two or more applicators may be located in the main unit 11 or on the side of the main unit 11. The length of coaxial cables may be linked with a frequency of transmitted electrical signal. In order to provide easier manipulation with one or more applicators 12a and/or 12b, the length of connection from the main unit 11 to e.g. applicator 12a (and therefore connecting tube 814) should be as long as possible. However, length of at least one coaxial cable between electrical elements in the main unit 11 may be linked with a frequency of transmitted electrical signal (e.g. RF signal) sent to at least treatment energy source (e.g. RF electrode to provide RF energy). Therefore the length of at least one coaxial cable inside the main unit (e.g. between a power source and the applicator connector 65a and/or 65b) may be as short as possible. The length of coaxial cable located in the main unit 11 may be in a range of 3 cm to 40 cm, or 7 cm to 30 cm, or 10 cm to 20 cm. In order to optimize manipulation with one or more applicators 12a or 12b connected to the main unit 11, the applicator connectors 65a and 65b may be located on the curved front side of the main unit 11.

The HMI 61 may include a touch screen display showing actual value and/or predetermined value of one or more treatment parameters. The touch screen may provide option to choose the displayed treatment parameters and/or adjust them. The HMI 61 may be divided into two display sections 61a and selection section 61b. The display section 61a may display actual value and/or predetermined value of one or more treatment parameters and other information for the user. The selection section 61b of the HMI 61 may be used for selection of treatment parameters and/or other adjustment of the treatment. HMI may be included in, coupled to or be part of one or more applicators 12, main unit 11, an additional treatment device 14 and/or in other one or more communication devices 15.

The HMI may be included in the main unit 11. The HMI may be fixed in a horizontal orientation on the main unit 11 or the HMI 61 may be oriented or tilted between 0° to 90° degrees with respect to a floor or other horizontal support surface. The angle between the HMI 61 plane and a floor may be adjusted by at least one joint or may be rotated around at least one Cartesian coordinates. The HMI 61 may be in form of detachable HMI, e.g. a tablet. The HMI 61 may be telescopically and/or rotationally adjusted according to one two or three Cartesian coordinates by a holder that may adjust distance of HMI 61 from the main unit 11 and/or orientation of the HMI 61 with regard to the main unit 11 and the user. The holder may include at least one, two or three implemented joint members.

One HMI 61 may be used for more than one type of the treatment device provided by the provider. The HMI software interface may be part of the main unit software or part of the software included in one or more additional treatment devices and/or communication devices. The software interface may be downloaded and/or actualized by connection with the communication device, the additional treatment device, flash memory device, the remote connection with sales, the service and/or the internet.

Figure 26:
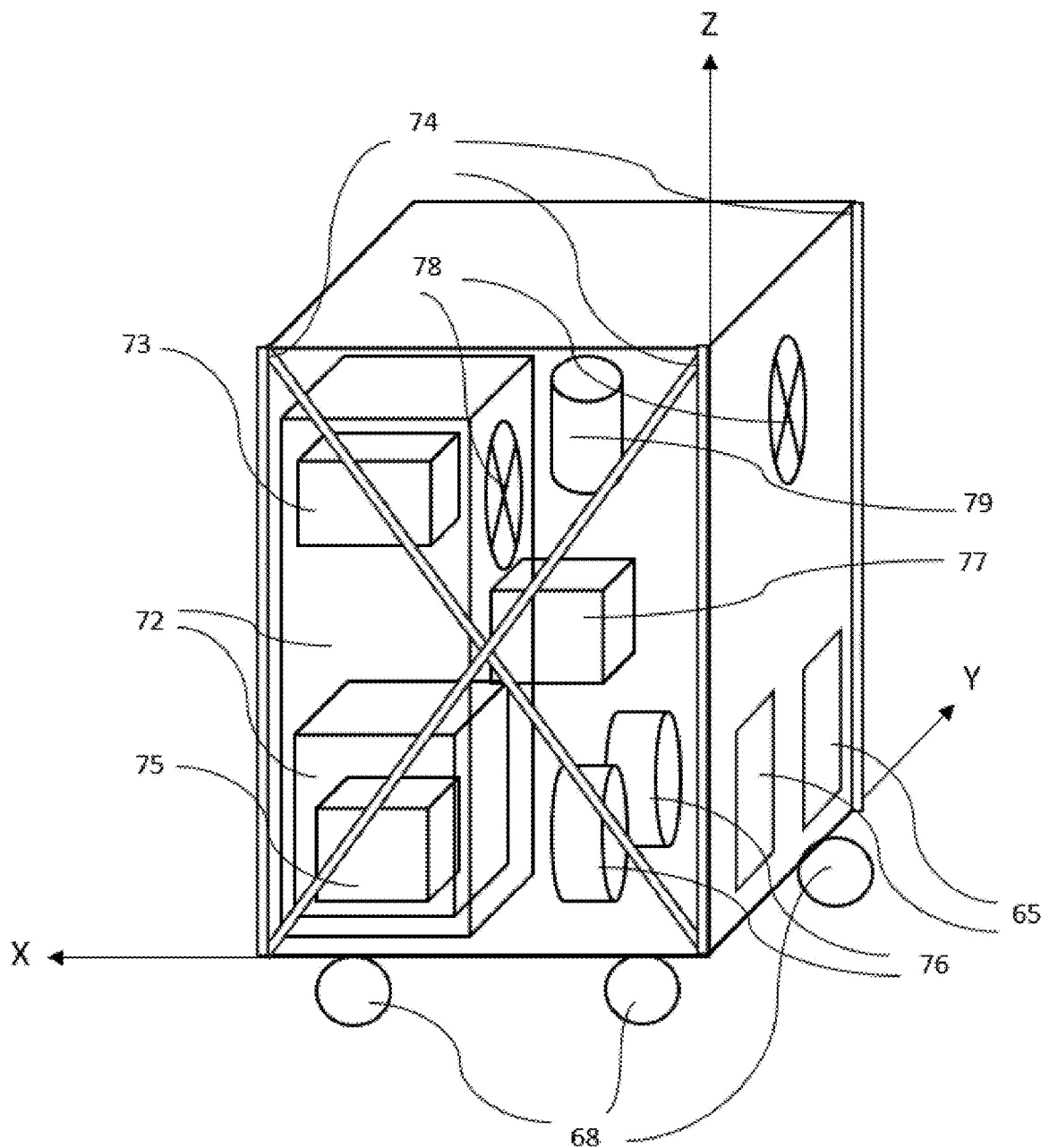
FIG. 26 illustrates an exemplary spatial arrangement of components within a main unit of a treatment device.

FIG. 26 shows exemplary layout of the interior of the main unit 11. The interior of the main unit 11 may include multiple electrical elements, control system, one or more control units of RF circuits, magnet circuits and/or other elements needed for correct function of the treatment device. Location of individual elements in the main unit 11 may be described by Cartesian coordinates with the zero values at the bottom edge of the front side facing the patient. The main unit 11 may include one or more struts 74. At least two struts 74 may create an X-shape that may be fixed at its ends to other vertical struts 74 to create construction for the main unit 11. The main unit 11 may include at least one cooling system 78 configured to cool electrical element such as one or more control units, PCBs, power sources, switches, energy storage devices and/or other electrical element of the treatment device. The cooling system 78 may be used for providing and/or cooling the cooling fluid provided to the applicator. The SYM element 79 may be located in the upper third of Z coordinate and at the first third of the X coordinate nonmatter of Y coordinate. Function of the SYM is explained below. The main unit 11 may also include one or more cases 72 formed from aluminium or other metal materials. The one or more cases 72 may provide electrical, electromagnetic and/or radiation insulation (later only as insulation) of one or more internal parts of the main unit 11 from other part of the main unit 11. For example, at least part of a RF circuit 73 may be located in the last third of X and Z coordinates in one of the cases. The power source 75, powering at least part of RF circuit and/or magnet circuit, may be located in the last third of X coordinate and in the first third of Z coordinate. An energy storage device 76 may be at least partially insulated from one or more RF circuit. When plurality of magnetic circuits is used, the plurality of magnet circuits may be at least partially insulated from each. In order to ensure short length of coaxial cable leading from the energy storage device 76 to applicator connector 65 as mentioned earlier, both elements (energy storage device 76 and applicator connector 65, e.g. 65a) may be located in the same half of the X and Z coordinate, such as at the first half of X and Z coordinate. Other electrical elements represented by box 77 of magnet circuit may be located in the first half of X coordinate and second third of Z coordinate.

Figure 7:
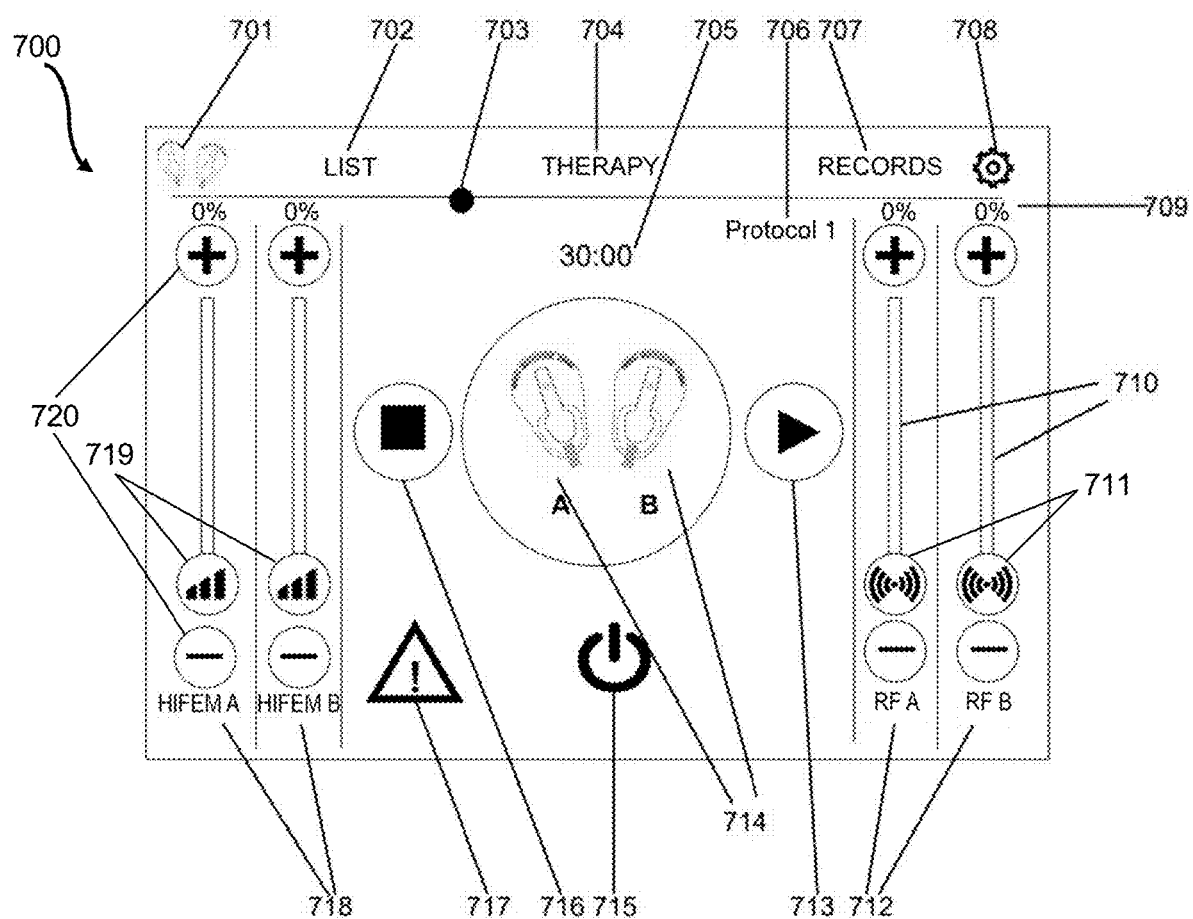
FIG. 7 illustrates an exemplary human machine interface (HMI).

FIG. 7 shows exemplary display interface 700 of the HMI 61. The HMI 61 may display one or more applicator symbols 701. One or more applicator symbols 701 and their colors may represent connection quality, number and/or type of available or connected applicators, additional treatment devices connected to the main unit 11 and/or involved in the treatment. The list 702 may redirect to a page or different display layout where a list of treatment protocols may be recorded or adjusted. The list 702 of treatment protocols may include one or more predetermined values of at one or more treatment parameter (e.g., intensity of magnetic field, intensity of RF field, intensity of magnetic impulses, intensity of magnetic pulses, pulse duration, burst duration, composition of individual burst, duty cycles, shape of envelope, time of treatment, composition of treatment parts, threshold temperature of the biological structure during the treatment, and/or other parameters). The list of treatment parameters may include one or more saved treatment protocols optimized for individual patients or body area. After choosing the treatment protocol, treatment parameters may be additionally optimized by user. Also, the treatment parameters may be adjusted by choosing additional patient's parameters, such as patient body type (e.g. skinny, slim, average weight, overweight, or obese), or a patient's BMI, gender, age group (e.g., younger than 30, 30-39, 40-49, 50-59, 60 and older). Also, the treatment parameters may be additionally optimized by selecting only of a part of treatment protocol.

The HMI 61 may include one or more sliders which may have several functions. For example, the slider 703 may be used as a navigator for selecting which page of the interface is being used, such as the list 702, a therapy icon 704, or a records 707. Also, the slider 703 may be used to indicate how much time is remaining to the end of the treatment.

The therapy icon 704 may represent the interface illustrated in FIG. 7. A timer 705 may represent treatment duration, remaining time of the treatment, and/or lapsed time of the treatment. The "Protocol 1" icon 706 may illustrate the type of number of a protocol selected and/or currently applied or prepared to be applied. The "records" 707 may redirect to another page of the interface with recorded history of treatments, information regarding treated patients, information regarding billing and renting system, information regarding billing information and/or credit cost of the treatment. The "records" 707 may display how many credits are left on the credit account, how many credits were spent, how long the treatment device was used, and/or other billing information. An icon illustrated by a symbol "setting" 708 may redirect user to a setting of the treatment device including the setting of e.g. a melody and/or intensity of the sound produced by the device and/or brightness of the display. The sound produced by the treatment device and/or brightness of the display may be different before and/or during the treatment. The "settings 708" interface may also enable to change date, time, language, type and/or parameters of connection between the main unit and the applicator, the additional treatment device, and/or the communication device. The "setting" 708 interface may include icons for starting a calibration and functionality scan of the treatment device and its connected parts. The "setting" 708 interface may provide software information, software history and/or software actualization, a button for contacting service and/or sending error protocol, type of operation mode (e.g. "basic" or "expert" with allowed additional setting of the treatment device), possibility to recharge credits for treatments, restoring to factory setting, and/or other settings.

Intensity signs 709 may be as illustrated in the form of percentile, number, power and/or in another format. The intensity signs 709 may be located adjacent to an icon that may adjust intensity of the treatment energy source. The intensity signs 709 may be located under, over and/or in an icon (e.g. as a number in an intensity bar 710) and/or as another visualization that may adjust the intensity of the treatment energy source. Each intensity bar 710 representing one treatment energy source of provided energy (e.g. RF field or magnetic field) may have its own intensity signs 709. The treatment device may include multiple applicators 714, for example, a first applicator A and a second applicator B may be connected to the main unit of the treatment device. In this way, applicators A and B may be applied to different muscles in the same muscle group or to pair muscles, such as a left and right buttock, left and right sides of an abdomen, a left and right thigh, among other paired muscles or cooperating muscles. Number of connected applicators and/or additional treatment devices providing the treatment energy may be lower or higher than two.

As shown in FIG. 7, each applicator may provide magnetic treatment 718 (left HMI part marked as HIFEM A and HIFEM B for the purpose of FIG. 7 and showed in exemplary interface human machine interface) and/or an RF treatment 712 (right HMI part marked as RF A and RF B for the purpose of FIG. 7 and showed in exemplary HMI).

The intensity of each RF field and/or magnetic field may be independently regulated e.g. by scrolling of individual magnetic intensity scroller 719 and/or RF intensity scroller 711 through intensity bars 710. One or more scrollers or intensity bars may be moved independently or may be moved together with another scroller or intensity bar in order to regulate plurality of magnetic fields, plurality of RF fields together and/or plurality of RF and magnetic fields provided by the one applicator together. Also, one or more scrollers or intensity bars may be controlled independently or may be moved together with another scroller or intensity bar in order to regulated plurality of magnetic fields, plurality of RF fields together and/or plurality of RF and magnetic fields provided by two applicators together. One or more intensity bars 710 may be distinguished by a color and may be adjusted by intensity scroller 719 or 711 and/or by an intensity buttons 720. The intensity buttons 720 may change (e.g. increase or decrease) RF field and/or magnetic field intensity by a fixed increment, such as 1% or 2% or 5% or 10% or in a range from 1% to 10% or in a range from 1% to 5% of maximal possible field intensity. Intensity of the magnetic field and/or the RF field may be adjusted independently for each treatment energy source. Also, intensity of the magnetic field and/or RF field may be adjusted by selection and/or connection of one or more applicators, additional treatment devices and/or treatment energy sources.

The operation of one or more RF electrodes and/or magnetic field generating devices may be synchronized and may be controlled by one, two or more intensity scrollers 719 and/or intensity buttons 720. The treatment may be started by a button start 713 that may be automatically (e.g. after starting the treatment) changed into a button pause. The treatment may be restarted and/or stopped by button stop 716 during the treatment. The interface may also show an indicator of a discomfort button 717 that may be activated by patient through a remote control when the treatment is uncomfortable. When the discomfort button 717 is activated treatment may be automatically and immediately interrupted (e.g. paused or stopped). When the discomfort button 717 is activated the treatment device may provide an human perceptible signal including an audible alert, including a sound signal. Further, the human perceptible signal may include a visual alert, including e.g. a flashing color. Based on the discomfort of the patient, the user may adjust e.g. the treatment parameters or treatment protocol, attachment or coupling of the applicator. The interface may also include a software power switch 715 to switch the treatment device on or off.

As shown in FIG. 7, the HMI may include two intensity bars (e.g. 710) for RF treatment and two intensity bars for magnetic treatment. Further, the HMI may include two intensity scrollers (e.g. 711) for RF treatment and two intensity bars (e.g. 719) for magnetic treatment. Furthermore, the HMI may include four intensity buttons for RF treatment and four intensity buttons (e.g. 720 for magnetic treatment. One intensity scroller, one intensity bar and/or two intensity buttons may be provided for one treatment circuit. Therefore, the FIG. 7 may show the HMI of treatment device including two treatment circuits for RF treatment and two treatment circuits for magnetic treatment.

The treatment device may include one or more applicators. The treatment device may include two, three, four, five or more applicators. Each applicator may include at least one, two or more different treatment energy sources, such as one or more RF electrodes providing the RF treatment and one or more magnetic field generating devices providing the magnetic treatment. For example, first applicator may include one RF electrode and one magnetic field generating device, while the second applicator may include another RF electrode and another magnetic field generating device. One applicator may be coupled to the main unit by one connecting tube. The connecting tubes of different applicator may be interconnected or separated for each applicator. Alternatively a plurality of applicators may be coupled to the main unit by one common connecting tube. At least one treatment parameter of at least one applicator may be changed independently from the other one or more applicators and/or additional treatment device.

One or more applicators, additional treatment devices and/or communication devices may be mechanically connected with the main unit by one or more wires and/or by the fluid conduits. One or more wires and/or fluid conduits may be located and lead through the connecting tube. The one or more wires coupled between main unit and the applicator may be used for transfer of electric signal (representing e.g. RF signal) to RF electrode positioned in an applicator in order to generate RF energy. The one or more wires may be used for providing electric current to magnetic field generating device positioned in the applicator in order to generate impulses of the magnetic field. Same wire and/or different wires coupling the applicator and the main unit 11 may be used for communication between the main unit 11 and the applicator 12 and/or for collecting feedback information. Feedback application may include e.g. measured signal parameters and/or impedimetric characteristics of the wire before and/or during the treatment. The fluid conduit between the main unit 11 and the applicator 12 may guide liquid, oil, water, vapors, gas and/or other temperature regulating cooling fluid.

One or more applicators may be coupled to patient's body and/or body area by one or more straps, one or more belts, or by creating vacuum under the applicator. Also, applicator may be coupled to the body area by a supporting matrix or by an adhesive layer located on at least part of the applicator's surface and contacting the patient's body or clothing. The applicator may be coupled to the body area by pushing the applicator to patient's body area or clothing by an adjustable mechanical positioning arm wherein the applicator may be detachably coupled to positioning arm including at least one, two or more joints. The belt may be at least partially elastic and may create a closed loop, such as by hook and loop fasteners (by Velcro), buckles, studs, and/or other fastening mechanisms may be used for adjusting a length. The belt may be coupled to body area and may include a fastening mechanism for coupling the applicator to the belt and/or patient's skin or clothing. Such fastening mechanism may be for example, a belt with pockets for the applicator. Coupling the applicator to the body area may include attaching or positioning of the applicator to the proximity or to the contact with the body area. One or more applicators may be coupled to the body area before or during the application of one or more types of treatment, (e.g. RF treatment or magnetic treatment). Also, the applicator may be coupled to the body area, skin or clothing by a cover from soft material, which may be folded around the applicator and/or the part of the body area. Furthermore, the applicator may be covered in soft material cover providing other coupling points for attachment of belt, folding soft material or any other coupling option mentioned herein.

The belt may be a length adjustable belt which may be at least partially flexible. One or more belts may couple or fix and/or attach one, two or more applicators to the patient's body or body area. The belt may be coupled to one applicator 800 or one belt may couple two or more applicators to the patient's body. When the plurality of applicators (e.g. two, three or more) are used, one applicator may be coupled to the body area of the patient by one belt while another applicator may be coupled to the body area by different belt. Alternatively, a plurality of applicators (e.g. two, three or more) may be coupled to the body area of the patient by one same belt. At least one applicator coupled by the belt may be fixed statically with regard to patient's body for at least part of the treatment. The at least one applicator that is coupled by the belt to patient's body may be repositioned once or more times during the treatment either manually by the operator or automatically to ensure optimal treatment effect and treatment comfort for the patient.

Coupling the applicator and/or additional treatment device to a patient's body may include placing the applicator in proximity of the patient's body and/or body area. In case of proximate coupling, the shortest distance between the applicator and the patient's skin may be in a range of 0.01 cm to 10 cm, or 0.01 cm to 5 cm, or 0.01 to 2 cm, or 0.01 to 1 cm, or 0.01 to 5 mm, or 0.01 to 2 mm. However, the applicator may be also placed in direct contact with the patient's skin. In case of direct contact, there may be no meaningful distance between the application and the patient's skin. In case of proximate or direct contact, the intervening material may be positioned between the applicator and patient's skin or clothing or body area. The intervening material may be an air gap, bolus, supporting matrix, part of the belt, textile, other clothing, gel, liquid absorbing material or metal.

Figure 22:
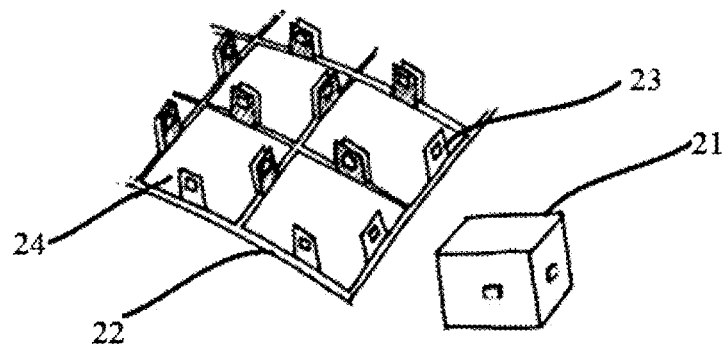
FIG. 22 illustrates a supporting matrix for attaching of an applicator and/or an additional treatment device to a patient's body.

FIG. 22 depicts an exemplary attachment of the applicator and/or additionally treatment device 21 to a patient's body with use of a supporting matrix 22. The supporting matrix 22, as illustrated in FIG. 22, may be shaped as a grid and/or scaffold. The grid and/or scaffold is at least partially flexible and attached to patient's body. The supporting matrix may be used for coupling the applicator and/or additional treatment device 21 in proximity to the patient's body in defined location referred as an applicator's spot 24 by a fastening member 23. The supporting matrix may be polymeric scaffold-like in FIG. 22, substrate like a textile/polymeric sheet and or other. The fastening member may be one or more elements such a locking mechanism, hinge, bayonet like system, Velcro for fastening the applicator and/or additional treatment device 21.

Figure 24:
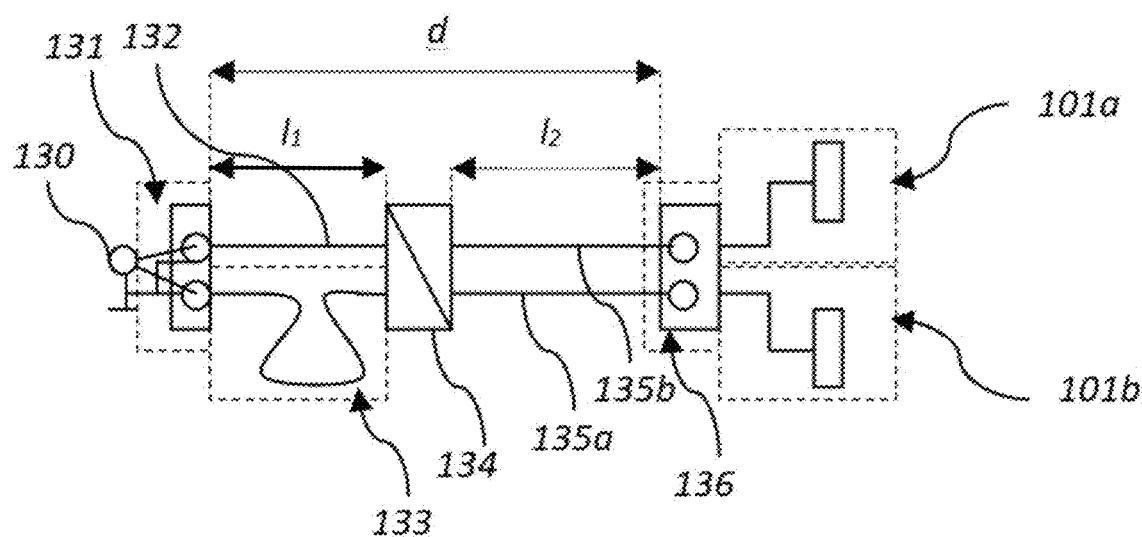
FIG. 24 illustrates an exemplary symmetrisation element SYM.
Figure 25:
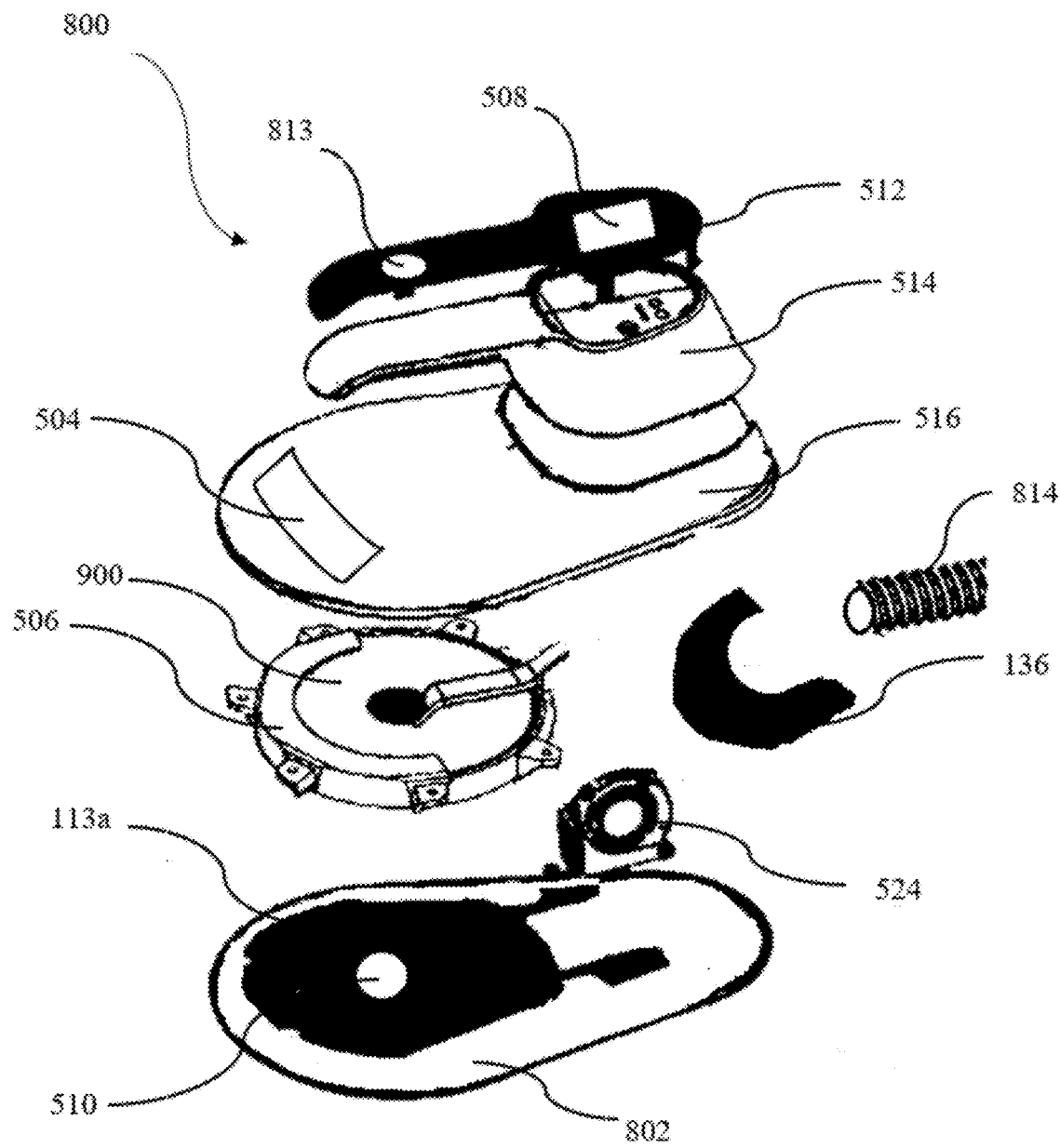
FIG. 25 illustrates an exploded view of applicator elements.

As shown in FIG. 25, the applicator 800 may include one or more parts defining casing of the applicator, which can be connected to the main unit by connecting tube 814. Also, the applicator may include one or more parts hidden in the applicator further defining function and functionality of the applicator. Casing of the applicator may include different parts e.g. a handle cover 512, a handle 514, a top cover 516, a second side portion 802 creating bottom cover of the applicator. Handle cover 512 may include a marker 813 and/or HMI 508 for e.g. displaying and/or adjusting actual value and/or predetermined value of one or more treatment parameters. The handle 514 may be used for manipulation with the applicator 800 and/or for coupling the applicator 800 to patient's body area. The top cover 516 may define interior of the applicator. The top cover 516 may include an air opening 504 enabling air flowing to or from the interior of the applicator to cool electrical elements located in the interior of the applicator. The electrical elements located inside the interior of the applicator may include e.g. RF electrode, magnetic field generating device and/or temperature sensor 510. The second side portion 802 creates a bottom cover of the applicator. The second side portion 802 may include one or more protruding shapes, grooves and/or other. Power, energy, one or more electromagnetic signal and/or cooling fluid may be delivered to applicator via connecting tube 814. In addition, cooling of one or more electrically powered element in the applicator (e.g. a magnetic field generating device 900 and/or substrate 113*a* with at least one RF electrode) may be provided by a fan 524 fixed to the top cover 516 and/or to the second side portion 802. The RF electrode substrate 113*a* may include a temperature sensor 510 configured to determine a temperature in the applicator, of at least part of bottom cover 517, of a body area and/or of a biological structure of a patient. The RF electrode located on the substrate may be connected to pairing element 136 reconnecting coaxial cables. The pairing element 136 is further described with regard to the FIG. 24. FIG. 25 also illustrates a frame 506 that may be used to fix the magnetic field generating device to the top cover 516 and/or to the second side portion 802. The frame 506 may be configured to eliminate noises and vibrations during magnet treatment.

The applicator may be designed as shown in exemplary FIGS. 8a-8d. The applicator 800 as illustrated in FIGS. 8a-8d may be used for treatment of body area.

One or more RF electrodes may be located in the applicator 800 between the magnetic field generating device and patient's body area. The RF electrode may be shaped to at least partially match a curvature of the first side portion 801, a second side portion 802, and/or a curvature of the patient's body area. The magnetic field generating device may at least partially match a curvature of the first side portion 801, the second side portion 802 and/or a curvature of the patient's body area. The RF electrode and/or the magnetic field generating device may be curved in order to focus and/or provide better targeting of the RF treatment and/or magnetic treatment. The first side portion 801 may be configured to maintain the position of the limb within the first side portion 801 during the treatment. The first side portion 801 may provide a stable position and/or equilibrium for the treated body area. The position of the limb of the patient may be maintained in the first side portion 801 even though the limb may move by the muscle contractions. The lateral movement and/or rotation of a limb may be limited due to the first side portion 801 and/or belt 817 in such way that the limb may be in stable position. The rotational movement with respect to the applicator 800 may be limited by coupling the applicator 800 to the body area, at least part the treated body limb by a belt. In addition, when part of the arm is treated by magnetic and/or RF treatment, at least part of the limb may be also attached to patient's trunk to minimize movement of the limb.

The second side portion 802 may be located on the opposite side of the applicator 800 with respect to the first side portion 801. The second side portion 802 may be substantially planar, or the second side portion 802 may be at least partially concave and/or convex. The applicator 800 may be coupled to the patient by a positioning mechanism, such as a belt 817, as it is illustrated in the FIGS. 8a and 8b.

Figure 8A:
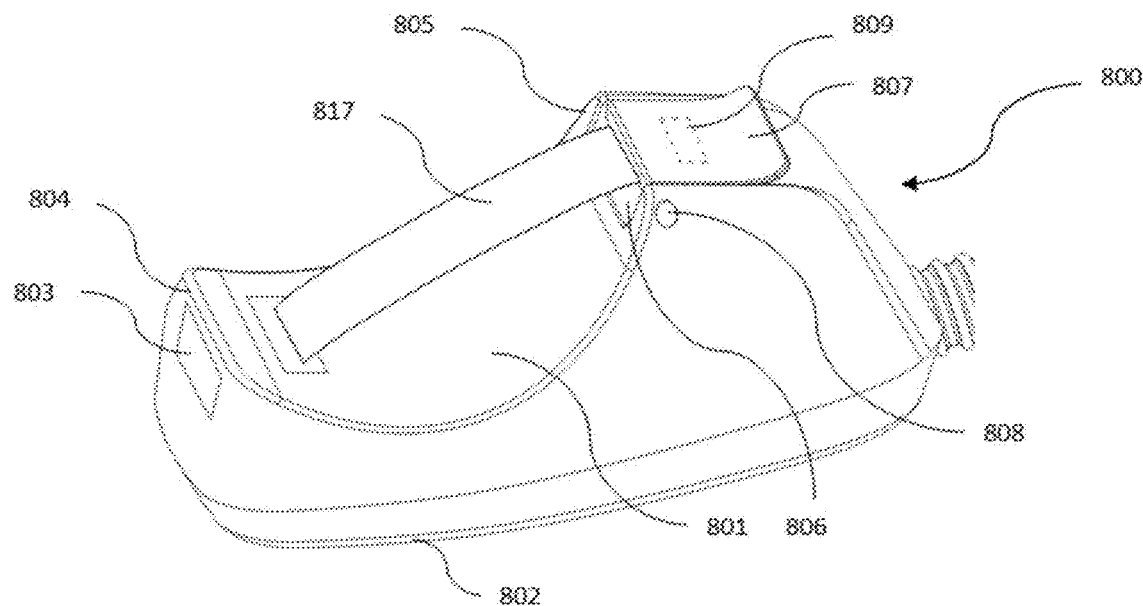
FIGS. 8a-8d illustrate parts of an exemplary applicator from the outer view.

FIG. 8a describes an applicator including the positioning mechanism which may be fixed in a recess 803 at a first end 804 of the first side portion 801 and a recess 806 at a second end 805 of the first side portion 801. The positioning mechanism, such as a belt or strap, may be fastened or its length may be adjusted by a clip 807. The clip 807 may move around the pin 808 in a clockwise or counter-clockwise direction. The clip 807 may be biased by a spring. Alternatively, the clip 807 may be locked by a suitable locking mechanism, or by any other movement restraining manner. The clip 807 may include a fastener 809 on lower side of the clip 807 for fixing a correct length of the positioning mechanism. The fastener 809 may be a hook-and-loop fastener, Velcro fastener, pin type fastener, among other mechanical fasteners. Coupling the applicator 800 to the patient's body as described above may be mostly used when the patient's body area is attached to the first side portion 801 of the applicator 800. The RF electrode and/or magnetic field generating device may be shaped to at least partially match a curvature of the first side portion 801. The RF electrode and/or the magnetic field generating device may be curved in order to focus and/or provide better targeting of the RF treatment and/or magnetic treatment.

Figure 8B:
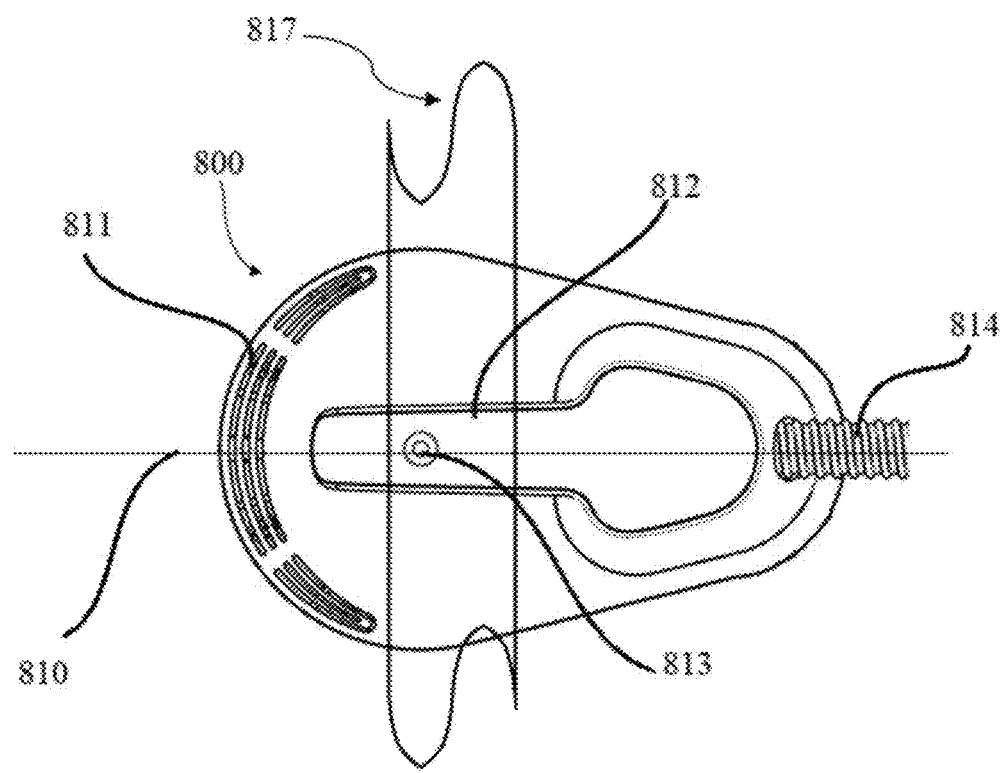
Figure 8C:
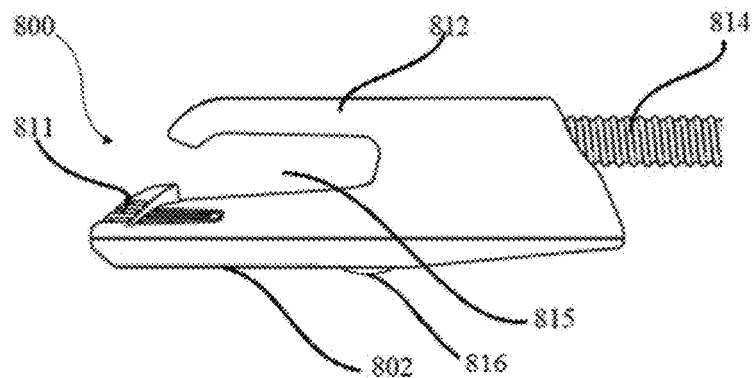

FIGS. 8b and 8c show an applicator including the positioning mechanism which may be guided perpendicularly to a curvature of the first side portion 801 and/or perpendicularly to an axis 810 of the applicator. The positioning mechanism may be positioned or guided through a concavity 815 of the handle and/or below, through or on a handle 812. Belt 817 may also be guided in any direction through and/or on the applicator 800 to hold the applicator 800 to the patient's skin. Coupling the applicator 800 to the patient's body as described above may be mostly used when the patient's body area is attached to the second side portion 802 of the applicator 800. The RF electrode and/or magnetic field generating device may be shaped to at least partially match the first side portion 801. The RF electrode and/or the magnetic field generating device may be flat or curved in order to focus and/or provide better targeting of the RF treatment and/or magnetic treatment.

FIG. 8b illustrates a top view of an applicator 800. Applicator 800 may include a marker 813 corresponding with the location of magnetic field generating device within the applicator 800. The marker 813 may be located above the centre of the magnetic field generating device. The marker 813 may enable easy and comfortable positioning of the applicator 800 by the user. A recess in a surface of the applicator 800 may be used as the marker 813. Alternatively, the marker 813 may be a different surface modification of a part of the applicator's cover, such as a different color, different roughness, presence of one or one light source (e.g. light emitting diode LED), a specific curvature of the casing of the applicator, logo of the manufacturing or distributing company and/or other. The casing of the applicator may include at least two colors. A first color may be on applicator's casing over the magnetic field generating device to enable correct positioning of the applicator, and the rest of the applicator may have a second color that differs from the first color. The color may be interpreted as a paint reflecting and/or absorbing specific wavelengths of light. Similar to marker 813, applicator may include a second marker to show a location of the at least one RF electrode.

As shown in in FIGS. 8b and 8c, applicator may include an outlet 811. The outlet 811 may enable circulation of the air in the applicator 800 and heat dissipation of heat generated by at one or more magnetic field generating devices and/or RF electrodes positioned in applicator and supplied by energy through one or more wire inside of a connecting tube 814. The connecting tube 814 may also include the fluid conduit that may provide or guide cooling fluid from the main unit 11 to the applicator 800.

The applicator 800 may further include one or more temperature sensors 816 as shown for example in FIG. 8c. The temperature sensor 816 may protrude from the casing of the applicator 800 e.g. such as from the surface of the second side portion 802 and/or from the first side portion 801. The temperature sensor 816 may protrude from the casing of the applicator 800 in order to create higher pressure to part of the treated body area by the applicator 800 and to provide better measurement of the temperature in the biological structure, of the body area and/or on the patient's body.

The second side portion 802 and/or the first side portion 801 may be heated and/or cooled. Heating of the second side portion 802 and/or the first side portion 801 may be used e.g. at the beginning of the treatment to reach treatment temperature sooner. Treatment temperature may include temperature of body area and/or biological structure increased by application of RF waves which may be appropriate for application of magnetic field. Cooling or heating by portions of the applicator may be used for maintaining constant temperature on the patient's skin. Also, cooling or heating by portions of the applicator may be used to achieve higher treatment temperatures in the patient's biological structure deeper than 0.5 cm under the patient's skin. Cooling a part of an applicator that is in contact with the patient (e.g., the second side portion 802 and/or the first side portion 801 of the applicator) may be used for minimizing a patient's sweating. The patient's skin may be cooled by cooling fluid (e.g. air) flowing and/or blowing from the applicator and/or other part of the treatment device. Cooling of the patient's skin may be provided by thermal diffusion between a cooled part of the applicator contacting patient's skin and the patient's skin. The cooled part of the applicator may be cooled by cooling fluid flowing in the applicator and/or by Peltier element using Peltier's effect.

Figure 8D:
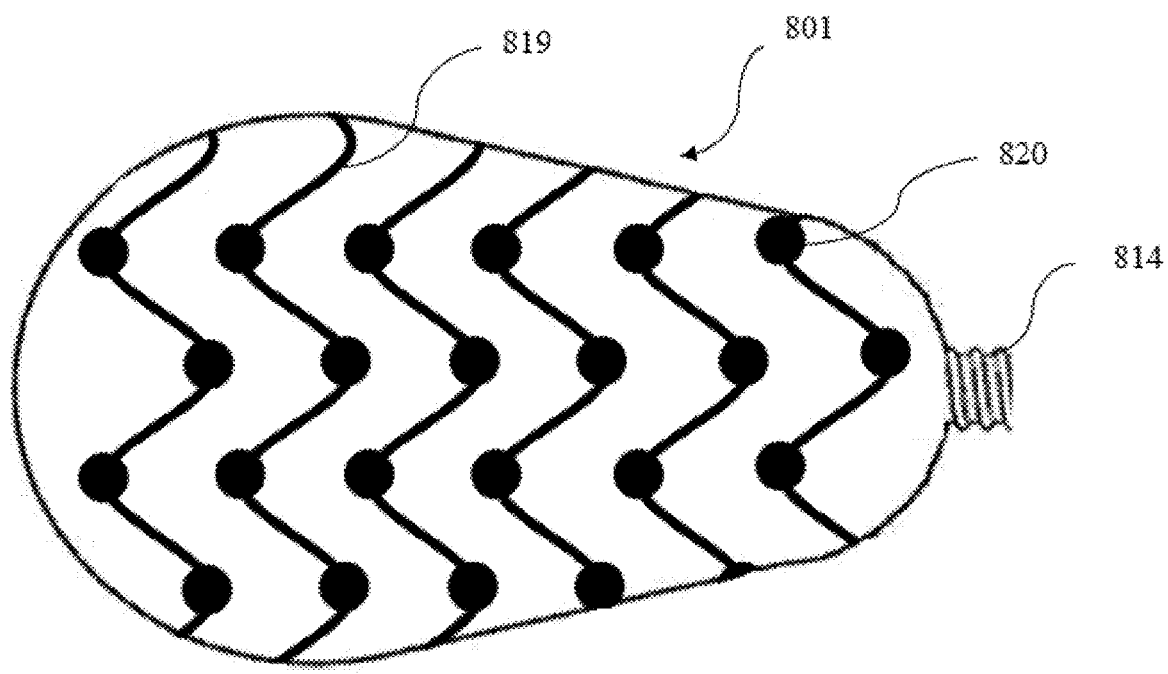

Patient's sweating may be uncomfortable for the patient and may adversely affect feedback information collection, contact with the applicator and patient's skin, and/or lead to lower adhesion of the applicator to the patient's skin. To prevent sweating of the patient's skin, cooling of contact applicator's area (e.g. first side portion 801 and/or second side portion 802) may be used. The second side portion 802 and/or the first side portion 801 may include grooves 819 that may be supplied by cooling fluid through applicator's apertures 820 where liquid and/or gas, (e.g. air, oil or water) may flow as illustrated in FIG. 8d. The first side portion or second side portion of the applicator may include applicator's holes or applicator's apertures 820 where air from the applicator 800 may be guided to remove heat, moisture and/or sweat from the patient's skin. The holes or apertures may be presented in the grooves 819. The holes may be used for providing an active substance on the patient. The contacting part of the applicator being in contact with the body area may include a fluid absorbing material, such as sponge, hydrophilic material, non-woven organic and/or polymeric textile, which may at least partially remove sweat from the patient's skin and/or improve conductivity between the patient and applicator 800. Reduction of patient's sweating in at least part of treated body area may be provided by reduction of sweat gland activity. Reduction of activity of sweat gland may be provided by application of a pulsed magnetic field, intensive light, heat shock provided by periodic hypothermia of patient's skin by applied active substance on and/or to the patient, such as glycopyrronium tosylate, and/or by other mechanisms.

Figure 23:
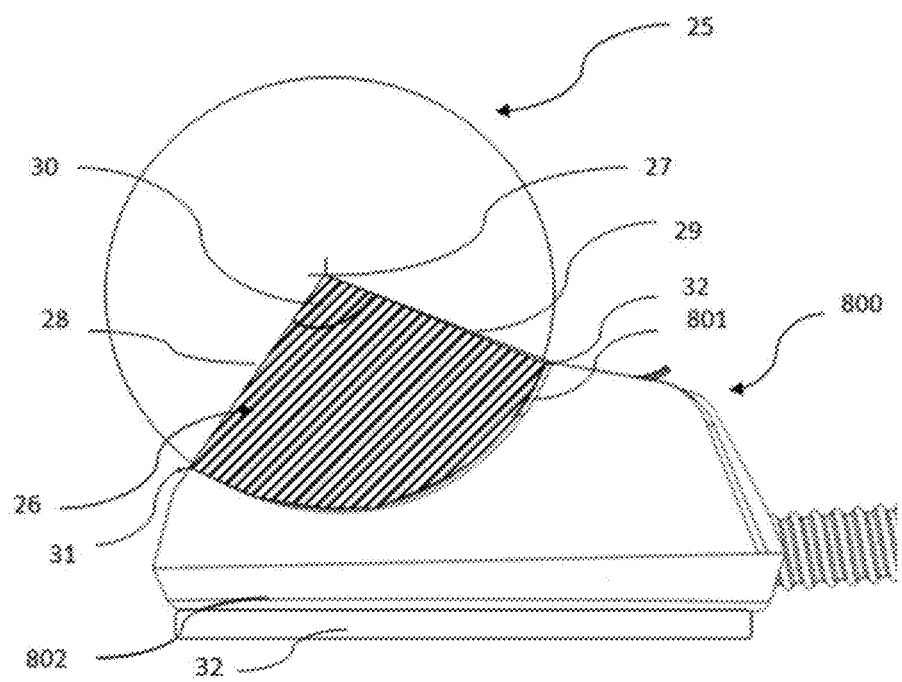
FIG. 23 illustrates a section of exemplary curved applicator's first side portion.

FIG. 23 illustrates an exemplary applicator including a concavity. The applicator may be designed with the first side portion 801 being at least partially convex. The first side portion 801 may alternatively be V-shaped or U-shaped. The curvature radius may correspond with a size of the patient's limb. The second side portion 802 may alternatively or additionally be at least partially convex.

The patient may lay in a supine position or sit on a patient support such as a bed, a couch or a chair. An arm of the patient may be set on the first side portion 801 of the applicator 800. The first side portion 801 may be in direct contact with the patient and RF treatment in combination with magnetic treatment may be applied. Also, a strap or belt may be guided through the concavity 815 to attach the applicator to the patient's body.

The first side portion 801 may have at least partial elliptical or circular shape according to a vertical cross section, wherein the total curvature 25 according to FIG. 23 may be defined as part of an ellipse or circle fitted to a curvature of at least part of the first side portion 801. A section where curvature of the first side portion 801 matches the fitted ellipse or circle may be called the section 26. The section 26 is defined as an angle 30 between two the line 28 and line 29. The line 28 and the line 29 cross a centre of symmetry 27 and points 31 and 33 located in the section 26 with the longest distance according to fitted part of an ellipse or circle copying curvature of the applicator 800. The centre of symmetry 27 is a centre of fitted ellipse and/or fitted circle. The angle 30 defining section 26 of the first side portion 801 may be at least 5° or in a range from 10° to 270°, 30° to 235°, 45° to 180°, or 60° to 135°. A curvature radius of at least part of fitted circle to the first side portion 801 may be in a range of 50 mm to 1250 mm, or in the range of 10 mm to 750 mm, or in the range of 50 mm to 500 mm, or in the range of 60 mm to 250 mm. The second side portion 802 may be curved on at least part of its surface wherein the section 26 of the second side portion 802 may be at least 5° or in a range from 10° to 270°, 30° to 235°, 45° to 180°, or 60° to 135°. Further a curvature radius of at least part of fitted circle to the second side portion 802 may be in a range of 50 mm to 1250 mm, 10 mm to 750 mm, 50 mm to 500 mm, or 60 mm to 250 mm.

One or more applicators and/or additional treatment devices may include a bolus 32, as shown for example in FIG. 23. The bolus 32 may refer to a layer of material located between the applicator or RF electrode positioned on the surface of the applicator and the patient's body area or skin (including epidermis of patient's skin or clothing). The bolus 32 may refer to a layer of material located between the RF electrode positioned on the surface of the applicator and the patient's body area or skin. Also, the bolus 32 may be an independent part from the applicator 800. The bolus 32 may be attached to the first side portion 801 and/or to the second side portion 802 of the applicator 800. The bolus 32 may be removable and detachable from the applicator 800. The bolus 32 may be mechanically coupled to the first side portion 801 and/or to the second side portion 802 of the applicator 800. The bolus 32 may be made of a solid, flexible material and/or a composition of solid and flexible materials may be used as a bolus. The bolus 32 may include a fluid material, such as water, gel, or fluid solution including ceramic, metal, polymeric and/or other particles enclosed in a flexible sac made of biocompatible material. The bolus 32 may be profiled, wherein a thickness of the bolus 32 as a layer between RF electrode and patient's skin may have a different thickness. Thickness of the bolus 32 may be higher in a location where an energy flux density of the RF treatment (including RF field) would be high enough to create uncomfortable hot spots and/or non-homogeneous temperature distribution. The bolus 32 allows for more homogenous biological structure heating and minimizes edge effects. Edge effects may also be minimized by different dielectric properties of the bolus across the bolus volume and/or bolus area. The bolus 32 may have higher thickness under the at least part of the edge of the RF electrode. The thickness of the bolus under the at least part of the edge of the RF electrode may be at least 5%, 10%, 15%, or 20% greater than a thickness of the bolus 32 under the at least part of a centre of the RF electrode wherein no apertures, cutout and/or protrusions are taken into account. The bolus 32 may have a higher thickness under at least part of the bipolar RF electrode and/or under at least part of a distance between at least two bipolar RF electrodes. The bolus 32 may be in such locations thicker by about at least 5%, 10%, 15%, or 20% than a thickness of the bolus 32 where the distance between two nearest points of two different bipolar RF electrodes is at least 5%, 10%, 15%, or 20% more. The bolus 32 may also improve transfer of treatment energy (e.g. magnetic field and/or RF field) to at least one biological structure and minimize energy reflection by providing gradual transition of dielectric properties between two different interfaces of the applicator and the biological structure. The bolus 32 may profile or focus the RF field and/or magnetic field to enhance the effect of the treatment, and/or provide deeper tissue penetration of the treatment.

The bolus 32 may also be a fluid absorbing material, such as a foam material, textile material, or gel material to provide better conductivity of the environment between the applicator and a patient's body. Better conductivity of the contact part of the applicator may be useful for better adjusting of the RF signal of the applied RF treatment to the patient's body and/or for better collecting of feedback information. The bolus 32 may mediate conductive contact between the RF electrode and the patient's skin or body area. Also, the bolus 32 may serve as a non-conductive or dielectric material modifying energy transfer to the patient's body, providing cooling of the patient's skin, removing sweat from the patient's skin and/or providing heating, such as capacitive heating of the patient's body. Fluid absorbing material serving as a bolus 32 may also provide better heat conductivity therefore temperature of the biological structure and/or the applicator may be faster, easier and more precisely regulated. The bolus 32 may also include additional RF electrode to provide the RF treatment.

As mentioned previously, the treatment device may include one, two, three, four, six or more applicators and/or additional treatment devices providing the magnetic treatment and/or the RF treatment. Each applicator, additional treatment device and/or treatment energy source (e.g. magnetic field generating device and/or the RF electrode) may have its own treatment circuit for energy transfer, wherein each treatment circuit may be independently regulated in each parameter of provided treatment energy by control system. Each applicator, treatment device, or treatment energy source may be adjusted and provide treatment independently and/or two or more applicators, treatment energy sources, and/or additional treatment devices may be adjusted as a group, and may be adjusted simultaneously, synchronously and/or may cooperate between each other.

When the treatment device includes two or more applicators, they may be coupled to contact or to be proximate to different parts of the body. In one example the first applicator may be coupled to contact or to be proximate to left buttock while the second applicator may be coupled to contact or to be proximate to right buttock. In another example, the first applicator may be coupled to contact or to be proximate to left side of abdominal area while the second applicator may be coupled to contact or to be proximate to right side of abdominal area. In still another example the first applicator may be coupled to contact or to be proximate to left thigh while the second applicator may be coupled to contact or to be proximate to right thigh. In still another example the first applicator may be coupled to contact or to be proximate to left calf while the second applicator may be coupled to contact or to be proximate to right calf. The plurality of applicators may be beneficial for treatment of cooperating muscles and/or pair muscles.

One or more applicators and/or the additional treatment devices may include the magnetic field generating device (e.g. a magnetic coil) generating magnetic field for a magnetic treatment. The magnetic field generating device may generate the RF field for the RF treatment. The essence is that the produced frequencies of the electromagnetic field has far different values. The magnetic field generating device may produce a dominant magnetic field vector for the magnetic treatment during lower frequencies of produced electromagnetic field. However, the magnetic field generating device may produce a dominant electromagnetic field vector for the magnetic treatment during higher frequencies of electromagnetic field which may be used for the RF treatment. The magnetic field generating device in the high frequency electromagnetic field domain may provide RF field similar to the RF field provided by the RF electrode. When one magnetic field generating device may be used for providing both the RF treatment and the magnetic treatment, the difference between frequencies for the RF treatment and the magnetic treatment production may be in a range from 500 kHz to 5 GHz, or from 500 kHz to 2.5 GHz or from 400 kHz to 800 kHz or from 2 GHz to 2.5 GHz. Also, when one magnetic field generating device is used for providing both the RF treatment and the magnetic treatment, the frequencies for the RF treatment may correspond with frequencies in the range of 100 kHz to 3 GHz, 400 kHz to 900 MHz, or 500 kHz to 3 GHz.

One or more applicators and/or additional treatment devices may include one or more RF electrodes and one or more magnetic field generating devices, wherein the RF electrodes have different characteristics, structure and/or design than the magnetic field generating device. The RF electrode may operate as a unipolar electrode, monopolar electrode, bipolar electrode, and/or as a multipolar electrode. One or more RF electrodes may be used for capacitive and/or inductive heating of biological structure or body area.

The applicator may include two bipolar RF electrodes. The bipolar electrodes may transfer the RF field between two bipolar RF electrodes located in at least one applicator. Bipolar electrodes may increase safety and targeting of provided RF treatment, as compared to electrodes of monopolar type. Bipolar electrodes may provide electromagnetic field passing through a patient's tissue located around and between RF electrodes, wherein due to impedance matching, it is possible to prevent creation of standing electromagnetic waves in the patient's tissue and prevent unwanted thermal injury of non-targeted tissue. Also, the distance between bipolar electrodes influences the depth of RF wave penetration allowing for enhanced targeting of the RF treatment.

The applicator may include a monopolar RF electrode or more monopolar electrodes. Monopolar electrodes may transfer radiofrequency energy between an active electrode and a passive electrode, wherein the active electrode may be part of the applicator and the passive electrode having larger surface area may be located at least 5 cm, 10 cm, or 20 cm from the applicator. A grounded electrode may be used as the passive electrode. The grounded electrode may be on the opposite side of the patient's body than the applicator is attached.

The magnetic treatment may be provided by the magnetic field generating device may be made from a conductive material, such as a metal, including for example copper. The magnetic field generating device may be formed as a coil of different size and shape. The magnetic field generating device may be a coil of multiple windings wherein one loop of the coil may include one or multiple wires. An individual loop of one or more wires may be insulated from the other turns or loops of one or more wires. Regarding the magnetic coil, each loop of wiring may be called turn. Further, individual wires in one turn or loop may be insulated from each other. The shape of the magnetic field generating device may be optimized with regard to the applicator size and design. The coil may be wound in order to match at least part of the applicator's shape according to the applicator's floor projection. The coil winding may be at least partially circular, oval and/or may have any other shapes that match to a shape of the applicator or a portion thereof. The loops of winding may be stacked on top of each other, may be arranged side by side, or stacking of the winding may be combined side by side and on top of other windings. The coil may be flat.

FIG. 9 illustrates a floor projection of an exemplary circular planar magnetic field generating device 900. The magnetic field generating device 900 may be characterized by dimensions including an outer diameter D, an inner diameter d, an inner radius r and an outer radius R. The magnetic field generating device 900 may be further characterized by areas A1 and A2. Area A2 may represent a winding area of the coil while A1 may represent a magnetic core or area without any magnetic core or windings.

The area A1 is associated with dimensions r and d. The area A1 may include no windings of the coil, and may be filled by air, oil, polymeric material. The area A1 may represent a magnetic core wherein the magnetic core may be an air core. Alternatively, the magnetic core may be a permeable material having high field saturation, such as a solid core from soft iron, iron alloys, laminated silicon steel, silicon alloys, vitreous metal, permendur, permalloy, powdered metals or ceramics and/or other materials.

The area A2 is associated with dimensions of outer radius R and outer diameter D.

The dimension of inner radius r may be in the range from 1% to 90% of the dimension of outer radius R, or in the range from 2% to 80% or from 3% to 60% or from 4% to 50%, from 8% to 30%, or from 20% to 40% or from 30% to 50% of the dimension of outer radius R. The dimensions of inner radius r and outer radius R may be used for achieving a convenient shape of the generated magnetic field.

The outer diameter D of the magnetic device may be in a range of 30 mm to 250 mm, or of 40 mm to 150 mm, or of 50 mm to 135 mm or of 90 mm to 125 mm, and the dimension of inner radius r may be in a range of 1% to 70% or 1% to 50% or 30% to 50%, 5% to 25%, or 8% to 16% of the dimension of outer radius R. For example, the dimension of outer radius R may be 50 mm and the dimension r may be 5 mm. The area A1 may be omitted and the magnetic field generating device may include only area A2 with the coil winding.

As discussed, the area A2 may include a plurality of windings. One winding may include one or more wires. The windings may be tightly arranged, and one winding may be touching the adjacent winding to provide magnetic field with high magnetic flux density. The winding area A2 may be in the range from 4 cm² to 790 cm², from 15 cm² to 600 cm², from 45 cm² to 450 cm² or from 80 cm² to 300 cm² or from 80 cm² to 150 cm² or from 80 cm² to 130 cm².

Alternatively, the windings may include a gap between each winding. The gap may be between 0.01% to 50%, or 0.1% to 25%, or 0.1% to 10%, or 0.1% to 5%, or 0.001% to 1% of the dimension R-r. Such construction may facilitate cooling and insulation of individual winding of the magnetic field generating device. Further, the shape of the generated magnetic field may be modified by such construction of the magnetic field generating device.

The wire of the coil winding may have a different cross-section area. The cross-sectional area of the winding wire may be larger at the centre of the winding where the coil winding radius is smaller. Such cross-section area of the wire may be from 2% to 50%, from 5% to 30%, or from 10% to 20% larger than the cross-sectional area of the same wire measured on the outer winding turn of the magnetic field generating device, wherein the coil winding radius is larger. The cross-sectional area of the winding wire of the magnetic field generating device may be larger on the outer coil winding turn of the magnetic field generating device where the coil winding radius is larger. Such cross-sectional area of the wire may be from 2% to 50%, from 5% to 30%, or from 10% to 20% larger than the cross-section area of the same wire measured on the inner turn of the magnetic field generating device wherein the coil winding radius is smaller.

The principles and parameters described above may be used in order to modify the shape of the provided magnetic field to the patient's body, provide a more homogenous and/or targeted muscle stimulation (e.g. muscle contraction), reduce expansion of the magnetic field generating device during the treatment and/or increase durability of the magnetic field generating device. The magnetic field generating device may expand and shrink during generation of time-varying magnetic field and this could cause damage of the magnetic field generating device. Different cross-sectional areas of used conductive material (e.g. wire, metallic stripe or creating winding of the magnetic field generating device) may minimize the destructive effect of expanding and shrinking the magnetic field generating device.

As discussed above, the cross-sectional area of the used conductive material, (e.g. wire, metallic stripe and/or creating winding of the magnetic field generating device) may vary between individual loops of wiring in a range of 2% to 50%, or of 5% to 30%, or of 10% to 20% in order to improve focusation of the provided magnetic treatment, to increase durability of the magnetic field generating device, to minimize heating of the magnetic field generating device, and/or for other reasons.

Further, stacking of the wiring and/or isolating and/or dilatation layer between individual conductive windings of the magnetic field generating device may not be constant and may be different based on the wire cross-sectional area, radius of the winding, required shape of provided magnetic field and/or other parameters.

Figure 9A:
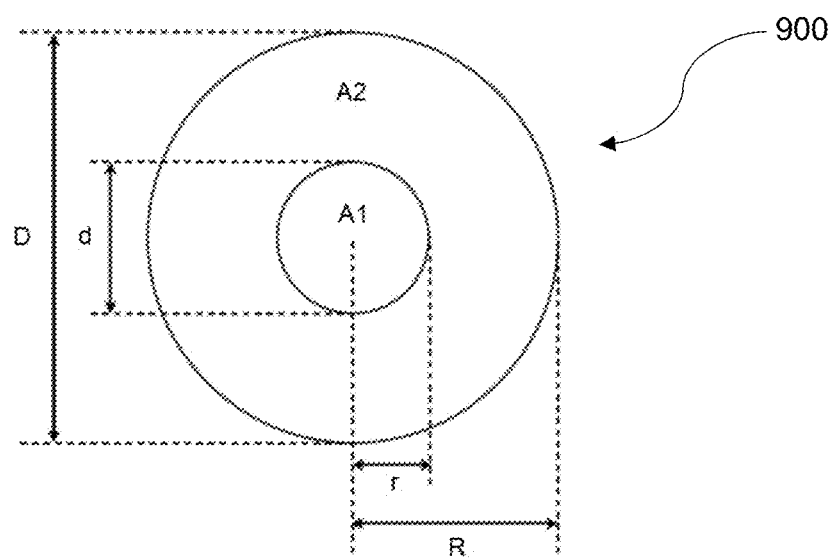
FIG. 9a illustrates an exemplary magnetic field generating device from the applicator's floor projection.
Figure 9B:
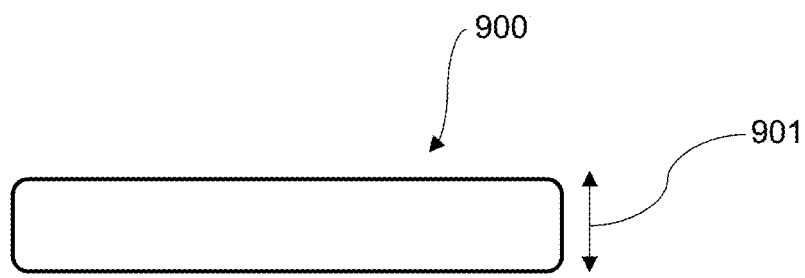
FIG. 9b illustrates a thickness of exemplary magnetic field generating device.

A thickness 901 of the magnetic field generating device 900 shown on FIG. 9b may be in a range of 0.3 cm to 6 cm, or of 0.5 cm to 5 cm, or of 1 cm to 3 cm from the applicator's side view.

A total surface of the magnetic field generating device surface according to the applicator's floor projection, i.e. area A1+A2, may be in a range from 5 cm² to 800 cm², 10 cm² to 400 cm², 20 cm² to 300 cm² or 50 cm² to 150 cm².

The ratio of the area A1 and winding area A2 may be in a range of 0.01 to 0.8, or 0.02 to 0.5 or 0.1 to 0.3 according to the applicator's floor projection. The ratio between the winding area A2 of the magnetic field generating device and the area of RF electrodes located in same applicator according to the applicator's floor projection may be in a range of 0.01 to 4, or 0.5 to 3, or 0.5 to 2, 0.3 to 1, or 0.2 to 0.5, or 0.6 to 1.7, or 0.8 to 1.5, or 0.9 to 1.2.

FIGS. 10a-10g show the location of one or more RF electrodes 101 with regard to at least one magnetic field generating device 900 in an applicator 800. The location of the RF electrodes 101, 102 and/or the magnetic field generating device 900 may crucially influence the effectiveness and targeting of the treatment energy sources. The RF electrodes and magnetic field generating device may be located within the applicator.

Figure 10A:
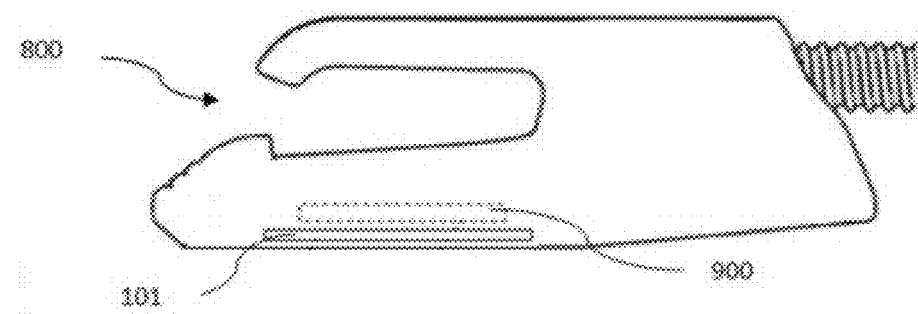
FIGS. 10a-10g illustrate possible locations of an exemplary RF electrode with regard to an exemplary magnetic field generating device.
Figure 10B:
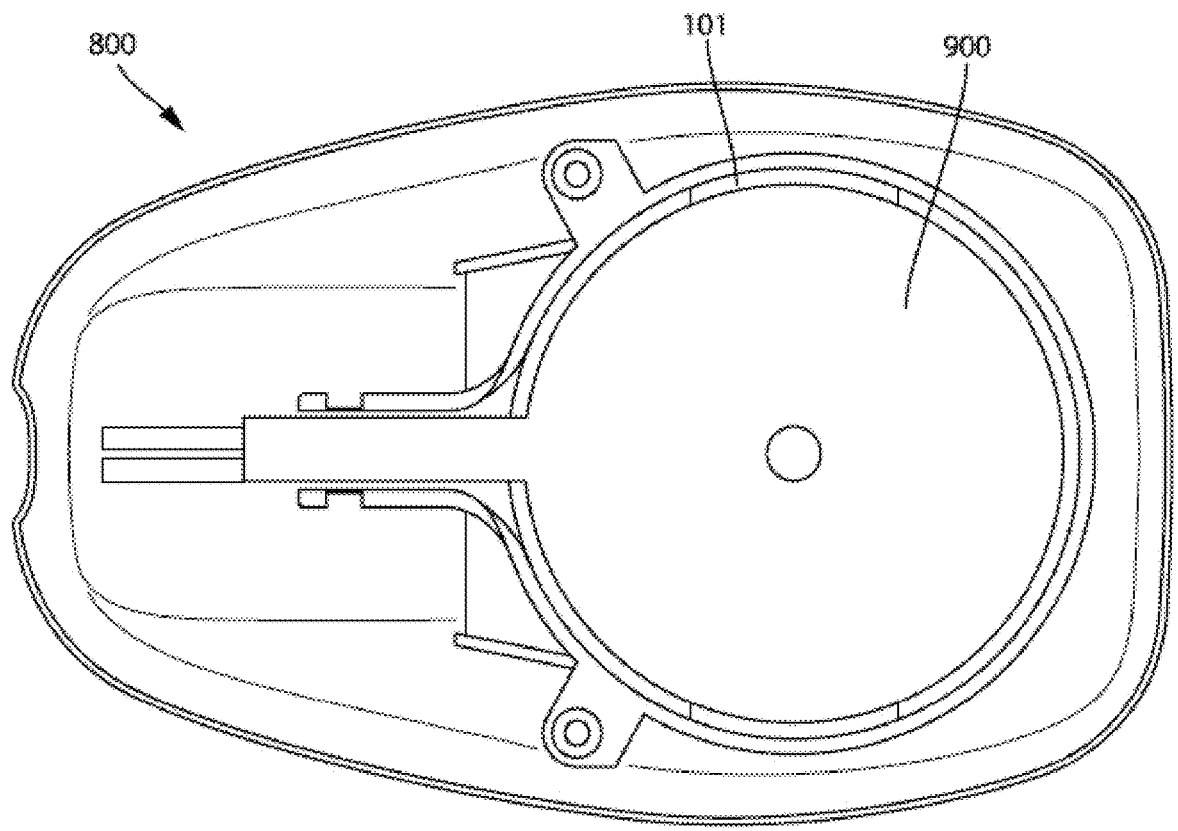
Figure 10C:
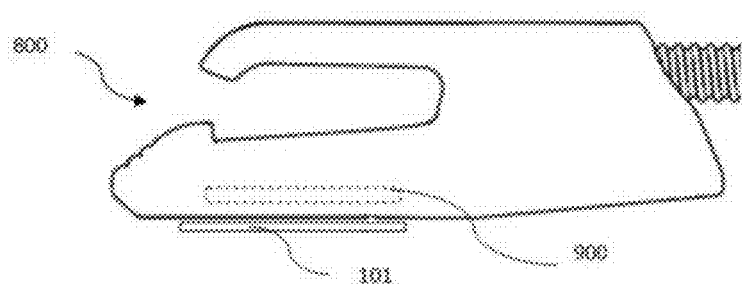

One or more RF electrodes 101, 102 may be located inside of the applicator 800, as illustrated in the FIGS. 10*a*, 10*b*, 10*d*, 10*e*, 10*f*, 10*g* and/or outside of the applicator 800, as illustrated in the FIG. 10*c*.

As shown in FIGS. 10*a*-10*e* and 10*g*, at least one RF electrode may be in at least partial overlay with the area A2 or A1 of at least one magnetic field generating device according to applicator's floor projection. Such arrangement may enable the best synergic effect of the magnetic and RF treatments, improve homogeneity of tissue heating by the RF treatment, improve targeting of the magnetic and RF treatment, and also minimize the health risk.

FIG. 10*a* illustrates a side view of the applicator including at least one RF electrode and magnetic field generating device. Shown applicator may include the at least one RF electrode 101 which may be located under the magnetic field generating device 900 in the applicator 800. FIG. 10*b* illustrates an upper view of the same type of applicator including RF electrode and magnetic field generating device. As shown in FIGS. 10*a* and 10*b*, the at least one RF electrode 101 may be very thin in order to reduce unwanted physical effects caused by the time-varying magnetic field. FIG. 10*b* illustrates that the at least one RF electrode 101 may be almost completely in overlay with the magnetic field generating device 900.

FIG. 10*c* illustrates another exemplary applicator including at least one RF electrode and magnetic field generating device. According to FIG. 10*c*, the at least one RF electrode 101 may be located outside of the applicator 800, such as on or adjacent to an exterior surface of the applicator 800. RF electrode outside of the applicator may have better insulation from the magnetic field generating device and/or from other conductive elements radiating electromagnetic field from the applicator. Better insulation may decrease the influence of unwanted physical effects induced in the at least one RF electrode 101 by radiating electromagnetic field and/or time-varying magnetic field. One or more RF electrodes 101 located outside of the applicator as illustrated in FIG. 10*c* may also have better contact with the patient's body and so operation of tuning electrical element of an RF circuit may be improved. Further, transferring of the RF treatment to at least one patient's target biological structure may be enhanced.

Figure 10D:
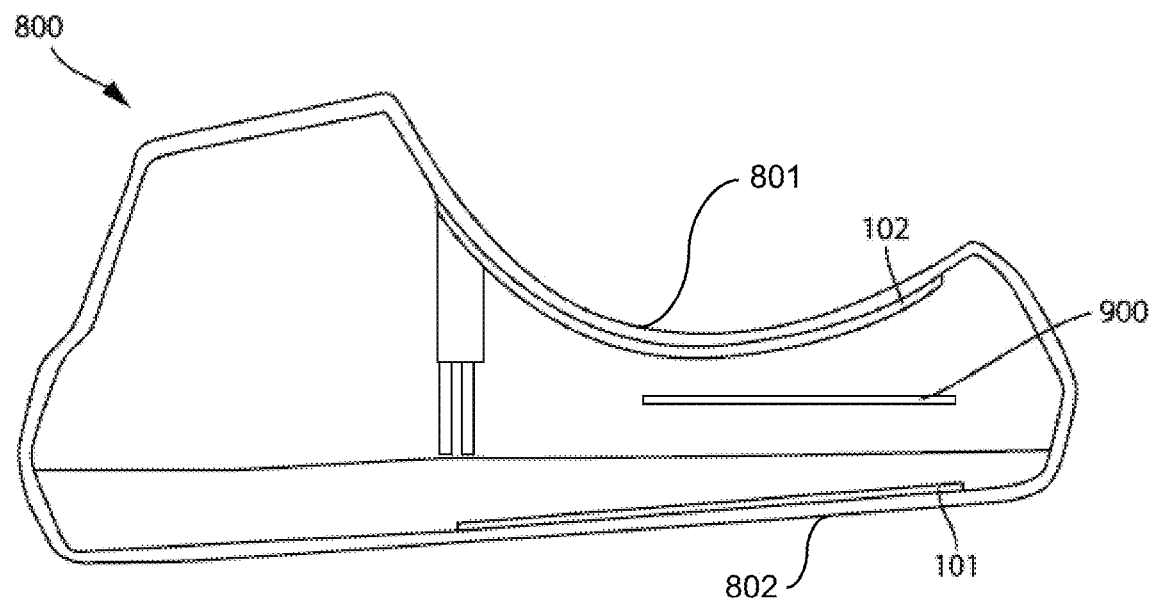

FIG. 10*d* illustrates another exemplary applicator including at least one RF electrode and magnetic field generating device. The at least one RF electrode 101 may be positioned below the magnetic field generating device 900. Applicator 800 may also include another at least one RF electrode 102 located above the magnetic field generating device 900, wherein both RF electrode and magnetic field generating device may be positioned in one applicator 800. The first side portion 801 having curved at least one RF electrode 102 in proximity or on its surface may be used for treating a curved body area (e.g. at least part of thighs, hips, neck and/or arms). The second side portion 802 with a flat at least one RF electrode 101 in proximity or on its surface may be used for treating body area where flat or nearly flat side of the applicator will be more suitable, such as an abdomen area or buttock.

Figure 10E:
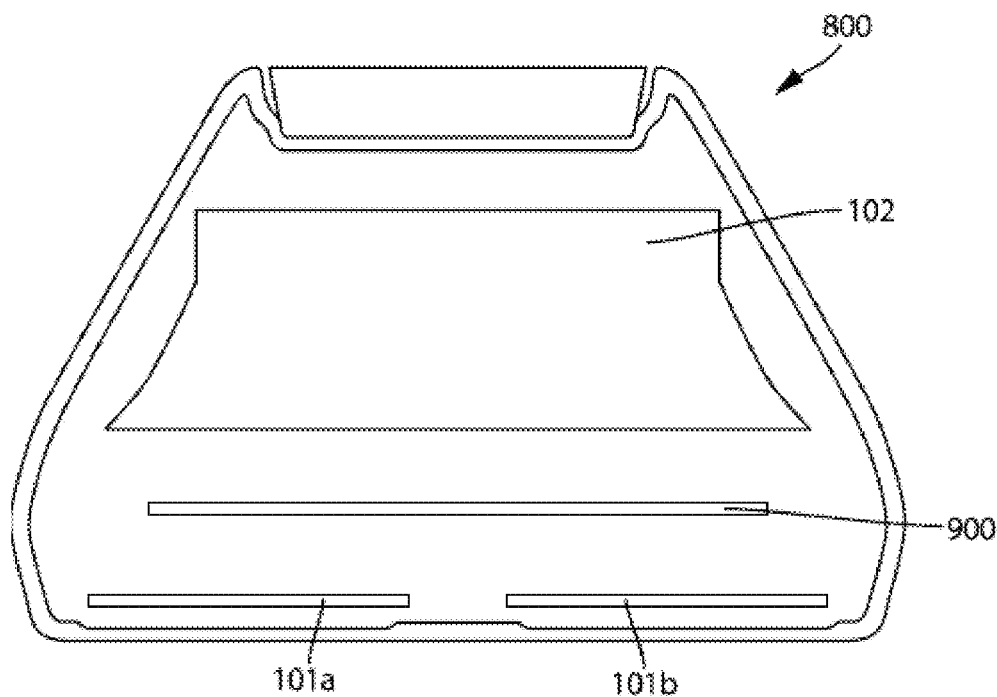

FIG. 10*e* shows a front side view of a similar applicator 800 as in FIG. 10*d*. FIG. 10*e* illustrates that the RF electrode 101 may be in fact two electrodes 101*a* and 101*b*. The electrodes 101*a* and 101*b* may be bipolar electrodes. Therefore, the applicator may include two bipolar electrodes 101*a* and 101*b* below the magnetic field generating device 900.

Figure 10F:
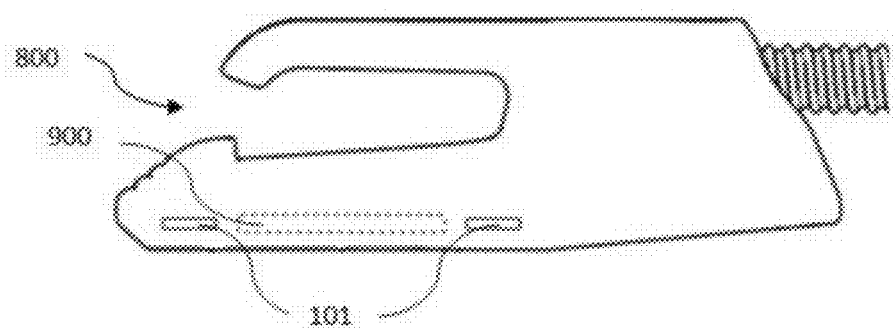

FIG. 10*f* illustrates another exemplary applicator 800 including RF electrode and magnetic field generating device. The applicator may include one or more RF electrodes 101 which may have minimal or no overlay with at least one magnetic field generating device 900 according to applicator's floor projection. The applicator may include two RF electrodes 101 having no or minimal overlay with magnetic field generating device.

Figure 10G:
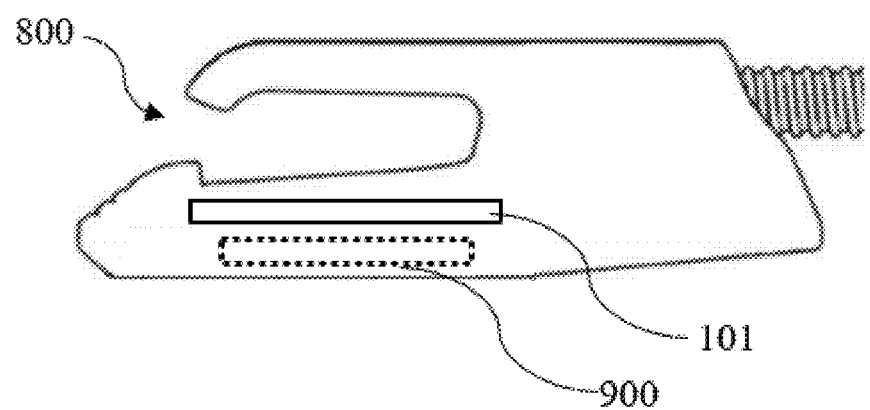

FIG. 10*g* illustrates another exemplary applicator 800 including RF electrode and magnetic field generating device. The applicator may at least one RF electrode 101 which may be located above the magnetic field generating device 900. The heating provided by RF electrode positioned above the magnetic field generating device may be provided also to magnetic field generating device itself.

One or more RF electrodes positioned on the one applicator and/or more the applicators 800 may be placed in contact with the patient. Also, one or more RF electrodes and/or applicators may be separated from the patient by an air gap, bolus, dielectric material, insulating material, gel, and/or other material.

One or more RF electrodes 101, 102 and/or magnetic field generating devices 900 within one applicator may be spaced from each other by an air gap, by material of a printed circuit board, insulator, cooling fluid, and/or other material. The distance between a conductive part of the magnetic field generating device and the nearest RF electrode may be in a range of 0.1 mm to 100 mm or 0.5 mm to 50 mm or 1 mm to 50 mm or 2 mm to 30 mm or 0.5 mm to 15 mm or 0.5 mm to 5 mm. Spacing between the magnetic field generating device and the RF electrode may be also provided in the form of an insulating barrier that separate a RF circuit from a magnetic circuit and prevents affecting one treatment circuit or treatment energy source by other treatment circuit or other treatment energy source. The magnetic field generating device positioned closer to patient's body may be able to stimulate and provide the treatment effect to at least part of at least one target biological structure more effectively and deeply than the magnetic field generating device that is in a larger distance from the patient's body.

The magnetic field generating device and/or one or more RF electrodes included in or on the applicator may be cooled during the treatment. Cooling of the magnetic field generating device and/or one or more RF electrodes may be provided by an element based on the Peltier effect and/or by flowing of a cooling fluid, such as air, water, oil and/or a fluid within the applicator or in proximity of the applicator. The cooling fluid may be flowed or guided around one or more magnetic field generating devices, one or more RF electrodes, between the magnetic field generating device and at least part of at least one RF electrode. Cooling fluid may flow only on the top and/or bottom of the magnetic field generating device. Cooling fluid may be a fluid, such as gas, oil, water and/or liquid. The cooling fluid may be delivered to the applicator from the main unit where the cooling fluid may be tempered. The cooling fluid may be delivered to applicator and to the proximity of magnetic field generating device and/or RF electrode. The cooling fluid may be delivered to the applicator by connecting tube coupled to the main unit. The connecting tube may include the fluid conduit, which may serve as path for the cooling fluid between applicator and the main unit.

The main unit may include one or more cooling tanks where the cooling fluid may be stored and/or cooled. Each cooling tank may include one or more pumps, wherein one pump may provide flow of the cooling fluid to one applicator. Alternatively, one pump may provide flow of the cooling fluid to plurality of applicators (e.g. two applicators). Further, the main unit may include one cooling tank storing and/or cooling the cooling fluid for one respective applicator or plurality of applicators. For example, when the treatment device includes two applicators, the main unit may include one cooling tank providing the cooling fluid for both applicators. In another example, when the treatment device includes two applicators, the main unit may include two cooling tanks providing cooling of the cooling fluid. Each cooling tank may provide cooling of the cooling fluid to one particular applicator either synchronously or independently. Cooling tank or fluid conduit may include a temperature sensor for measuring temperature of cooling fluid.

The fluid conduit may be a plastic tube. The plastic tube may lead from cooling tank to the applicator and then back to cooling tank. When the treatment device includes e.g. two applicators, the fluid conduit may lead from the cooling tank to one applicator and then back to cooling tank while the second fluid conduit may lead from the same or different cooling tank to second applicator and then back to the cooling tank. However, fluid conduit may lead from cooling tank to first applicator, then lead to second applicator and finally to cooling tank.

When the RF electrode is positioned in the proximity of magnetic field generating device, the time-varying magnetic field generated by the magnetic field generating device may induce unwanted physical effects in the RF electrode. Unwanted physical effects induced by time-varying magnetic field may include e.g. induction of eddy currents, overheating of RF electrode, skin effect, and/or causing other electric and/or electromagnetic effects like a phase shift in the RF electrode. Such unwanted physical effects may lead to treatment device malfunction, energy loss, decreased treatment effect, increased energy consumption, overheating of at least applicator's part, e.g., RF electrode, collecting false feedback information, malfunctioning of signal adjustment provided to the RF electrode and/or other unwanted effects.

The described invention provides options, methods or designs how to prevent and/or minimize one or more unwanted physical effects induced in the RF electrode by the magnetic field. The same options methods or designs may help to minimize shielding of magnetic field by RF electrode. One option may include arrangement of the RF electrode in minimal or no overlay with the magnetic field generating device according to the floor projection of the applicator. Another option may include an RF electrode of special design as described below. Still another option may include reducing of thickness of the RF electrode. Still another option may include providing the RF electrode from a conductive material that reduces induction of unwanted physical effects and heating of the RF electrode. One or more RF electrode providing RF energy during the treatment by described treatment device may use at least one of these options, at least two options and or combination of these options and their characterization as described below.

One option of minimizing or eliminating unwanted physical effects induced in the RF electrode by a magnetic field may include arrangement of the RF electrode in minimal or no overlay with the magnetic field generating device according to the floor projection of the applicator.

Figure 11:
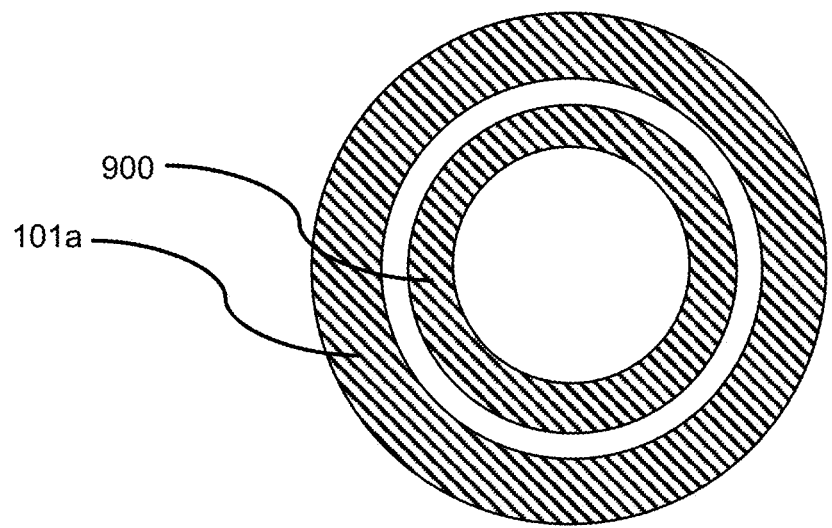
FIG. 11 illustrates a floor projection of a location of an exemplary RF electrode locating with regard to an exemplary magnetic field generating device.

FIG. 11 illustrates an example in which the RF electrode 101a may be located under, next to and/or above the magnetic field generating device 900 and have no or minimal overlay with the magnetic field generating device 900 according to the applicator's floor projection. As shown on FIG. 11 the electrode 101a may be located outside of area A2.

Figure 12:
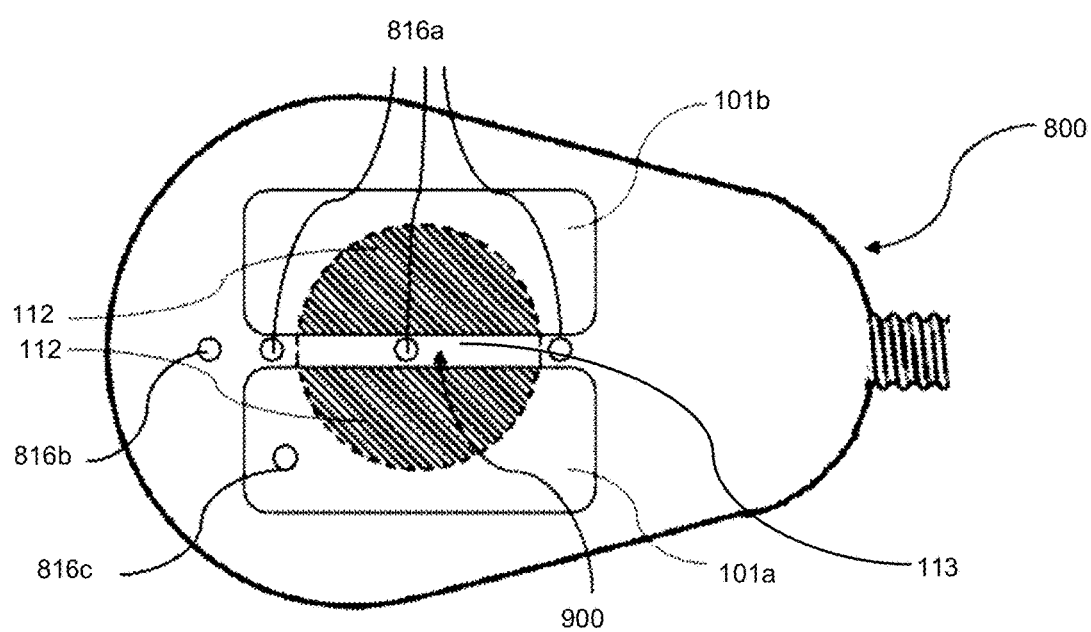
FIG. 12 illustrates a floor projection of an applicator including RF electrodes and a magnetic field generating device with partial overlay according to applicator's floor projection.

FIG. 12 illustrates another exemplary applicator including a magnetic field generating device and one or more RF electrode. The applicator 800 may include two RF electrodes 101a and 101b spaced by gap 113. Two RF electrodes 101a and/or 101b may be in at least partial overlay 112 with the winding area A2 and or area A1 of the magnetic field generating device 900 according to the applicator's floor projection. The partial overlay 112 is represented by hatched area in the FIG. 12. The floor projection may be represented by a picture of the applicator 800 taken from the bottom of the applicator by X-ray. Such partial overlay 112 may be in a range from 1% to 100%, or from 1% to 99%, or from 1% to 70%, or from 5% to 50%, or from 5% to 40%, or from 10% to 30%, or from 25% to 100%, or from 10% to 100%, or from 30% to 95%, or from 40% to 100%, or from 70% to 100%, or from 80% to 95% or from 30 to 70% of the area of one RF electrode area according to the floor projection of the applicator. Overlay of two areas may refer to a ratio between these two different areas.

One or more temperature sensors 816a may be located between bipolar RF electrodes 101a, 101b as illustrated in FIG. 12. One or more temperature sensor 816a may be at least partially encircled by at least one RF electrode 101a and 101b according to the applicator's floor projection as illustrated by temperature sensors 816a in FIG. 12. The highest amount of RF energy may flow between bipolar electrodes 101a and 101b. Therefore a volume of the body area or the treated tissue between or directly below bipolar electrodes may have the highest temperature and should be measured as an actual temperature or temperature reference to predetermined temperature. However, the temperature sensor may be placed inside applicator or on the surface of the applicator.

A characteristic shape of the RF electrode may create inhomogeneous temperature distribution of the heat during the treatment. It may be useful to place the temperature sensor 816b such that it is not located between RF bipolar electrodes 101a, 101b in such way that the temperature sensor is not encircled by bipolar electrodes 101a, 101b. The temperature sensor may be placed inside applicator or on the surface of the applicator. Also, the temperature sensor 816c may be located under the RF electrode. The material of the first side portion 801 and/or the second side portion 802 covering at least part of the temperature sensor 816 (e.g. 816a, 816b or 816c) and contacting the patient's body may be manufactured from the same material as the first side portion 801 and/or the second side portion 802. However, the material of the first side portion 801 or second side portion 802 covering the temperature sensor 816 may be from a different material than the remainder of the first side portion 801 or second side portion 802, such as a material with a higher thermal conductivity, e.g. ceramic, titanium, aluminum, or other metallic material or alloy. The temperature sensor 816 may be a thermistor. The temperature sensor 816 (e.g. 816a, 816b or 816c) may be fixed or coupled to the first side portion 801 and/or second side portion 802 by thermal conductive material, such as a thermal epoxy layer, with good thermal conductivity. Wire connection between the temperature sensor 816 and rest of the treatment device may be represented by one, two or more conductive wires with diameter in a range of 0.05 mm to 3 mm, or of 0.01 mm to 1 mm, or of 0.1 mm to 0.5 mm. The wire connection including a conductive wire with described diameter may be advantageous because of minimizing of thermal transfer between the wire and the temperature sensor 816. The wire connection to the temperature sensor 816 may have thermal conductivity in a range of 5 $W \cdot m^{-1} \cdot K^{-1}$ to 320 $W \cdot m^{-1} \cdot K^{-1}$, or 6 W·m$^{-1}$·K$^{-1}$ to 230 W·m$^{-1}$·K$^{-1}$, or 6 W·m$^{-1}$·K$^{-1}$ to 160 W·m$^{-1}$·K$^{-1}$, or 20 W·m$^{-1}$·K$^{-1}$ to 110 W·m$^{-1}$·K$^{-1}$, or 45 W·m$^{-1}$·K$^{-1}$ to 100 W·m$^{-1}$·K$^{-1}$, or 50 W·m$^{-1}$·K$^{-1}$ to 95 W·m$^{-1}$·K$^{-1}$. A material of wire connection may be e.g.: nickel, monel, platinum, osmium, niobium, potassium, steel, germanium, aluminium, cobalt, magnesium copper and/or their alloys. At least part of the wire connection connected to the temperature sensor 816 may be thermally insulated by sheathing or shielding, such as by rubber tubing. The temperature sensor 816 may be an optical temperature sensor, such as an infrared IR thermosensor, which may be part of the applicator and/or in the main unit. During treatment, the optical temperature sensor may be located in contact with the patient's skin or in a range of 0.1 cm to 3 cm, or 0.2 cm to 2 cm from the patient's skin. The optical temperature sensor may collect information from the patient's skin through the optical cable.

One or more RF electrodes located with at least partial overlay under the magnetic field generating device may provide synergic effect of the magnetic treatment and the RF treatment. Stronger or more intensive treatment result may be provided with RF electrodes located with at least partial overlay under the magnetic field generating device. The generated RF field and the magnetic field from treatment energy sources in such configuration may be targeted to the same body area and/or target biological structures. This may result in better heating of stimulated muscles and adjacent tissues, better suppressing of uncomfortable feeling caused by muscle stimulation (e.g. muscle contraction), better regeneration after treatment and/or better prevention of panniculitis and other tissue injury.

Another option of minimizing or elimination of unwanted physical effects induced in the RF electrode by magnetic field may include special design of the RF electrode.

It is a part of the invention, that the unwanted physical effects induced by magnetic field in RF electrode positioned in proximity or at least partial overlay with the magnetic field generating device may be further minimized or eliminated by using a segmented RF electrode. The segmented RF electrode may comprise apertures, cutouts and/or protrusions. The areas of apertures and/or cutouts may be created by air, dielectric and/or other electrically insulating material. The electrode may comprise various protrusions. The plurality of apertures and/or cutouts may be visible from the floor projection of such electrode. Another parameter minimizing or eliminating the presence of the unwanted physical effects may be the thickness of the RF electrode. If a conductive material of the RF electrode is thin and an area of the RF electrode is at least partially separated by an insulator, loops of eddy currents induced by magnetic field may be very small and so induction in such areas is minimized.

The RF electrode may include one or more apertures or cutouts which may segment the conductive area of the RF electrode and/or perimeter of the RF electrode. The RF electrode is therefore segmented in comparison to regular electrode by disruption of the surface area (i.e., an electrode with no apertures or cutouts). The two or more apertures or cutouts of the one RF electrode may be asymmetrical. The one or more aperture and cutout may have e.g. rectangular or circular shape. An aperture may be any hole and/or opening in the electrode area of the RF electrode according to applicator's floor projection. The apertures and/or cutouts may have regular, irregular, symmetrical and/or asymmetrical shape. The apertures and/or cutouts may be filled by e.g. air, dielectric and/or other electrically insulating material (e.g. dielectric material of printed circuit board). When the RF electrode includes two or more apertures or cutouts, the apertures or cutouts may have the same point of symmetry and/or line of symmetry. The distance between two closest points located on the borders of two different apertures and cutouts of RF electrode may be in a range from 0.1 mm to 50 mm or 0.1 mm to 15 mm or from 0.1 mm to 10 mm or from 0.1 mm to 8 mm. When the RF electrode is in at least partial overlay with magnetic field generating device, the RF electrode may include larger apertures and cutouts in part of the conductive surface, which is closer to the center of the magnetic field generating device.

Figure 13A:
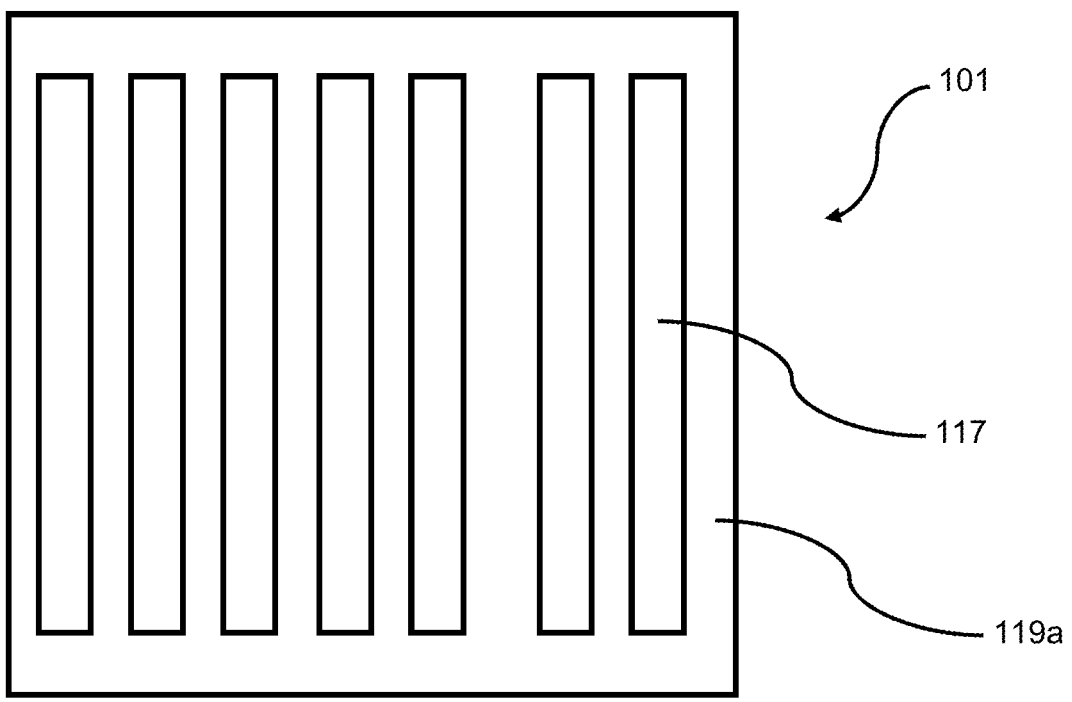
FIGS. 13a-13b illustrate an exemplary RF electrode with apertures.

FIG. 13a illustrates an exemplary RF electrode wherein the RF electrode 101 includes an electrode area 119a and defines one or more apertures 117 in the conductive area of the RF electrode. The apertures 117 may be elongated slots having a rectangular shape. One aperture 117 may be parallel to another apertures.

Figure 13B:
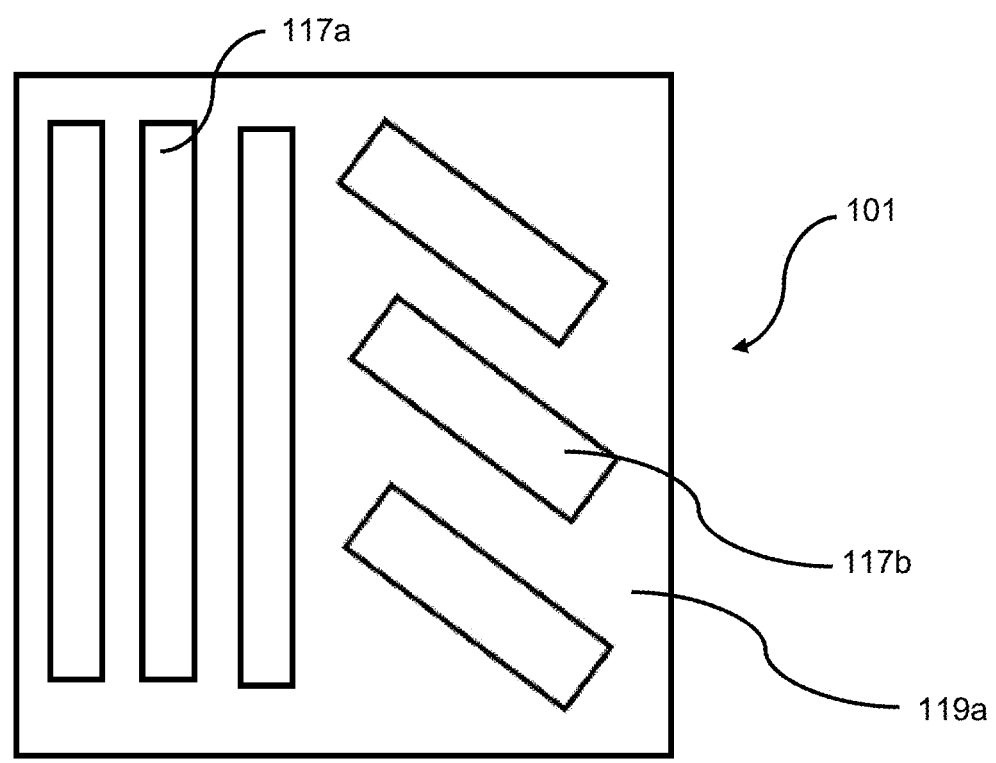

FIG. 13b illustrates another exemplary of RF electrode wherein the RF electrode 101 includes an electrode area 119a and one or more apertures 117a and 117b in the conductive area of the RF electrode. Apertures 117a are not parallel to apertures 117b.

Figure 13C:
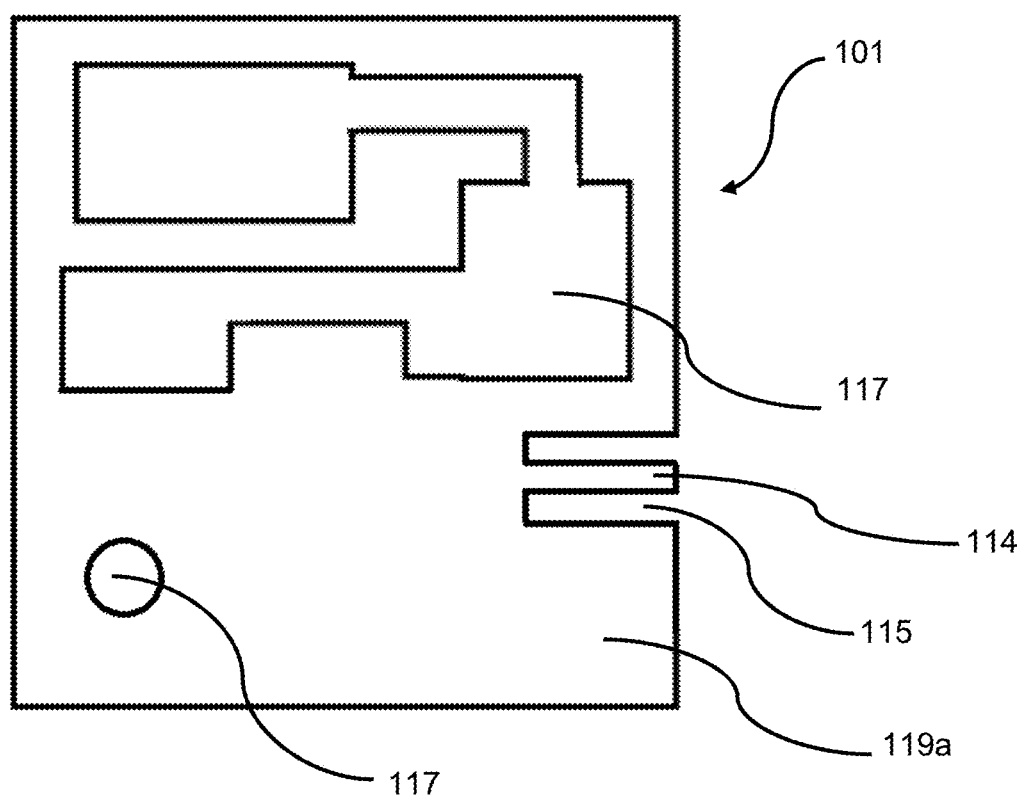
FIG. 13c illustrates an exemplary RF electrode with apertures, protrusions and cutouts.

FIG. 13c illustrates another exemplary RF electrode wherein the RF electrode 101 includes an electrode area 119a and combination of one or more apertures 117 in the conductive area, cutout 115 in the conductive area and protrusion 114 of the RF electrode.

Figure 13D:
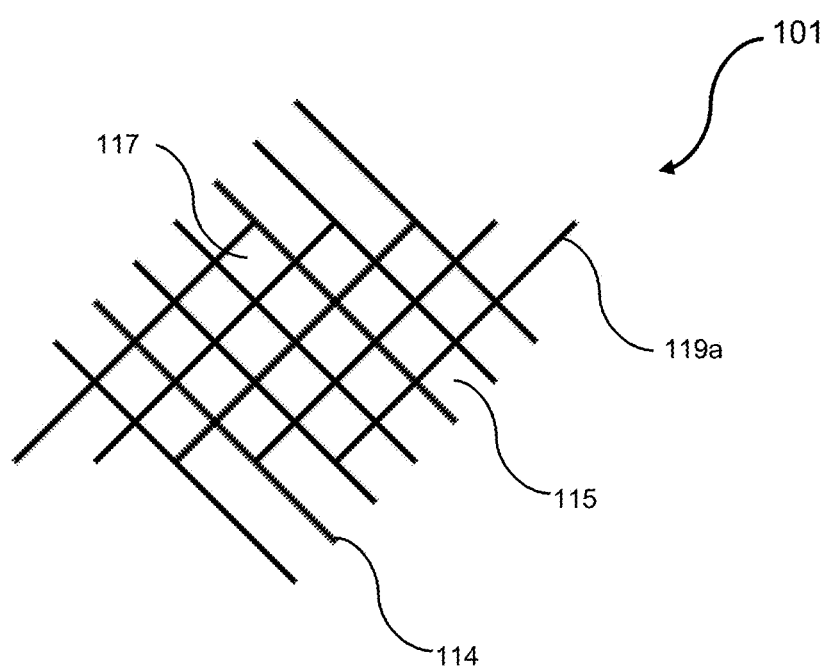
FIG. 13d illustrates another exemplary RF electrode with apertures and cutouts.

FIG. 13d illustrates another exemplary RF electrode wherein the RF electrode 101 includes a combination of one or more apertures 117 at the conductive area and the cutouts 115 in the electrode area. The lines represent thin line (e.g. single wire) of electrode area 119a of RF electrode. The RF electrode may be a grid of conductive wires or mesh of conductive wires. The protrusion 114 may define one or more cutouts 115 at a perimeter of the electrode.

Figure 13E:
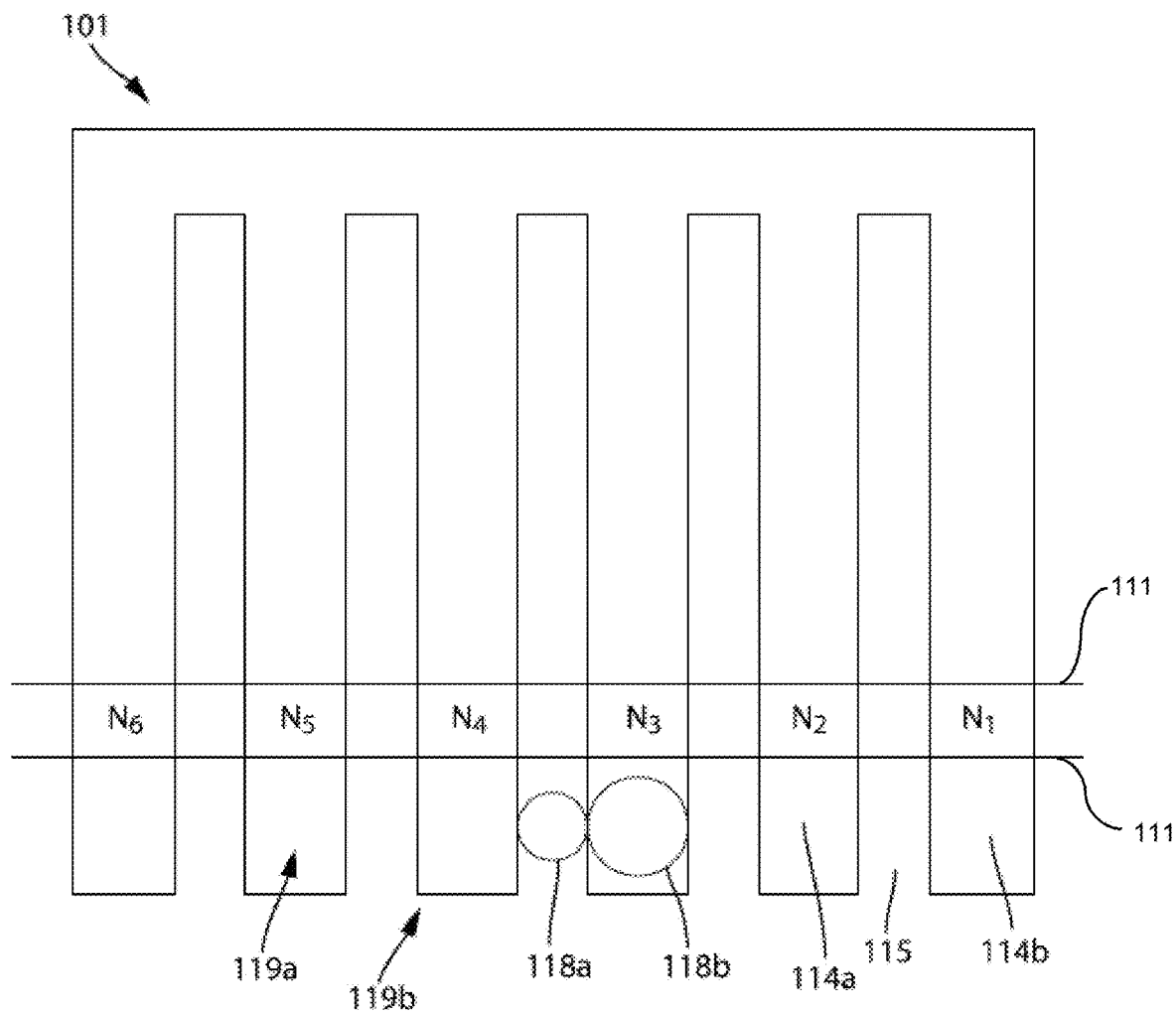
FIG. 13e illustrates an exemplary RF electrode with protrusions.

FIG. 13e illustrates another exemplary RF electrode including protrusions and cutouts. The RF electrode 101 has an electrode area 119a, a border length 119b, and a plurality of protrusions illustrated as $N_{\#}$. The protrusions may define protrusion cutouts (e.g. cutout 115 wherein the cutout may be an opening or gap). The RF electrode 101 may include at least two, three or five protrusions 114 (e.g. 114a, 114b) or more. The protrusions 114 may be separated from one another by cutout 115. Similarly, the RF electrode 101 may include one, two, three or more protrusion cutouts. A first protrusion 114a and a second protrusion 114b of the plurality of protrusions may be arranged generally parallel to one another. The protrusions 114 may be spaced at a fixed interval and may be regularly arranged. Protrusions 114a, 114b may be shaped as rods or pins having a generally linear shape. Protrusions 114a and 114b may be made of a conductive material. Cutout 115 may be filled by air, dielectric, or other electrically insulating material. The distance between protrusions is such distance, that at least one circle 118a which may be hypothetically inscribed into cutout 115 and between two protrusions 114a and 114b. The at least one circle 118a may have a diameter in a range from 0.001 to 30 mmm or 0.005 mm to 15 mm, or from 0.01 mm to 10 mm or 0.01 mm to 8 mm or from 0.01 mm to 7 mm, or from 0.01 mm to 5 mm or from 0.01 mm to 3 mm or from 0.01 mm to 2 mm, wherein each circle may have at least one tangential point located on the first protrusion 114a and at least one tangential point located on the second protrusion 114b. Each circle 118a may have different tangential points. The cutout 115 may be symmetrical and/or asymmetrical along its length. The cutout 115 may create a constant distance between protrusions 114a and 114b. The distance between protrusions 114a and 114b may not be constant along the length of the protrusions. The smallest distance between two nearest protrusions 114a, 114b may be with increasing length of the protrusions increasing and/or decreasing.

The protrusions 114 or cutouts 115 may have symmetrical, asymmetrical, irregular and/or regular shape. The size, shape and/or symmetry of individual protrusions 114 may be the same and/or different across the RF electrode 101. For example, each protrusion 114 may have the same shape, the same dimensions, and/or symmetry.

The protrusions 114 may be characterized by the hypothetically inscribed circle 118b directly into protrusion. The hypothetically inscribed circle 118b to the protrusion 114 may have diameter in a range of 0.001 mm to 30 mm, or of 0.01 mm to 15 mm, or of 0.2 mm to 10 mm, or of 0.2 mm to 7 mm or of 0.1 to 3 mm. The hypothetically inscribed circle may not cross the border of the protrusion in which it is inscribed. The magnetic flux density B measured on at least part of the RF electrode surface area may be in a range of 0.1 T to 5 T, or in range of 0.2 T to 4 T, or in range of 0.3 T to 3 T, or of 0.5 T to 5 T, or in range of 0.7 T to 4 T, or in range of 1 T to 3 T. The magnetic flux density B measured on at least part of the RF electrode surface area may be measured during the treatment. The RF electrode surface area may include surface area of conductive surface of the RF electrode.

The number of protrusions $N_\#$ included in one RF electrode means the highest possible number of conductive areas electrically insulated from each other that may be created between and/or by two parallel cuts 111 across the surface of the RF electrode. The distance between two parallel cuts 111 may be in a range of 1 mm to 50 mm or 2 mm to 35 or 5 mm to 20 mm. The number of protrusions $N_\#$ may be in range of 5 to 1000, or of 10 to 600, or of 20 to 400, or of 50 to 400, or of 100 to 400 or of 15 to 200, or of 30 to 100, or of 40 to 150, or of 25 to 75.

The total number of protrusions in one RF electrode regardless of the parallel cuts 111 may be in the range of 5 to 1000, or of 10 to 600, or of 20 to 400, or of 50 to 400, or of 100 to 400 or of 15 to 200, or of 30 to 100, or of 40 to 150, or of 25 to 140.

The total number of apertures or cutouts in one RF electrode regardless of the parallel cuts 111 may be in the range of 5 to 1000, or of 10 to 600, or of 20 to 400, or of 50 to 400, or of 100 to 400 or of 15 to 200, or of 30 to 100, or of 40 to 150, or of 25 to 140.

The number of apertures, cutouts and/or protrusions in one RF electrode located below the coil including its core may be in a range 5 to 1000, or of 10 to 600, or of 20 to 400, or of 50 to 400, or of 100 to 400 or of 15 to 200, or of 30 to 100, or of 40 to 150, or of 25 to 140.

Number of an individual protrusions included in one RF electrode may be in range of 1 to 8000 or of 2 to 8000 or of 5 to 8000 or of 3 to 5000 or of 5 to 1000 or of 5 to 500 or of 10 to 500 or of 5 to 220 or of 10 to 100 in the area of size 2 cm multiplied 1 cm.

The magnetic flux density B and/or amplitude of magnetic flux density as measured on at least part of the RF electrode 101 may be in a range of 0.1 T to 5 T, 0.2 T to 4 T, 0.3 T to 3 T, 0.7 T to 5 T, 1 T to 4 T, or 1.5 T to 3 T during the treatment. The electrode may be defined by a protrusion density $\rho_p$ according to Equation 1, $$\rho_p = \frac{n}{lB} \quad \text{Equation 1}$$

wherein n symbolize a number of a protrusions intersecting a magnetic field line of force of magnetic flux density $B\ [T]$ and $l\ [cm]$ symbolizes a length of intersected the magnetic field line of force by these protrusions. The length l may be at least 1 cm long and magnetic field line of force may have a magnetic flux density $B\ [T]$ of at least 0.3 T or 0.7 T. The protrusion density according to the treatment device may be in at least part of the RF electrode in a range of 0.3 cm$^{-1}$·T$^{-1}$ to 72 cm$^{-1}$·T$^{-1}$, or of 0.4 cm$^{-1}$·T$^{-1}$ to 10 cm$^{-1}$·T$^{-1}$, or of 0.4 cm$^{-1}$·T$^{-1}$ to 7 cm$^{-1}$·T$^{-1}$, or of 0.5 cm$^{-1}$·T$^{-1}$ to 6 cm$^{-1}$·T$^{-1}$, or of 0.8 cm$^{-1}$·T$^{-1}$ to 5.2 cm$^{-1}$·T$^{-1}$.

Protrusions may be wider (i.e. they may have a greater thickness) where the magnetic flux density is lower and thinner where magnetic flux density is higher. Further, protrusion density $\rho_p$ may be higher where the magnetic flux density is higher.

An electrode area of one or more RF electrodes in one applicator or one additional treatment device may be in a range from 1 cm² to 2500 cm², or 25 cm² to 800 cm², or 30 cm² to 600 cm², or 30 cm² to 400 cm², or from 50 cm² to 300 cm², or from 40 cm² to 200 cm² according to the applicator's floor projection.

The RF electrode may have a border ratio. Border ratio may be defined as the ratio between circumference and area of the electrode. An example of border ratio is shown in FIG. 13e, where the circumference may be depicted as the border length 119b and area of the RF electrode is depicted by the electrode area 119a of the RF electrode according to the applicator's floor projection. The electrode area 119a is the area of the RF electrode without wires supplying the RF electrodes and without sum of the circumference of all apertures and/or cutouts. The border length 119b is the sum of electrode's circumference and all circumferences of apertures inscribed inside the electrode, if there exist any. The border ratio of the RF electrode may be in a range of 150 m$^{-1}$ to 20 000 m$^{-1}$ or of 200 m$^{-1}$ to 10 000 m$^{-1}$ or of 200 m$^{-1}$ to 4000 m$^{-1}$ or of 300 m$^{-1}$ to 10 000 m$^{-1}$ or of 300 m$^{-1}$ to 4000 m$^{-1}$ or of 500 m$^{-1}$ to 4000 m$^{-1}$ or 10 m$^{-1}$ to 20 000 m$^{-1}$ or 20 m$^{-1}$ to 10 000 m$^{-1}$ or 30 m$^{-1}$ to 5 000 m$^{-1}$.

According to the applicator's floor projection, at least one RF electrode may have a border ratio in a range of 150 m$^{-1}$ to 20000 m$^{-1}$ or of 250 m$^{-1}$ to 10000 m$^{-1}$ or of 200 m$^{-1}$ to 4000 m$^{-1}$ or of 300 m$^{-1}$ to 1000 m$^{-1}$ or of 400 m$^{-1}$ to 4000 m$^{-1}$ or of 400 m$^{-1}$ to 1200 m$^{-1}$ or of 500 m$^{-1}$ to 2000 m$^{-1}$ or 10 m$^{-1}$ to 20 000 m$^{-1}$ or 20 m$^{-1}$ to 10 000 m$^{-1}$ or 30 m$^{-1}$ to 5 000 m$^{-1}$ in a locations where a magnetic flux density B on at least part of the RF electrode's surface may be in a range of 0.1 T to 7 T, or of 0.3 T to 5 T, or of 0.5 to 3 T, or of 0.5 T to 7 T, or in a range of 0.7 T to 5 T, or in range of 1 T to 4 T. With increasing magnetic flux density B across the RF electrode area may be an increased border ratio.

The ratio between the border ratio and the magnetic flux density B on RF electrode surface area may be called a charging ratio. The charging ratio may be related to square surface area of RF electrode of at least 1.5 cm² and magnetic flux density in a range of 0.1 T to 7 T, or of 0.3 T to 5 T, or of 0.5 to 3 T, or of 1 T to 5 T, or of 1.2 T to 5 T. The charging ratio of at least part of the RF electrode may be in a range from 70 m$^{-1}$·T$^{-1}$ to 30000 m$^{-1}$·T$^{-1}$, or from 100 m$^{-1}$·T$^{-1}$ to 5000 m$^{-1}$·T$^{-1}$, or from 100 m$^{-1}$·T$^{-1}$ to 2000 m$^{-1}$·T$^{-1}$, or from 120 m$^{-1}$·T$^{-1}$ to 1200 m$^{-1}$·T$^{-1}$, or from 120 m$^{-1}$·T$^{-1}$ to 600 m$^{-1}$·T$^{-1}$ or from 230 m$^{-1}$·T$^{-1}$ to 600 m$^{-1}$·T$^{-1}$. Square surface area of RF electrode may include a surface area having square shape.

With higher border ratio and/or charging ratio, induced unwanted physical effects in the RF electrode may be lower because the RF electrode may include partially insulated protrusions from each other. With higher border ratio and/or charging ratio, possible hypothetically inscribed circles into protrusions has to be also smaller and so loops of induced eddy current has to be smaller. Therefore, induced eddy currents are smaller and induced unwanted physical effect induced in the RF electrode is lower or minimized.

The ratio between an area of one side of all RF electrodes (floor projection) and one side of all winding areas of all magnetic field generating devices (area A2 as shown in FIG. 9a) in one applicator and according to its floor projection may be in a range of 0.1 to 15, or of 0.5 to 8, or of 0.5 to 4, or of 0.5 to 2.

Figure 16:
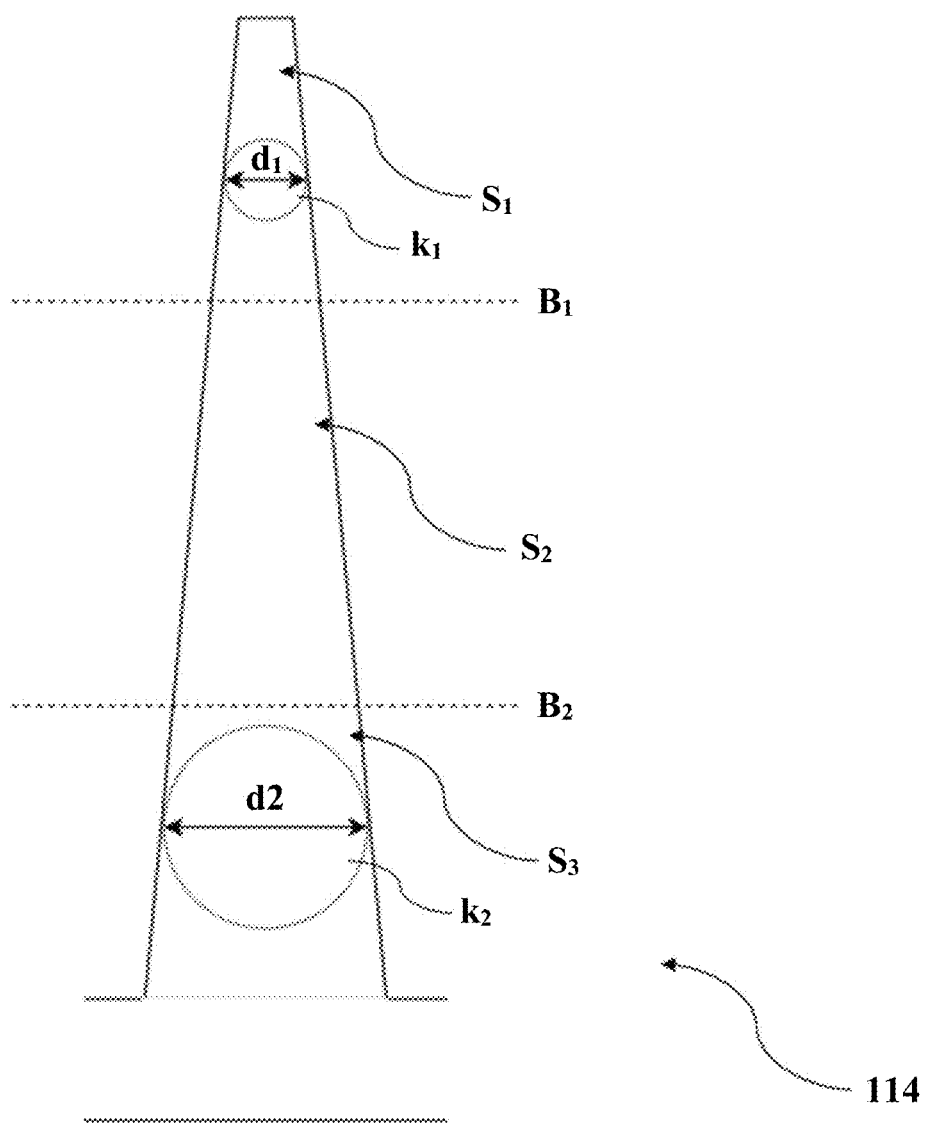
FIG. 16 illustrates one exemplary protrusion intersecting magnetic field lines with a difference higher than 0.1 T.

As illustrated in FIG. 16, if one protrusion 114 is intersected by magnetic field lines $B_1$ and $B_2$ where absolute value of $|B_1|$ is higher than absolute value of $|B_2|$ and $|B_1|-|B_2|0.05<1$ T, then the protrusion may be divided into three areas by lines of forces $B_1$ and $B_2$. In other words, the protrusion 114, as is illustrated in FIG. 16, may be divided into thirds $S_1$, $S_2$, $S_3$ that have the same length according to direction of magnetic field gradient and $S_1$ is exposed to higher magnetic flux density than $S_3$. Area $S_1$ may be placed in the highest magnetic flux density, $S_2$ may be placed in middle magnetic flux density and $S_3$ may be placed in the lowest magnetic flux density. The maximal hypothetically inscribed circle $k_1$ with diameter $d_1$ inscribed in the area $S_1$ may have smaller diameter than the maximal inscribed circle $k_2$ with diameter $d_2$ inscribed in the area $S_3$. The diameter $d_2$ may be greater than diameter $d_1$ of 2% to 1500%, or of 5% to 500%, or of 10% to 300%, or of 10% to 200%, or of 10% to 100%, or of 5% to 90%, or of 20% to 70%, or 5% to 20% of the diameter $d_1$. In such case, protrusions may be thinner where the magnetic flux density is higher, such as at least partially pyramidal shape of the protrusion may be created. In addition, protrusions may be thinner where magnetic flux density is higher.

The RF electrode may have different sizes and shapes. According to the invention, bipolar electrodes may be parallel electrodes, such as shown in FIGS. 14a-14e, or concentric electrodes it is shown in FIGS. 15a-15c. The same type of RF electrodes 101 illustrated in FIGS. 14a-14e and FIGS. 15a-15c that may be located close to the second side portion of the applicator may be used as RF electrodes 102 located close to the first side portion and/or for any other one or more RF electrodes.

Shape and arrangement of RF electrodes of at least one applicator may be based on size shape and symmetry of body location (anatomy) where at least one applicator will be attached. Positioning and different shapes of the RF electrode may be beneficial in order to avoid creating of hot spots, provide homogeneous heating of as large treated body area, as possibility to avoid needs of moving with one or more applicators.

Figure 14A:
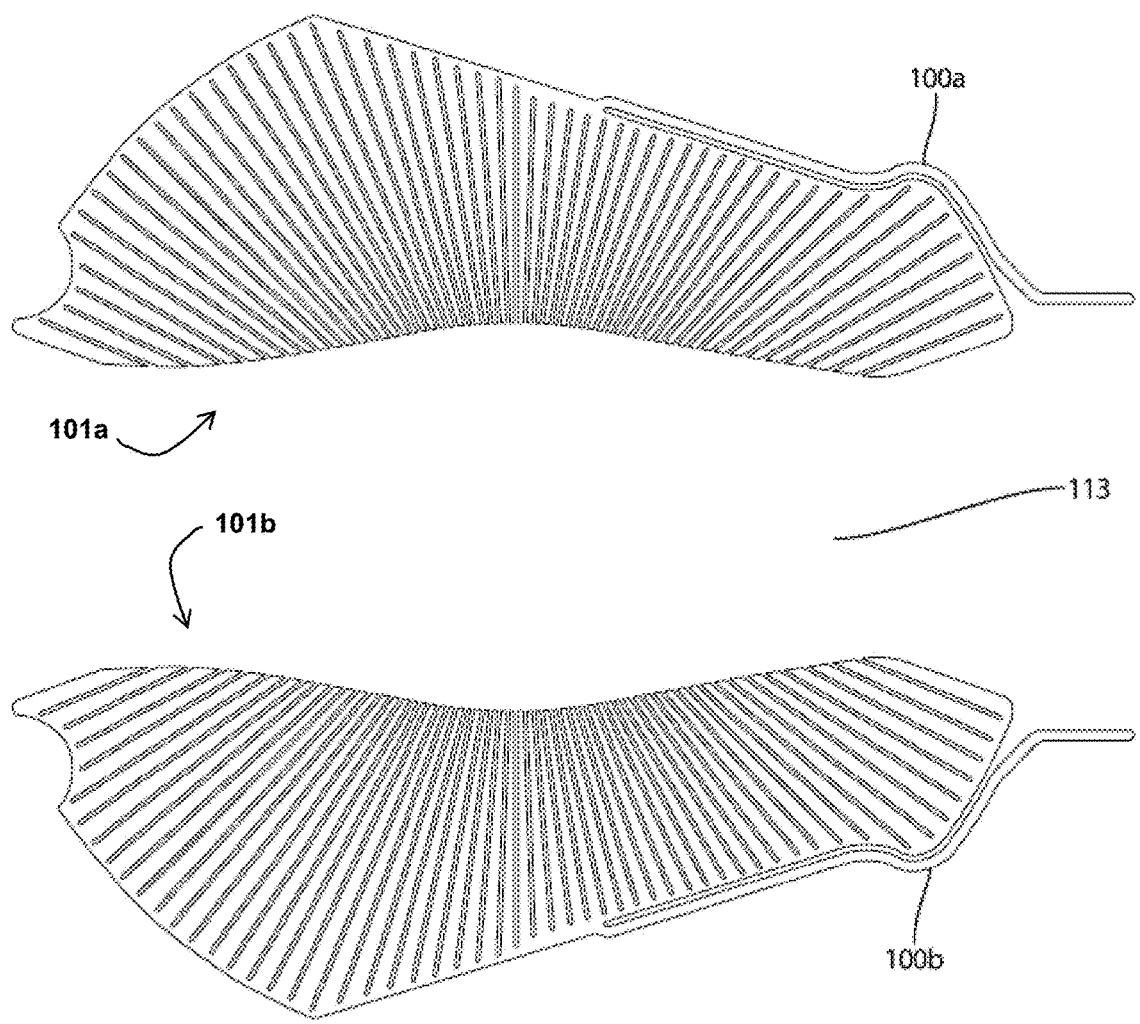
FIGS. 14a-14e illustrate a parallel pair of bipolar RF electrodes with protrusions.
Figure 14B:
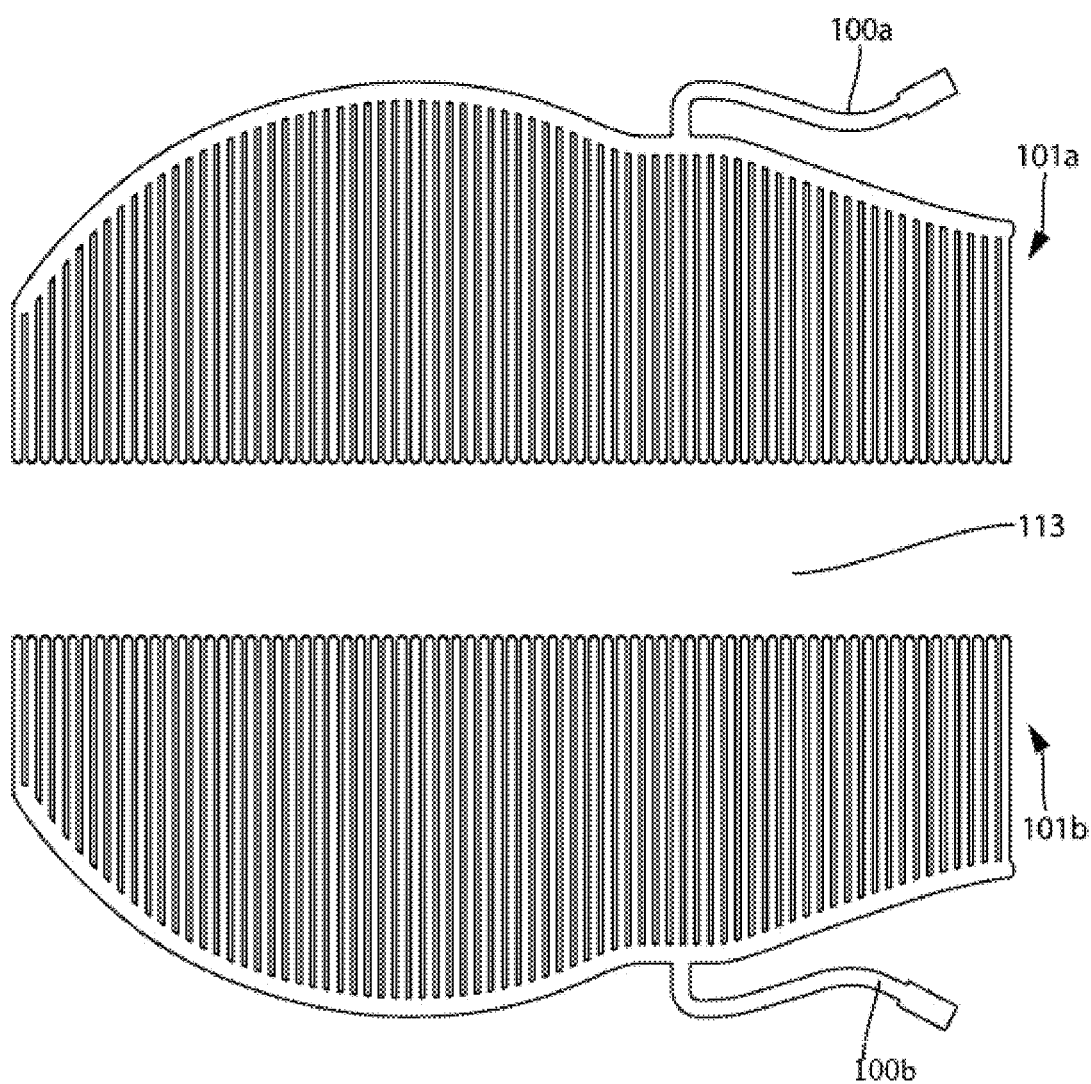
Figure 14C:
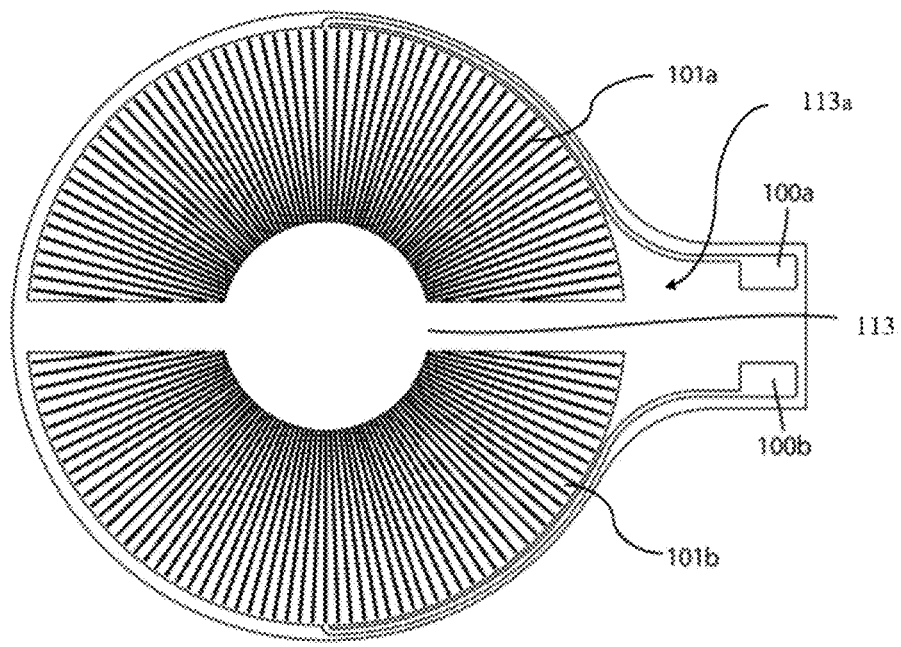
Figure 14D:
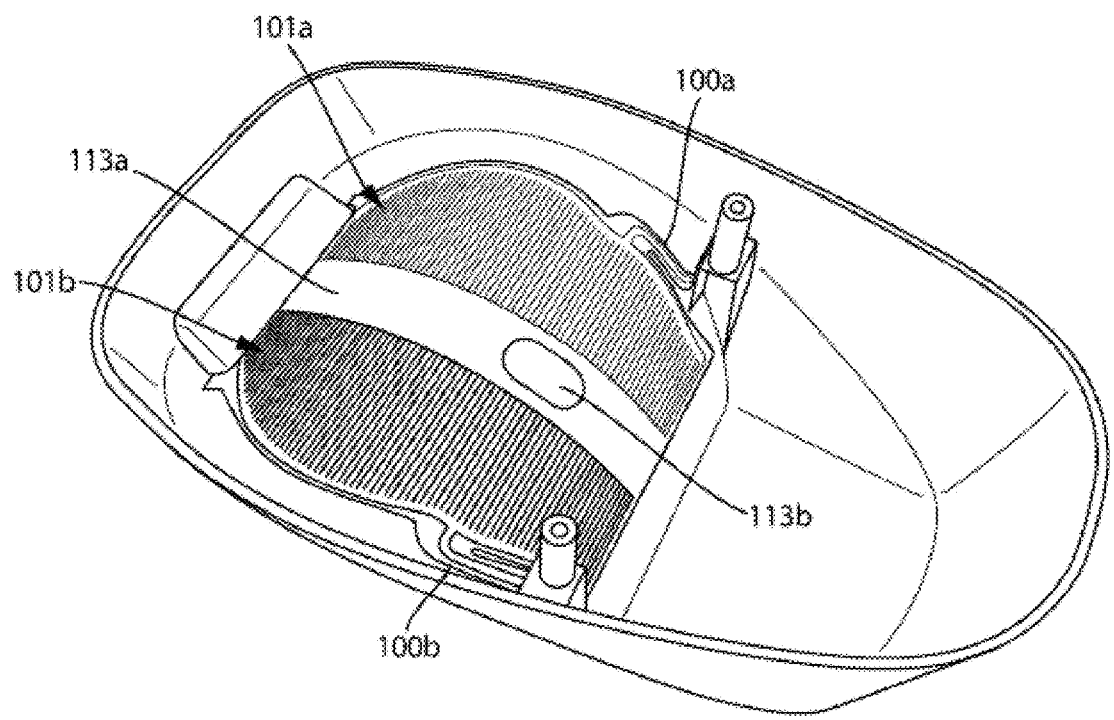
Figure 14E:
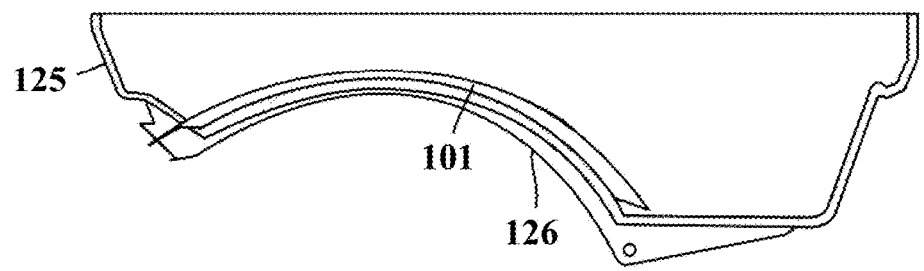
Figure 15A:
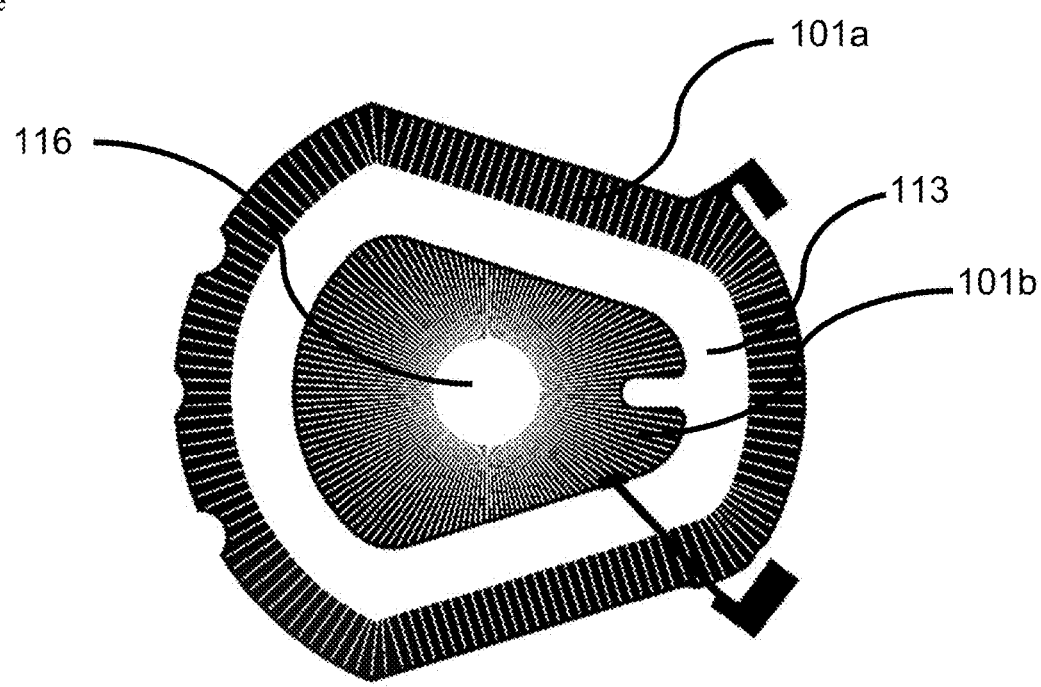
FIGS. 15a-15c illustrate bipolar RF electrode pairs with protrusions, wherein a first RF electrode at least partially encircle a second RF electrode of RF electrodes pair.
Figure 15B:
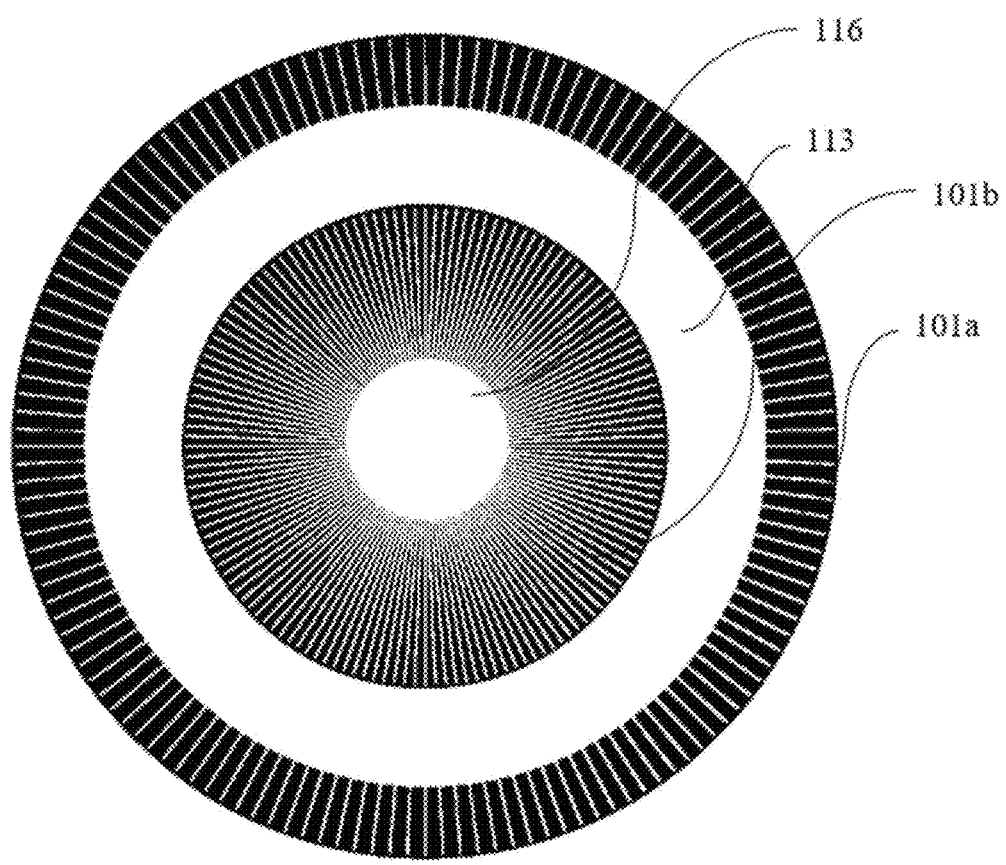
Figure 15C:
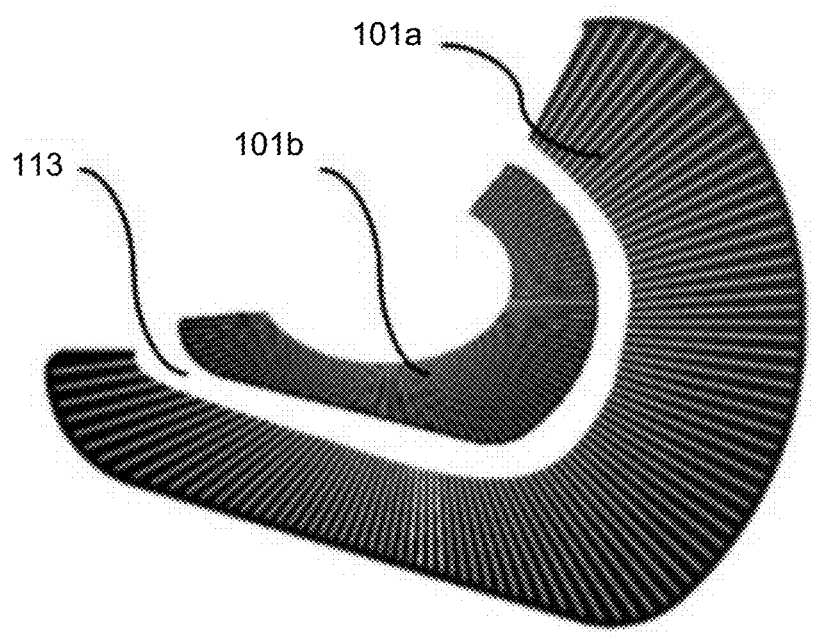

FIG. 14a illustrates an example of symmetrical positioning of RF electrodes. FIG. 14b illustrates another example of symmetrical positioning of RF electrodes. FIG. 14c illustrates still another example of symmetrical positioning of RF electrodes. FIG. 14d illustrates view of an applicator including symmetrical positioning of RF electrodes. FIG. 14e illustrates a side view of an applicator including example of symmetrical positioning of RF electrodes.

According to examples of RF electrodes shown in FIGS. 14a-14e, the applicator may include at least one pair of parallel bipolar RF electrodes 101a and 101b spaced by a gap 113. The RF electrodes are powered by wiring 100a and 100b. As illustrated in FIGS. 14a, 14b and 14d, RF electrodes 101a, 101b may be symmetrical, and may be mirror images. The shape of individual RF electrodes 101a and 101b may be irregular or asymmetrical wherein the length and/or area of at least 40%, 50%, 70%, 90%, or 99% of all protrusions in one RF electrode may be different. Body anatomy and testing may prove that such kind of RF electrodes could provide the most comfortable and efficient treatment of body areas, such as abdomen area, buttock, arms and/or thighs.

As illustrated in FIG. 14c, RF electrodes 101a, 101b may be at least partially symmetrical according to at least one axis or point of symmetry, such as according to linear symmetry, point symmetry, and rotational symmetry. For example, each electrode may be semi-circular or C-shaped. Further, the gap 113 between RF electrodes 101a and 101b may be irregular and/or may be designed according to at least one axis of symmetry, such as linear axis of symmetry with mirror symmetry. Thus, in case when electrodes 101a and 101b may be semi-circular, gap 113 may be circular. Use of such symmetrical electrode may be beneficial for treating body area where such symmetry may be required to highlight symmetry of body area (e.g. buttocks or hips).

The gap 113 between RF electrodes 101a and 101b may include air, cooling fluid, oil, water, dielectric material, fluid, and/or any other electric insulator, such as a substrate from composite material used in printed board circuits. The RF electrode 101a and 101b may be formed from copper foil and/or layer deposited on such substrate. The gap 113 may influence a shape of the electromagnetic field (e.g. RF field) produced by RF electrodes and the depth of electromagnetic field penetration into a patient's body tissue. Also, the distance between the at least two RF electrodes 101a and 101b may create the gap 113 which may have at least partially circular, elliptic and/or parabolic shape, as illustrated in FIGS. 14a. The gap 113 may have regular shape for spacing RF electrodes with constant distance as illustrated in FIG. 14b.

The gap 113 between the RF electrodes 101a and 101b may be designed to provide a passage of amount in the range of 2% to 70% or 5% to 50% or 15% to 40% of the magnetic field generated by the magnetic field generating device. The distance between the nearest parts of at least two different RF electrodes in one applicator may be in a range of 0.1 cm to 25 cm, or of 0.2 cm to 15 cm, or of 2 cm to 10 cm, or of 2 cm to 5 cm.

The gap 113 between two RF electrodes may be designed in a plane of the RF bipolar electrodes wherein the gap 113 may at least partially overlay a location where the magnetic flux density generated by the magnetic field generating device has the highest absolute value. The gap 113 may be located in such location in order to optimize treatment efficiency and minimize energy loss.

It should be noted that strong magnetic field having high derivative of the magnetic flux density dB/dt may induce unwanted physical effects even in the RF electrode with protrusions, apertures and/or cutouts. The gap 113 may be positioned or located in the location where the absolute value of magnetic flux density is highest. As a result, the plurality of RF electrodes positioned around the gap 113 may be then affected by lower amount of magnetic flux density.

Plurality of RF electrodes (e.g. two RF electrodes 101a and 101b) may be located on a substrate 113a as shown in the FIG. 14d. Substrate 113a may be used as filler of the gap 113 between RF electrodes and of one or more cutouts 115. As shown in FIGS. 14d and 25, the substrate 113a and one or more RF electrodes may be curved into required shape and/or radius to fit to patient's body area. RF electrodes 101a or 101b may be curved along a lower cover 125 of applicator 800, particularly along a curved portion 126 of lower cover 125. As shown in FIG. 14d, the substrate 113a may define a substrate gap 113b for at least one sensor, such as temperature sensor. Substrate gap 113b may further enable passage of one or more wires, cooling fluid, and/or for implementing another treatment energy source, such as a light treatment energy source (e.g. LED, laser diode) providing illumination or additional heating of the biological structure and/or body area.

FIGS. 15a, 15b and 15c illustrate two RF electrodes 101a and 101b, wherein at least one RF electrode 101a may at least partially surround another RF electrode 101b. The RF electrodes 101a and 101b may be spaced by gap 113 including e.g. substrate 113a with the same insulating properties as described above with respect to FIGS. 14a-14e. RF electrode 101b may include a hole 116 in order to minimize shielding of magnetic field and inducing of unwanted physical effects induced in the RF electrode 101b. The hole 116 may be located in the RF electrode plane where the magnetic flux density of the magnetic field generated by magnetic field generating device reaches highest values during the treatment. The hole 116 may be circular, or may have other shapes, such as oval, square, triangle, or rectangle, among others. The hole 116 may have an area of 0.05 $cm^2$ to 1000 $cm^2$, or 0.05 $cm^2$ to 100 $cm^2$, or of 3 $cm^2$ to 71 $cm^2$, or of 3 $cm^2$ to 40 $cm^2$, or of 3 $cm^2$ to 20 $cm^2$, or of 3 $cm^2$ to 15 $cm^2$, or of 0.5 $cm^2$ to 2.5 $cm^2$. The RF electrodes may be fully or partially concentric.

FIG. 15a illustrates two RF electrodes 101a and 101b may which be noncircular with at least one linear and/or point symmetry. Shown electrodes 101a and 101b may have no centre of symmetry. Shown RF electrode 101a may include a hole 116 in its centre where the magnetic flux density is the highest in order to minimize induction of unwanted physical effect in the RF electrode by magnetic field.

FIG. 15b illustrates two RF electrodes 101a and 101b may have a circular shape with rotational symmetry. The RF electrodes 101a and 101b may have the same centre of symmetry. Shown RF electrode 101a may include a hole 116 in its centre where the magnetic flux density is the highest in order to minimize induction of unwanted physical effects in the RF electrode by magnetic field.

FIG. 15c illustrates two RF electrodes 101a and 101b may have no symmetry and no centre of symmetry.

Another option of minimizing or elimination of unwanted physical effects induced in the RF electrode by magnetic field may include reducing the thickness of the RF electrode.

Thickness of the conductive layer of RF electrode of the invention may be in a range of 0.01 mm to 10 mm, or of 0.01 mm to 5 mm, or of 0.01 mm to 3 mm, or of 0.01 mm to 1 mm, or 0.1 mm to 1 mm, or of 0.005 mm to 0.1 mm, or of 0.01 mm to 0.2 mm. One type of the RF electrode may be designed by a similar method as printed circuit boards (PCB) are prepared, wherein a thin, conductive layer may be deposited into and/or onto a substrate with insulating properties. The substrate may include one, two or more conductive layers from a material such as copper, silver, aluminum, alloys of nickel and zinc, austenitic stainless steel and/or other materials, creating the RF electrode. The thickness of substrate material may be in a range of 0.01 mm to 10 mm, or of 0.01 mm to 5 mm, or of 0.01 mm to 3 mm, or of 0.01 mm to 2 mm, or of 0.1 mm to 2 mm, or of 0.5 mm, to 1.5 mm or of 0.05 mm to 1 mm. The substrate material may be polymeric, ceramic, copolymeric sheet, phenol resin layer, epoxy resin layer, fiberglass fabric other textile fabric, polymeric fabric and/or other. The substrate may be at least partially flexible and/or rigid.

The RF electrode may be system of thin, conductive wires, flat stripes, sheets or the like.

Still another option of minimizing or elimination of unwanted physical effects induced in the RF electrode by magnetic field may include forming the RF electrode from a conductive material that reduces induction of unwanted physical effects and heating of the RF electrode.

The RF electrodes may be made of specific conductive materials reducing induction of unwanted physical effects in the RF electrode. Such materials may have relative permeability in a range of 4 to 1,000,000, or of 20 to 300,000, or of 200 to 250,000, or of 300 to 100,000, or of 300 to 18,000, or of 1,000 to 8,000. Material of the RF electrode may include carbon, aluminum, copper, nickel, cobalt, manganese, zinc, iron, titanium, silver, brass, platinum, palladium and/or others from which may create alloys, such as Mu-metal, permalloy, electrical steel, ferritic steel, ferrite, stainless steel of the same. In addition, the RF electrode may be made from mixed metal oxides and/or fixed powder from metal oxides, metal from m-metal elements to minimize induction of eddy currents and heating of the RF electrode and also in order to minimize energy loss of time-varying magnetic field.

One or more RF electrodes providing RF energy during the treatment by described treatment device may use at least one options, at least two options and or combination of options how to minimize or eliminate unwanted physical effects induced by magnetic field as described above. Also one or more characterization of the option may be used for manufacture, design and operation of the treatment device of invention.

The treatment device combining RF treatment with magnetic treatment may include one or more treatment circuits. The treatment circuit for RF treatment may include power source, RF electrode and/or all electrical elements described herein for RF cluster. The treatment circuit for magnetic treatment may include power source, magnetic field generating device, all electrical elements described herein for magnetic cluster HIFEM. Plurality of treatment circuits providing same or different treatment may include common power source. Alternatively, each treatment circuit may include its own power source. Operation of all treatment circuits may be regulated by one master unit or one or more control units. The HMI, master unit and/or one or more control unit may be used for selection, control and/or adjustment of one or more treatment parameters for each applicator and/or each treatment energy source (e.g. RF electrode or magnetic field generating device. Treatment parameters may be selected, controlled and/or adjusted by HMI, master unit and/or one or more control unit independently for each applicator.

Figure 17:
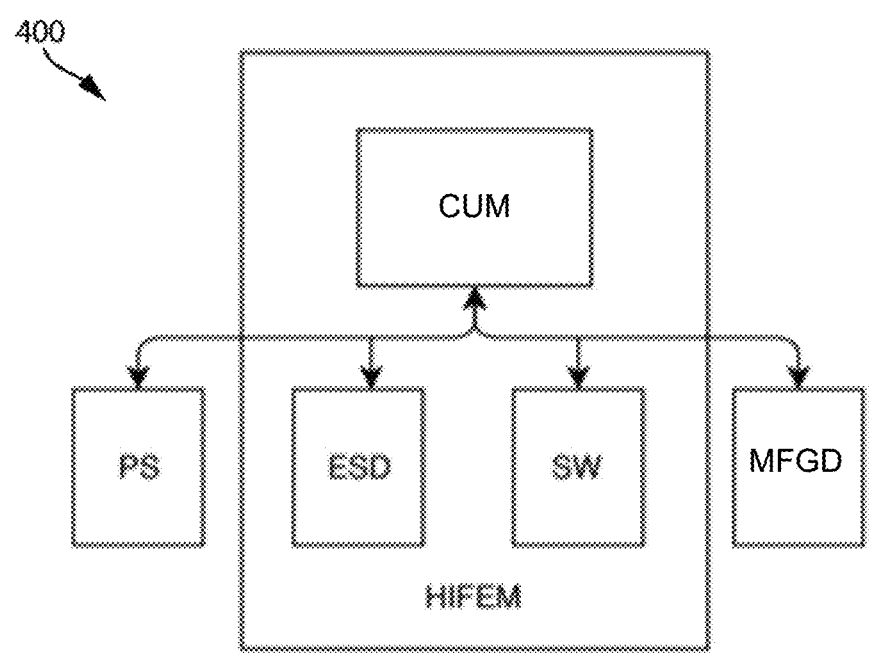
FIG. 17 illustrates an exemplary schema of a magnet circuit.

FIG. 17 illustrates exemplary electrical elements of a magnetic circuit 400. The electrical signal passing through the magnetic circuit 400 may be transformed into a form of one or more pulses of electrical signal. The electric pulses may be provided to magnetic field generating device in order to generate impulses of time-varying magnetic field. Individual electrical elements of the magnetic circuit may be a power source (PS), an energy storage device (ESD), a switch (SW), magnetic field generating device (MFGD) and control unit of magnetic circuit (CUM). The magnetic circuit may include treatment cluster for magnetic treatment called as HIFEM cluster. The HIFEM cluster may include e.g. ESD, SW and/or CUM. Control unit of magnetic circuit CUM may be part of the control system. Control unit of magnetic cluster CUM and/or other electrical element of magnetic circuit may be slave of the master unit. The HIFEM cluster, control system and/or CUM may provide or control storage of electric energy in ESD by controlling the amount of stored electrical energy. HIFEM cluster, control system and/or CUM may provide modification of electrical signal, adjustment of parameters of electric signal transferred through HIFEM cluster, safe operation of the circuit and/or charging or recharging of the ESD. For example, the HIFEM cluster or control system may provide adjustment of magnetic flux density of magnetic field provided by MFGD by adjustment of voltage and/or current of electrical pulses transferred to MFGD. Modification of the electrical signal may include a distortion of signal transmitted in magnetic circuit, envelope distortion in shape, amplitude and/or frequency domain, adding noise to the transferred electrical signal and/or other degradation of transmitted original signal entering the magnetic circuit.

Figure 18A:
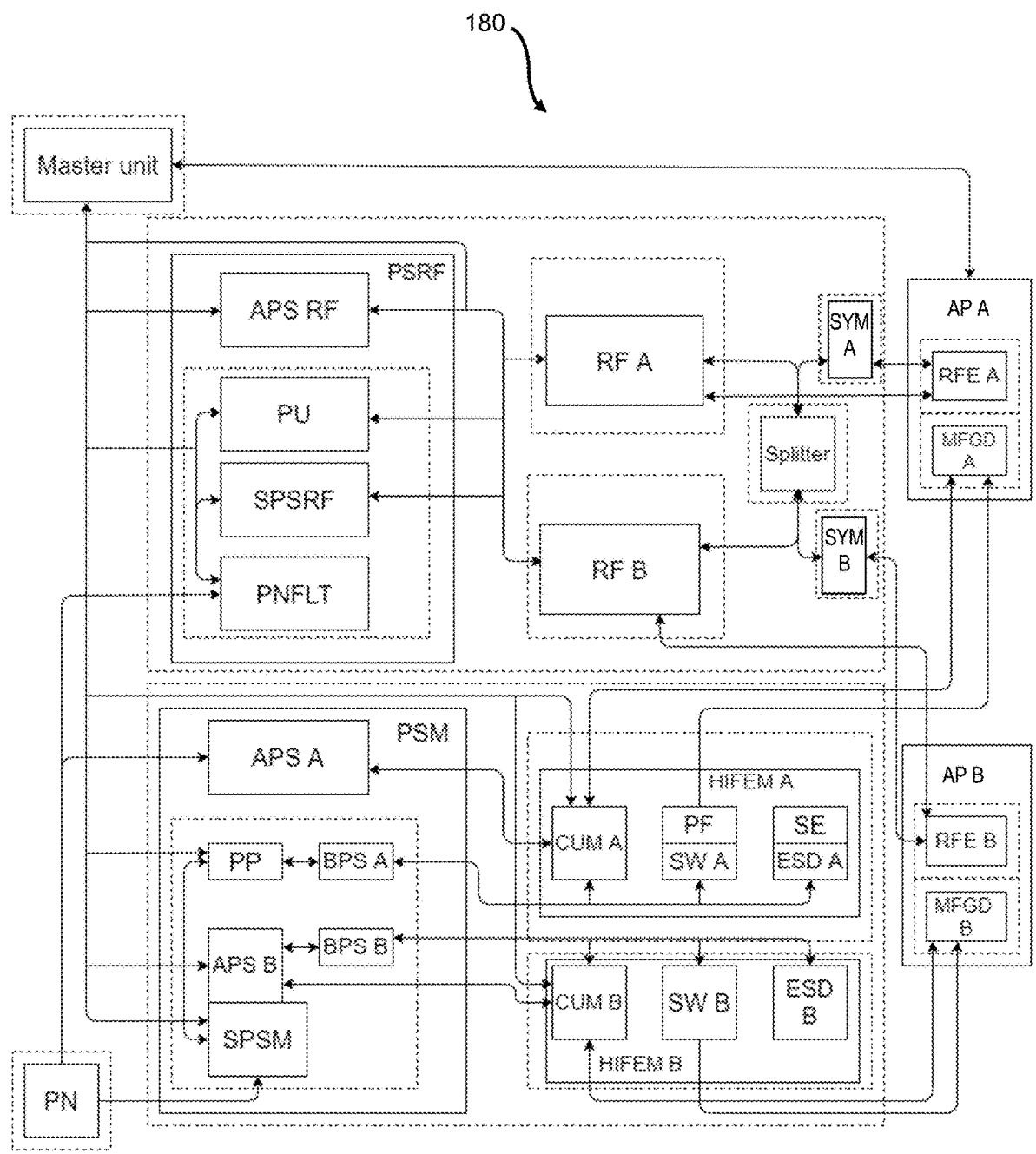
FIG. 18a illustrates an exemplary schema of electrical elements of treatment device.

The energy storage device ESD, may accumulate electrical energy, which may be provided to magnetic field generating device in the form of electric signal (e.g. in form of high power impulses) of energy. The ESD may include one, two, three or more capacitors. The ESD may also include one or more other electrical elements such as a safety element, such as a voltage sensor, a high voltage indicator, and/or discharging resistors, as shown in FIG. 18*a*. The voltage sensor and the high voltage indicator may provide feedback information to the switch SW and or to control unit CUM. The discharging resistor being a part of the may provide discharging of at least one capacitor in case of hazardous situation. Discharging of one or more ESD may be controlled by the control unit CUM. Released electrical energy from the ESD may be delivered as high power impulse and/or pulse to at least part of the magnetic circuit e.g. to the magnetic field generating device MFGD.

A capacitance of energy storage device may be in the range of 5 nF to 100 mF, or in the range of 25 nF to 50 mF, or in the range of 100 nF to 10 mF, or in the range of 1 µF to 1 mF, or in the range of 5 µF to 500 µF or in the range of 10 µF to 180 µF, or in the range of 20 µF to 80 µF.

The energy storage device may be charged on a voltage in a range from 250 V to 50 kV, 700 V to 5 kV, 700 V to 3 kV, or 1 kV to 1.8 kV.

The energy storage device may provide a current pulse discharge in a range from 100 A to 5 kA, 200 A to 3 kA, 400 A to 3 kA, or 700 A to 2.5 kA. The current may correspond with a value of the peak magnetic flux density generated by the magnetic field generating device.

By discharging of the energy storage device, a high power current pulse may be produced with an energy in a range of 5 J to 300 J, 10 J to 200 J, or 30 J to 150 J.

The switch SW may include any switching device, such as a diode, pin diode, MOSFET, JFET, IGBT, BJT, thyristor and/or a combination thereof. The switch may include a pulse filter providing modification of the electrical signal. The pulse filter may suppress switching voltage ripples created by the switch during discharging of the ESD.

The magnetic circuit may be commanded to repetitively switch on/off the switch SW and discharge the energy storage device ESD to the magnetic field generating device, e.g. the coil in order to generate the time-varying magnetic field.

An inductance of the magnetic field generating device may be up to 1 H, or in the range of 1 nH to 500 mH, 1 nH to 50 mH, 50 nH to 10 mH, 500 nH to 1 mH, or in the range of 1 µH to 500 µH or in the range of 10 µH to 60 µH.

The magnetic field generating device may emit no radiation (e.g. gamma radiation).

The magnet circuit may include a series connection of the switch SW and the magnetic field generating device. The switch SW and the magnetic field generating device together may be connected in parallel with the energy storage device ESD. The energy storage device ESD may be charged by the power source PS. After that, the energy storage device ESD may be discharged through the switch SW to the magnetic field generating device MFGD. During a second half-period of LC resonance, the polarity on the energy storage device ESD may be reversed in comparison with the power source PS. As a result, there may be twice the voltage of the power source. Hence, the power source and all parts connected in the magnetic circuit may be designed for a high voltage load and protective resistors may be placed between the power source and the energy storage device.

The magnetic field generating device MFGD and an energy storage device ESD may be connected in series. The magnetic field generating device MFGD may be disposed in parallel to the switch SW. The energy storage device ESD may be charged through the magnetic field generating device. To provide an energy impulse to generate a magnetic impulse (or pulse to generate a magnetic pulse), controlled shorting of the power source takes place through the switch SW. In this way the high voltage load at the terminals of the power source PS during the second half-period of LC resonance associated with known devices is avoided. The voltage on the terminals of the power source PS during second half-period of LC resonance may have a voltage equal to the voltage drop on the switch SW.

The switch may be any kind of switching device. Depending on the type of the switch, the load of the power source may be reduced to a few Volts, e.g., 1-10 volts. Consequently, it is not necessary to protect the power source from a high voltage load, e.g., thousands of Volts. Accordingly, the use of protective resistors and/or protection circuits may be reduced or eliminated.

Figure 18B:
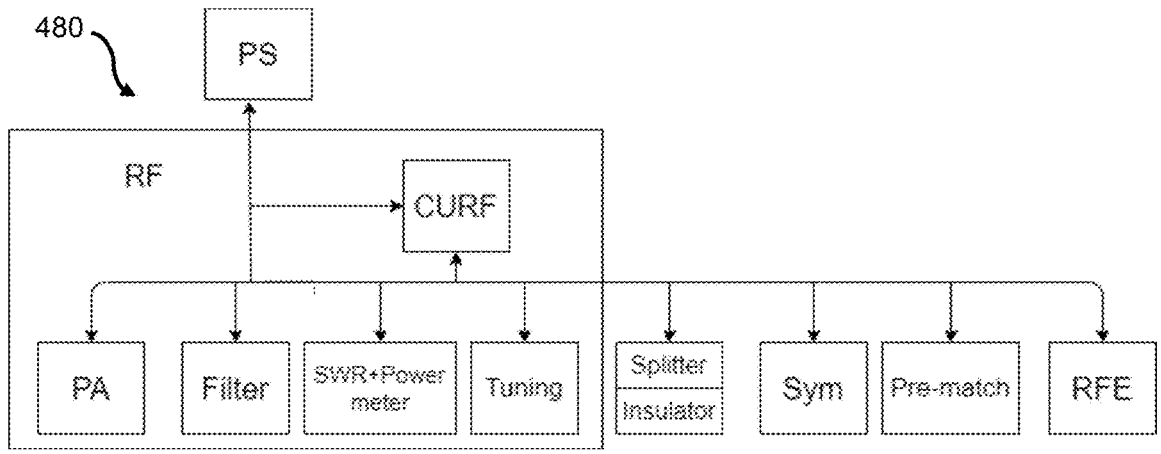
FIG. 18b illustrates exemplary schema of a RF circuit.

FIG. 18*b* illustrates exemplary electrical elements of an RF circuit 480. The RF circuit may provide an adjusted and/or modified electromagnetic signal (electrical signal) to an RF electrode (RFE). The RF circuit may include power source (PS), treatment cluster for RF treatment (area marked as RF), control unit of RF cluster (CURF), power amplifier (PA), filter, standing wave ratio combined with power meter (SWR+Power meter), tuning element (tuning), splitter, insulator, symmetrisation element (SYM), pre-match and RF electrode (RFE). Treatment cluster for RF treatment may include e.g. control unit of RF cluster (CURF), power amplifier (PA), filter, standing wave ratio combined with power meter (SWR+Power meter) and/or tuning element (tuning). Control unit of RF circuit CURF may be part of the control system. Control unit of RF circuit CURF and/or other electrical element of RF circuit may be slave of the master unit. One or more electrical elements described as a part of RF circuit may be dismissed, some of the electrical elements may be merged to one with similar function and/or some of the electrical elements may be added to improve functionality of the circuit.

The power source of the RF circuit may provide electric signal of voltage in a range of 1 V to 5 kV, or 5 V to 140 V, or 10 V to 120 V, or 15 V to 50 V, or 20 V to 50 V.

The CURF may control operation of any electrical element of RF circuit. The CURF may regulate or modify parameters of the electrical signal transferred through the RF circuit. Parameters of the signal, e.g., voltage, phase, frequency, envelope, value of the current, amplitude of the signal and/or other may be influenced by individual electrical elements of the RF circuit that may be controlled by CURF, control system and/or electrical properties of individual electrical elements of RF circuit. Electrical elements influencing signal in the RF circuit may be, for example, a power source (PS), a power amplifier (PA), a filter, a SWR+Power meter, a tuning, a splitter, an insulator, symmetrisation element changing unbalanced signal to balanced signal (SYM), pre-match and/or RF electrode generating RF waves. Modification of the electrical signal may include a distortion of signal transmitted in RF circuit, envelope distortion in shape, amplitude and/or frequency domain, adding noise to the transferred electrical signal and/or other degradation of transmitted original signal entering the RF circuit.

The power amplifier PA may produce RF signal of respective frequency for generation of RF waves by RF electrode. The power amplifier may be MOSFET, LDMOS transistor or vacuum tube. The PA may be able to increase an amplitude of provided signal and/or modified signal to electric signal (e.g. RF signal).

The filter may include one or more filters which may suppress unwanted frequency of signal transmitted from the power amplifier. One or more filters may filter and provide treatment with defined band of frequencies. One or more filters may be used to filter the electrical signal such as electric signal in the RF circuit, according to signal frequency domain to let pass only band of wanted frequencies. The filter may be able to filter out unsuitable signal frequencies based on internal software and/or hardware setting of the filter. The filter may operate according to communication with other one or more electrical elements e.g. the CURF. The one or more filters may be located between a power source of RF signal PSRF and the RFE.

The SWR+Power meter may measure output power of RF energy and evaluate the quality of impedance matching between the power amplifier and applicator. The SWR+Power meter may include a SWR meter that may measure the standing wave ratio in a direction of a wave transmission. The SWR+Power meter may include a power meter that may measure amplitude of such standing waves. The SWR+Power meter may communicate with the CURF and/or with the tuning element. The SWR+Power meter may provide a feedback information in order to prevent creation of the standing wave in the patient's body, provide better signal adjustment by the tuning element and to provide safer treatment and energy transfer to biological structure more effectively in more targeted manner.

Tuning element may provide improvement of the impedance matching. The tuning element may include, e.g. capacitor, LC and/or RLC circuit. The tuning element may provide controlled tuning of the RF circuit system capacity, wherein the RF circuit system includes individual electrical elements of the RF circuit and also currently treated tissue of the patient under the influence of the provided RF waves. Tuning of the RF circuit may be provided before and/or during the treatment. The tuning element may also be called a transmatch.

The symmetrisation element SYM may convert the signal from unbalanced input to balanced output. The SYM may be a balun and/or a balun transformer including wound coaxial cable to balance signal between RF electrodes. The SYM element may provide signal symmetrisation between the first and the second bipolar RF electrode e.g. by creating $\lambda/2$ phase shift of the RF signal guided through the coaxial cables to the first and the second bipolar RF electrode.

The splitter may split the RF signal transferred/delivered in the RF circuit by a coaxial cable. Divided signal may have the same phase of each divided signal part and/or the divided signals may have constant phase shift from each other. For example, the splitter may provide one part of the RF signal to a first RF electrode and second part of the RF signal to a second RF electrode of a bipolar electrode. The splitter may be shared for one two or more independent RF circuits or each RF circuit may have its own splitter.

An insulator may be combined with the splitter and/or may be located before and/or after splitter with regard of transporting RF signal to the RF electrode. The insulator may be electrical insulation of at least part of the RF circuit from the magnetic circuit. The insulator may be used to minimize influence of the magnetic circuit to the RF circuit.

The pre-match may be used in the devices using coaxial cables. The pre-match may include a small coil, condenser and/or resistor.

The RF electrode (RFE), acting as a treatment energy source, may include one or more unipolar RF electrodes, one or more monopolar RF electrodes and/or one or more pairs of bipolar RF electrodes.

The power source PS of the RF circuit, power amplifier PA, filter, SWR+Power meter, tuning, SYM, splitter, insulator and/or pre-match may be at least partially and/or completely replaced by an HF generator supplying the rest of the circuit, including the RF electrode, with a high frequency electric signal.

FIG. 24 illustrates one of examples of the symmetrisation element SYM. Input coaxial cable 130 provides electrical signal (e.g. RF signal) to the splitter 131 that may split RF signal into two branches. The splitter 131 may also include an insulating element, such as at least one, two, three or more serial connected capacitors creating insulating length in a range of 4 mm to 100 mm, or 20 mm to 50 mm. The SYM may be established or represented by the different length of the coaxial cables guided or leading to pair of bipolar RF electrodes. The difference in length between coaxial cables 132 and 133 in location $l_1$ may be in a range of 0.4 to 0.6, or 0.46 to 0.55 of the $\lambda$, where $\lambda$ may be wavelength of the guided RF signal in the coaxial cable 132 and/or coaxial cable 133. The length of the coaxial cable 132 may be in a range of 1 cm to 5 m, 5 cm to 90 cm or 10 cm to 50 cm. The length of the coaxial cables 132+135b may be in a range of k/4 10%, or ±5%, or their multiples by positive integer. The length of the coaxial cable 133 may be in a range of 2 m to 12 m, or 2.2 m to 8 m. The length of the coaxial cable 133 may be in a range of $\lambda/2\pm10\%$, or ±5%, plus the length of cable 132. The length of the coaxial cables 133+135a may be in a range of $3\lambda/4\pm10\%$, or ±5%. In a summary the coaxial cables 132+135b are shifted in relation to the coaxial cables 133+135a of $\lambda/2$ 10%, or ±5%. This part of the SYM may cause phase shift 180° of the RF signal delivered to one RF electrodes 101a and 101b. The RF electrodes 101a and 101b may be part of one applicator or the RF electrode 101a may be part of first applicator and RF electrode 101b may be part of second applicator. A connector 134 may be used for connecting one or more applicators to the main unit. The part 12 may represent a connecting tube of the applicator. The length of the coaxial cables 135a and 135b in this connecting tube may be in a range of 1 m to 6 m, or of 1.1 m to 4 m or of $\lambda/4\pm10\%$ or ±5%. A pairing element 136 may be conductive connection of the conductive shielding part of the coaxial cables 135a and 135b. The pairing element 136 may have a surface area in a range of 0.5 $cm^2$ to 100 $cm^2$, 1 $cm^2$ to 80 $cm^2$ or 1.5 $cm^2$ to 50 $cm^2$. The pairing element 136 may include material of height electric conductivity, such as copper, silver, gold, nickel, or aluminum, wherein the impedance of the pairing element 136 may be near to zero. The pairing element 136 or between pairing element and electrode may be placed a capacitor, resistor and/or inductor.

The RF circuit and/or the magnetic circuit may be at least partially located in one or more applicators. The wire connection between the applicator, an additional treatment device and/or the main unit may be also considered as a part of the RF circuit and/or magnetic circuit element because of the impedance, resistivity and/or length of the wire connection. One or more electrical elements of the magnetic circuit shown in FIG. 17, RF circuit shown in FIGS. 18b and 18a may be dismissed, may be sorted in different order and/or two or more electrical elements may create one individual combined electrical element. Adjusting of the signal provided to the RF circuit may be at least partially provided by or inside another different circuit of the treatment device e.g.: magnetic circuit and/or other.

FIG. 18a illustrates an exemplary schema 180 of electrical elements of treatment device. The exemplary schema include two independent power sources including power source for RF treatment (PSRF) and power source for magnetic treatment (PSM) connected to one power network (PN). The PSRF may provide electromagnetic signal to two independent treatment clusters for RF treatment RF A and/or RF B. The PSM may provide electromagnetic signal to one or more clusters of magnetic treatment HIFEM A and/or HIFEM B. One or more the power sources may be also powering other parts of the treatment device, such as a human machine interface (HMI), or the master unit, among others. Each magnetic circuit and/or RF circuit may have its own control units (CUM A, CUM B and CURF A and CURF B). CURF A and CURF B may be control units of RF treatment cluster for RF treatment A (RF A) and treatment cluster for RF treatment B (RF B) respectively.

Control units may include one or more PCBs or microprocessors. One or more control units may communicate between each other and/or with the master unit that may be selected as a master unit for other control units in master-slave communication. The master unit may be the first or only control unit that communicates with the HMI. The master unit may control units CUM A and CUM B. The master unit may be a control unit including one or more PCBs and/or microprocessors. Master unit or control unit A (CUM A) or control unit B (CUM B) may be coupled to human machine interface. Also, the master unit may be human machine interface HMI or be coupled to the human machine interface HMI.

FIG. 18a illustrates two parts of the treatment device, wherein the first part may provide the RF treatment and the second part may provide the magnetic treatment. Two parts of the treatment device may be insulated from each other. The treatment device may include one or more insulated electrical elements and/or parts of the treatment device and individual circuits from each other in a manner of shielding voltage barrier, distance barrier and/or radiation barrier. Examples of insulated parts may be represented by a dashed line in FIG. 18a. It is also possible that individual electrical elements of the treatment device may be insulated from at least one part of the treatment device. Insulation of such parts and/or electrical elements may be provided by material of high dielectric constant, by distance of individual parts and/or electrical elements, by system of capacitors or resistors. Also, any shielding known from electronic, physics, by aluminium boxes and/or by other manner may be used.

The RF treatment and/or magnetic treatment may be provided by at least one, two, three, four or more treatment circuit (which may be located in the main unit) and/or applicators wherein one treatment circuit may include RF cluster or magnetic cluster. Each applicator A and B (AP A and AP B) may include at least one electrical element of one, two or more treatment circuits. Each applicator may include at least one, two or more different treatment energy sources, such as one or more RF electrodes providing the RF treatment and one or more magnetic field generating devices providing the magnetic treatment. As shown in FIG. 18a, the treatment device may include first applicator (AP A) and second applicator (AP B). The first applicator (AP A) may include first RF electrode (RFE A) from first RF circuit and first magnetic field generating device (MFGD A) from first magnetic circuit. The second applicator (AP B) may include second RF electrode (RFE B) from second RF circuit and second magnetic field generating device (MFGD B) from second magnetic circuit. In different example, first applicator may include first magnetic field generating device and first pair of bipolar RF electrodes, while second applicator may include second magnetic field generating device and second pair of bipolar RF electrodes. Two applicators may be connected to main unit separately and may be individually positioned to proximity of the body area before or during the treatment, when they are coupled to the body area in contact with the body area.

FIG. 18a also illustrates other individual parts of the treatment device, such as treatment cluster for RF treatment (RF A), treatment cluster for RF treatment (RF B), treatment cluster for magnetic treatment HIFEM A, treatment cluster for magnetic treatment HIFEM B in the magnetic circuit, power source for RF treatment (PSRF), power source for magnetic treatment (PSM), applicator A (AP A), applicator B (AP B). All parts, except the applicators, may be located in the main unit. Shown splitter, symmetrisation element (SYM A), and symmetrisation element (SYM B) are parts of two RF circuits. The splitter shown on FIG. 18a may be common for the RF circuits. The power source for RF treatment (PSRF) may include steady power source of RF circuit (SPSRF), auxiliary power source of RF circuit (APS RF), power network filter PNFLT and/or power unit (PU). Individual electrical elements may not be included with other electrical elements in PSRF. The power source for magnetic treatment (PSM) may include auxiliary power source A (APS A), auxiliary power source B (APS B), steady power source of magnetic circuit (SPSM), power pump (PP), board power source A (BPS A) and/or board power source B (BPS B). Individual electrical elements may not be included with other electrical elements in PSM. Treatment cluster for magnetic treatment HIFEM A of the magnetic circuit may include control unit A (CUM A), energy storage device A (ESD A), switch A (SW A), safety element (SE) and/or pulse filter (PF). Treatment cluster for magnetic treatment HIFEM B of the magnetic circuit may include control unit B (CUM B), energy storage device B (ESD B) and/or switch B (SW B). Although not shown on FIG. 18a, the treatment cluster for magnetic treatment HIFEM B may also include pulse filter (PF) and/or safety element (SE). Individual electrical elements may be insulated from each other. However, individual electrical elements and/or circuit parts may be merged and/or shared with other circuit parts. As an example, one control unit may be at least partially shared with two or more RF circuits and/or magnetic circuits, and one control unit may regulate power or power network or power source providing power for the RF circuit and also for the magnetic circuit. Another example may be at least one auxiliary power source and/or steady power source shared with at least two RF and/or magnetic circuits.

Treatment cluster for magnetic treatment HIFEM A may provide magnetic treatment independently on treatment cluster for magnetic treatment HIFEM B. Alternatively, the treatment device may include just one treatment cluster for magnetic treatment HIFEM or the treatment device may include two or more individual treatment clusters for magnetic treatment HIFEM, wherein some of the treatment cluster for magnetic treatment HIFEM may share individual electrical elements such as a control unit, energy storage device, pulse filter and/or other.

As shown in FIG. 18a, the treatment cluster for magnetic treatment HIFEM, e.g. HIFEM A, may include the control unit, e.g. CUM A. The control unit, e.g. CUM A, may control a charging and/or discharging of the energy storage device, e.g. ESD A, processing feedback information and/or adjusting parameters of individual electrical elements and/or treatment clusters for magnetic treatment HIFEM. In addition, the control unit (e.g. CUM A) may control adjusting parameters or operation of electrical elements, e.g. BPS A from circuit part PSM, switch, PF, ESD A from the treatment cluster for magnetic treatment HIFEM A and/or processing information from the sensors in the applicator AP A and/or AP B. The control unit (e.g. CUM A) may also communicate with another one or more magnetic and/or RF circuits and/or including master unit. The power source PSM, the energy storage device ESD and/or the switch SW may be at least partially regulated by the control unit of the magnetic circuit, e.g. CUM A. The control unit (e.g. CUM A) or master unit and/or one or more individual electrical elements of the circuit may be regulated by any other electrical element based on mutual communication between them. The master unit may be able to adjust treatment parameters of the magnetic treatment and/or the RF treatment based on feedback information provided from the sensors and/or based on communication with other control units, e.g. the master unit. One control unit CUM or CURF may regulate independently one or more circuits providing magnetic and/or RF treatment. At least one control unit may use peer-to-peer communication and/or master-slave communication with other control units (e.g. CUM A may be slave control unit of the master unit).

The treatment device may include one, two, three or more ESD, wherein each ESD may include one, two, three or more capacitors. One ESD may provide energy to one, two, three or more treatment energy sources, such as magnetic field generating devices providing magnetic treatment. Each coil may be coupled to its own respective ESD or more than one ESD. The ESD may include one or more other electrical elements such as a safety element SE, such as a voltage sensor, a high voltage indicator, and/or discharging resistors, as shown in FIG. 18a. The voltage sensor and the high voltage indicator may provide feedback information to the switch SW and/or to control unit, e.g., CUM A. The discharging resistor as part of the SE may provide discharging of at least one capacitor in case of hazardous situation. Discharging of one or more ESD may be controlled by the control unit e.g. CUM A or CUM B. The signal provided from the energy storage device ESD through the switch SW to the magnetic field generating device may be modified by a pulse filter (PF). The PF may be part of the switch SW and/or may be positioned between the switch SW and the magnetic field generating device, e.g., MFGD A. The PF may suppress switching voltage ripples created by the switch during discharging of the ESD. The proposed circuit may repetitively switch on/off the switch SW and discharge the energy storage device ESD to the magnetic field generating device, e.g. the MGFD A in order to generate the time-varying magnetic field. As shown in FIG. 18a, one or more electrical elements of the magnetic circuit and/or RF circuit may be omitted and/or combined to another. For example, one or more individual electrical elements of PSRF and/or PSM may be combined to one, but independency of individual circuits may be decreased. Also electrical elements the PF, the SE and/or other may be independent electrical element. Also individual treatment circuits, e.g. RF circuits, may be different from each other as can be seen in FIGS. 18a and 18b, wherein electrical elements, such as a filter, a SWR+Power meter, a tuning, a splitter, an insulator, a SYM and/or a pre-match may be dismissed and/or combined to one. Dismissing and/or combining of individual electrical elements may results in decreased efficiency of energy transfer to patients body without tuning, higher energy loss because of absence the SYM, pre-match and/or tuning, malfunctioning of signal adjusting in the circuit and incorrect feedback information without the SWR+Power meter, the splitter and the insulator and/or the treatment device may be dangerous to patient without the filter, the SWR+Power meter, the SYM and/or the tuning element.

Control units CUM A and CUM B may serve as slaves of the master unit which may command both control units CUM A and CUM B to discharge the electrical current to respective magnetic field generating devices (e.g. MFGD A and MFGD B). Therefore, the control of each control unit CUM A and CUM B is independent. Alternatively, CUM B may be slave of the CUM A, while CUM A itself may be slave of master unit. Therefore, when master unit commands the CUM A to discharge electrical current into the magnetic field generating device (e.g. MFGD A), the CUM A may command the CUM B to discharge electrical current to another magnetic field generating device (e.g. MFGD B) positioned in different applicator. In another alternative, additional control unit may be positioned between master unit and control units CUM A and CUM B, wherein such additional control unit may provide e.g. timing of discharges. By both these approaches, the pulses of magnetic field may be applied synchronously or simultaneously.

When the treatment device includes more than one magnetic field generating device and method of treatment include using more than one magnetic field generating device (e.g., a coil), each coil may be connected to respective magnetic circuit. However, one coil may be connected to plurality of magnetic circuits. Also, the power source PSM may be used for at least two magnetic field generating devices.

The power source, e.g. PSM and/or PSRF may provide an electric energy to at least one or at least one individual electrical element of RF circuit, magnetic circuit, and/or to other part of the treatment device e.g. to the master unit, HMI, energy storage device (e.g. ESD A and/or ESD B), to control unit (e.g. CUM A and/or CUM B) and/or to the switch (eg. SW A or SW B). The power source may include one or more elements transforming electric energy from the power network connection PN as illustrated in FIG. 18a. Several individual electrical elements of the power source, of the RF circuit and/or magnetic circuit may be constructed as one common electrical element and do not have to be constructed as individual electrical elements as illustrated in FIG. 18a. Each RF and/or magnetic circuit may have its own power source and/or at least one electrical element of the power source powering just one of the RF and/or the magnetic circuit. Also, at least part of one power source may be powering at least two different circuits before and/or during at least part of the treatment. The power source may include one or more parts shared with individual electrical circuits that may be at least partially electrically isolated from each other.

One or more electrical elements of the power source for RF treatment (e.g. a steady power source of magnetic circuit (SPSM), an auxiliary power sources APS A and/or APS B, a power pump PP, board power source BPS A and/or BPS B) may provide electric energy to individual electrical elements of the RF circuit and/or magnetic circuit directly and/or indirectly. Directly provided electric energy is provided through conductive connection between two electrical elements wherein no other electrical element of the circuit is in serial connection between directly powered electrical elements. Insulating and/or other electrical elements of the circuits such as resistors, insulating capacitors and the like may be not considered to be an electrical element. Indirectly powered electrical elements may be powered by one or more other elements providing electric energy through any other element that may change parameters of provide electric energy, such as current value, frequency, phase, amplitude and/or other.

The power source PSM illustrated in FIG. 18a in more detail may include connection to a power network PN. The PN may provide filtering and/or other adjustment of an input electric signal from the power network, such as the frequency and current value. The PN may also be used as an insulating element creating a barrier between the treatment device and the power network. The PN may include a one or more of capacitors, resistors and/or filters filtering signal returning from the treatment device The PN may include a plug or connection to a plug. The PN may be coupled to a plug or power grid. The PSM may include one or more steady power source (e.g. steady power source of magnetic circuit SPSM), auxiliary power sources (e.g. APS A and/or APS B), one or more power pumps PP; and/or one or more board power sources (e.g. BPS A and/or BPS B). As illustrated in FIG. 18a, the treatment device may include at least two electrically insulated magnetic and/or RF circuits that may be controlled at least partially independently, e.g. intensity of generated magnetic field by the magnetic field generating devices MFGD A and the MFGD B connected to treatment clusters for magnetic treatment HIFEM A and HIFEM B may be different. Steady power source (SPSM) may provide steady output voltage under different power network conditions. Steady power source SPSM may be connected to the auxiliary power source (e.g. APS A and/or APS B). Two auxiliary power sources may be combined and create one electrical element. Steady output voltage produced by steady power source and/or by auxiliary power source may be in a range of 1 V to 1000 V, or 20 V to 140 V, or 50 V to 700 V, or 120 V to 500 V, or 240 V to 450 V.

One or more auxiliary power sources may be powering one or more control units of the individual circuits. APS may be also powering one or more board power source BPS, e.g. BPS A and/or BPS B. APS may be also powering master unit HMI and/or other elements of the treatment device. Because of APS, at least one control unit and/or master unit may provide processing/adjusting of the electric signal in RF and/or magnet circuit precisely, independently and/or also individual electrical element of the treatment device may be protected from the overload. The board power source (e.g. element BPS A and/or BPS B) may be used as a source of electric energy for at least one element of magnetic circuit (e.g. energy storage device ESD A and/or B). Alternatively, one or more elements of the power source PSM may be combined and/or dismissed.

The power source may serve as high voltage generator providing voltage to a magnetic circuit and/or RF circuit. The voltage provided by power source may be in a range from 500 V to 50 kV, or from 700 V to 5 kV, or from 700 V to 3 kV, or from 1 kV to 1.8 kV. The power source is able to deliver a sufficient amount of electrical energy to each circuit, such as to any electrical element (e.g. the energy storage device ESD A) and to the magnetic field generating device (e.g. MFGD A). The magnetic field generating device may repeatedly generate a time-varying magnetic field with parameters sufficient to cause muscle contraction.

According to FIG. 18a, RF circuits have their own power source PSRF that may be at least partially different from the PSM. The PSRF may include element electrical PNFLT suppressing electromagnetic emission from the internal parts of the PN and/or from the any part of the RF circuit. Electrical element PNFLT may represent power network filter. However, PNFLT may be also part of the PN. The PSRF may include SPSRF providing steady output voltage under different power network conditions to auxiliary power source of a RF circuit APS RF, control unit of the RF circuit, a power unit PU and/or other electrical elements using direct current supply. As further illustrated in FIG. 18a, APS RF may include its own mechanism transforming alternating current to direct current independently to SPSRF. The APS RF may be able to power control unit of the treatment cluster for RF treatment RF A and/or master unit while SPSRF may independently power control unit of the treatment cluster for RF treatment RF B. The power unit PU of the RF circuit may be powering one or more RF circuits or at least one electrical element of the RF circuit, such as power amplifiers and/or other electrical elements of the treatment cluster for RF treatment RF A and/or treatment cluster for RF treatment RF B creating and/or adjusting high frequency signal.

At least one electrical element described as PSM, PSRF, APS, SPSM and/or SPSRF may be shared by at least one RF circuit and magnetic circuit.

Control units CURF may work as slave of the master unit, which may command CURF to provide RF signal through RF circuit to RF electrode. In case of two control units CURF both control units work as slaves of the master unit which may command both control units CURF to provide RF signal to respective RF electrodes. Therefore, the control of each control unit from possible plurality of CURF is independent. Alternatively, first CURF may be slave of second CURF, while first CURF itself may be slave of master unit. Therefore, when master unit commands the first CURF to discharge electrical current into the first RF electrode, the first CURF may command the second CURF to discharge electrical current to second RF electrode positioned in different applicator. In another alternative, additional control unit may be positioned between master unit and plurality of control units CURF, wherein such additional control unit may provide e.g. timing of discharges. By both these principles, the pulses of RF field may be applied continuously or in pulsed manned.

Treatment clusters for magnetic HIFEM A and HIFEM B shown in FIGS. 17, 18a and 18b may be controlled through one or more sliders or scrollers related to HMI parts marked as HIFEM A and HIFEM B 718 shown on FIG. 7. Through related intensity scrollers, intensity bars and/or intensity sliders shown on human machine interface HMI, the user may control or adjust speed of operation of one or more electrical elements of treatment clusters for magnetic energy HIFEM A and/or HIFEM B.

Also, treatment cluster for RF treatment RF A and treatment cluster for RF treatment RF B shown in FIGS. 17, 18a and 18b may be controlled through sliders, bars or intensity scrollers related to HMI parts marked as RF A and RF B 712 shown on FIG. 7. Through related intensity scrollers, intensity bars and/or intensity sliders shown on human machine interface HMI, the user may control or adjust speed of operation of one or more electrical elements of treatment clusters for RF treatment RF A and/or RF B. Also, by using the related intensity scrollers, intensity bars and/or intensity sliders the user may control or adjust speed of electrical signal transmission through or between one or more electrical elements of treatment clusters for RF treatment RF A or RF B.

The treatment device may include two or more applicator, each applicator may include one magnetic field generating device and one or two RF electrodes. Inductance of first magnetic field generating device positioned in first applicator may be identical as inductance of second magnetic field generating device positioned in the second applicator. Also, number of turns, winding area and/or area without winding of the first magnetic field generating device in the first applicator may be identical as number of turns, winding area and/or area without winding of the second magnetic field generating device in the second applicator. The first magnetic field generating device in the first applicator may provide identical magnetic field as the second magnetic field generating device in the second applicator. The identical magnetic fields provided by plurality of magnetic field generating devices during same or another treatment sessions may have same treatment parameters e.g. number of pulses in train, number of pulses in burst, same amplitude of magnetic flux density of impulses, same shape of envelope or other. However, reasonable deviation e.g. from amplitude of magnetic flux density may be tolerated in the identical magnetic field. The deviation of amplitudes of magnetic flux density or average magnetic flux density as measured by fluxmeter or oscilloscope may be in the range of 0.1% to 10% or 0.1% to 5%.

Alternatively, the inductance of magnetic field generating devices in both applicator may be different. Also, magnetic fields provided by plurality of magnetic field magnetic devices during the same or another treatment sessions may have different treatment parameters.

When the treatment device has two or more applicators, each applicator may include one magnetic field generating device and one or two RF electrodes. The size or area of one RF electrode positioned in first applicator may be identical to another RF electrode positioned in the second applicator. First applicator and second applicator may provide identical RF fields provided during same or another treatment sessions, wherein identical RF fields may have same treatment parameters e.g. wavelength, phase, time duration and intensity of RF field.

Alternatively, the size of area of RF electrodes in both applicators may be different. Also, magnetic fields provided by plurality of magnetic field generating devices during the same or another treatment sessions may have different treatment parameters.

Figure 19:
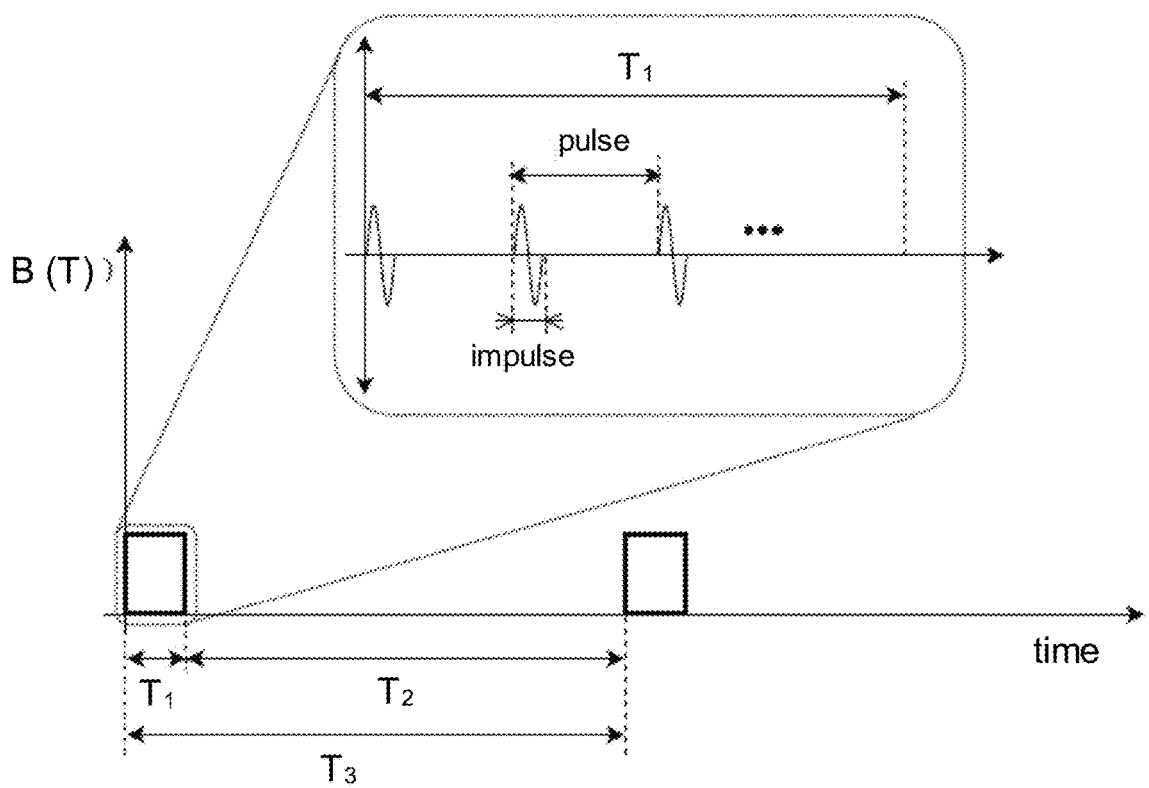
FIG. 19 illustrates an exemplary composition of magnetic field including impulses or pulses.

FIG. 19 shows exemplary composition of magnetic field (e.g. time-varying magnetic field) provided by the magnetic field generating device. Also, the FIG. 19 may show also composition of RF field. Therefore, especially in description of FIG. 19, the term "impulse" may refer to "magnetic impulse" or "RF impulse". Similarly, the term "pulse" may refer to "magnetic pulse" or "RF pulse". Also, term "train" may refer to "magnetic train". Term "magnetic train" may include train of magnetic pulses wherein the train of magnetic pulses may be understood as plurality of magnetic subsequent pulses wherein one pulse follows another. As the magnetic pulse may include one magnetic impulse, the term "magnetic train" may include also train of magnetic impulses. The term "burst" may refer to "magnetic burst".

As shown in FIG. 19, an impulse may refer to a time period of applied treatment energy (e.g. magnetic field) with sufficient intensity to cause at least partial treatment effect, such as an at least partial muscle contraction, muscle contraction, change of temperature of the biological structure and/or nerve stimulation. The magnetic impulse may include one biphasic shape as shown on FIG. 19. The magnetic impulse may include amplitude of magnetic flux density.

A magnetic pulse may refer to a time period including impulse and passive time period of the pulse. The magnetic pulse may refer to a time period of one magnetic impulse and passive time period, i.e. time duration between two impulses from rise/fall edge to subsequent of following rise/fall edge. The passive time duration of a pulse may include either applying no treatment energy to the patient's body and/or application of the treatment energy insufficient to cause at least a partial treatment effect due to insufficient treatment energy intensity (e.g. magnetic flux density) and/or frequency of delivered treatment energy. Such time period may be called pulse duration. As shown on FIG. 19, each pulse may include one biphasic shape lasting for a time period called an impulse duration. Alternatively, the impulses or pulses may be monophasic.

As further shown on FIG. 19, the plurality of pulses may form the train. The train may refer to a plurality of pulses, wherein one train may comprise at least two pulses wherein pulses follow one by another. Train may last time period lasting $T_1$ shown in FIG. 19.

The magnetic train may include plurality of magnetic pulses in the range of 2 magnetic pulses to 200 000 magnetic pulses or 2 magnetic pulses to 150 000 magnetic pulses or 2 magnetic pulses to 100 000 magnetic pulses. Magnetic train may cause multiple at least partial muscle contractions or muscle contractions followed one by one, at least one incomplete tetanus muscle contraction, at least one supra-maximal contraction or at least one complete tetanus muscle contraction. During application of one train, magnetic field may provide one muscle contraction followed by muscle relaxation. The muscle relaxation may be followed by another muscle contraction during the application of one train. During one train, the muscle work cycle (which may include muscle contraction followed by muscle relaxation) may be repeated at least twice, three, four or more times.

The burst may refer to one train provided during time period $T_1$ and a time period $T_2$ which may represent a time period when no treatment effect is caused. The time period $T_2$ may be a time period providing passive treatment where no treatment energy is applied to a patient's body and/or applied treatment energy is insufficient to cause the treatment effect. The time period $T_3$ shown in FIG. 19 may represent the time duration of the burst.

The magnetic train of a time-varying magnetic field may be followed by a static magnetic field and/or the magnetic train may be followed by a time-varying magnetic field of frequency and/or magnetic flux density insufficient to cause at least a partial muscle contraction or muscle contraction. For example, the burst may provide at least one at least partial muscle contraction followed by no muscle contraction. In another example, the burst may provide at least one muscle contraction followed by no muscle contraction. The treatment may include a number of magnetic bursts in a range of 15 to 25,000, or in a range of 40 to 10,000, or in a range of 75 to 2,500, or in a range of 150 to 1,500, or in a range of 300 to 750 or up 100,000. The repetition rate in the subsequent bursts may incrementally increase/decrease with an increment of 1 to 200 Hz, or of 2 to 20 Hz, or of 5 Hz to 15 Hz, or more than 5 Hz. Alternatively, the amplitude of magnetic flux density may vary in the subsequent bursts, such as incrementally increase/decrease with an increment of at least 1%, 2%, or 5% or more of the previous pulse frequency. During application of one burst, magnetic field may provide one muscle contraction followed by muscle relaxation. The muscle relaxation may be followed by another muscle contraction during the application of same burst. During one burst, the muscle work cycle (which may include muscle contraction followed by muscle relaxation) may be repeated at least twice, three, four or more times.

Also, a treatment duty cycle may be associated with an application of a pulsed treatment energy of the magnetic field as illustrated in FIG. 19. The treatment duty cycle may refer to a ratio between time of active treatment $T_1$ and sum of time of an active and a passive treatment during one cycle $T_3$.

An exemplary treatment duty cycle is illustrated in FIG. 19. Duty cycle of 10% means that $T_1$ of active treatment last 2 s and passive treatment $T_2$ last 18 s. In this exemplary treatment the period including active and passive treatment period $T_3$ lasts 20 seconds. The treatment duty cycle may be defined as a ratio between $T_1$ and $T_3$. The treatment duty cycle may be in a range from 1:100 (which means 1%) to 24:25 (which means 96%) or 1:50 (which means 2%) to 4:6 (which means 67%) or 1:50 (which means 2%) to 1:2 (which means 50%) or 1:50 to 1:3 (which means 33%) or 1:50 (which means 2%) to 1:4 (which means 25%) or 1:20 (which means 5%) to 1:8 (which means 12.5%) or 1:100 (which means 1%) to 1:8 (which means 12.5%) or at least 1:4 (which means at least 25%).

An exemplary application of a burst repetition rate of 4 Hz may be the time-varying magnetic field applied to the patient with a repetition rate of 200 Hz and with a treatment duty cycle of 50% in trains lasting 125 ms, i.e. each train includes 25 pulses. An alternative exemplary application of a burst repetition rate of 6 bursts per minute may be the time-varying magnetic field applied to the patient with a repetition rate of 1 Hz and with a treatment duty cycle of 30% in trains lasting 3 s; i.e., each train includes 3 pulses.

The FIG. 19 may also show exemplary composition of magnetic component provided by the RF electrode.

When the treatment device uses plurality of applicators (e.g. two), each applicator may include one magnetic field generating device. As each magnetic field generating device may provide one respective magnetic field, the plurality of applicators may provide different magnetic fields. In that case the amplitude of magnetic flux density of magnetic impulses or pulses may be same or different, as specified by user through HMI and/or by one or more control units.

The impulses of one magnetic field provided by one magnetic field generating device (e.g. magnetic coil) may be generated and applied synchronously as the impulses of another magnetic field provided by another magnetic field generating device. During treatment session with the treatment device including two magnetic field generating device, the impulses of one magnetic field provided by one magnetic field generating device may be generated synchronously with the impulses of second magnetic field provided by second magnetic field generating device. Synchronous generation may include simultaneous generation.

The synchronous generation of magnetic impulses may be provided by synchronous operation of switches, energy storage devices, magnetic field generating devices and/or other electrical elements of the plurality of magnetic treatment circuit. However, the synchronous operation of electrical elements of magnetic treatment circuit may be commanded, adjusted or controlled by user through HMI, master unit and/or more control unit.

Figure 27A:
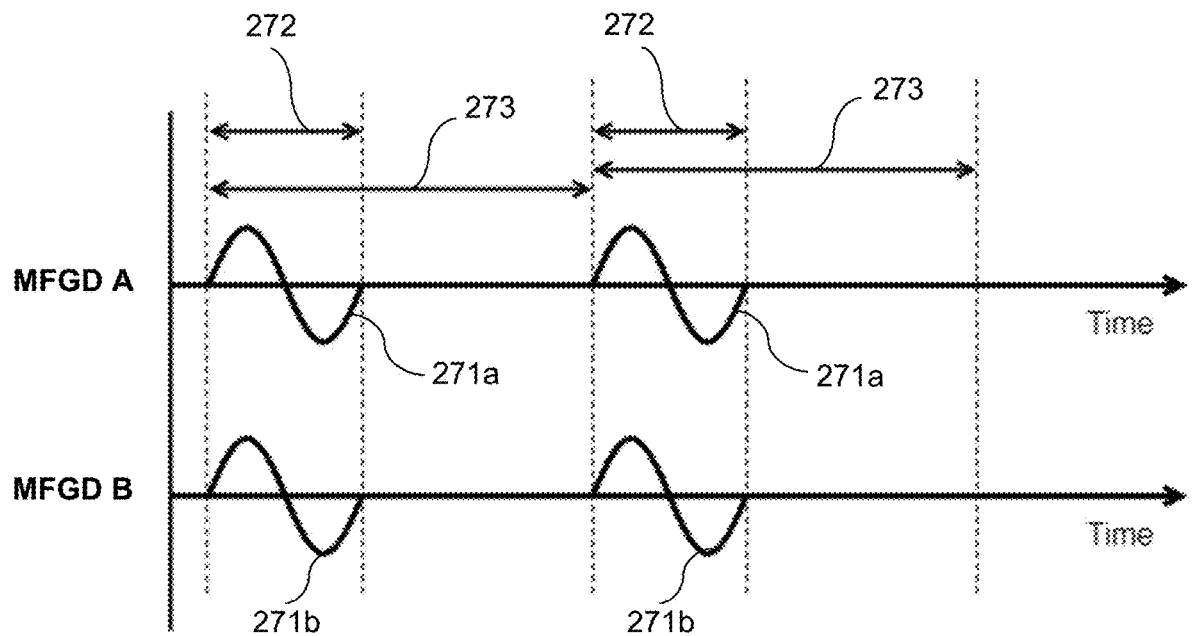
FIGS. 27a-27d illustrate an example of synchronous application of magnetic fields.

The FIG. 27*a* shows simultaneous type of synchronous generation of magnetic impulses on two exemplary magnetic field generating devices. The magnetic field generating device A (MFGD A) may generate first magnetic field including plurality of biphasic magnetic impulses 271*a*. The magnetic field generating device B (MFGD B) may generate second magnetic field including plurality of magnetic impulses 271*b*. The magnetic impulses of both magnetic fields are generated during the impulse duration 272 of the magnetic impulses 271*a* of the first magnetic field. Also, the impulse of both magnetic fields are generated within the pulse duration 273 of the first magnetic field. Simultaneous generation of magnetic field means that the magnetic impulse 271*a* of the first time-varying magnetic field is generated at the same the time as the magnetic impulse 271*b* of the second time-varying magnetic field.

The synchronous generation of magnetic fields may include generating a first pulse of the first time-varying magnetic field such that the first pulse lasts for a time period, wherein the time period lasts from a beginning of a first impulse of the first time-varying magnetic field to a beginning of a next consecutive impulse of the first time-varying magnetic field and generating a second pulse of the second time-varying magnetic field by the second magnetic field generating device such that the second pulse lasts from a beginning of a first impulse of the second time-varying magnetic field to a beginning of a next consecutive impulse of the second time-varying magnetic field. Synchronous generation of magnetic field means that the first impulse of the second time-varying magnetic field is generated during the time period of the first pulse.

Figure 27B:
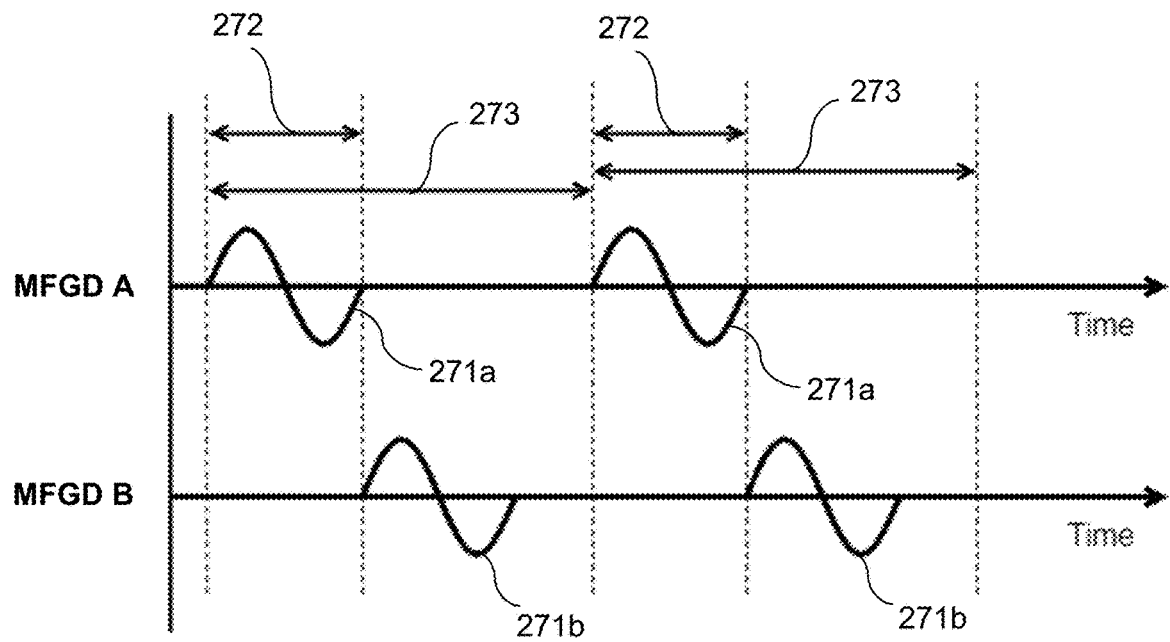

FIG. 27*b* shows an example of synchronous generation of magnetic impulses. The magnetic field generating device A (MFGD A) may generate first magnetic field including plurality of biphasic magnetic impulses 271*a*. The magnetic field generating device B (MFGD B) may generate second magnetic field including plurality of magnetic impulses 271*b*. The magnetic impulses 271*b* of second magnetic field may be generated during the pulse duration 273 of pulse of the first magnetic field, but outside of impulse duration 272 of impulse of first magnetic field.

Figure 27C:
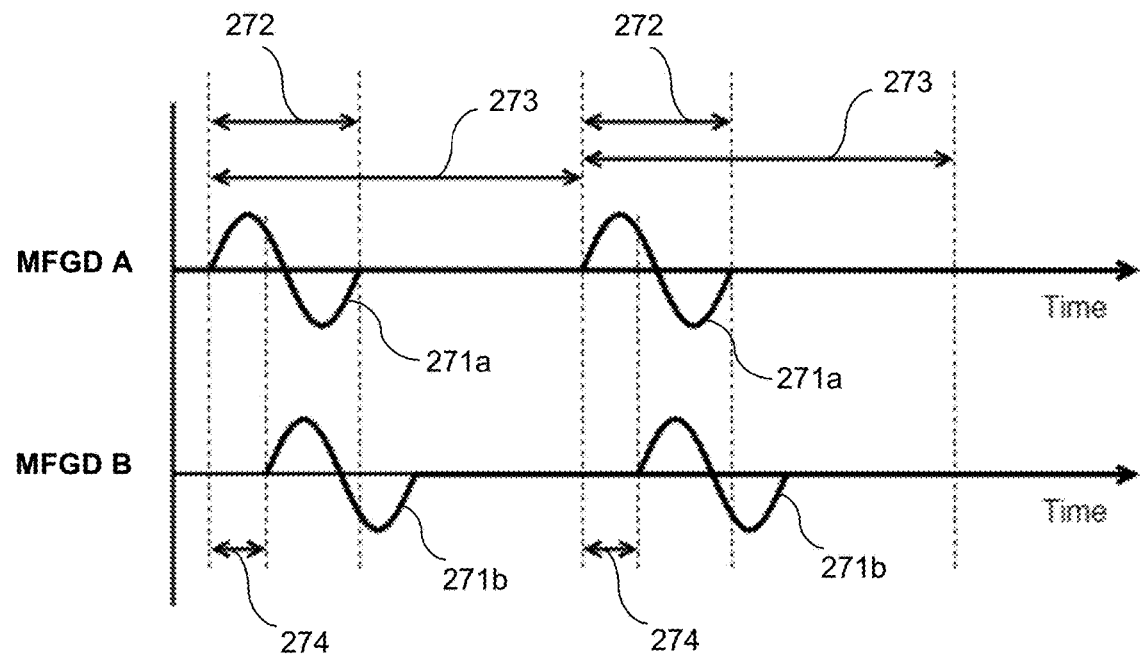

FIG. 27*c* shows another example of synchronous generation of magnetic impulses. The magnetic field generating device A (MFGD A) may generate first magnetic field including plurality of biphasic magnetic impulses 271*a*. The magnetic field generating device B (MFGD B) may generate second magnetic field including plurality of magnetic impulses 271*b*. The magnetic impulse 271*b* of second magnetic field may be generated during the pulse duration 273 of pulse of the first magnetic field. Also, the magnetic impulse 271*b* of second magnetic field may be generated during the impulse duration 272 of pulse of the first magnetic field. The beginning of the magnetic impulse 271*b* of second magnetic field may be distanced from the beginning of the impulse 271*a* of the first magnetic field by a time period called impulse shift 274. The impulse shift may be in a range of 5 l to 10 ms or 5 μs to 1000 μs or 1 μs to 800 μs.

Figure 27D:
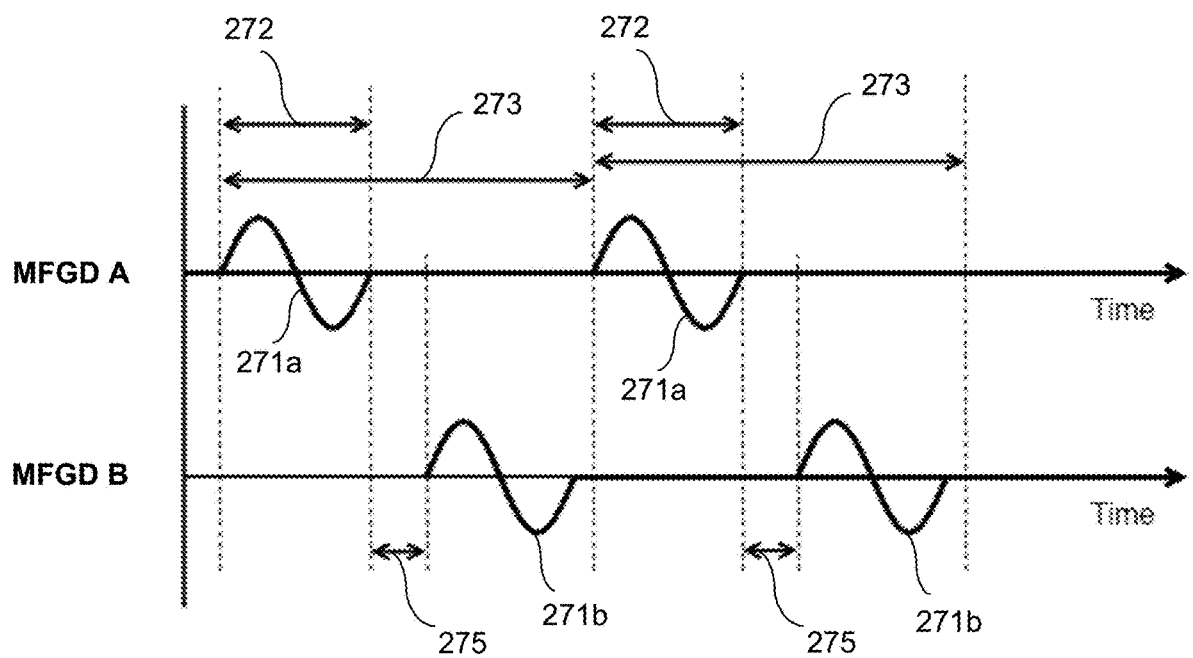

FIG. 27*d* shows still another example of synchronous generation of magnetic impulses. The magnetic field generating device A (MFGD A) may generate first magnetic field including plurality of biphasic magnetic impulses 271*a*. The magnetic field generating device B (MFGD B) may generate second magnetic field including plurality of magnetic impulses 271b. The magnetic impulse 271b of second magnetic field may be generated within the pulse duration 273 of the pulse of the first magnetic field. The magnetic impulse 271b of second magnetic field may be generated outside of impulse duration 272 of the impulse of the first magnetic field. The beginning of the magnetic impulse 271b of second magnetic field may be distanced from the end of the magnetic impulse 271a of the first magnetic field by a time period called impulse distance period 275. The impulse distance period may last in a range of 5 1 to 10 ms or 5 μs to 1000 μs or 1 μs to 800 μs.

Beside synchronous generation, the magnetic impulses of plurality of magnetic fields may be generated separately. Separated generation of magnetic impulses of magnetic fields may include generation of impulses of one magnetic field are generated outside of pulse duration of another magnetic field.

Figure 27E:
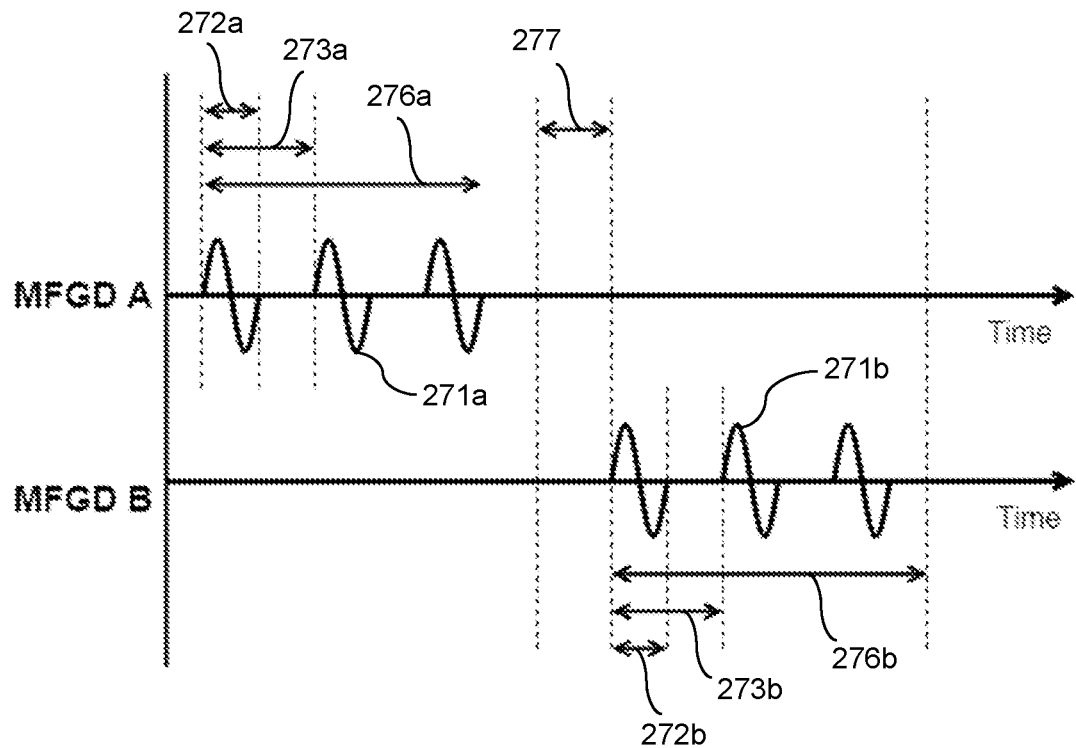
FIG. 27e illustrates an example of separate application of magnetic fields.

FIG. 27e shows example of separate generation of magnetic impulses. The magnetic field generating device A may generate first magnetic field including train of biphasic magnetic impulses 271a having impulse duration 272a. Each magnetic impulse 271a is part of a pulse having pulse duration 273a. The impulse duration 272a of first magnetic field may be part of pulse duration 273a of first magnetic field. The train of first magnetic field may have train duration 276a. The magnetic field generating device B may generate another magnetic field including another train of plurality of magnetic impulses 271b having impulse duration 272b. Each magnetic impulse 271b is part of a pulse having pulse duration 273b. The impulse duration 272b of second magnetic field may be part of pulse duration 273b of second magnetic field. The train of second magnetic field may have train duration 276b. The train having train duration 276a is generated by magnetic field generating device A in different time than train having train duration 276b generated by magnetic field generating device B. Both train may be separated by separation period 277 may be in the range of 1 ms to 30 s. During separation period 277, no magnetic field generating device may be active meaning that the energy storage device providing current pulses may not store any energy.

All examples of synchronous or separated generation of magnetic impulses may be applied during one treatment session. Also, the impulse shift and/or impulse distance period may be calculated for any magnetic impulse 271b of second or another magnetic field, which may be positioned according to any example given by FIGS. 27B-27E. The impulse shift and/or impulse distance period may be measured and calculated from oscilloscope measurement. The synchronous generation of magnetic impulses may lead and be extrapolated to synchronous generation of magnetic pulses and/or trains by two or more magnetic field generating devices. Similarly, the separated generation of magnetic impulses may lead and be extrapolated to synchronous generation of magnetic pulses and/or trains by two or more magnetic field generating devices.

The adjustment or control provided by master unit and/or one or more control units may be used for creation or shaping of magnetic envelope or RF envelope. For example, the magnetic impulses or RF impulses may be modulated in amplitude of each impulse or plurality of impulses to enable assembly of various envelopes. Similarly, the amplitude of RF energy may be modulated in amplitude to assemble various envelopes. The master unit and/or one or more control units may be configured to provide the assembly of one or more envelopes described herein. Differently shaped magnetic envelopes and/or RF envelopes (referred herein also as envelopes) may be differently perceived by the patient. The envelope or all envelopes as shown on Figures of this application may be fitted curve through amplitude of magnetic flux density of impulses, pulses or trains and/or amplitudes of power output of RF impulses of RF waves.

The envelope may be a magnetic envelope formed from magnetic impulses. The magnetic envelope formed from impulses may include plurality of impulses, e.g. at least two, three, four or more subsequent magnetic impulses. The subsequent magnetic impulses of such magnetic envelope may follow each other. In case of such envelope, the envelope duration may begin by first impulse and end with the last impulse of the plurality of impulses. The envelope may include one train of magnetic impulses. The envelope may be a fitted curve through amplitudes of magnetic flux density of impulses. The envelope formed by magnetic impulses may therefore define train shape according to modulation in magnetic flux density, repetition rate and/or impulse duration of magnetic impulses. Accordingly, the envelope may be an RF envelope formed by RF impulses and their modulation of envelope, repetition rate or impulse duration of RF impulse of RF wave.

The envelope may be a magnetic envelope formed by magnetic pulses. The magnetic envelope formed by pulses may include plurality of pulses (e.g. at least two, three, four or more subsequent magnetic pulses), wherein pulses follow each other without any missing pulse. In such case, the envelope duration may begin by impulse of first pulse and end with a passive time duration of last impulse of the plurality of pulses. The envelope formed by magnetic pulses may therefore define train shape in according to modulation in magnetic flux density, repetition rate and/or impulse duration. The envelope may include one train of magnetic pulses. The train consists of magnetic pulses in a pattern that repeats at least two times during the protocol. The magnetic envelope may be a fitted curve through amplitudes of magnetic flux density of pulses.

The envelope may be a magnetic envelope formed from magnetic trains. The magnetic envelope formed from trains may include plurality of trains (e.g. at least two, three, four or more subsequent magnetic trains), wherein trains follow each other with time duration between the train. In such case, the envelope duration may begin by impulse of first pulse of the first train and end with a passive time duration of the plurality of pulses. The plurality of trains in one envelope may be separated by missing pulses including impulses. The number of missing pulses may be in a range of 1 to 20 or 1 to 10.

The envelope may be modulated on various offset values of magnetic flux density. The offset value may be in the range of 0.01 T to 1 T or 0.1 to 1 T or 0.2 to 0.9 T. The offset value may correspond to non-zero value of magnetic flux density.

During one treatment session, treatment device may apply various number of envelopes. Two or more envelopes of magnetic field may be combined to create possible resulting shape.

In examples mentioned above, the envelope may begin by first impulse. Further, the envelope continue through duration of first respective pulse including first impulse. Further, the envelope may end with a passive time duration of last pulse, wherein the last pulse may follow the first pulse. This option is shown on following figures showing exemplary shapes of envelope of magnetic pulses. As shown on following figures, the shape of envelope may be provided by modulation of magnetic flux density. The shape of RF envelope may be provided by modulation of amplitude of power or impulses of RF waves.

Figure 28:
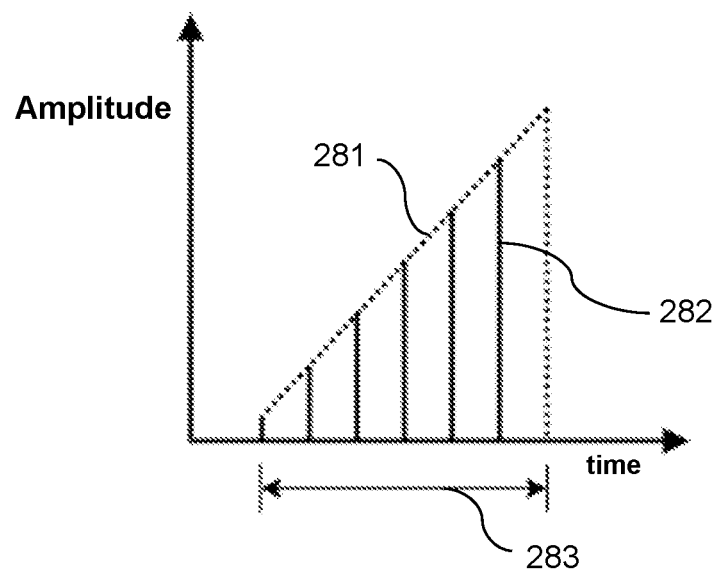
FIG. 28 illustrates an exemplary increasing envelope of magnetic field.

FIG. 28 is an exemplary illustration of an increasing envelope 281 formed from magnetic impulses 282, wherein one magnetic impulse 282 is followed by one passive time period of the magnetic pulse. Amplitude of magnetic flux density of subsequent impulses in the increasing envelope is increasing. The amplitude of magnetic flux density of one impulse is higher than amplitude of magnetic flux density of preceding impulse. Similarly, the amplitude of magnetic flux density of second impulse is higher than amplitude of magnetic flux density of the first impulse. The increasing amplitude may be used for muscle preparation. The envelope duration 283 of the increasing envelope 281 begins from first impulse of the first pulse to end of the passive time duration of last pulse. Similarly, the amplitude of RF waves may be modulated in amplitude to assemble increasing envelope 281.

Figure 29:
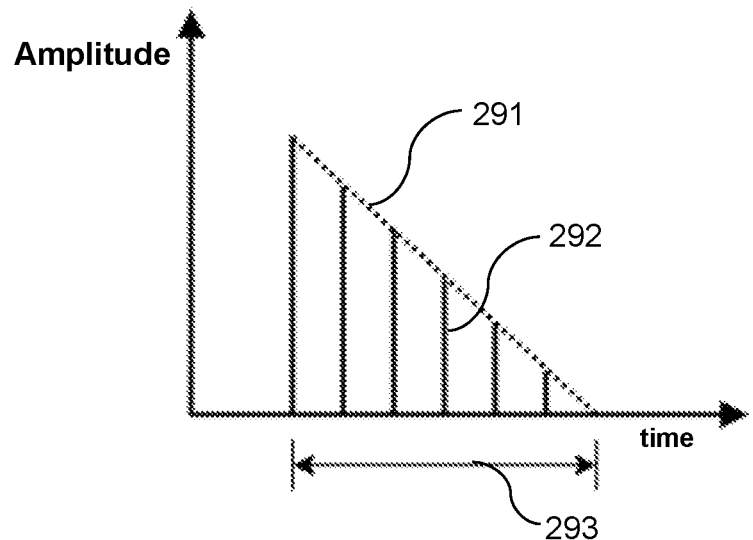
FIG. 29 illustrates an exemplary decreasing envelope of magnetic field.

FIG. 29 is an exemplary illustration of a decreasing envelope 291 formed from magnetic impulses 292. Amplitude of magnetic flux density of subsequent impulses in the decreasing envelope is decreasing. The amplitude of magnetic flux density of one impulse is lower than amplitude of magnetic flux density of preceding impulse. Similarly, the amplitude of magnetic flux density of second impulse is lower than amplitude of magnetic flux density of the first impulse. The envelope duration 293 of the decreasing envelope 291 begins from first impulse of the first pulse to end of the passive time duration of last pulse. Similarly, the amplitude of RF waves may be modulated in amplitude to assemble decreasing envelope 291.

Figure 30:
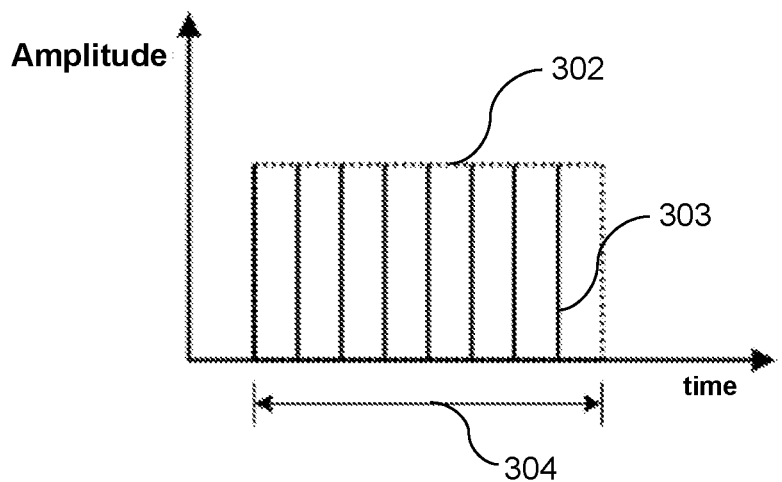
FIG. 30 illustrates an exemplary rectangular envelope of magnetic field.

FIG. 30 is an exemplary illustration of a rectangular envelope 302 formed from magnetic impulses 303. Amplitude of magnetic flux density of impulses in the rectangular envelope may be constant. However, the amplitude of magnetic flux density of subsequent impulses may oscillate around predetermined value of amplitude of magnetic flux density in range of 0.01% to 5%. The amplitude of magnetic flux density of first impulse may be identical as the amplitude of magnetic flux density of the second impulse, wherein the second impulse follows the first impulse. The envelope duration 304 of the rectangular envelope 302 begins from first impulse of the first pulse to end of the passive time duration of last pulse. The rectangular envelope may be used for inducing of muscle contraction or muscle twitches. Similarly, the amplitude of RF waves may be modulated in amplitude to assemble rectangular envelope 302.

Figure 31:
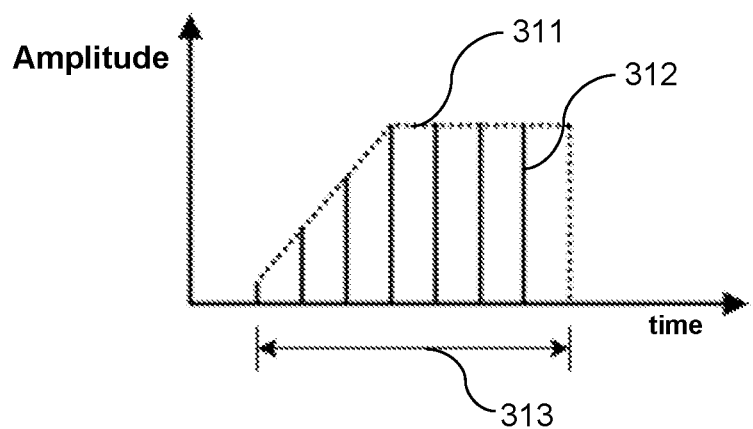
FIG. 31 illustrates an exemplary combined envelope of magnetic field.

FIG. 31 is an exemplary illustration of a combined envelope 311, which may be hypothetically seen as combination of increasing envelope and rectangular envelope. Combined envelope 311 includes magnetic impulses 312. Amplitude of magnetic flux density of impulses in the combined envelope may be increasing for in a range of 1% to 95% or 5% to 90% or 10% to 80% of the time duration of the whole combined envelope. The amplitude of magnetic flux density of subsequent impulses in the rectangular part of the combined envelope may oscillate around predetermined value of amplitude of magnetic flux density in range of 0.01% to 5%. The envelope duration 313 of the combined envelope 311 begins from first impulse of the first pulse to end of the passive time duration of last pulse. The combined envelope as shown on FIG. 31 may be used for preparation of muscle and inducing of muscle contraction or muscle twitches. Similarly, the amplitude of RF waves may be modulated in amplitude to assemble envelope 311.

Figure 32:
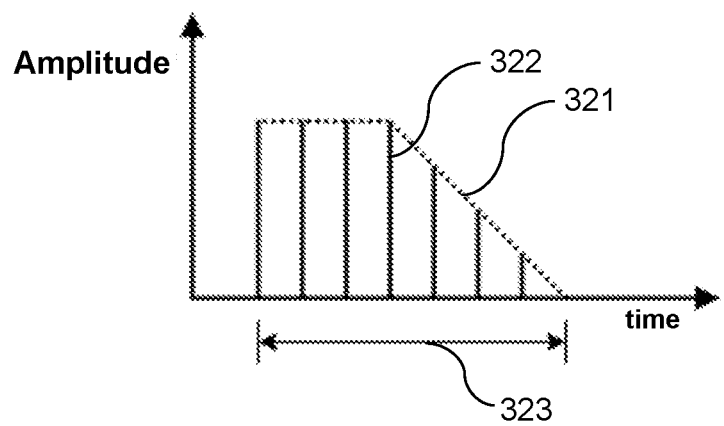
FIG. 32 illustrates another exemplary combined envelope of magnetic field.

FIG. 32 is an exemplary illustration of a combined envelope 321, which may be hypothetically seen as combination of rectangular envelope and decreasing envelope. Combined envelope 321 includes magnetic impulses 322. Amplitude of magnetic flux density of impulses in the combined envelope may be decreasing for in a range of 1% to 95% or 5% to 90% or 10% to 80% of the time duration of the whole combined envelope. The amplitude of magnetic flux density of subsequent impulses in the rectangular part of the combined envelope may oscillate around predetermined value of amplitude of magnetic flux density in range of 0.01% to 5%. The envelope duration 323 of the combined envelope 321 begins from first impulse of the first pulse to end of the passive time duration of last pulse. The combined envelope as shown on FIG. 32 may be used for inducing of muscle contraction or muscle twitches and subsequent end of the muscle stimulation. Similarly, the amplitude of RF waves may be modulated in amplitude to assemble combined envelope 321.

Figure 33:
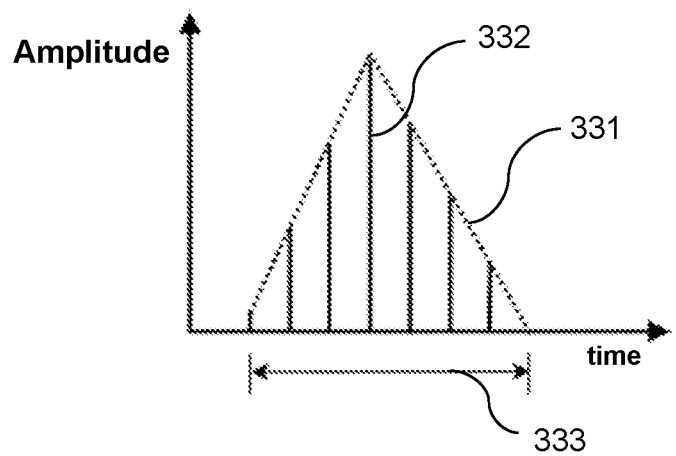
FIG. 33 illustrates an exemplary triangular envelope of magnetic field.

FIG. 33 is an exemplary illustration of triangular envelope 331, which can be understood as a combination of the increasing envelope immediately followed by the decreasing envelope. Triangular envelope 331 may include magnetic impulses 332. The triangular shape of the envelope may not be symmetrical. Also, the straightness of one or more lines of the triangular shape may be interrupted by another type of envelope mentioned herein, e.g. rectangular envelope. One triangular envelope may closely follow another triangular envelope or be joined to another triangular envelope. By joining two triangular envelopes, the resulting envelope may have the saw-tooth shape. The envelope duration 333 of the triangular envelope 331 begins from first impulse of the first pulse to end of the passive time duration of last pulse. Similarly, the amplitude of RF waves may be modulated in amplitude to assemble triangular envelope 331.

Figure 34:
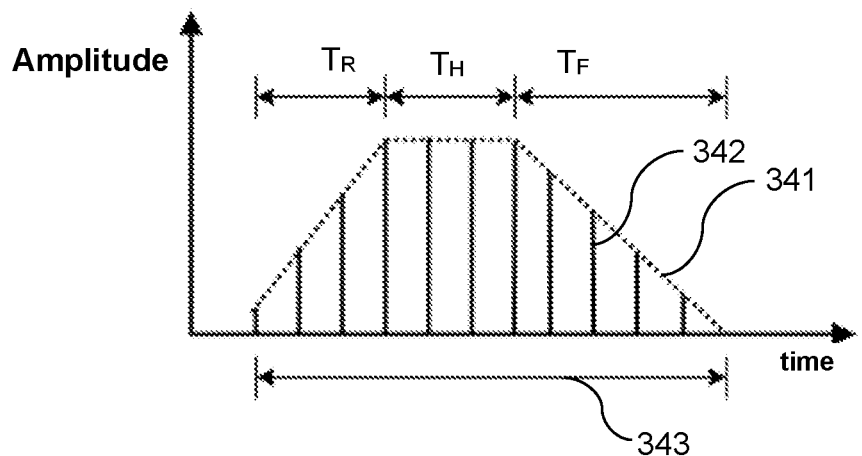
FIG. 34 illustrates an exemplary trapezoidal envelope of magnetic field.

FIG. 34 is an exemplary illustration of a trapezoidal envelope 341. The trapezoidal envelope 341 may include magnetic impulses 342. The trapezoidal envelope may include increasing (rising) time period $T_R$, hold time period $T_H$ and decreasing (fall) time period $T_F$. During increasing time period, the amplitude of magnetic flux density of subsequent impulses is increasing. Further, during increasing time period the amplitude of magnetic flux density of one impulse is higher than amplitude of magnetic flux density of preceding impulse. During hold time period, the amplitude of magnetic flux density of subsequent impulses may oscillate around predetermined value of amplitude of magnetic flux density in range of 0.01% to 5%. During decreasing time period, the amplitude of magnetic flux density of subsequent impulses is decreasing. Further, during decreasing time period the amplitude of magnetic flux density of one impulse is lower than amplitude of magnetic flux density of preceding impulse. Hold period may be interrupted by another hold time period of having different predetermined value of the magnetic flux density. The envelope duration 343 of the trapezoidal envelope 341 begins from first impulse of the first pulse to end of the passive time duration of last pulse. Similarly, the amplitude of RF waves may be modulated in amplitude to assemble trapezoidal envelope 341.

A trapezoidal envelope may be perceived by the patient as the most comfortable for muscle tissue stimulation. Trapezoidal envelope respects natural course of muscle contraction, i.e. the muscle contraction may be time-varying. Strength of natural muscle contraction increases, holds at the highest strength and decreases. The trapezoidal envelope corresponds with natural muscle contraction, i.e. the strength of the muscle contraction may correspond with the magnetic flux density. The magnetic flux density during the duration of the trapezoidal envelope increases, holds and decreases. Same shape of envelope may have RF electrode formed from RF impulses having appropriate amplitude.

The trapezoidal envelope may be at least once interrupted by one or more impulses, pulses, bursts and/or trains that do not fit to the trapezoidal envelope shape, but after this interruption the trapezoidal envelope may continue.

Also, the trapezoidal envelope may include plurality of trains, e.g. two, three four or more trains. In case of trapezoidal shape, the envelope may include three trains. The first train may include impulses with increasing magnetic flux density. Magnetic flux density of one impulse may be higher than magnetic flux density of the second impulse following the first impulse. The second train may include impulses with constant magnetic flux density. However, the operation of the treatment device may not provide strictly constant magnetic flux density for each impulse, therefore the magnetic flux density may oscillate in range of 0.1 to 5%. The third train may include impulses with decreasing magnetic flux density. Magnetic flux density of one impulse may be lower than magnetic flux density of the second impulse following the first impulse.

Furthermore. trapezoidal envelope may include plurality of bursts, e.g. two, three four or more bursts. In case of trapezoidal shape, the envelope may include three bursts. The first burst may include impulses with increasing magnetic flux density. Magnetic flux density of one impulse may be higher than magnetic flux density of the second impulse following the first impulse. The second bursts may include impulses with constant magnetic flux density. However, the operation of the treatment device may not provide strictly constant magnetic flux density for each impulse, therefore the magnetic flux density may oscillate in range of 0.1 to 5%. The third bursts may include impulses with decreasing magnetic flux density. Magnetic flux density of one impulse may be lower than magnetic flux density of the second impulse following the first impulse.

Figure 20:
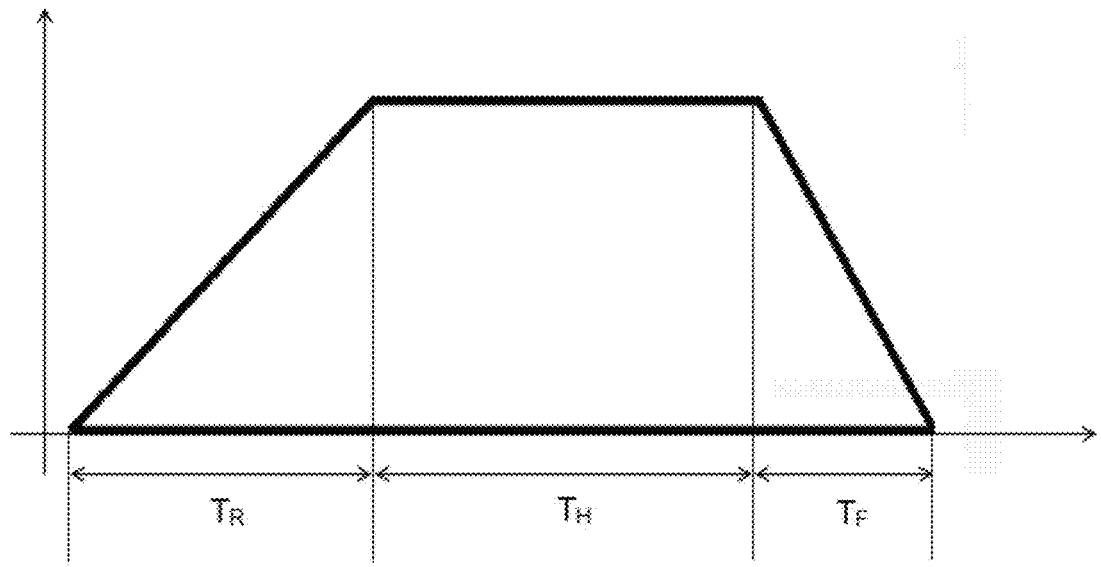
FIG. 20 illustrates a trapezoidal envelope.

FIG. 20 illustrates another exemplary trapezoidal envelope. The vertical axis may represent magnetic flux density, and the horizontal axis may represent time. A trapezoidal envelope may be a fitted curve through amplitudes of magnetic flux density of impulses applied during a train, where $T_R$ is time period with increasing magnetic flux density called increasing transient time, i.e. the amplitude of the magnetic flux density may increase. $T_H$ is time period with maximal magnetic flux density, i.e. the amplitude of the magnetic flux density may be constant. $T_F$ is time period with decreasing magnetic flux density, i.e. the amplitude of the magnetic flux density may decrease. A sum of $T_R$, $T_H$ and $T_F$ may be trapezoidal envelope duration that may corresponds with muscle contraction.

The trapezoidal envelope may decrease energy consumption. Due to lower energy consumption, the trapezoidal shape may enable improved cooling of the magnetic field generating device. Further, the resistive losses may be reduced due to lower temperature of the magnetic field generating device. Different repetition rates may cause different types of muscle contractions. Each type of muscle contraction may consume different amounts of energy.

Figure 35:
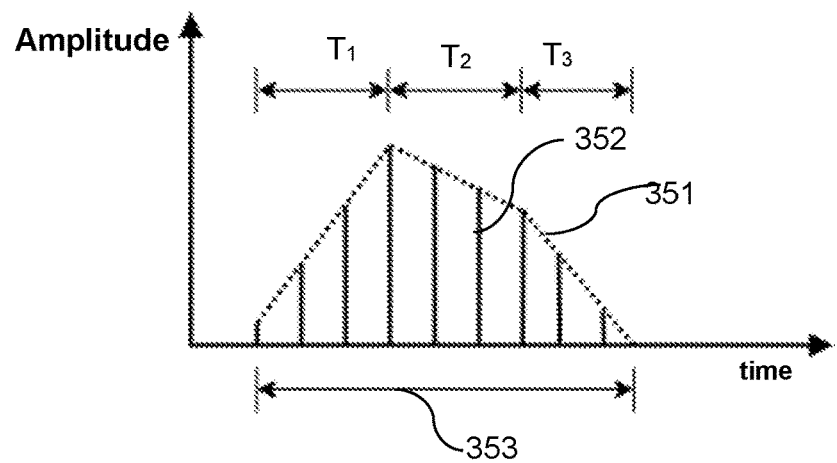
FIG. 35 illustrates another exemplary trapezoidal envelope of magnetic field.

FIG. 35 is an exemplary illustration of a trapezoidal envelope 351 including an increasing time period $T_1$, a first decreasing time period $T_2$ and a second decreasing time period $T_3$. The trapezoidal envelope 351 includes magnetic impulses 352. Increasing time period includes impulses with increasing amplitude of magnetic flux density. First decreasing time period and second decreasing time period includes impulses with decreasing amplitude of the magnetic flux density. On the shown example, first decreasing time period follows the increasing time period and precedes the second decreasing time period. The amplitude of magnetic flux density of subsequent impulses is shown to decrease more steeply during the second decreasing time period. Alternatively, the amplitude of magnetic flux density of subsequent impulses may decrease more steeply during the first decreasing time period. The envelope duration 353 of the trapezoidal envelope 351 begins from first impulse of the first pulse to end of the passive time duration of last pulse. Accordingly, the envelope may be a magnetic envelopes formed from RF impulses. Similarly, the amplitude of RF waves may be modulated in amplitude to assemble trapezoidal envelope 351.

Figure 36:
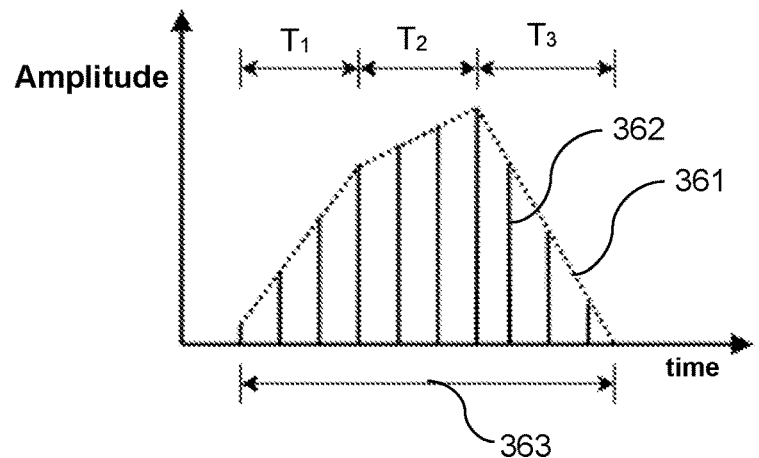
FIG. 36 illustrates another exemplary trapezoidal envelope of magnetic field.

FIG. 36 is an exemplary illustration of a trapezoidal envelope 361 including a first increasing time period, a second increasing time period and a decreasing time period. The trapezoidal envelope 361 includes magnetic impulses 362. First increasing time period and second increasing time period include impulses with increasing amplitude of magnetic flux density. First increasing time period and second increasing time period include impulses with increasing amplitude of the magnetic flux density. On the shown example, second increasing time period follows the first increasing time period and precedes the decreasing time period. The amplitude of magnetic flux density of subsequent impulses is shown to increase more steeply during the first increasing time period. Alternatively, the amplitude of magnetic flux density of subsequent impulses may increase more steeply during the second increasing time period. The envelope duration 363 of the trapezoidal envelope 361 begins from first impulse of the first pulse to end of the passive time duration of last pulse. Similarly, the amplitude of RF waves may be modulated in amplitude to assemble trapezoidal envelope 361.

Figure 37:
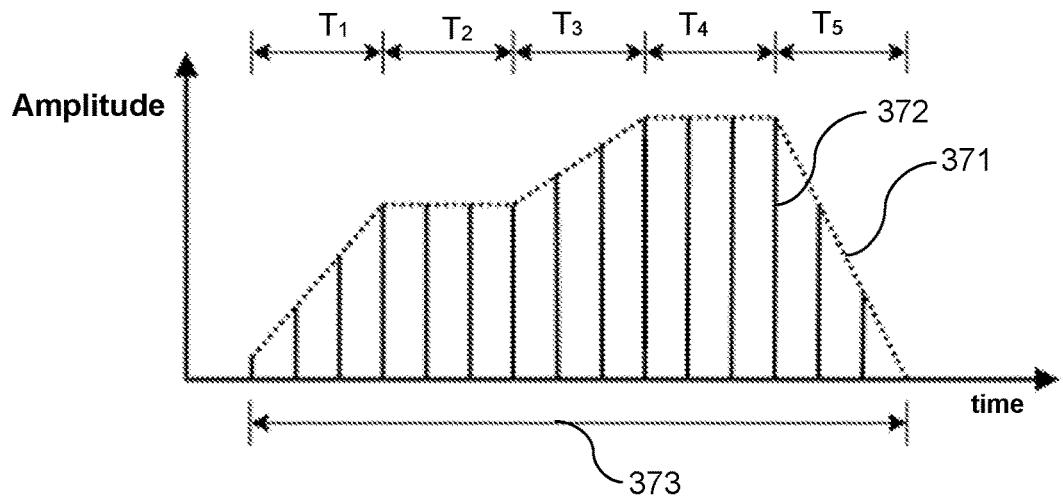
FIG. 37 illustrates an exemplary step envelope of magnetic field.

FIG. 37 is an exemplary illustration of a step envelope 371 including a first increasing time period $T_1$, first hold time period $T_2$, second increasing time period, second hold time period and a decreasing time period. The step envelope 371 includes magnetic impulses 372. During first and second increasing time periods the amplitude of magnetic flux density of subsequent impulses may increase. During decreasing time period the amplitude of magnetic flux density of subsequent impulses may decrease. During hold time period the amplitude of magnetic flux density of subsequent impulses may be constant or may oscillate around predetermined value of amplitude of magnetic flux density in range of 0.01% to 5%. The envelope duration 373 of the step envelope 371 begins from first impulse of the first pulse to end of the passive time duration of last pulse. Similarly, the amplitude of RF waves may be modulated in amplitude to assemble step envelope 371.

Figure 38:
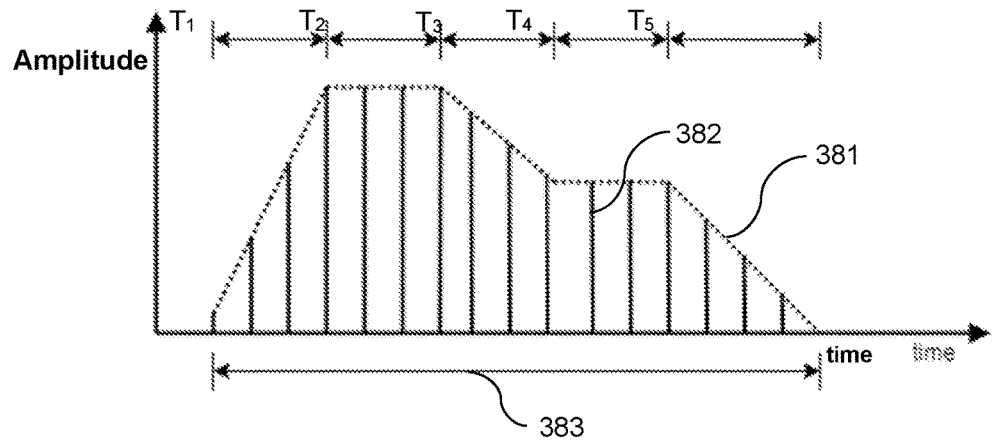
FIG. 38 illustrates another exemplary step envelope of magnetic field.

FIG. 38 is an exemplary illustration of a step envelope 381 including a first increasing time period $T_1$, first hold time period $T_2$, first decreasing time period $T_3$, second hold time period $T_4$ and a second decreasing time period $T_5$. The step envelope 381 includes magnetic impulses 382. During increasing time period the amplitude of magnetic flux density of subsequent impulses may increase. During first and second decreasing time periods the amplitude of magnetic flux density of subsequent impulses may decrease. During hold time period the amplitude of magnetic flux density of subsequent impulses may be constant or may oscillate around predetermined value of amplitude of magnetic flux density in range of 0.01% to 5%. The envelope duration 383 of the step envelope 381 begins from first impulse of the first pulse to end of the passive time duration of last pulse.

Similarly, the amplitude of RF waves may be modulated in amplitude to assemble envelope 381.

Figure 39:
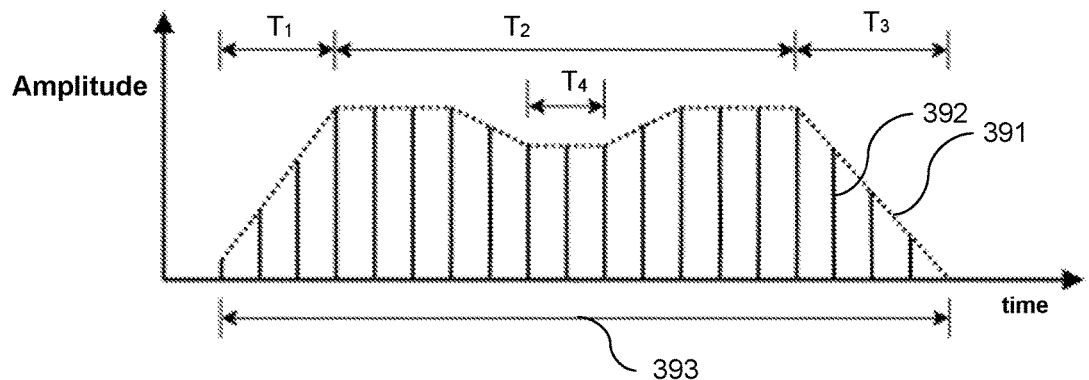
FIG. 39 illustrates another exemplary trapezoidal envelope of magnetic field.

FIG. 39 is an exemplary illustration of another type of trapezoidal envelope 391 including magnetic impulses 392. The trapezoidal envelope may include increasing time period $T_1$, hold time period $T_2$ and decreasing time period $T_3$. During increasing time period, the amplitude of magnetic flux density of subsequent impulses is increasing. Further, during increasing time period the amplitude of magnetic flux density of one impulse is higher than amplitude of magnetic flux density of preceding impulse. During hold time period, the amplitude of magnetic flux density of subsequent impulses may oscillate around predetermined value of amplitude of magnetic flux density in range of 0.01% to 5%. During decreasing time period, the amplitude of magnetic flux density of subsequent impulses is decreasing. Further, during decreasing time period the amplitude of magnetic flux density of one impulse is lower than amplitude of magnetic flux density of preceding impulse. Hold period may include another hold time period $T_4$ of having different predetermined value of the magnetic flux density. The envelope duration 393 of the envelope 391 begins from first impulse of the first pulse to end of the passive time duration of last pulse. Similarly, the amplitude of RF waves and/or RF impulses may be modulated in amplitude to assemble envelope 391.

Figure 40:
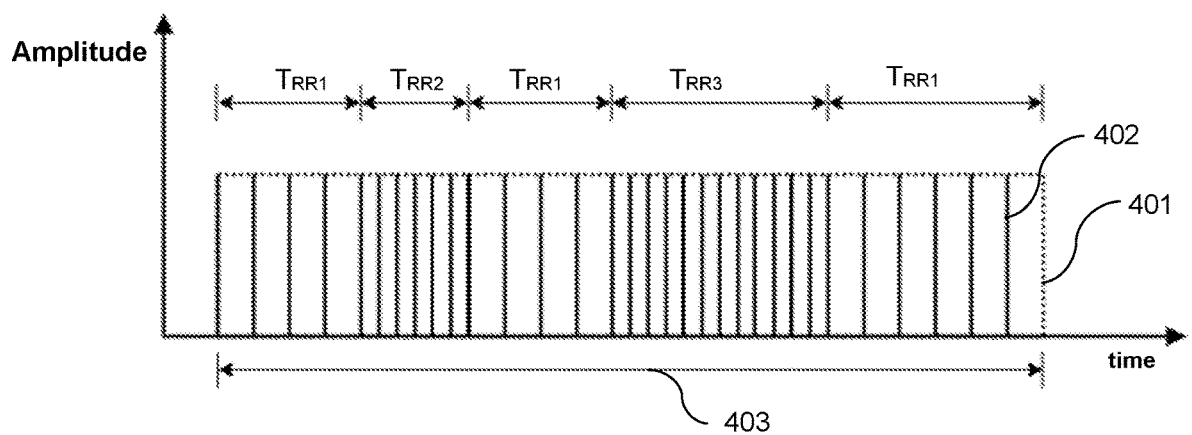
FIG. 40 illustrates an example of envelope of magnetic field including modulation in domain of repetition rate.

The envelope may include combined modulation of magnetic flux density and repetition rate. FIG. 40 shows exemplary illustration of rectangular envelope 401 with constant amplitude of magnetic flux density. The rectangular envelope 401 may include magnetic impulses 402. Time periods $T_{RR2}$ and $T_{RR3}$ shows impulses having higher repetition frequency than rest of the magnetic impulses during $T_{RR1}$ of shown rectangular envelope. Shown time periods $T_{RR2}$ and $T_{RR3}$ may provide stronger muscle contraction than the rest of the shown rectangular envelope. However, all shown envelopes may include modulation in repetition rate domain. The envelope duration 403 of the rectangular envelope 401 begins from first impulse of the first pulse to end of the passive time duration of last pulse. Accordingly, the envelope may be a magnetic envelopes formed from RF impulses. Their amplitude may also form an amplitude, called RF envelope. Similarly, the amplitude and/or repetition rate of RF impulses may be modulated in amplitude to assemble envelopes 401.

Figure 41:
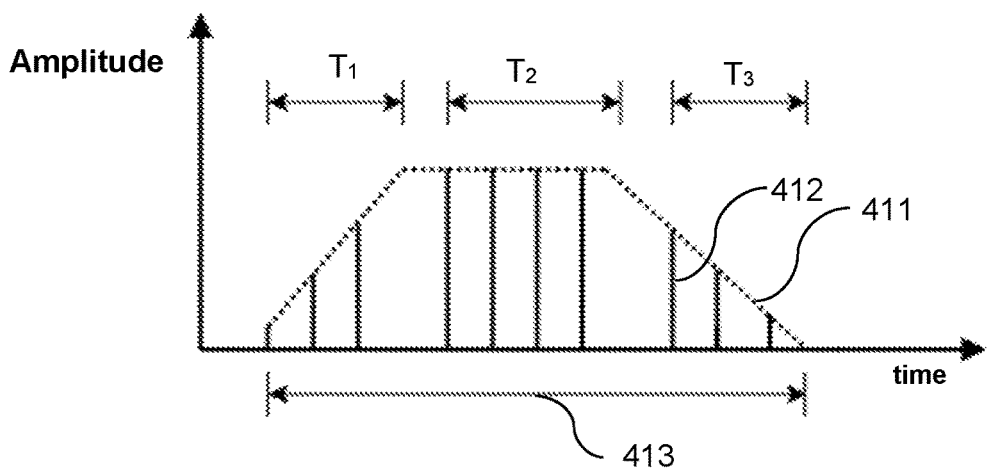
FIG. 41 illustrates an exemplary trapezoidal envelope formed from trains of magnetic field.

As mentioned, the envelope may be formed from magnetic trains separated by one or more missing pulses. FIG. 41 shows the envelope formed from magnetic trains including magnetic impulses 412. As shown, first train including train of impulses with increasing magnetic flux density has duration $T_1$. Second train of including impulses with constant or oscillating magnetic flux density has duration $T_2$. Third train of including impulses with decreasing magnetic flux density has duration $T_3$. The envelope 411 including plurality of trains has trapezoidal shape. The time durations between durations $T_1$ and $T_2$ or durations $T_2$ and $T_3$ may represent time gaps where the missing pulses including missing impulses would be positioned. The envelope duration 413 of the envelope 411 begins from first impulse of the first pulse to end of the passive time duration of last pulse. Similarly, the amplitude of RF waves or RF impulses may be modulated in amplitude to assemble envelopes 411.

Figure 42:
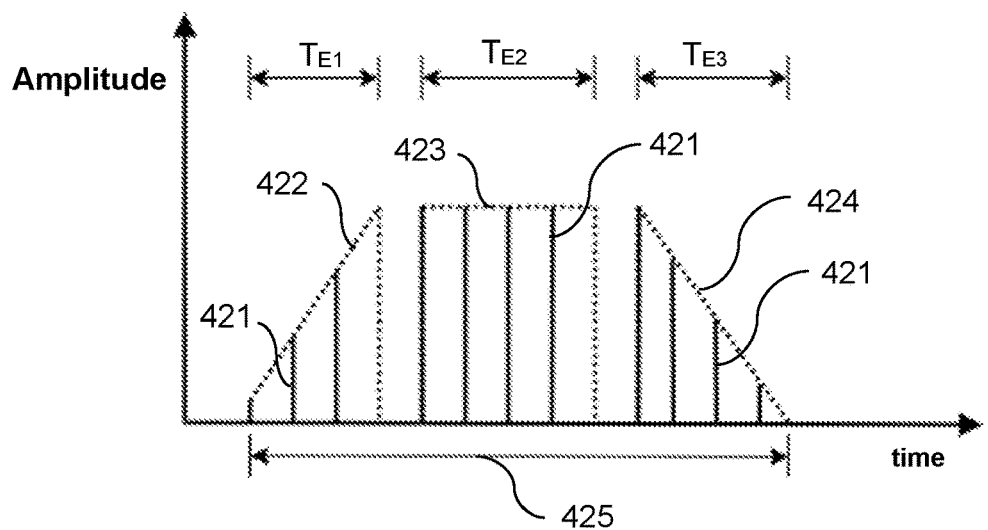
FIG. 42 illustrates another exemplary combined envelope of magnetic field.

During treatment, the magnetic envelopes may be combined. FIG. 42 shows an example of combination of magnetic envelopes. The increasing envelope 422 having increasing shape includes train of magnetic impulses 421. The increasing envelope 422 may have duration TEL The rectangular envelope 423 includes train of magnetic impulses 421. The rectangular envelope may have duration $T_{E2}$. The decreasing envelope 424 includes train of magnetic impulses 421. The decreasing envelope 424 may have duration $T_{E3}$. A resulting subperiod of treatment protocol formed by combination of the first, second and third envelope, may provide same or similar treatment effect as trapezoidal envelope shown e.g. on FIG. 34 and FIG. 20. A resulting subperiod of treatment protocol has duration 425 from first impulse of the first pulse to end of the passive time duration of last pulse of the treatment subperiod. Similarly, the amplitude of RF waves and/or RF impulses may be modulated in amplitude to assemble combination of envelopes.

Figure 43:
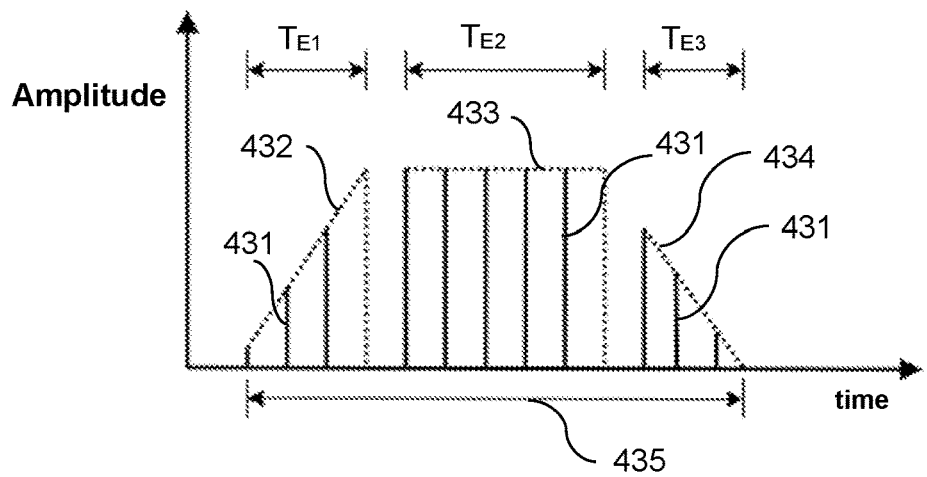
FIG. 43 illustrates another exemplary combined envelope of magnetic field.

FIG. 43 illustrates another example of combination of magnetic envelopes, wherein the decreasing period has different magnetic flux density than rectangular envelope. This example may illustrate, that combination of magnetic envelopes may include envelopes with different magnetic flux density. The increasing envelope 432 having increasing shape includes train of magnetic impulses 431. The increasing envelope may have duration TEL The rectangular envelope 433 includes train of magnetic impulses 431. The rectangular envelope may have duration $T_{E2}$. The decreasing envelope includes train of magnetic impulses 431. The decreasing envelope 434 may have duration $T_{E3}$. A resulting subperiod of treatment protocol formed by combination of the first, second and third envelope, may provide same or similar treatment effect as trapezoidal envelope shown e.g. on FIGS. 34 and 20. A resulting subperiod of treatment protocol has duration 435 from first impulse of the first pulse to end of the passive time duration of last pulse of the treatment subperiod. Similarly, the amplitude of RF waves or RF impulses may be modulated in amplitude to assemble combination of envelopes.

Figure 44:
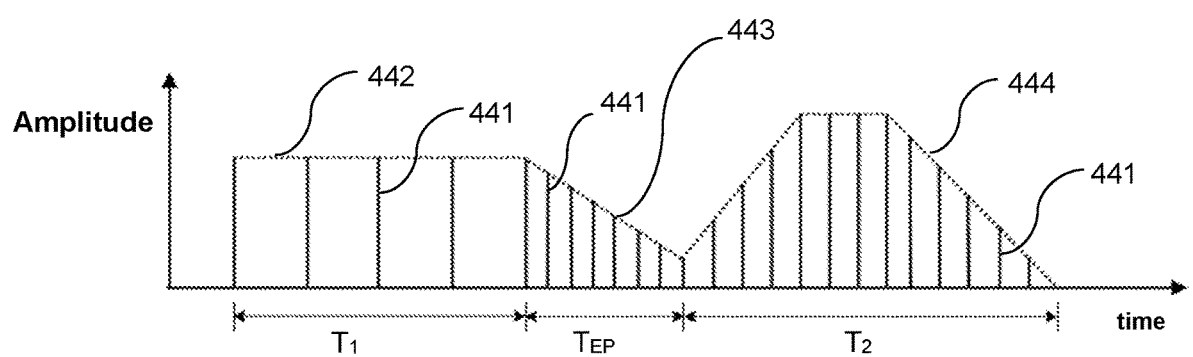
FIG. 44 illustrates two exemplary envelopes of magnetic field with an example of inter-envelope period.

FIG. 44 two exemplary envelopes of magnetic field with an example of inter-envelope period i.e. time period between envelopes. Time period between envelopes may include time of no magnetic stimulation. However, the time period between envelopes may include magnetic impulses providing insufficient or unrecognizable muscle stimulation (including e.g. muscle contraction and muscle relaxation). The magnetic impulses generated during time period between envelopes may also form envelope. The magnetic impulses providing insufficient or unrecognizable muscle stimulation may be generated by discharging of energy storage device to magnetic field generating coil in order to discharge the resting capacity. The energy storage device may be then charged by power source to higher amount of electrical current and/or voltage in order to provide high power current impulses to magnetic field generating device. Rectangular envelope 442 having duration $T_1$ may include magnetic impulses 441. Trapezoidal envelope 444 having duration $T_2$ may include magnetic impulses 441. The inter-envelope time period having duration $T_{EP}$ may include envelope 443 (e.g. having decreasing shape) given by magnetic flux density of magnetic impulses 441 within the inter-envelope time period. Alternatively, the inter-envelope time period may include single impulses providing muscle twitches. Accordingly, the envelope may be a magnetic envelopes formed from RF impulses. Their amplitude may also form an amplitude, called RF envelope. The time period between RF envelopes may include time of no heating.

The RF treatment (RF field) may be generated by treatment energy source (e.g. RF electrode) in continual operation, pulsed operation or operation including cycles. The continual operation is provided during continual RF treatment. The pulsed operation is provided during pulsed RF treatment.

During the continual operation, RF electrode may generate RF field for the whole treatment or in one time duration during the treatment, as commanded by master unit one or more control units. The RF electrode may generate RF wave having a sine shape. In other words, the RF electrode may generate radio frequency waveform having sine shape. Other shapes are possible, e.g. sawtooth, triangle or square according to amplitudes of RF wave.

The continual RF treatment may have one of the highest synergic effects with provided magnetic treatment due to continual heating of the patient's target biological structures, highest effect to polarization of the patient's target biological structures and to ensure deep magnetic field penetration and high effect of generated magnetic field to a patient's tissue, such as to promote muscle contraction.

During the pulsed generation the RF electrode may generate RF field for two or more active time periods of the treatment, wherein the time periods may be separated by passive time periods. Active time period of pulsed RF treatment may represent the time period during which the RF electrode is active and generates RF field. The active time period may be in the range of 1 s to 15 minutes or 30 s to 10 minutes or 5 s to 900 s or 30 s to 300 s or 60 s to 360 s. The passive time period of RF pulsed treatment may represent the time period during which the RF electrode is inactive and does not generate RF field. The passive time period of RF pulsed treatment may be in the range of 1 s to 15 minutes or 10 s to 10 minutes or 5 s to 600 s or 5 s to 300 s or from 10 s to 180 s. Pulsed generation and its parameters may vary during the treatment.

The user may select, control or adjust various treatment protocols of the treatment device through the control unit or the master unit of the treatment device. Also, the master unit and/or control unit may select, control or adjust treatment protocols body area or another option selected by the user. In addition, the master unit and/or control unit may select, control or adjust treatment various treatment parameters according to feedback provided by any sensor mentioned above.

The treatment protocol may include a selection of one or more treatment parameters and their predetermined values as assigned to respective protocol. Further, the treatment protocol may include various types of combined treatment by magnetic treatment and RF treatment.

Regarding the treatment parameters, the user may control or adjust various treatment parameters of the treatment device through the control system including master unit or one or more control units of the treatment device. The master unit and/or control unit may control or adjust treatment parameters according to treatment protocol, body area or another option selected by the user. In addition, the master unit and/or control unit may control or adjust treatment various treatment parameters according to feedback provided by any sensor mentioned above. The master unit or one or more control unit may provide adjustment of treatment parameters of magnetic field including magnetic flux density, amplitude of magnetic flux density, impulse duration, pulse duration, repetition rate of impulses, repetition rate of pulses, train duration, number of impulses and/or pulses in train, burst duration, composition of magnetic burst, composition of magnetic train, number of envelopes, duty cycle, shape of envelopes and/or maximal of the magnetic flux density derivative. The master unit or one or more control unit may provide adjustment of treatment parameters of RF field including frequency of RF field, duty cycle of RF field, intensity of RF field, energy flux provided by RF field, power of RF field, amplitude of power of RF field and/or amplitude of power of RF waves, wherein the RF waves may refer to electrical component of RF field. Treatment parameters may be controlled or adjusted in following ranges.

In addition, treatment parameters may include, for example, the treatment time, temperature of magnetic field generating device, temperature of RF electrode, temperature of the applicator, temperature of the cooling tank, selection of targeted body area, number of connected applicator, temperature of cooling fluid (as measured in a fluid conduit, connecting tube, applicator or cooling tank by an appropriate temperature sensor), selected body area and/or others.

Different magnetic flux density, pulse duration, composition of trains and/or bursts may have different influence on muscle tissue. One part of a magnetic treatment may cause, for example, muscle training in order to increase muscle strength, muscle volume, muscle toning, and other parts of the magnetic treatment may cause muscle relaxation. The signal provided to the RF electrode may be modulated with regard to capacity of the circuit created by two bipolar RF electrodes and the patient's body, preventing creation of standing radiofrequency waves in the applicator and/or a patient, or other. The modulation of the radiofrequency field may be provided in the frequency domain, intensity domain, impulse duration, and/or other parameters. The goal of individual radiofrequency treatment, magnetic treatment and/or their combination is to reach the most complex and/or efficient treatment of the target biological structure. The modulation in the time domain may provide active and passive periods of stimulation. Passive period may occur when the RF treatment and/or magnetic treatment includes a period with no muscle stimulation and/or no change of temperature or other treatment effect provided by RF field of target biological structure. During a passive period, there may not be generated a magnetic field and/or RF field. Also, during a passive period, magnetic field and RF field may be generated but the intensity of the magnetic field and/or the RF field may not be sufficient to provide treatment effect of at least one of the target biological structure.

The magnetic flux density of the magnetic field may be in a range from 0.1 T to 7 T, or in a range from 0.5 T to 7 T, or in a range from 0.5 T to 5 T, or in range from 0.5 T to 4 T, or in range from 0.5 T to 2 T. Such definition may include the amplitude of magnetic flux density of the magnetic field. Shown ranges of magnetic flux density may be used for causing muscle contraction. The magnetic flux density and/or amplitude of the magnetic flux density may be measured by fluxmeter or by oscilloscope.

A repetition rate may refer to a frequency of firing the magnetic impulses. The repetition rate may be derived from the time duration of the magnetic pulse. The repetition rate of the magnetic impulses may be in the range of 0.1 Hz to 700 Hz, or from 1 Hz to 700 Hz, or from 1 Hz to 500 Hz, or in the range of 1 Hz to 300 Hz or 1 Hz to 150 Hz. As each magnetic pulse includes one magnetic impulse, the repetition rate of magnetic pulses is equal to repetition rate of magnetic impulses. The duration of magnetic impulses may be in a range from 1 µs to 10 ms or from 3 µs to 3 ms or from 3 µs to 3 ms or from 3 µs to 1 ms or 10 µs to 2000 µs or 50 µs to 1000 µs or from 100 µs to 800 µs. The repetition rate of impulses may be measured from recording of the oscilloscope measurement.

The train duration may be in the range of 1 ms to 300 s or from 1 ms to 80 s or from 2 ms to 60 s or 4 ms to 30 s, or from 8 ms to 10s, or from 25 ms to 3 s. A time between two subsequent trains may be in a range of 5 ms to 100 s, or of 10 ms to 50 s, or of 200 ms to 25 s, or of 500 ms to 10 s, or of 750 ms to 5 s or from 300 ms to 20 s. The repetition rate may be measured from recording of the oscilloscope measurement.

The burst duration may be in a range of 10 ms to 100 seconds, or from 100 ms to 15 s, or from 500 ms to 7 s, or from 500 ms to 5 s. The repetition rate of magnetic bursts may be in a range of 0.01 Hz to 150 Hz, or of 0.02 Hz to 100 Hz, or in the range of 0.05 Hz to 50 Hz, or 0.05 Hz to 10 Hz, or of 0.05 Hz to 2 Hz. The repetition rate may be measured from recording of the oscilloscope measurement.

Another parameter to provide effective magnetic treatment and causing muscle contraction is a derivative of the magnetic flux density defined by dB/dt, where: dB is magnetic flux density derivative [T] and dt is time derivative [s]. The magnetic flux density derivative is related to magnetic field. The magnetic flux density derivative may be defined as the amount of induced electric current in the tissue and so it may serve as one of the key parameters to in providing muscle contraction. The higher the magnetic flux density derivative, the stronger muscle contraction is. The magnetic flux density derivative may be calculated from the equation mentioned above.

The maximal value of the magnetic flux density derivative may be up to 5 MT/s, or in the ranges of 0.3 to 800 kT/s, 0.5 to 400 kT/s, 1 to 300 kT/s, 1.5 to 250 kT/s, 2 to 200 kT/s, or 2.5 to 150 kT/s.

The frequency of the RF field (e.g. RF waves) may be in the range of hundreds of kHz to tens of GHz, e.g. in the range of 100 kHz to 3 GHz, or 500 kHz to 3 GHz, 400 kHz to 900 MHz or 500 kHz to 900 MHz or around 13.56 MHz, 40.68 MHz, 27.12 MHz, or 2.45 GHz.

An energy flux provided by RF field (e.g. RF waves) may be in the range of 0.001 W/cm$^2$ to 1,500 W/cm$^2$, or 0.001 W/cm$^2$ to 15 W/cm$^2$, or 0.01 W/cm$^2$ to 1,000 W/cm$^2$, or of 0.01 W/cm$^2$ to 5 W/cm$^2$, or of 0.08 W/cm$^2$ to 1 W/cm$^2$ or of 0.1 W/cm$^2$ to 0.7 W/cm$^2$. The term "around" should be interpreted as in the range of 5% of the recited value.

The voltage of electromagnetic signal provided by power source of treatment circuit for RF treatment may be in the range of 1 V to 5 kV, or 5 V to 140 V, or 10 V to 120 V, or 15 V to 50 V, or 20 V to 50 V.

The temperature in the biological structure, temperature on the surface of treated body area, temperature in the body area, temperature of the inside of the applicator, temperature of the RF electrode and/or temperature of the magnetic field generating device may be measured e.g. by the temperature sensor 816 implemented in the applicator shown in FIG. 8c. The temperature of the RF electrode and/or magnetic field generating device may be maintained in a range from 38° C. to 150° C., 38° C. to 100° C., or from 40° C. to 80° C., 40° C. to 60° C. or 41° C. to 60° C., or 42° C. to 60° C. The temperature on the surface of treated body area, temperature in the treated body and/or in the biological structure may be increased to the temperature in a range of 38° C. to 60° C., or of 40° C. to 52° C., or of 41° C. to 50° C., or of 41° C. to 48° C., or of 42° C. to 48° C., or of 42° C. to 45° C. The values of temperature described above may be achieved during 5 s to 600 s, 10 s to 300 s, or 30 s to 180 s after RF treatment and/or magnetic treatment starts. After that, the value temperature may be maintained constant during the treatment with maximal temperature deviation in a range of 5° C. 3° C., or 2° C., or 1° C.

At the beginning of the treatment a starting temperature on the patient's skin and/or in the biological structure may be increased to the starting temperature in range from 42° C. to 60° C., or from 45° C. to 54° C., or from 48° C. to 60° C., or from 48° C. to 52° C. and/or to a temperature 3° C., or 5° C., or 8° C. above the temperature when apoptotic process begins but not over 60° C. After 45 s to 360 s, or after 60 s to 300 s, or after 120 s to 400 s, or after 300 s to 500 s when the starting temperature was reached, the intensity of the RF field may be decreased and a temperature on the patient's skin and/or temperature in the biological structure may be maintained at the temperature in a range from 41° C. to 50° C., or from 42° C. to 48° C. According to another method of the treatment, the temperature of the biological structure may be during the treatment at least two times decreased and increased in a range of 2° C. to 10° C., 2° C. to 8° C., or 3° C. to 6° C. while at least one applicator is attached to the same patient's body area, such as an abdominal area, buttock, arm, leg and/or other body area.

Temperature in the biological structure may be calculated according to mathematic model, correlation function, in combination with at least one or more measured characteristic. Such measured characteristic may include temperature on the patient's skin, capacitance between RF electrodes, Volt-Ampere characteristic of RF bipolar electrodes and/or Volt-Ampere characteristic of connected electrical elements to RF electrodes.

The treatment duration may be from 5 minutes to 120 minutes, or from 5 minutes to 60 minutes, or from 15 minutes to 40 minutes. During one week, one, two or three treatments of the same body area may be provided. Also, one pause between two subsequent treatments may be one, two or three weeks.

The sum of energy flux density of the RF treatment and the magnetic treatment applied to the patient during the treatment, may be in a range from 0.03 mW/mm$^2$ to 1.2 W/mm$^2$, or in the range from 0.05 mW/mm$^2$ to 0.9 W/mm$^2$, or in the range from 0.01 mW/mm$^2$ to 0.65 W/mm$^2$. A portion of the energy flux density of magnetic treatment during the simultaneous application of RF treatment and active magnetic treatment may be in a range from 1% to 70%, 3% to 50%, 5% to 30%, or 1% to 20% of treatment time.

The power output of RF energy (i.e. RF field) provided by one RF electrode may be in a range of 0.005 W to 350 W or 0.1 W to 200 W or 0.1 W to 150 W.

Figure 21:
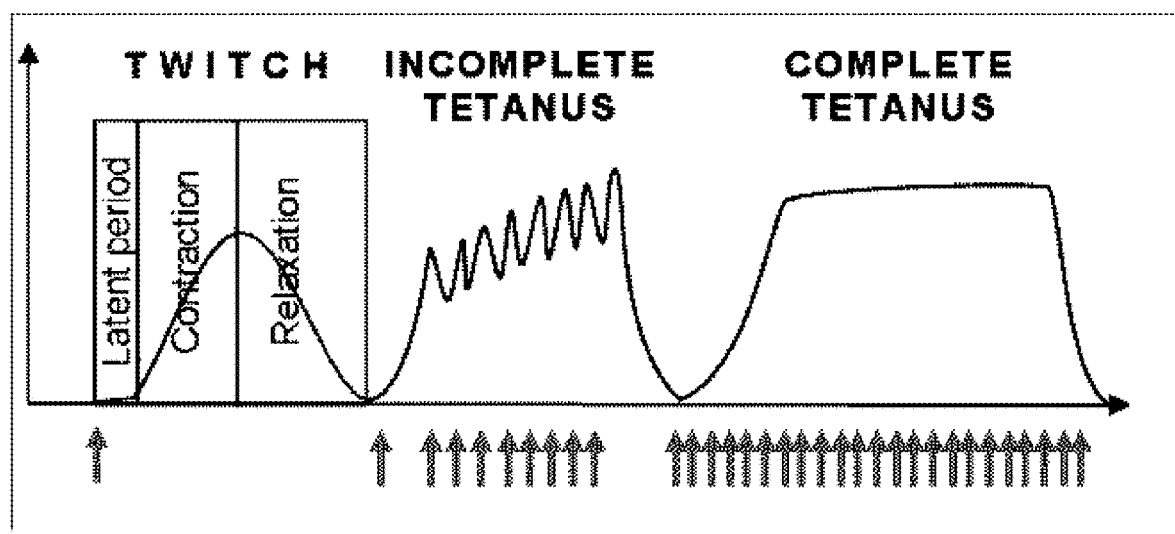
FIG. 21 illustrates different types of muscle stimulation.

FIG. 21 illustrates different types of muscle contraction, which may be provided by treatment device and achieved by application of magnetic field or combination of magnetic field and RF field. The muscle contraction may differ in energy consumption and muscle targeting, e.g., muscle strengthening, muscle volume increase/decrease, muscle endurance, muscle relaxation, warming up of the muscle and/or other effects. The vertical axis may represent a strength of the muscle contraction, and the horizontal axis may represent time. The arrows may represent magnetic impulses and/or pulses applied to the muscle of the patient.

Low repetition rate of the time-varying magnetic field pulses, e.g. in a range of 1 Hz to 15 Hz, may cause a twitch. Low repetition rate may be sufficiently low to enable the treated muscle to fully relax. The energy consumption of the treated muscle may be low due to low repetition rate. However, the low repetition rate may cause for active relaxation of muscle e.g. between two contractions.

Intermediate repetition rate of the time-varying magnetic field pulses may cause incomplete tetanus muscle contraction, intermediate repetition rate may be in a range of 15 Hz to 29 Hz. Incomplete tetanus muscle contraction may be defined by a repetition rate in a range of 10 Hz to 30 Hz. The muscle may not fully relax. The muscle may be partially relaxed. The muscle contraction strength may increase with constant magnetic flux density applied.

Higher repetition rate of the time-varying magnetic field pulses may cause complete tetanus muscle contraction. Higher repetition rates may be for example in a range of 30 Hz to 150 Hz, or 30 Hz to 90 Hz, or 30 Hz to 60 Hz. The complete tetanus muscle contraction may cause the strongest supramaximal muscle contraction. The supramaximal muscle contraction may be stronger than volitional muscle contraction. The energy consumption may be higher. The strengthening effect may be improved. Further, it is believed that at repetition rates of at least 30 Hz, the adipose cells may be reduced in volume and/or in number.

Even higher repetition rate of the time-varying magnetic field pulses over 90 Hz may suppress and/or block pain excitement transmission at different levels or neural system and/or pain receptors. The higher repetition rate may be at least 100 Hz, at least 120 Hz, or at least 140 Hz, or in a range of 100 Hz to 230 Hz, or 120 Hz to 200 Hz, or 140 Hz to 180 Hz. The application of time-varying magnetic field to the muscle of the patient may cause a pain relieving effect.

High repetition rate of the time-varying magnetic field pulses in a range of 120 Hz to 300 Hz, or 150 Hz to 250 Hz, or 180 Hz to 350 Hz, or higher than 200 Hz may cause a myorelaxation effect.

A quality of the muscle contraction caused by the time-varying magnetic field may be characterized by parameters such as a contractile force of the muscle contraction, a muscle-tendon length, a relative shortening of the muscle or a shortening velocity of the muscle.

The contractile force of the muscle contraction may reach a contractile force of at least 0.1 N/cm$^2$ and up to 250 N/cm$^2$. The contractile force may be in a range from 0.5 N/cm$^2$ to 200 N/cm$^2$, or in the range from 1 N/cm$^2$ to 150 N/cm$^2$, or in the range from 2 N/cm$^2$ to 100 N/cm$^2$.

The muscle-tendon length may reach up to 65% of a rest muscle-tendon length. The muscle-tendon length may be in a range of 1 to 65% of the rest muscle-tendon length, or in a range of 3 to 55% of the rest muscle-tendon length, or in a range of 5% to 50% of the rest muscle-tendon length.

The muscle may be shortened during the muscle contraction up to 60% of a resting muscle length. The muscle shortening may be in a range of 0.1% to 50% of the resting muscle length, or in the range of 0.5% to 40% of the resting muscle length, or in the range of 1% to 25% of the resting muscle length.

The muscle may shorten at a velocity of up to 10 cm/s. The muscle shortening velocity may be in a range of 0.1 cm/s to 7.5 cm/s, or in the range of 0.2 cm/s to 5 cm/s, or in the range of 0.5 cm/s to 3 cm/s.

A time-varying magnetic field may be applied to the patient in order to cause a muscle shaping effect by muscle contraction. The muscle may obtain increased tonus and/or volume. Strength of the muscle may increase as well.

Regarding the types of combined treatment by RF treatment and magnetic treatment, the treatment device may be configured to provide different treatment energies (e.g. RF field and magnetic field) in various time periods during one treatment session. The user may control or adjust the treatment through the HMI. HMI may be coupled to master unit and/or one or more control units. Also, the master unit and/or control unit may control or adjust application of different treatment energies according to treatment protocol, body area or another option selected by the user. In addition, the master unit and/or control unit may control or adjust application of different treatment energies according to feedback provided by any sensor mentioned above. Therefore, master unit and/or one or more control units may control or adjust the treatment and providing of treatment energies (e.g. RF treatment and magnetic treatment) in various time periods during one treatment session. All shown types of applications of magnetic treatment and RF treatment may be provided by treatment device.

One type of combined application of magnetic treatment with RF treatment may be simultaneous application. During simultaneous application both magnetic treatment and RF treatment may applied in same time during whole or most of treatment session. In one example, simultaneous application may be achieved by application of one or more sections of magnetic field with application of continuous RF field. In another example, pulsed magnetic treatment may be applied during continual RF treatment. In still another example, simultaneous application may be achieved by continual application of RF treatment together with e.g. one, or two long train of magnetic pulses. In such case, long train of magnetic pulses should include magnetic pulses having repetition rate of values in range of 1 Hz to 15 Hz or 1 Hz to 10 Hz. When only one or two long magnetic trains are used for the whole treatment session, train duration of such trains may be in the range of 5 s to 90 minutes or 10 s to 80 minutes or 15 minutes to 45 minutes.

Muscle contraction caused by the time-varying magnetic field with or during simultaneous RF treatment may include more affected muscle fibres. Also, the targeted biological structure (e.g. muscle) may be more contracted with applied lower magnetic flux density of magnetic field as compared to situation without simultaneous RF treatment.

Simultaneous application of the RF treatment and the magnetic treatment into the same body area may improve dissipation of heat created by the RF treatment. This effect is based on increased blood circulation in treated body area or vicinity of treated area. Also, induced muscle work may improve homogeneity of heating and dissipation of heat induced and provided by RF field.

Another type of combined application of magnetic treatment with RF treatment may be separate application. During separate application both magnetic treatment and RF treatment may applied in different time during treatment session. RF treatment may be provided before, after, and/or between magnetic envelopes, bursts, trains, pulses and/or impulses od magnetic treatment.

The ratio between a time when the magnetic treatment is applied and a time when the RF treatment is applied may be in a range of 0.2% to 80% or 2% to 60% or 5% to 50% or 20% to 60%. The time of applied magnetic treatment for this calculation is the sum of all pulse durations during the treatment.

Another type of combined application of magnetic treatment with RF treatment may be dependent application. Application of one treatment energy may be dependent on start or one or more treatment parameter of another treatment energy. Dependent application may be started or regulated according to feedback from one or more sensor. For example, start of application of RF treatment may be dependent on start of magnetic treatment or start of train, burst and/or envelope. When the thermal dissipation provided by a muscle work (including muscle contraction and/or relaxation) is not provided, health risk of unwanted tissue damage caused by overheating may occur. In another example, start of application of magnetic treatment may be dependent on the start, time duration or intensity of RF treatment. The magnetic treatment may preferably start after the biological structure is sufficiently heated. The magnetic treatment providing at least partial muscle contraction or muscle contraction may improve blood and lymph flow, provide massage of the adjacent tissues and provides better redistribution of the heat induced in the patient's body by the RF treatment.

The treatment protocol may be divided into two or more treatment sections. The number of treatment section may be in the range of 2 to 50 or 2 to 30 or 2 to 15 for one protocol.

Each treatment section of the treatment protocol may include different treatment parameters and/or types of combined treatment of magnetic treatment and RF treatment as described above.

One treatment section may last for a section time, wherein section time may be in a range of 10 s to 30 minutes or 15 s to 25 minutes or 20 s to 20 minutes. Different sections may have different treatment effects in one or more treated biological structures, e.g., a muscle and adipose tissue. For example, one treatment section may provide high intensity muscle exercise where muscle contractions are intensive and a high number of such contractions is provided, wherein a higher repetition rate of magnetic pulses with high energy flux density may be used during one treatment section. Another treatment section may have a muscle relaxation effect, wherein the low and/or the high repetition rate of magnetic pulses may be used and/or also lower magnetic flux density of magnetic field may be used.

Treatment protocol may include different setting of power output of RF treatment, as commanded or controlled by control system of the treatment device. One setting may be a constant power output, wherein the power output during the treatment protocol may be same. Another setting may be an oscillating power output of RF treatment. The power output of RF treatment may oscillate around predetermined value of power output in a range of 0.1% to 5% of predetermined power output. Still another setting may be a varying power output of RF energy, wherein the power output of RF treatment is varied during treatment protocol. The variation of power output of RF treatment may be provided in one or more power output variation steps, wherein one power output variation step may include one change of value of power output of RF treatment applied by one or more RF electrodes. The change of power output of RF treatment from one value to another value during power output variation step may be in the range of 0.1 W to 50 W or 0.1 W to 30 W or 0.1 W to 20 W. The power output variation step may have time duration in the range of 0.1 s to 10 min or 0.1 s to 5 min.

Regarding the variation of power output of RF energy, the power output of RF energy may have different values during different time period of treatment protocol. Therefore, RF treatment may have different value of power output during first time period followed by power output variation step followed by second time period having different value of power output of RF treatment. The first time period having one value of power output of RF treatment may be in a range of 1 s to 15 min or 10 s to 10 min. The second time period having another value of power output of RF treatment may be in a range of 1 s to 45 min or 4 s to 59 min or 5 s to 35 min. For example, RF treatment may have value of power output about 20 W during first time and 10 W during second time period.

First exemplary treatment protocol may include two treatment section. First treatment section may include envelopes of magnetic pulses, wherein the envelopes may include pulses having repetition rate in the range of 1 to 10 Hz. Envelopes of first treatment section may have rectangular or trapezoidal shape. Duration of first treatment section may be from 3 minutes to 15 minutes. Second treatment section may include envelopes of magnetic pulses, wherein the envelopes may include pulses having repetition rate in the range of 15 to 45 Hz. Envelopes of second treatment section may have rectangular or trapezoidal shape. Duration of first treatment section may be from 3 minutes to 15 minutes. The treatment sections may be repeated one after another. The RF treatment may be applied continuously during the whole treatment protocol. The RF treatment may include one or two power output variation steps.

Second exemplary treatment protocol may include three treatment section. First treatment section may include envelopes of magnetic pulses, wherein the envelopes may include pulses having repetition rate in the range of 5 to 50 Hz. Envelopes of first treatment section may have rectangular or trapezoidal shape. Duration of first treatment section may be from 3 minutes to 15 minutes. Second treatment section may include envelopes of magnetic pulses, wherein the envelopes may include pulses having repetition rate in the range of 15 to 45 Hz. Envelopes of second treatment section may have rectangular or trapezoidal shape. Duration of first treatment section may be from 3 minutes to 15 minutes. Third treatment section may include envelopes of magnetic pulses, wherein the envelopes may include pulses having repetition rate in the range of 10 to 40 Hz. Envelopes of third treatment section may have rectangular or trapezoidal shape. Duration of third treatment section may be from 3 minutes to 15 minutes. The treatment sections may be repeated one after another. The RF treatment may be applied continuously during the whole treatment protocol. The RF treatment may include one or two power output variation steps. The one power output variation step may be initiated in a range of 1 or 20 minutes after the start of the treatment protocol. In one example, the one power output variation step may be initiated three minutes after the start of the treatment protocol.

All of the examples, embodiments and methods may be used separately or in any combination.

Novel systems and methods have been described. The invention should be interpreted in the broadest sense, hence various changes and substitutions may be made of course without departing from the spirit and scope of the invention. The invention therefore should not be limited, except by the following claims and their equivalents.

Following patent applications are incorporated herein by reference in their entireties:

U.S. patent application Ser. No. 14/789,156 filed Jul. 1, 2015; U.S. patent application Ser. No. 14/789,658 filed Jul. 1, 2015; U.S. patent application Ser. No. 14/783,110 filed Oct. 1, 2015; U.S. patent application Ser. No. 14/926,365 filed Oct. 29, 2015; U.S. patent application Ser. No. 14/951,093 filed Nov. 24, 2015; U.S. patent application Ser. No. 15/073,318 filed Mar. 17, 2016; U.S. patent application Ser. No. 15/099,274 filed Apr. 14, 2016; U.S. patent application Ser. No. 15/151,012 filed May 10, 2016; U.S. patent application Ser. No. 15/344,811 filed Nov. 7, 2016; U.S. patent application Ser. No. 15/178,455 filed Jun. 9, 2016; U.S. patent application Ser. No. 15/396,073 filed Dec. 30, 2016; U.S. patent application Ser. No. 15/404,384 filed Jan. 12, 2017; U.S. Provisional Patent Application No. 62/357,679 filed Jul. 1, 2016; U.S. Provisional Patent Application No. 62/440,905 filed Dec. 30, 2016; U.S. Provisional Patent Application No. 62/440,912 filed Dec. 30, 2016; U.S. Provisional Patent Application No. 62/440,922 filed Dec. 30, 2016; U.S. Provisional Patent Application No. 62/441,805 filed Jan. 3, 2017; U.S. Provisional Patent Application No. 62/440,936 filed Dec. 30, 2016; U.S. Provisional Patent Application No. 62/440,940 filed Dec. 30, 2016; U.S. patent application Ser. No. 15/446,951 filed Mar. 1, 2017; U.S. patent application Ser. No. 15/473,390 filed Mar. 29, 2017; U.S. patent application Ser. No. 15/601,719 filed May 22, 2017; U.S. patent application Ser. No. 15/677,371 filed Aug. 15, 2017; U.S. patent application Ser. No. 15/860,443 filed Jan. 2, 2018; U.S. patent application Ser. No. 15/862,410 filed Jan. 4, 2018; U.S. patent application Ser. No. 15/954,783 filed Apr. 17, 2018; U.S. patent application Ser. No. 16/034,752 filed Jul. 13, 2018; U.S. patent application Ser. No. 16/034,793 filed Jul. 13, 2018; U.S. patent application Ser. No. 16/042,093 filed Jul. 23, 2018; U.S. patent application Ser. No. 16/196,798 filed Nov. 20, 2018; U.S. patent application Ser. No. 16/196,837 filed Nov. 20, 2018; U.S. patent application Ser. No. 16/218,735 filed Dec. 13, 2018; U.S. patent application Ser. No. 16/219,724 filed Dec. 13, 2018; U.S. Provisional Patent Application No. 62/786,731 filed Dec. 31, 2018; U.S. patent application Ser. No. 16/266,570 filed Feb. 4, 2019; U.S. patent application Ser. No. 16/266,494 filed Feb. 4, 2019; U.S. patent application Ser. No. 16/294,034 filed Mar. 6, 2019; U.S. patent application Ser. No. 16/560,790 filed Sep. 4, 2019; U.S. patent application Ser. No. 16/567,866 filed Sep. 11, 2019; U.S. patent application Ser. No. 16/664,524 filed Oct. 25, 2019; U.S. patent application Ser. No. 16/673,784 filed Nov. 4, 2019; U.S. patent application Ser. No. 16/673,683 filed Nov. 4, 2019; U.S. patent application Ser. No. 16/674,144 filed Nov. 5, 2019; U.S. patent application Ser. No. 16/827,330 filed Mar. 23, 2020 and International Patent Application No. PCT/IB2016/053930 filed Jun. 30, 2016.

List of abbreviations related to FIGS. 17, 18 and 18*a*. The (A/B) means that respective element of the list may be shown with respective letter. For example, ESD (A/B) means that ESD A and/or ESD B are shown in at least one Figure.

PS power source
ESD (A/B) energy storage device
SW (A/B) switch
HIFEM (A/B) treatment cluster for magnetic treatment
MFGD (A/B) magnetic field generating device
CUM (A/B) control unit of magnetic circuit
APS RF auxiliary power source of RF circuit
PU power unit
SPSRF steady power source of RF circuit
PNFLT power network filter
PSRF power source for RF treatment
RF (A/B) treatment cluster for RF treatment
SYM (A/B) symmetrisation element
AP (A/B) applicator
RFE (A/B) RF electrode
APS (A/B) auxiliary power source
PSM power source for magnetic treatment
BPS (A/B) board power source
SPSM steady power source of magnetic circuit
PN power network
PF pulse filter
SE safety element
PA power amplifier
CURF control unit of RF circuit

What is claimed is:

1. A treatment device for providing a magnetic treatment and a radiofrequency treatment to a body area of a patient, comprising:
an energy storage device configured to store electrical energy;
a magnetic field generating device;
a switching device configured to discharge the electrical energy from the energy storage device to the magnetic field generating device, such that a time-varying magnetic field is generated and provides muscle contraction to a muscle in the body area of the patient,
wherein the time-varying magnetic field has a magnetic flux density in a range of 0.1 Tesla to 7 Tesla and a repetition rate in a range of 0.1 Hz to 700 Hz; and
a radiofrequency electrode configured to generate a radiofrequency field to heat tissue in the body area of the patient,
wherein a body of the radiofrequency electrode comprises a plurality of openings in a range of 5 to 1000 openings.

2. The device of claim 1, wherein the magnetic field generating device comprises an air core.

3. The device of claim 2, further comprising an applicator comprising a casing, wherein the magnetic field generating device is positioned within the casing.

4. The device of claim 1, wherein a shortest distance between the magnetic field generating device and the radiofrequency electrode is in a range of 0.1 mm to 100 mm.

5. The device of claim 4, wherein the magnetic field generating device and the radiofrequency electrode are separated by an insulating material or an air gap.

6. The device of claim 1, wherein the radiofrequency electrode comprises a conductive layer deposited on an insulating substrate, and wherein a thickness of the conductive layer is in a range of 0.01 mm to 5 mm.

7. The device of claim 6, wherein the body of the radiofrequency electrode further comprises a plurality of protrusions, wherein adjacent protrusions of the plurality of protrusions define the plurality of openings, and wherein at least one of the plurality of openings is further defined by a hypothetical circle fitting within the opening between adjacent protrusions, such that a maximum diameter of the hypothetical circle fitting within the opening between the adjacent protrusions is in a range of 0.01 mm to 10 mm.

8. The device of claim 1, wherein the radiofrequency electrode further comprises an electrically insulating material or a dielectric material disposed within each opening of the plurality of openings.

9. A treatment device for providing a magnetic treatment and a radiofrequency treatment to a body area of a patient, comprising:
an energy storage device configured to store electrical energy;
a magnetic field generating device;
a switching device configured to discharge the electrical energy from the energy storage device to the magnetic field generating device, such that a time-varying magnetic field is generated and provides muscle contraction to a muscle in the body area of the patient,
wherein the time-varying magnetic field has a magnetic flux density in a range of 0.5 Tesla to 7 Tesla and a repetition rate in a range of 0.1 Hz to 700 Hz; and
a radiofrequency electrode configured to generate a radiofrequency field to heat tissue in the body area of the patient,
wherein the radiofrequency electrode is a first radiofrequency electrode of a bipolar pair of radiofrequency electrodes, and
wherein the radiofrequency electrode is configured to be positioned between the magnetic field generating device and the body area of the patient.

10. The device of claim 9, wherein the magnetic field generating device and the radiofrequency electrode are separated by an air gap.

11. The device of claim 9, wherein the magnetic field generating device and the radiofrequency electrode are separated by an insulating material.

12. The device of claim 11, wherein the insulating material is a part of a printed circuit board.

13. The device of claim 9, wherein a distance between the magnetic field generating device and the radiofrequency electrode is in a range of 0.5 mm to 50 mm.

14. The device of claim 13, wherein the radiofrequency electrode comprises a conductive wire.

15. The device of claim 9, wherein the radiofrequency electrode comprises a conductive layer having a thickness in a range of 0.01 mm to 5 mm.

16. The device of claim 15, wherein the radiofrequency electrode is deposited on an insulating substrate having a thickness in a range of 0.01 mm to 10 mm.

17. A treatment device for providing a magnetic treatment and a radiofrequency treatment to a body area of a patient, comprising:
 an energy storage device configured to store electrical energy;
 an applicator comprising:
  a casing comprising a top cover and a bottom cover;
  a magnetic field generating device housed within the casing; and
  a radiofrequency electrode positioned between the magnetic field generating device and the bottom cover; and
 a switching device configured to discharge the electrical energy from the energy storage device to the magnetic field generating device, such that the magnetic field generating device generates a time-varying magnetic field to cause a muscle in the body area of the patient to contract,
 wherein the time-varying magnetic field has a magnetic flux density in a range of 0.5 Tesla to 7 Tesla and a repetition rate in a range of 0.1 Hz to 700 Hz, and
 wherein the radiofrequency electrode is configured to generate a radiofrequency field to heat tissue in the body of the patient.

18. The device of claim 17, wherein the radiofrequency electrode is connected to a power amplifier configured to generate a radiofrequency signal having a frequency in a range of 100 kHz to 3 GHz.

19. The device of claim 18, wherein the radiofrequency electrode is a first radiofrequency electrode from a bipolar pair of radiofrequency electrodes positioned within the applicator.

20. The device of claim 19, further comprising a control system comprising a microprocessor, wherein the applicator further comprises a temperature sensor, and wherein the temperature sensor communicates with the control system.

21. The device of claim 19, wherein a distance between the pair of radiofrequency electrodes is in a range of 0.1 cm to 25 cm.

22. The device of claim 17, wherein the radiofrequency electrode comprises a conductive layer having a thickness in a range of 0.01 mm to 10 mm.

23. The device of claim 17, wherein the radiofrequency electrode comprises a conductive layer deposited on an insulating substrate.

24. The device of claim 17, wherein the radiofrequency electrode comprises 5 to 1000 openings in a body of the radiofrequency electrode.

25. A treatment device for providing a magnetic treatment and a radiofrequency treatment to a body area of a patient, comprising:
 an energy storage device configured to store electrical energy;
 an applicator comprising:
  a casing of the applicator;
  a magnetic field generating device housed within the casing; and
  a radiofrequency electrode comprising a conductive layer;
 a switching device configured to discharge the electrical energy from the energy storage device to the magnetic field generating device, such that the magnetic field generating device generates a time-varying magnetic field to cause a muscle in the body area of the patient to contract; and
 a human machine interface comprising a display interface comprising:
  a plurality of intensity scrollers or buttons;
  two intensity bars configured to indicate intensity of the magnetic treatment; and
  two intensity bars configured to represent indicate intensity of the radiofrequency treatment,
 wherein the time-varying magnetic field has a magnetic flux density in a range of 0.5 Tesla to 7 Tesla and a repetition rate in a range of 0.1 Hz to 700 Hz,
 wherein the radiofrequency electrode is configured to generate a radiofrequency field to heat tissue in the body of the patient,
 wherein a first scroller or button of the plurality of intensity scrollers or buttons is configured to independently control intensity of a magnetic treatment provided by the magnetic field generating device, and is configured to effect a change in one or more of the intensity bars configured to indicate the intensity of the magnetic treatment, and
 wherein a second scroller or button of the plurality of intensity scrollers or buttons is configured to independently control intensity of a radiofrequency treatment provided by the radiofrequency electrode, and is configured to effect a change in one or more of the intensity bars configured to indicate the intensity of the radiofrequency treatment.

26. The device of claim 25, wherein the display interface comprises two intensity buttons configured to control the intensity of the radiofrequency treatment and two intensity buttons configured to control the intensity of the magnetic treatment.

27. The device of claim 26, wherein the entirety of the radiofrequency electrode is positioned within the casing of the applicator.

28. The device of claim 25, further comprising:
 a main unit comprising the energy storage device, a power source for the radiofrequency treatment, and a connector to which the applicator is connected; and
 a connecting tube configured to connect the applicator to the connector,
 wherein the connecting tube comprises one or more wires configured to provide an electrical signal to the radiofrequency electrode.

29. The device of claim 28, wherein the applicator further comprises an outlet configured to dissipate heat generated by the magnetic field generating device.

30. The device of claim 29, wherein the magnetic field generating device is a planar magnetic coil.

* * * * *